United States Patent
Schunk et al.

(10) Patent No.: US 9,302,988 B2
(45) Date of Patent: Apr. 5, 2016

(54) FLUOROMETHYL-SUBSTITUTED PYRROLE CARBOXAMIDES

(71) Applicant: GRÜNENTHAL GMBH, Aachen (DE)

(72) Inventors: Stefan Schunk, Aachen (DE); Melanie Reich, Aachen (DE); Henning Steinhagen, Sulzbach a.T. (DE); Nils Damann, Köln (DE); Michael Haurand, Aachen (DE); Achim Kless, Aachen (DE); Philip Skone, Herts (GB); Richard Hamlyn, Cambridgeshire (GB); Robert Kirby, Cambridge (GB); Marc Rogers, Cambridgeshire (GB); Kathy Sutton, Herts (GB)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/013,081

(22) Filed: Aug. 29, 2013

(65) Prior Publication Data

US 2014/0066426 A1    Mar. 6, 2014

Related U.S. Application Data

(60) Provisional application No. 61/694,326, filed on Aug. 29, 2012.

(30) Foreign Application Priority Data

Aug. 29, 2012   (EP) .................................. 12006120

(51) Int. Cl.

| | | |
|---|---|---|
| *C07D 207/323* | (2006.01) | |
| *C07D 207/34* | (2006.01) | |
| *C07D 403/12* | (2006.01) | |
| *C07D 401/06* | (2006.01) | |
| *C07D 401/12* | (2006.01) | |
| *C07D 403/06* | (2006.01) | |
| *C07D 405/12* | (2006.01) | |
| *C07D 409/12* | (2006.01) | |
| *C07D 413/06* | (2006.01) | |
| *C07D 413/12* | (2006.01) | |
| *C07D 417/06* | (2006.01) | |
| *C07D 487/04* | (2006.01) | |

(52) U.S. Cl.
CPC .......... *C07D 207/34* (2013.01); *C07D 207/323* (2013.01); *C07D 401/06* (2013.01); *C07D 401/12* (2013.01); *C07D 403/06* (2013.01); *C07D 403/12* (2013.01); *C07D 405/12* (2013.01); *C07D 409/12* (2013.01); *C07D 413/06* (2013.01); *C07D 413/12* (2013.01); *C07D 417/06* (2013.01); *C07D 487/04* (2013.01)

(58) Field of Classification Search
CPC ................................................... C07D 207/323
See application file for complete search history.

(56) References Cited

U.S. PATENT DOCUMENTS

| 7,968,591 B2 | 6/2011 | Oberboersch et al. |
| 2009/0137573 A1 | 5/2009 | Oberboersch et al. |

FOREIGN PATENT DOCUMENTS

WO     2012 004604 A1    1/2012

OTHER PUBLICATIONS

Winters et al. (Bioorg. Med. Chem. Lett., 24 (2014), p. 2053-2056).*
Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chs. 9-10 provided.*
Tyagarajan et al; "A potent and selective indole N-type calcium channel (Cav2.2) blocker for the rtreatment of pain"; Bioorganic & Medicinal Chemistry Letters 21 (2011) pp. 869-873.
Bennett, G.J. and Xie, Y.K., "A peripheral mononeuropathy in rat that produces disorders of pain sensation like those seen in man", Pain 1988, 33(1), 87-107.
D'Amour and Smith; "A method for determining loss of pain sensation"; (J. Pharm. Exp. Ther. 72, 74-79 (1941).
Dubuisson, D. et al.; "The formalin test: a quantitative study of the analgesic effects of morphine, meperidine, and brain stem stimulation in rats and cats"; Pain 1977, 4, 161-174.
Remington's Pharmaceutical Sciences, A.R. Gennaro (Editor), 17th edition, Mack Publishing Company, Easton, Pa, 1985, in particular in Part 8, Chapters 76 to 93.
Kim, S.H. and Chung, J.M., An experimental model for peripheral neuropathy produced by segmental spinal nerve ligation in the rat, Pain 1992, 50(3), 355-363.
Miljanich, G.P.; "Ziconotide: Neuronal calcium channel blocker for treating severe chroni pain"; Current Medicinal Chemistry, 2004, 11, 3029-2040.
Rauck, Richard L. et al; "Intrathecal Ziconotide for Neuropathic Pain: A Review"; Pain Practice, vol. 9, Issue 5, 2009, 327-337.
Staats, et al; "Intrathecal ziconotide in the treatment of refractory pain in patients with cancer or AIDS"; JAMA, 2003; 291: 63-70 (Reprinted JAMA, Jan. 7, 2004, vol. 291, No. 1, 63-70).

* cited by examiner

*Primary Examiner* — Robert Havlin
(74) *Attorney, Agent, or Firm* — Norris McLaughlin & Marcus, P.A.

(57) ABSTRACT

The invention relates to pyrrole carboxamides bearing a fluoromethyl-moiety as voltage gated calcium channel blockers, to pharmaceutical compositions containing these compounds and also to these compounds for use in the treatment and/or prophylaxis of pain and further diseases and/or disorders.

9 Claims, No Drawings

FLUOROMETHYL-SUBSTITUTED PYRROLE CARBOXAMIDES

CROSS-REFERENCE TO RELATED APPLICATIONS

This application claims priority of U.S. Provisional Patent Application No. 61/694,326, filed on Aug. 29, 2012, and European Patent Application No. 12 006 120.5, filed on Aug. 29, 2012, the entire contents of which patent applications are incorporated herein by reference.

FIELD OF THE INVENTION

The invention relates to substituted pyrrole-2-yl-carboxamides bearing a fluorinated methyl moiety in 5-position as voltage gated Ca-channel (CaV) blockers, to pharmaceutical compositions containing these compounds and also to these compounds for use in the treatment and/or prophylaxis of pain and further diseases and/or disorders.

BACKGROUND OF THE INVENTION

Ion channels are proteins that form pores in membranes of biological cells and control the flow of ions down their electrochemical gradient. They are involved in the regulation of a wide range of cellular functions in both excitable and nonexcitable cells and provide attractive therapeutic targets for the treatment of various diseases.

In the somatosensory context, CaV2.2 channels, specific cellular plasma membrane calcium channels that belong to a diverse superfamily of voltage-gated calcium channels (VGCCs), were demonstrated to play an important role in spinal nociceptive processing.

The critical role of CaV2.2 in pain processing was underlined by the clinical efficacy of the intrathecally delivered, selective CaV2.2 channel antagonist Ziconotide (SNX-111; Prialt™), a synthetic peptide derived from a ω-(omega)-conotoxin peptide (Miljanich, 2004, Curr. Med. Chem., 11(23), p. 3029-40; Staats et al., 2004, JAMA, 291(1), p. 63-70). Inthrathecal administration of Ziconotide is required in order to reach the ion channel in presynaptic terminals of sensory neurons in the spinal cord. Common side effects of Ziconotide include memory impairment, dizziness, nystagmus, speech disorder, nervousness, somnolence and abnormal gait (Rauck et al., 2009, Pain Pract., 9, p. 327-37), which have been attributed to the inhibition of CaV2.2 channels in the brain by Ziconotide.

Therefore, a demand remains for the development of orally available CaV2.2 calcium channel blockers that show the desired qualities and effectively block CaV2.2 calcium channels in the nociceptive signaling pathway.

SUMMARY OF THE INVENTION

The present invention describes small molecule CaV2.2 channel blockers.

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by CaV2.2 calcium channels.

This object is achieved by the subject matter described herein.

It has surprisingly been found that the compounds of general formula (I), as given below, display outstanding affinity to CaV2.2 calcium channels and are therefore particularly suitable for the prophylaxis and/or treatment of disorders or diseases which are at least partially mediated by CaV2.2 calcium channels.

The present invention therefore relates to a compound of general formula (I),

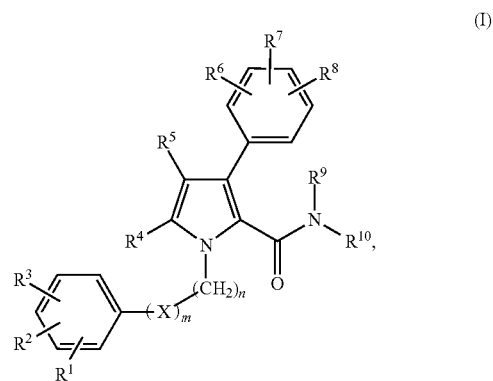

wherein n represents 0, 1 or 2; m represents 0 or 1 with the proviso that n m;

X is selected from the group consisting of O, S, NH or N—$C_{1-6}$-alkyl;

$R^1$, $R^2$ and $R^3$, are each independently of one another selected from the group consisting of H; F; Cl; Br; I; $NO_2$; CN; $C_{1-6}$-alkyl; $CF_3$; $CF_2H$; $CFH_2$; $CF_2Cl$; $CFCl_2$; C(=O)—H; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—$NH_2$; O—S(=O)$_2$—N(H)($C_{1-6}$-alkyl); O—S(=O)$_2$—N($C_{1-6}$-alkyl)$_2$; $NH_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—$NH_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—$NH_2$; N(H)—S(=O)$_2$—N(H)($C_{1-6}$-alkyl); N(H)—S(=O)$_2$N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—$NH_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); or S(=O)$_2$—N($C_{1-6}$-alkyl)$_2$, whereby in each case $C_{1-6}$-alkyl may be branched or unbranched; unsubstituted or mono- or polysubstituted;

a $C_{3-6}$ cycloaliphatic residue or a 3 to 7 membered heterocycloaliphatic residue, in each case unsubstituted or mono- or polysubstituted;

$R^4$ represents $CH_2F$; $CHF_2$, or $CF_3$;

$R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or poly-substituted;

$R^6$, $R^7$ and $R^8$, are each independently of one another selected from the group consisting of H; F; Cl; Br; I; $NO_2$; CN; $C_{1-6}$-alkyl; $CF_3$; $CF_2H$; $CFH_2$; $CF_2Cl$; $CFCl_2$; C(=O)—H; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—$NH_2$; O—S(=O)$_2$—N(H)($C_{1-6}$-alkyl); O—S(=O)$_2$—N($C_{1-6}$-alkyl)$_2$; $NH_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—$NH_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—$NH_2$; N(H)—S(=O)$_2$—N(H)($C_{1-6}$-alkyl); N(H)—S(=O)$_2$N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—$NH_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); or S(=O)$_2$—N($C_{1-6}$-alkyl)$_2$, whereby in each case $C_{1-6}$-alkyl may be branched or unbranched; unsubstituted or mono- or poly-substituted;

a $C_{3-6}$ cycloaliphatic residue or a 3 to 7 membered heterocycloaliphatic residue, in each case unsubstituted or mono- or polysubstituted;

$R^9$ represents H, a $C_{1-10}$ aliphatic residue, branched or unbranched, unsubstituted or mono- or poly-substituted; a $C_{3-10}$ cycloaliphatic residue or a 3 to 10 membered heterocycloaliphatic residue, in each case unsubstituted or mono- or poly-substituted and in each case optionally connected via a $C_{1-8}$ aliphatic group, branched or unbranched, which in turn may be unsubstituted or mono- or polysubstituted;

$R^{10}$ represents H, a $C_{1-10}$ aliphatic residue, branched or unbranched, unsubstituted or mono- or polysubstituted; a $C_{3-10}$ cycloaliphatic residue, a 3 to 10 membered heterocycloaliphatic residue or a heteroaryl residue, in each case unsubstituted or mono- or poly-substituted and in each case optionally connected via a $C_{1-8}$ alkylene group, branched or unbranched, which in turn may be unsubstituted or mono- or polysubstituted; or $R^9$ and $R^{10}$ together with the nitrogen atom connecting them form a 3 to 10 membered heterocycloaliphatic residue, which may be unsubstituted or mono- or polysubstituted;

optionally in the form of a single stereoisomer or a mixture of stereoisomers, in the form of the free compound and/or a physiologically acceptable salt and/or a physiologically acceptable solvate thereof.

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The term "physiologically acceptable salt" preferably comprises in the sense of this invention a salt of at least one compound according to the present invention and at least one physiologically acceptable acid or base.

A physiologically acceptable salt of at least one compound according to the present invention and at least one physiologically acceptable acid preferably refers in the sense of this invention to a salt of at least one compound according to the present invention with at least one inorganic or organic acid which is physiologically acceptable—in particular when used in human beings and/or other mammals. Examples of physiologically acceptable acids are: hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid.

A physiologically acceptable salt of at least one compound according to the present invention and at least one physiologically acceptable base preferably refers in the sense of this invention to a salt of at least one compound according to the present invention as an anion with at least one preferably inorganic cation, which is physiologically acceptable—in particular when used in human beings and/or other mammals.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents. Examples of physiologically acceptable solvents are water, alkanols, esters, ethers or ketones. Particularly preferred solvates are hydrates.

The terms "alkyl", "$C_{1-4}$-alkyl", and "$C_{1-6}$-alkyl" preferably comprise in the sense of this invention acyclic saturated aliphatic hydrocarbon residues, which can be respectively branched or unbranched and can be unsubstituted or can be mono- or polysubstituted, e.g. mono-, di- or trisubstituted, and which contain 1 to 6 carbon atoms, i.e. 1, 2, 3, 4, 5 or 6 carbon atoms, or 1 to 4, i.e. 1, 2, 3 or 4 carbon atoms, respectively, i.e. $C_{1-6}$ aliphatic residues and $C_{1-6}$ aliphatic residues, i.e. $C_{1-6}$ alkanyls as well as $C_{1-6}$ alkanyls. Preferred $C_{1-6}$ alkanyl residues are selected from the group consisting of methyl, ethyl, n-propyl, 2-propyl, n-butyl, isobutyl, sec.-butyl, tert.-butyl, n-pentyl, isopentyl, neopentyl, and n-hexyl. Preferred $C_{1-6}$ alkanyl residues are selected from the group consisting of methyl, ethyl, n-propyl, 2-propyl, n-butyl, isobutyl, sec.-butyl, and tert.-butyl.

In relation to the terms "alkyl", "$C_{1-4}$-alkyl" and "$C_{1-6}$-alkyl", the term "monosubstituted" or "polysubstituted" such as di- or tri-substituted refers in the sense of this invention, with respect to the corresponding residues or groups, to the single substitution or multiple substitution, e.g. disubstitution or trisubstitution, of one or more hydrogen atoms each independently of one another by at least one substituent. The term "polysubstituted" such as di- or tri-substituted with respect to polysubstituted residues and groups such as di- or tri-substituted residues and groups includes the polysubstitution of these residues and groups either on different or on the same atoms, for example trisubstituted on the same carbon atom, as in the case of $CF_3$ or $CH_2CF_3$ or at various points, as in the case of $CH(OH)$—$CH_2CH_2$—$CHCl_2$. The multiple substitution can be carried out using the same or using different substituents.

The terms "$C_{1-10}$ aliphatic residue", "$C_{1-8}$ aliphatic residue", and "$C_{1-6}$ aliphatic residue" comprise in the sense of this invention acyclic saturated or unsaturated aliphatic hydrocarbon residues, which can be branched or unbranched and also unsubstituted or mono- or polysubstituted, which contain 1 to 10, or 1 to 8, or 1 to 4 carbon atoms respectively, i.e. $C_{1-10}$ alkanyls ($C_{1-10}$ alkyls), $C_{2-10}$ alkenyls and $C_{2-10}$ alkynyls as well as $C_{1-8}$ alkanyls ($C_{1-8}$ alkyls), $C_{2-8}$ alkenyls and $C_{2-8}$ alkynyls as well as $C_{1-6}$ alkanyls ($C_{1-6}$ alkyls), $C_{2-4}$ alkenyls and $C_{2-4}$ alkynyls, respectively. Alkenyls comprise at least one C—C double bond (a C=C-bond) and alkynyls comprise at least one C—C triple bond (a C≡C-bond). Preferably, aliphatic residues are selected from the group consisting of alkanyl (alkyl) and alkenyl residues, more preferably are alkanyl (alkyl) residues. Preferred $C_{1-10}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl and n-decyl. Preferred $C_{1-8}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl and n-octyl. Preferred $C_{1-6}$ alkanyl residues are selected from the group consisting of methyl, ethyl, n-propyl, 2-propyl, n-butyl, isobutyl, sec.-butyl and tert.-butyl. Preferred $C_{2-10}$ alkenyl residues are selected from the group consisting of ethenyl (vinyl), propenyl (—$CH_2CH=CH_2$, —$CH=CH$—$CH_3$, —$C(=CH_2)$—$CH_3$), butenyl, pentenyl, hexenyl heptenyl, octenyl, nonenyl and decenyl. Preferred $C_{2-8}$ alkenyl residues are selected from the group consisting of ethenyl (vinyl), propenyl (—$CH_2CH=CH_2$, —$CH=CH$—$CH_3$, —$C(=CH_2)$—$CH_3$), butenyl, pentenyl, hexenyl heptenyl and octenyl. Preferred $C_{2-4}$ alkenyl residues are selected from the group consisting of ethenyl (vinyl), propenyl (—$CH_2CH=CH_2$, —$CH=CH$—$CH_3$, —$C(=CH_2)$—$CH_3$) and butenyl. Preferred $C_{2-10}$ alkynyl residues are selected from the group consisting of ethynyl, propynyl (—$CH_2$—$C≡CH$, —$C≡C$—$CH_3$), butynyl, pentynyl, hexynyl, heptynyl, octynyl, nonynyl and decynyl. Preferred $C_{2-8}$ alkynyl residues are selected from the group consisting of ethynyl, propynyl (—$CH_2$—$C≡CH$, —$C≡C$—$CH_3$), butynyl, pentynyl, hexynyl, heptynyl and octynyl. Preferred $C_{2-4}$ alkynyl residues are selected from the group consisting of ethynyl, propynyl (—$CH_2$—$C≡CH$, —$C≡C$—$CH_3$) and butynyl.

The terms "$C_{3-6}$ cycloaliphatic residue" and "$C_{3-10}$ cycloaliphatic residue" mean for the purposes of this invention cyclic aliphatic hydrocarbons containing 3, 4, 5 or 6 carbon atoms and 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloaliphatic residues can be bound to the respective superordinate general structure via any desired and possible ring member of the cycloaliphatic residue. The cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues, which in each case can in turn be unsubstituted or mono- or polysubstituted. $C_{3-10}$ cycloaliphatic residue can furthermore be singly or multiply bridged such as, for example, in the case of adamantyl, bicyclo[2.2.1]heptyl or bicyclo[2.2.2]octyl. Preferred $C_{3-10}$ cycloaliphatic residues are selected from the group consisting of cyclopropyl, cyclobutyl, cyclopentyl, cyclohexyl, cycloheptyl, cyclooctyl, cyclononyl, cyclodecyl, adamantyl, cyclopentenyl, cyclohexenyl, cycloheptenyl, cyclooctenyl,

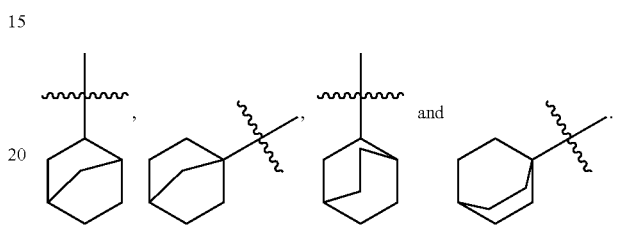

Preferred $C_{3-6}$ cycloaliphatic residues are selected from the group consisting of cyclopropyl, cyclobutyl, cyclopentyl, cyclohexyl, cyclopentenyl and cyclohexenyl. Particularly preferred $C_{3-10}$ cycloaliphatic and $C_{3-6}$ cycloaliphatic residues are $C_{3-6}$ cycloaliphatic residues such as cyclopropyl, cyclobutyl, cyclopentyl, cyclohexyl, cyclopentenyl and cyclohexenyl, in particular cyclopropyl.

The terms "3 to 7-membered heterocycloaliphatic residue" or "3-7-membered heterocycloaliphatic residue", and "3 to 10-membered heterocycloaliphatic residue" or "3-10-membered heterocycloaliphatic residue" mean for the purposes of this invention heterocycloaliphatic saturated or unsaturated (but not aromatic) residues having 3 to 7, i.e. 3, 4, 5, 6 or 7 ring members, and 3 to 10, i.e. 3, 4, 5, 6, 7, 8, 9 or 10 ring members, respectively, in which in each case at least one, if appropriate also two or three carbon atoms are replaced by a heteroatom or a heteroatom group each selected independently of one another from the group consisting of O, S, S(=O), S(=O)$_2$, N, NH and N($C_{1-6}$-alkyl) such as N($CH_3$), wherein the ring members can be unsubstituted or mono- or polysubstituted. The cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues, which in each case can in turn be unsubstituted or mono- or polysubstituted. The heterocycloaliphatic residue can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cycloaliphatic, aromatic or heteroaromatic ring systems, i.e. with a cycloaliphatic, heterocycloaliphatic, aryl or heteroaryl residue, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 14 ring members, wherein the ring system can be formed with further saturated, (partially) unsaturated, (hetero)cycloaliphatic or aromatic or heteroaromatic rings, i.e. with a cycloaliphatic, heterocycloaliphatic, aryl or heteroaryl residue, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

The term "connected via a $C_{1-6}$ aliphatic group" or "via a $C_{1-8}$ aliphatic group" with respect to residues as heterocycloaliphatic residue and cycloaliphatic residue mean for the purpose of the invention that these residues have the above-defined meanings and that each of these residues is bound to the respective superordinate general structure via a $C_{1-6}$ aliphatic group or via a $C_{1-8}$ aliphatic group, respectively. The $C_{1-6}$ aliphatic group and the $C_{1-8}$ aliphatic group can in all cases be branched or unbranched, unsubstituted or mono- or polysubstituted. The $C_{1-6}$ aliphatic group can in all cases be furthermore saturated or unsaturated, i.e. can be a $C_{1-6}$-alkylene group, a $C_{2-6}$-alkenylene group or a $C_{2-6}$-alkynylene group. The same applies to a $C_{1-8}$ aliphatic group, i.e. a $C_{1-8}$ aliphatic group can in all cases be furthermore saturated or unsaturated, i.e. can be a $C_{1-8}$-alkylene group, a $C_{2-8}$-alkenylene group or a $C_{2-8}$-alkynylene group. Preferably, the $C_{1-6}$ aliphatic group is a $C_{1-6}$-alkylene group or a $C_{2-6}$-alkenylene group, more preferably a $C_{1-6}$-alkylene group. Preferably, the $C_{1-8}$ aliphatic group is a $C_{1-8}$-alkylene group or a $C_{2-8}$-alkenylene group, more preferably a $C_{1-8}$-alkylene group. Preferred $C_{1-6}$-alkylene groups are selected from the group consisting of —CH$_2$—, —CH$_2$—CH$_2$—, —CH(CH$_3$)—, CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)— and —C(CH$_3$)(CH$_2$CH$_3$)—. Preferred $C_{2-6}$-alkenylene groups are selected from the group consisting of —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C(CH$_3$)— and —C(CH$_2$CH$_3$)=CH—. Preferred $C_{2-6}$-alkynylene groups are selected from the group consisting of —C≡C—, —C≡C—CH$_2$—, —C≡C—CH$_2$—CH$_2$—, —C≡C—CH(CH$_3$)—, —CH$_2$—C≡C—CH$_2$— and —C≡C—C≡C—. Preferred $C_{1-8}$-alkylene groups are selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$— and —CH$_2$—(CH$_2$)$_4$—CH$_2$—. Preferred $C_{2-8}$-alkenylene groups are selected from the group consisting of —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C(CH$_3$)—, —C(CH$_2$CH$_3$)=CH—, —CH=CH—CH$_2$—CH$_2$—CH$_2$—, —CH$_2$—CH=CH—CH$_2$—CH$_2$—, —CH=CH—CH=CH—CH$_2$—CH$_2$— and —CH=CH—CH=CH—CH=CH—. Preferred $C_{2-8}$-alkynylene groups are selected from the group consisting of —C≡C—, —C≡C—CH$_2$—, —C≡C—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

In relation to the terms "alkyl", "$C_{1-4}$-alkyl", "$C_{1-6}$-alkyl", "aliphatic residue", "aliphatic group", "cycloaliphatic residue" and "heterocycloaliphatic residue", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; I; NO$_2$; CN; =O; =NH; =N(OH); =N(O—$C_{1-6}$-alkyl); CF$_3$; CF$_2$H; CFH$_2$; CF$_2$Cl; CFCl$_2$; $C_{1-6}$-alkyl; ($C_{1-8}$ alkylene)-OH; C(=O)—H; C(=O)—$C_{1-6}$-alkyl; C(=O)—OH; C(=O)—O—$C_{1-6}$-alkyl; C(=O)—N(H)(OH); C(=O)—NH$_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; OCF$_3$; OCF$_2$H; OCFH$_2$; OCF$_2$Cl; OCFCl$_2$; O—$C_{1-6}$-alkyl; O—($C_{1-8}$ alkylene)-OH; O—($C_{1-8}$ alkylene)-O—$C_{1-8}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—NH$_2$; O—S(=O)$_2$—N(H)($C_{1-6}$-alkyl); O—S(=O)$_2$—N($C_{1-6}$-alkyl)$_2$; NH$_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—NH$_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—NH$_2$;

N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$—OH; N(H)—S(=O)$_2$—$C_{1-6}$-alkyl; N(H)—S(=O)$_2$—O—$C_{1-6}$-alkyl; N(H)—S(=O)$_2$—NH$_2$; N(H)—S(=O)$_2$—N(H)($C_{1-6}$-alkyl); N(H)—S(=O)$_2$—N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—NH$_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; SCF$_3$; SCF$_2$H; SCFH$_2$; SCF$_2$Cl; SCFCl$_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); S(=O)$_2$—N($C_{1-6}$-alkyl)$_2$; a $C_{3-6}$ cycloaliphatic residue or a 3 to 7 membered heterocycloaliphatic residue. The term "polysubstituted" with respect to polysubstituted residues and groups includes the polysubstitution of these residues and groups either on different or on the same atoms, for example trisubstituted on the same carbon atom, as in the case of CF$_3$, CH$_2$CF$_3$ or 1,1-difluorocyclohexyl, or at various points, as in the case of CH(OH)—CH=CH—CHCl$_2$ or 1-chloro-3-fluorocyclohexyl. A substituent can if appropriate for its part in turn be mono- or polysubstituted. The multiple substitution can be carried out using the same or using different substituents.

Preferred substituents of "alkyl", "$C_{1-4}$-alkyl", "$C_{1-6}$-alkyl", "aliphatic residue" and "aliphatic group" are selected from the group consisting of F; Cl; Br; I; NO$_2$; CF$_3$; CN; =O; =NH; $C_{1-6}$-alkyl; ($C_{1-8}$-alkylene)-OH; C(=O)—H; C(=O)—$C_{1-6}$-alkyl; C(=O)—OH; C(=O)—O—$C_{1-6}$-alkyl; C(=O)—NH$_2$; C(=O)—N(H)($C_{1-6}$-alkyl); C(=O)—N($C_{1-6}$-alkyl)$_2$; OH; O—$C_{1-6}$-alkyl; O—C(=O)—$C_{1-6}$-alkyl; O—($C_{1-8}$ alkylene)-OH; O—($C_{1-8}$ alkylene)-O—$C_{1-8}$ alkyl; OCF$_3$; NH$_2$; N(H)($C_{1-6}$-alkyl); N($C_{1-6}$-alkyl)$_2$; N(H)—C(=O)—$C_{1-6}$-alkyl; N(H)—S(=O)$_2$—$C_{1-6}$-alkyl; N($C_{1-6}$-alkyl)-S(=O)$_2$—$C_{1-6}$-alkyl; N(H)—C(=O)—NH$_2$; N(H)—C(=O)—N(H)($C_{1-6}$-alkyl); N(H)—C(=O)—N($C_{1-6}$-alkyl)$_2$; N(H)—S(=O)$_2$—NH$_2$; N(H)—S(=O)$_2$—N(H)($C_{1-6}$-alkyl); N(H)—S(=O)$_2$—N($C_{1-6}$-alkyl)$_2$; N($C_{1-6}$-alkyl)-S(=O)$_2$—NH$_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; SCF$_3$; S—$C_{1-6}$-alkyl; S(=O)$_2$ $C_{1-6}$-alkyl; S(=O)$_2$OH; S(=O)$_2$O—$C_{1-6}$-alkyl and S(=O)$_2$—NH$_2$; S(=O)$_2$—N(H)($C_{1-6}$-alkyl); and S(=O)$_2$—N($C_{1-6}$-alkyl)$_2$.

Particularly preferred substituents of "alkyl", "$C_{1-4}$-alkyl", "$C_{1-6}$-alkyl", "aliphatic residue" and "aliphatic group" are selected from the group consisting of F; Cl; Br; I; NO$_2$; CF$_3$; CN; =O; $C_{1-6}$-alkyl; ($C_{1-8}$-alkylene)-OH; C(=O)—H; C(=O)—$C_{1-6}$-alkyl; C(=O)—OH; C(=O)—O—$C_{1-6}$-alkyl; C(=O)—NH$_2$; C(=O)—N(H)($C_{1-6}$-alkyl); C(=O)—N($C_{1-6}$-alkyl)$_2$; OH; O—$C_{1-6}$-alkyl; O—C(=O)—$C_{1-6}$-alkyl; O—($C_{1-6}$-alkylene)-OH; O—($C_{1-8}$-alkylene)-O—$C_{1-6}$-alkyl; OCF$_3$; NH$_2$; N(H)($C_{1-6}$-alkyl); N($C_{1-6}$-alkyl)$_2$; N(H)—C(=O)—$C_{1-6}$-alkyl; N(H)—S(=O)$_2$—$C_{1-6}$-alkyl; N($C_{1-6}$-alkyl)-S(=O)$_2$—$C_{1-6}$-alkyl; N(H)—C(=O)—NH$_2$; N(H)—C(=O)—N(H)($C_{1-6}$-alkyl); N(H)—C(=O)—N($C_{1-6}$-alkyl)$_2$; N($C_{1-6}$-alkyl)-S(=O)$_2$—NH$_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; SCF$_3$; S—$C_{1-6}$-alkyl; S(=O)$_2$ $C_{1-6}$-alkyl; S(=O)$_2$OH; S(=O)$_2$O—$C_{1-6}$-alkyl; S(=O)$_2$—NH$_2$; S(=O)$_2$—N(H)($C_{1-6}$-alkyl) and S(=O)$_2$—N($C_{1-6}$-alkyl)$_2$.

Most preferred substituents of "alkyl", "$C_{1-4}$-alkyl", "$C_{1-6}$-alkyl", "aliphatic residue" and "aliphatic group" are selected from the group consisting of F; Cl; Br; I; CF$_3$; C(=O)—NH$_2$; C(=O)—N(H)($C_{1-6}$-alkyl); C(=O)—N($C_{1-6}$-alkyl)$_2$; OH; O—$C_{1-6}$-alkyl; O—($C_{1-8}$-alkylene)-OH; O—($C_{1-8}$-alkylene)-O—$C_{1-8}$-alkyl; NH$_2$; N(H)($C_{1-6}$-alkyl); N($C_{1-6}$-alkyl)$_2$; N(H)—C(=O)—$C_{1-6}$-alkyl; N(H)—S(=O)$_2$—$C_{1-6}$-alkyl; N($C_{1-6}$-alkyl)-S(=O)$_2$—$C_{1-6}$-alkyl; N(H)—S(=O)$_2$—NH$_2$; SH; S—$C_{1-6}$-alkyl; S(=O)$_2$ $C_{1-6}$-alkyl and S(=O)$_2$—N(H)($C_{1-6}$-alkyl).

Particularly preferred substituents of "cycloaliphatic residue" and "heterocycloaliphatic residue" are selected from the group consisting of F; Cl; Br; I; NO$_2$; CF$_3$; CN; =O; $C_{1-6}$-alkyl; $C_{3-6}$ cycloaliphatic residue; 3 to 7 membered heterocycloaliphatic residue; $C_{3-6}$ cycloaliphatic residue or 3 to 6 membered heterocycloaliphatic bridged via a $C_{1-6}$ aliphatic group; CHO; C(=O)—$C_{1-6}$-alkyl; CO$_2$H; C(=O)O—$C_{1-6}$-alkyl; CONH$_2$; C(=O)NH—$C_{1-6}$-alkyl; C(=O)N($C_{1-6}$-alkyl)$_2$; OH; O—$C_{1-6}$-alkyl; OCF$_3$; O—($C_{1-8}$-alkylene)-OH; O—($C_{1-8}$-alkylene)-O—$C_{1-6}$-alkyl; O—C(=O)—$C_{1-6}$-alkyl; NH$_2$; NH—$C_{1-6}$-alkyl; N($C_{1-6}$-alkyl)$_2$; NH—C(=O)—$C_{1-6}$-alkyl; SH; S—$C_{1-6}$-alkyl; SCF$_3$; S(=O)$_2$—$C_{1-6}$-alkyl; S(=O)$_2$OH; S(=O)$_2$O—$C_{1-6}$-alkyl and S(=O)$_2$—NH—$C_{1-6}$-alkyl.

The compounds according to the invention are defined by substituents, for example by $R^1$, $R^2$ and $R^3$ (1$^{st}$ generation substituents) which are for their part if appropriate themselves substituted (2$^{nd}$ generation substituents). Depending on the definition, these substituents of the substituents can for their part be resubstituted (3$^{rd}$ generation substituents). If, for example, $R^1$=a $C_{1-6}$-alkyl (1$^{st}$ generation substituent), then the $C_{1-6}$-alkyl can for its part be substituted, for example with a NH—$C_{1-6}$-alkyl (2$^{nd}$ generation substituent). This produces the functional group $R^1$=($C_{1-6}$-alkyl-NH—$C_{1-6}$-alkyl). The NH—$C_{1-6}$-alkyl can then for its part be resubstituted, for example with Cl (3$^{rd}$ generation substituent). Overall, this produces the functional group $R^1$=$C_{1-6}$-alkyl-NH—$C_{1-6}$-alkyl, wherein the $C_{1-6}$-alkyl of the NH—$C_{1-6}$-alkyl is substituted by Cl.

However, in a preferred embodiment, the 3$^{rd}$ generation substituents may not be resubstituted, i.e. there are then no 4$^{th}$ generation substituents.

In another preferred embodiment, the 2$^{nd}$ generation substituents may not be resubstituted, i.e. there are then not even any 3$^{rd}$ generation substituents. In other words, in this embodiment, in the case of general formula (I), for example, the functional groups for $R^1$ to $R^9$ can each if appropriate be substituted; however, the respective substituents may then for their part not be resubstituted.

In some cases, the compounds according to the invention are defined by substituents which are or carry a cycloaliphatic residue or a heterocycloaliphatic residue, respectively, in each case unsubstituted or mono- or polysubstituted, or which form together with the carbon atom(s) or heteroatom(s) connecting them, as the ring member or as the ring members, a ring, for example a cycloaliphatic or a heterocycloaliphatic ring system. Both these cycloaliphatic or heterocycloaliphatic ring systems and the (hetero)cycloaliphatic ring systems formed in this manner can if appropriate be condensed with a cycloaliphatic residue, preferably a $C_{3-6}$ cycloaliphatic residue, or with a heterocycloaliphatic residue, preferably a 3 to 7 membered heterocycloaliphatic residue, e.g. with a cycloaliphatic residue such as cyclohexyl, or a heterocycloaliphatic residue such as morpholinyl, wherein the cycloaliphatic or heterocycloaliphatic residues condensed in this way can for their part be respectively unsubstituted or mono- or polysubstituted.

Within the scope of the present invention, the symbol

used in the formulae denotes a link of a corresponding residue to the respective superordinate general structure.

If a residue occurs multiply within a molecule, then this residue can have respectively different meanings for various substituents: if, for example, both $R^1$ and $R^2$ denote a 3 to 10 membered heterocycloaliphatic residue, then the 3 to 10 membered heterocycloaliphatic residue can e.g. represent morpholinyl for $R^1$ and can represent piperazinyl for $R^2$.

In a preferred embodiment of the compound according to the present invention $R^1$, $R^2$ and $R^3$ are each independently of one another selected from the group consisting of H; F; Cl; Br; I; $NO_2$; CN; $C_{1-6}$-alkyl; $CF_3$; $CF_2H$; $CFH_2$; $CF_2Cl$; $CFCl_2$; C(=O)—H; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—$NH_2$; O—S(=O)$_2$—N(H)($C_{1-6}$-alkyl); O—S(=O)$_2$—N($C_{1-6}$-alkyl)$_2$; $NH_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—$NH_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—$NH_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—$NH_2$; N(H)—S(=O)$_2$—N(H)($C_{1-6}$-alkyl); N(H)—S(=O)$_2$N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—$NH_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); or S(=O)$_2$—N($C_{1-6}$-alkyl)$_2$, whereby in each case $C_{1-6}$-alkyl may be branched or unbranched; unsubstituted or mono- or polysubstituted; a $C_{3-6}$ cycloaliphatic residue or a 3 to 7 membered heterocycloaliphatic residue, in each case unsubstituted or mono- or polysubstituted.

Preferably,
$R^1$, $R^2$ and $R^3$ are each independently of one another selected from the group consisting of H; F; Cl; CN; $C_{1-6}$-alkyl; $CF_3$; $CF_2H$; $CFH_2$; OH; $OCF_3$; O—$C_{1-6}$-alkyl; O—C(=O)—$C_{1-6}$-alkyl; $NH_2$; N(H)($C_{1-6}$-alkyl); N($C_{1-6}$-alkyl)$_2$; $SCF_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$ alkyl)$_2$, whereby in each case $C_{1-6}$-alkyl may be branched or unbranched, or a $C_{3-6}$ cycloaliphatic residue, unsubstituted or mono- or polysubstituted.

More preferably,
$R^1$, $R^2$ and $R^3$ are independently of one another selected from the group consisting of H, F, Cl, $CFH_2$, $CF_2H$, $CF_3$, CN, $CH_2$—$OCH_3$, S(=O)$_2$—$CH_3$, $OCF_3$, $CH_3$, O—$CH_3$, O—$CH_2CH_3$ and N($CH_3$)$_2$.

Even more preferably,
$R^1$, $R^2$ and $R^3$ are independently of one another selected from the group consisting of H, F, Cl, CN, $CFH_2$, $CF_2H$, $CF_3$, $OCF_3$, $CH_3$, S(=O)$_2$—$CH_3$, O—$CH_3$, and O—$CH_2CH_3$.

Still more preferably,
$R^1$, $R^2$ and $R^3$ are independently of one another selected from the group consisting of H, F, Cl, $CF_3$, $OCF_3$, $CH_3$, S(=O)$_2$—$CH_3$ and O—$CH_3$.

Particularly preferred,
$R^1$, $R^2$ and $R^3$ are independently of one another selected from the group consisting of H, F, Cl, $CF_3$, $CH_3$ and O—$CH_3$.

Even more particularly preferred,
$R^1$, $R^2$ and $R^3$ are independently of one another selected from the group consisting of H, F, Cl, $CH_3$ and O—$CH_3$.

In one preferred embodiment of the compound according to the present invention, $R^1$, $R^2$ and $R^3$ denote H.

In another preferred embodiment of the compound according to the present invention at least one of $R^1$, $R^2$ and $R^3$ is H.

In another preferred embodiment of the compound according to the present invention one or two of $R^1$, $R^2$ and $R^3$, denote(s) H.

In another preferred embodiment of the compound according to the present invention one of $R^1$, $R^2$ and $R^3$ represents H.

In another preferred embodiment of the compound according to the present invention two of $R^1$, $R^2$ and $R^3$ represent H.

In another preferred embodiment of the compound according to the present invention
$R^2$ and $R^3$ are independently of one another selected from the group consisting of H; F; Cl; CN; $C_{1-6}$-alkyl; $CF_3$; $CF_2H$; $CFH_2$; OH; $OCF_3$; O—$C_{1-6}$-alkyl; O—C(=O)—$C_{1-6}$-alkyl; $NH_2$; N(H)($C_{1-6}$-alkyl); N($C_{1-6}$-alkyl)$_2$; $SCF_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$, whereby in each case $C_{1-6}$-alkyl may be branched or unbranched, or a $C_{3-6}$ cycloaliphatic residue, unsubstituted or mono- or polysubstituted, and $R^1$ represents H.

Preferably,
$R^2$ and $R^3$ are independently of one another selected from the group consisting of H, F, Cl, $CFH_2$, $CF_2H$, $CF_3$, CN, $C_{1-6}$-alkyl; $CH_2$—OH, $CH_2$—$OCH_3$, $OCF_3$, OH, O—$CH_3$, O—$CH_2CH_3$, $NH_2$, NH($CH_3$), and N($CH_3$)$_2$, more preferably are independently of one another selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and N($CH_3$)$_2$, even more preferably are independently of one another selected from the group consisting of H, F, Cl, $CFH_2$, $CF_2H$, $CF_3$, $OCF_3$, $CH_3$, O—$CH_3$, and O—$CH_2CH_3$, still more preferably are independently of one another selected from the group consisting of H, F, Cl, $CF_3$, $OCF_3$, $CH_3$ and O—$CH_3$, in particular are independently of one another selected from the group consisting of H, F, Cl, $CH_3$, $CF_3$ and O—$CH_3$, even more particularly preferred are independently of one another selected from the group consisting of H, F, Cl, $CH_3$ and O—$CH_3$, and $R^1$ represents H.

In yet another preferred embodiment of the compound according to the present invention,
$R^3$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, CH($CH_3$)$_2$, S(=O)$_2$—$CH_3$, O—$CH_3$, O—$CH_2CH_3$, $NH_2$, NH($CH_3$), and N($CH_3$)$_2$,
and both $R^1$ and $R^2$ represent H.

Preferably,
$R^3$ is selected from the group consisting of F, Cl, $CFH_2$, $CF_2H$, $CF_3$, CN, $CH_2$—OH, $CH_2$—$OCH_3$, $OCF_3$, OH, $CH_3$, $S(=O)_2$—$CH_3$, O—$CH_3$, O—$CH_2CH_3$, $NH_2$, $NH(CH_3)$, and $N(CH_3)_2$, more preferably is selected from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of F, Cl, $CFH_2$, $CF_2H$, $CF_3$, $OCF_3$, $CH_3$, O—$CH_3$, and O—$CH_2CH_3$, still more preferably is selected from the group consisting of F, Cl, $CF_3$, $OCF_3$, $CH_3$ and O—$CH_3$, in particular is selected from the group consisting of F, Cl, $CF_3$, $CH_3$ and O—$CH_3$, even more particularly preferred is selected from the group consisting of F, Cl, $CH_3$ and O—$CH_3$,
and both $R^1$ and $R^2$ represent H.

In yet a further preferred embodiment of the compound according to the present invention
$R^2$ is selected from the group consisting of H; F; Cl; CN; $C_{1-6}$-alkyl; $CF_3$; $CF_2H$; $CFH_2$; OH; $OCF_3$; O—$C_{1-6}$-alkyl; O—C(=O)—$C_{1-6}$-alkyl; $NH_2$; $N(H)(C_{1-6}$-alkyl); $N(C_{1-6}$-alkyl$)_2$; $SCF_3$; S(=O)—$C_{1-6}$-alkyl; $S(=O)_2$—$C_{1-6}$-alkyl; $S(=O)_2$—OH; $S(=O)_2$—O—$C_{1-6}$-alkyl; $S(=O)_2$—$NH_2$; $S(=O)_2$—$N(H)(C_{1-6}$-alkyl); or $S(=O)_2$—$N(C_{1-6}$ alkyl$)_2$, whereby in each case $C_{1-6}$-alkyl may be branched or unbranched,
$R^3$ is selected from the group consisting of H; F; Cl; CN; $C_{1-6}$-alkyl; $CF_3$; $CF_2H$; $CFH_2$; OH; $OCF_3$; O—$C_{1-6}$-alkyl; O—C(=O)—$C_{1-6}$-alkyl; $NH_2$; $N(H)(C_{1-6}$-alkyl); $N(C_{1-6}$-alkyl$)_2$; $SCF_3$; S(=O)—$C_{1-6}$-alkyl; $S(=O)_2$—$C_{1-6}$-alkyl; $S(=O)_2$—OH; $S(=O)_2$—O—$C_{1-6}$-alkyl; $S(=O)_2$—$NH_2$; $S(=O)_2$—$N(H)(C_{1-6}$-alkyl); or $S(=O)_2$—$N(C_{1-6}$-alkyl$)_2$, whereby in each case $C_{1-6}$-alkyl may be branched or unbranched,
and $R^1$ represents H.
Preferably,
$R^2$ is selected from the group consisting of H, F, Cl, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, $S(=O)_2$—$CH_3$, O—$CH_3$, O—$CH_2CH_3$, $NH_2$, $NH(CH_3)$, and $N(CH_3)_2$, preferably is selected from the group consisting of F, Cl, $CFH_2$, $CF_2H$, $CF_3$, CN, $CH_2$—OH, $CH_2$—$OCH_3$, $OCF_3$, OH, $CH_3$, $S(=O)_2$—$CH_3$, O—$CH_3$, O—$CH_2CH_3$, $NH_2$, $NH(CH_3)$, and $N(CH_3)_2$, more preferably is selected from the group consisting of F, Cl, $CFH_2$, $CF_2H$, $CF_3$, CN, $CH_2$—$OCH_3$, $OCF_3$, $CH_3$, $S(=O)_2$—$CH_3$, O—$CH_3$, O—$CH_2CH_3$ and $N(CH_3)_2$, even more preferably is selected from the group consisting of F, Cl, $CFH_2$, $CF_2H$, $CF_3$, $OCF_3$, $CH_3$, $S(=O)_2$—$CH_3$, O—$CH_3$ and O—$CH_2CH_3$, still more preferably is selected from the group consisting of F, Cl, $CF_3$, $S(=O)_2$—$CH_3$, $OCF_3$, $CH_3$ and O—$CH_3$, in particular is selected from the group consisting of F, Cl, $CF_3$, $S(=O)_2$—$CH_3$, $CH_3$ and O—$CH_3$, even more particularly preferred is selected from the group consisting of F, Cl, $CH_3$ and O—$CH_3$,
$R^3$ is selected from the group consisting of H, F, Cl, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, preferably is selected from the group consisting of F, Cl, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of H, F, Cl, $CFH_2$, $CF_2H$, $CF_3$, $OCF_3$, $CH_3$, O—$CH_3$, and O—$CH_2CH_3$, still more preferably is selected from the group consisting of H, F, Cl, $CF_3$, $OCF_3$, $CH_3$ and O—$CH_3$, in particular is selected from the group consisting of H, F, Cl, $CF_3$, $CH_3$ and O—$CH_3$, even more particularly preferred is selected from the group consisting of H, F, Cl, $CH_3$ and O—$CH_3$, and $R^1$ represents H.

In another particularly preferred embodiment according to the present invention the part structure (SF-I)

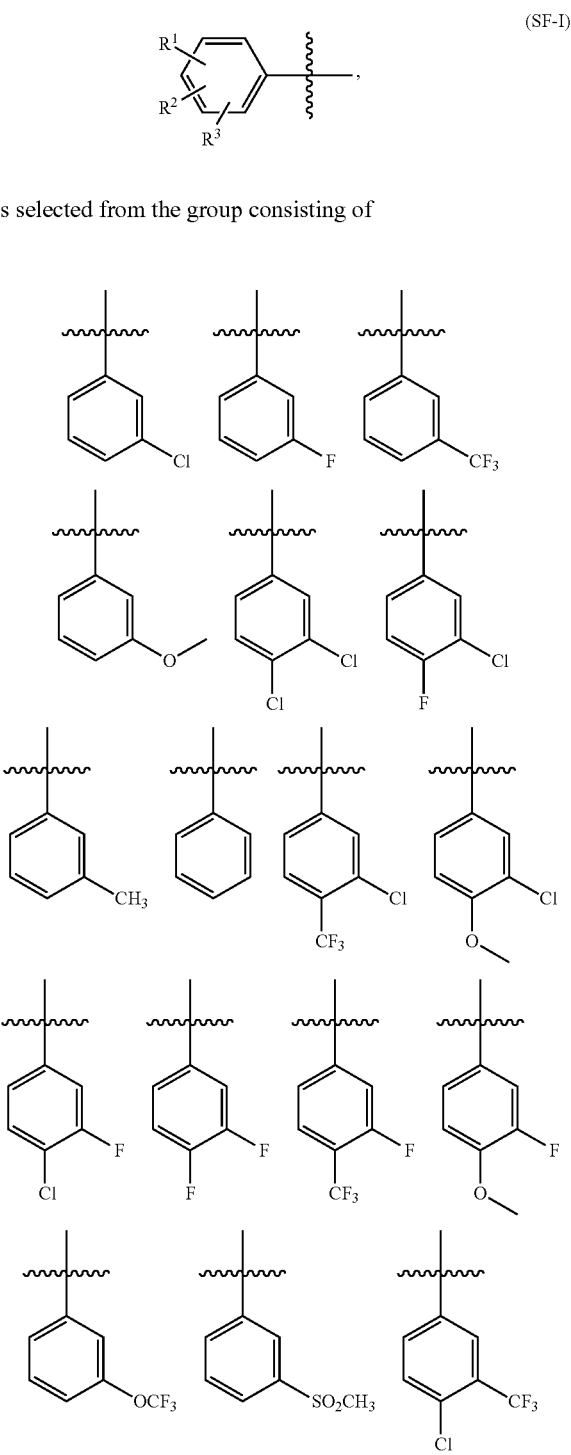

is selected from the group consisting of

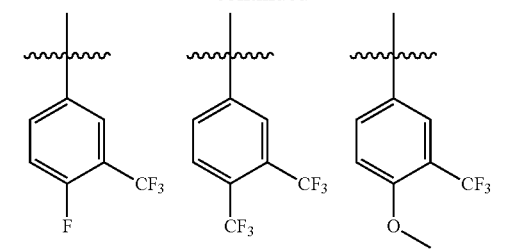
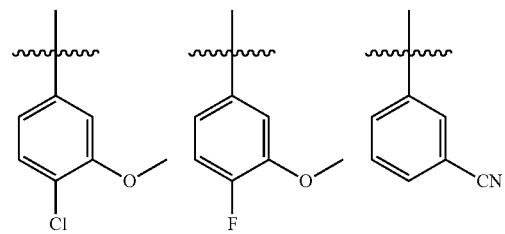
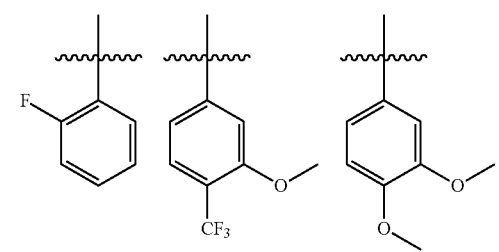
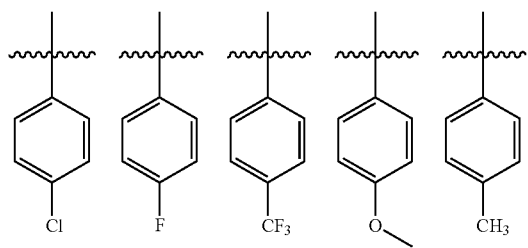
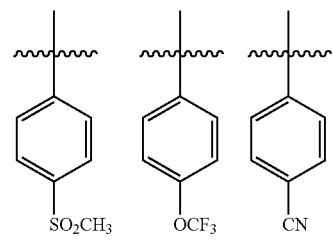
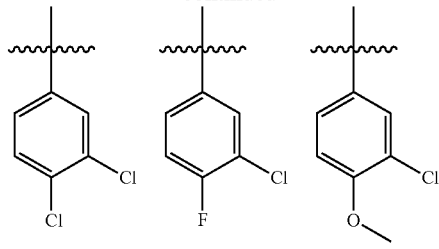
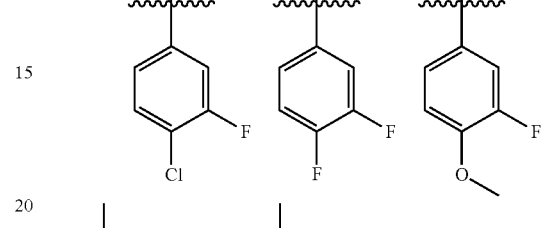
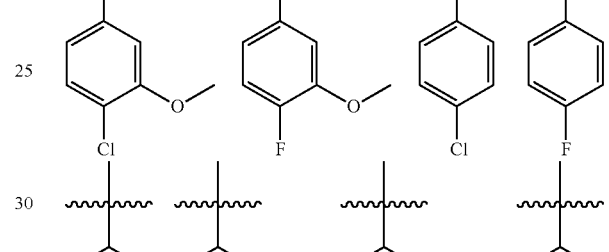
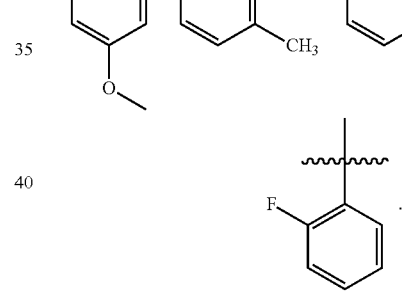
Most preferred, the part structure (SF-I) is selected from the group consisting of
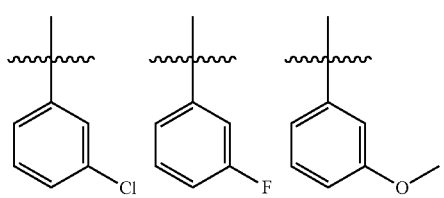
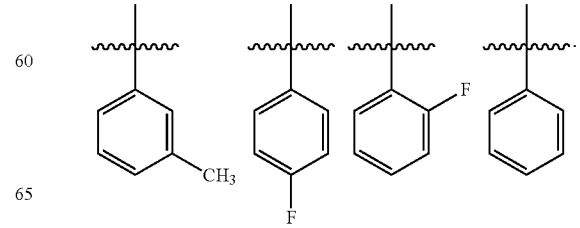
Even more particularly preferred, the part structure (SF-I) is selected from the group consisting of
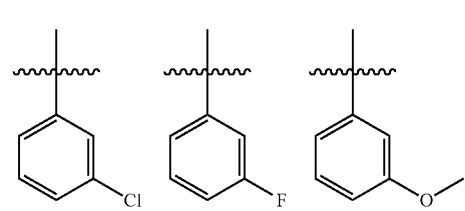

In a preferred embodiment of the compound according to the present invention,
n represents 0, 1 or 2;
m represents 0 or 1 with the proviso that n≥m,
wherein
X is selected from the group consisting of O, S, NH or N—$C_{1-6}$-alkyl;

In another preferred embodiment of the compound according to the present invention,
n represents 0 or 1 and m represents 0.

In a particularly preferred embodiment of the compound according to the present invention,
n represents 0 and m represents 0.

In another particularly preferred embodiment of the compound according to the present invention,
n represents 1 and m represents 0.

In yet a further preferred embodiment of the compound according to the present invention,
n represents 1 or 2 and m represents 1.
Preferably,
n represents 2 and m represents 1.
More preferably,
n represents 2, m represents 1 and X is selected from the group consisting of O, S, NH and N—$C_{1-6}$-alkyl.
Even more preferably,
n represents 2, m represents 1 and X is selected from the group consisting of O, NH and N—$C_{1-6}$-alkyl.

In a particularly preferred embodiment of the compound according to the present invention,
n represents 2, m represents 1 and X represents O.

In another particularly preferred embodiment of the compound according to the present invention,
n represents 1, m represents 0 and
$R^1$, $R^2$ and $R^3$ are each independently of one another selected from the group consisting of H; F; Cl; CN; $C_{1-6}$-alkyl; $CF_3$; $CF_2H$; $CFH_2$; OH; $OCF_3$; O—$C_{1-6}$-alkyl; O—C(=O)—$C_{1-6}$-alkyl; $NH_2$; N(H)($C_{1-6}$-alkyl); N($C_{1-6}$-alkyl)$_2$; $SCF_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$, whereby in each case $C_{1-6}$-alkyl may be branched or unbranched, or a $C_{3-6}$ cycloaliphatic residue, unsubstituted or mono- or polysubstituted.

In a particularly preferred embodiment of the compound according to the present invention,
n represents 1, m represents 0 and $R^1$, $R^2$ and $R^3$ represent H.

In another particularly preferred embodiment of the compound according to the present invention,
n represents 1, m represents 0 and
$R^1$, $R^2$ and $R^3$ are each independently of one another selected from the group consisting of H; F; Cl; CN; $C_{1-6}$-alkyl; $CF_3$; $CF_2H$; $CFH_2$; OH; $OCF_3$; O—$C_{1-6}$-alkyl; O—C(=O)—$C_{1-6}$-alkyl; $NH_2$; N(H)($C_{1-6}$-alkyl); N($C_{1-6}$-alkyl)$_2$; $SCF_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$, whereby in each case $C_{1-6}$-alkyl may be branched or unbranched, or a $C_{3-6}$ cycloaliphatic residue, unsubstituted or mono- or polysubstituted.
with the proviso that at least one of $R^1$, $R^2$ and $R^3$ does not represent H.
More preferably,
n represents 1, m represents 0 and
$R^1$, $R^2$ and $R^3$ are each independently of one another selected from the group consisting of H; F; Cl; $C_{1-6}$-alkyl; CN; $CF_3$; $CF_2H$; $CFH_2$; S(=O)$_2$—$CH_3$; OH; $OCF_3$ or $OCH_3$,
with the proviso that at least one of $R^1$, $R^2$ and $R^3$ does not represent H.
More preferably,
n represents 1, m represents 0 and
$R^1$, $R^2$ and $R^3$ are each independently of one another selected from the group consisting of H; F; Cl; CN; $CH_3$; $CF_3$; $CF_2H$; $CFH_2$; S(=O)$_2$—$CH_3$; OH; $OCF_3$ or $OCH_3$,
with the proviso that at least one of $R^1$, $R^2$ and $R^3$ does not represent H.

In another preferred embodiment of the compound according to the present invention
$R^4$ represents $CH_2F$, $CHF_2$ or $CF_3$.
Preferably,
$R^4$ represents $CHF_2$ or $CF_3$.

In a particularly preferred embodiment of the compound according to the present invention $R^4$ represents $CF_3$.

In another particularly preferred embodiment of the compound according to the present invention $R^4$ represents $CHF_2$.

In a further preferred embodiment of the compound according to the present invention,
$R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or polysubstituted;.
Preferably,
$R^5$ is selected from the group consisting of H, methyl, ethyl, n-propyl, iso-propyl, n-butyl, sec-butyl, iso-butyl, tert-butyl, cyclopropyl, methoxy, ethoxy, methylsulfonyl, 2-oxetyl, 3-oxetyl, 2-tetrahydrofuranyl and 3-tetrahydrofuranyl.
More preferably,
$R^5$ is selected from the group consisting of H, methyl, ethyl, iso-propyl and cyclopropyl.
Even more preferably,
$R^5$ represents H or methyl.

In a particularly preferred embodiment of the compound according to the present invention $R^5$ represents methyl ($CH_3$).

In another particularly preferred embodiment of the compound according to the present invention $R^5$ represents H.

In another preferred embodiment of the compound according to the present invention,
$R^6$, $R^7$ and $R^8$ are each independently of one another selected from the group consisting of H; F; Cl; Br; I; $NO_2$; CN; $C_{1-6}$-alkyl; $CF_3$; $CF_2H$; $CFH_2$; $CF_2Cl$; $CFCl_2$; C(=O)—H; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—$NH_2$; O—S(=O)$_2$—N(H)($C_{1-6}$-alkyl); O—S(=O)$_2$—N($C_{1-6}$-alkyl)$_2$; $NH_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—$NH_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—$NH_2$; N($C_{1-6}$-alkyl)-C(=O)—N(H)($C_{1-6}$-alkyl); N($C_{1-6}$-alkyl)-

C(=O)—N($C_{1-6}$-alkyl)$_2$; N(H)—S(=O)$_2$OH; N(H)—S(=O)$_2$—$C_{1-6}$-alkyl; N(H)—S(=O)$_2$—O—$C_{1-6}$-alkyl; N(H)—S(=O)$_2$—NH$_2$; N(H)—S(=O)$_2$—N(H)($C_{1-6}$-alkyl); N(H)—S(=O)$_2$N($C_{1-6}$-alkyl)$_2$; N($C_{1-6}$-alkyl)-S(=O)—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—NH$_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; SCF$_3$; SCF$_2$H; SCFH$_2$; SCF$_2$Cl; SCFCl$_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); or S(=O)$_2$—N($C_{1-6}$-alkyl)$_2$, whereby in each case $C_{1-6}$-alkyl may be branched or unbranched; unsubstituted or mono- or polysubstituted; a $C_{3-6}$ cycloaliphatic residue or a 3 to 7 membered heterocycloaliphatic residue, in each case unsubstituted or mono- or polysubstituted.

Preferably, $R^6$, $R^7$ and $R^8$ are each independently of one another selected from the group consisting of H; F; Cl; CN; $C_{1-6}$-alkyl; CF$_3$; CF$_2$H; CFH$_2$; OH; OCF$_3$; O—$C_{1-6}$-alkyl; O—C(=O)—$C_{1-6}$-alkyl; NH$_2$; N(H)($C_{1-6}$-alkyl); N($C_{1-6}$-alkyl)$_2$; SCF$_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); or S(=O)$_2$—N($C_{1-6}$-alkyl)$_2$; whereby in each case $C_{1-6}$-alkyl may be branched or unbranched; or a $C_{3-6}$ cycloaliphatic residue, unsubstituted or mono- or polysubstituted.

More preferably, $R^6$, $R^7$ and $R^8$ are independently of one another selected from the group consisting of H, F, Cl, $C_{1-6}$-alkyl; CFH$_2$, CF$_2$H, CF$_3$, CN, CH$_2$—OCH$_3$, OCF$_3$, CH$_3$, O—CH$_3$, O—CH$_2$CF$_3$, O—CH$_2$CH$_3$ and N(CH$_3$)$_2$.

Even more preferably, $R^6$, $R^7$ and $R^8$ are independently of one another selected from the group consisting of H, F, Cl, CFH$_2$, CF$_2$H, CF$_3$, CN, OCF$_3$, CH$_3$, O—CH$_3$, O—CH$_2$CF$_3$ and O—CH$_2$CH$_3$.

Still more preferably, $R^6$, $R^7$ and $R^8$ are independently of one another selected from the group consisting of H, F, Cl, CF$_3$, CN, OCF$_3$, CH$_3$ and O—CH$_3$.

Particularly preferred, $R^6$, $R^7$ and $R^8$ are independently of one another selected from the group consisting of H, F, Cl, CF$_3$, OCF$_3$ and O—CH$_3$.

In a preferred embodiment of the compound according to the present invention at least one of $R^6$, $R^7$ and $R^8$ is ≠H.

In another preferred embodiment of the compound according to the present invention one or two of $R^6$, $R^7$ and $R^8$, preferably $R^7$ and/or $R^8$, denote(s) H.

In another preferred embodiment of the compound according to the present invention one of $R^6$, $R^7$ and $R^8$ represents H.

In another preferred embodiment of the compound according to the present invention $R^6$ and $R^7$ are independently of one another selected from the group consisting of H; F; Cl; CN; $C_{1-6}$-alkyl; CF$_3$; CF$_2$H; CFH$_2$; OH; OCF$_3$; O—$C_{1-6}$-alkyl; O—C(=O)—$C_{1-6}$-alkyl; NH$_2$; N(H)($C_{1-6}$-alkyl); N($C_{1-6}$-alkyl)$_2$; SCF$_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); or S(=O)$_2$—N($C_{1-6}$-alkyl)$_2$, whereby in each case $C_{1-6}$-alkyl may be branched or unbranched, and $R^8$ represents H.

Preferably, $R^6$ and $R^7$ are independently of one another selected from the group consisting of H, F, Cl, $C_{1-6}$-alkyl, CFH$_2$, CF$_2$H, CF$_3$, CN, CH$_2$—OH, CH$_2$—OCH$_3$, OCF$_3$, OH, O—CH$_2$CF$_3$, O—CH$_2$CH$_3$, NH$_2$, NH(CH$_3$), and N(CH$_3$)$_2$, more preferably are independently of one another selected from the group consisting of H, F, Cl, CFH$_2$, CF$_2$H, CF$_3$, CN, CH$_2$—OCH$_3$, OCF$_3$, CH$_3$, O—CH$_3$, O—CH$_2$CF$_3$, O—CH$_2$CH$_3$ and N(CH$_3$)$_2$, even more preferably are independently of one another selected from the group consisting of H, F, Cl, CFH$_2$, CF$_2$H, CF$_3$, OCF$_3$, CH$_3$, O—CH$_3$, and O—CH$_2$CH$_3$, still more preferably are independently of one another selected from the group consisting of H, F, Cl, CF$_3$, OCF$_3$, CH$_3$ and O—CH$_3$, and $R^8$ represents H.

In yet another preferred embodiment of the compound according to the present invention, $R^6$ is selected from the group consisting of F; Cl; $C_{1-6}$-alkyl; CN; CF$_3$; CF$_2$H; CFH$_2$; OH; OCF$_3$; alkyl; O—C(=O)—$C_{1-6}$-alkyl; NH$_2$; N(H)($C_{1-6}$-alkyl); N($C_{1-6}$-alkyl)$_2$; SCF$_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); or S(=O)$_2$—N($C_{1-6}$-alkyl)$_2$, whereby in each case $C_{1-6}$-alkyl may be branched or unbranched, and both $R^7$ and $R^8$ represent H.

Preferably, $R^6$ is selected from the group consisting of F, Cl, $C_{1-6}$-alkyl, CFH$_2$, CF$_2$H, CF$_3$, CN, CH$_2$—OH, CH$_2$—OCH$_3$, OCF$_3$, OH, CH$_3$, O—CH$_3$, O—CH$_2$CH$_3$, NH$_2$, NH(CH$_3$), and N(CH$_3$)$_2$, more preferably is selected from the group consisting of F, Cl, CFH$_2$, CF$_2$H, CF$_3$, CN, CH$_2$—OCH$_3$, OCF$_3$, CH$_3$, O—CH$_3$, O—CH$_2$CH$_3$ and N(CH$_3$)$_2$, even more preferably is selected from the group consisting of F, Cl, CFH$_2$, CF$_2$H, CF$_3$, OCF$_3$, CH$_3$, O—CH$_3$, and O—CH$_2$CH$_3$, still more preferably is selected from the group consisting of F, Cl, CF$_3$, OCF$_3$, CH$_3$ and O—CH$_3$, and both $R^7$ and $R^8$ represent H.

In yet a further preferred embodiment of the compound according to the present invention $R^6$ is selected from the group consisting of F; Cl; $C_{1-6}$-alkyl; CN; CF$_3$; CF$_2$H; CFH$_2$; OH; OCF$_3$; alkyl; O—C(=O)—$C_{1-6}$-alkyl; NH$_2$; N(H)($C_{1-6}$-alkyl); N($C_{1-6}$-alkyl)$_2$; SCF$_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); or S(=O)$_2$—N($C_{1-6}$-alkyl)$_2$, whereby in each case $C_{1-6}$-alkyl may be branched or unbranched, $R^7$ is selected from the group consisting of F; Cl; $C_{1-6}$-alkyl; CN; CF$_3$; CF$_2$H; CFH$_2$; OH; OCF$_3$; alkyl; O—C(=O)—$C_{1-6}$-alkyl; NH$_2$; N(H)($C_{1-6}$-alkyl); N($C_{1-6}$-alkyl)$_2$; SCF$_3$; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); or S(=O)$_2$—N($C_{1-6}$-alkyl)$_2$, whereby in each case $C_{1-6}$-alkyl may be branched or unbranched, and $R^8$ represents H.

Preferably, $R^6$ is selected from the group consisting of F, Cl, $C_{1-6}$-alkyl, CFH$_2$, CF$_2$H, CF$_3$, CN, CH$_2$—OH, CH$_2$—OCH$_3$, OCF$_3$, OH, O—CH$_3$, O—CH$_2$CH$_3$, NH$_2$, NH(CH$_3$), and N(CH$_3$)$_2$, more preferably is selected from the group consisting of F, Cl, CFH$_2$, CF$_2$H, CF$_3$, CN, CH$_2$—OCH$_3$, OCF$_3$, CH$_3$, O—CH$_3$, O—CH$_2$CH$_3$ and N(CH$_3$)$_2$, even more preferably is selected from the group consisting of F, Cl, CFH$_2$, CF$_2$H, CF$_3$, OCF$_3$, CH$_3$, O—CH$_3$, and O—CH$_2$CH$_3$, still more preferably is selected from the group consisting of F, Cl, CF$_3$, OCF$_3$, CH$_3$ and O—CH$_3$, $R^7$ is selected from the group consisting of H, F, Cl, $C_{1-6}$-alkyl, $CFH_2$, $CF_2H$, $CF_3$, CN, $CH_2$—OH, $CH_2$—$OCH_3$, $OCF_3$, OH, O—$CH_3$, O—$CH_2CH_3$, $NH_2$, $NH(CH_3)$, and $N(CH_3)_2$, more preferably is selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of H, F, Cl, $CFH_2$, $CF_2H$, $CF_3$, $OCF_3$, $CH_3$, O—$CH_3$, and O—$CH_2CH_3$, still more preferably is selected from the group consisting of H, F, Cl, $CF_3$, $OCF_3$, $CH_3$ and O—$CH_3$, and $R^8$ represents H.

In another particularly preferred embodiment according to the present invention the part structure (SF-II)

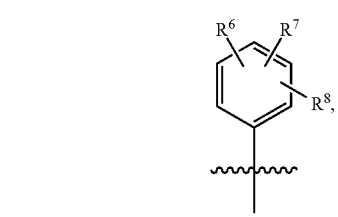

(SF-II)

is selected from the group consisting of

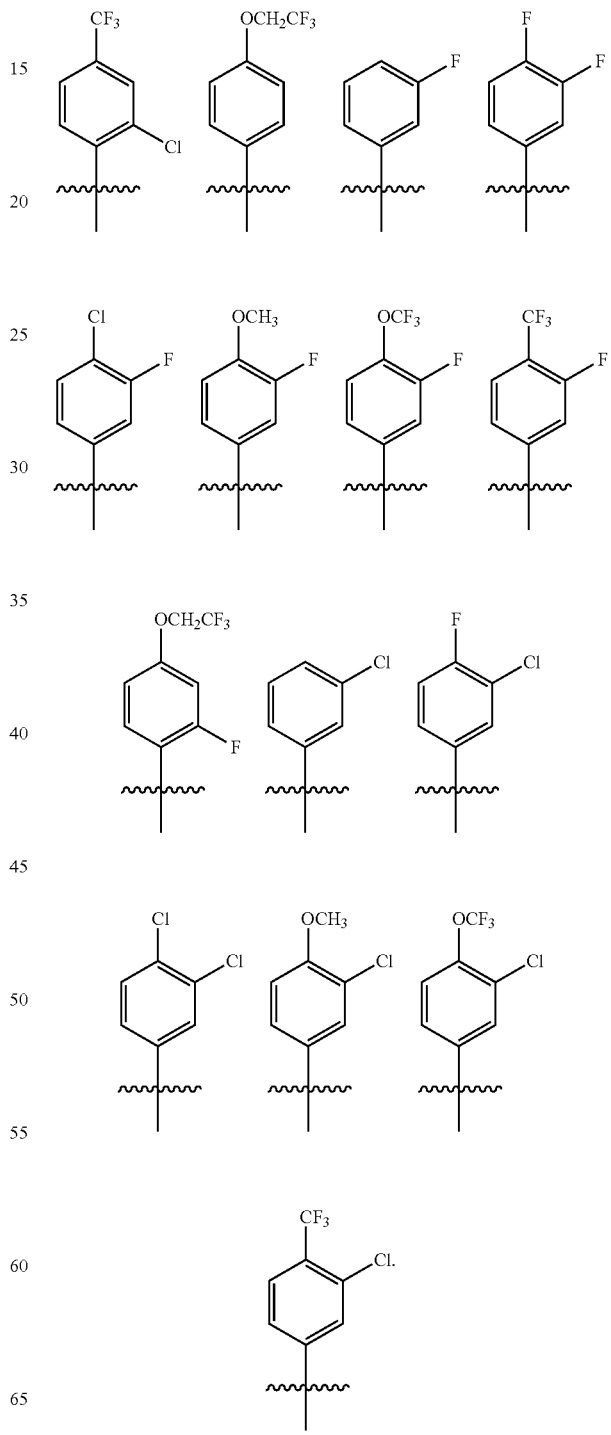

Even more particularly preferred, the part structure (SF-II) is selected from the group consisting of

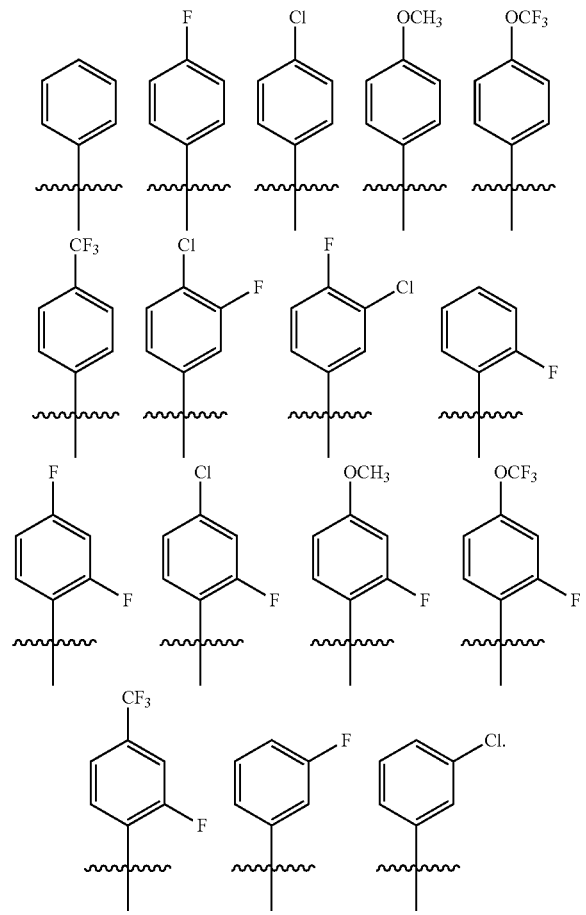

Most preferred, the part structure (SF-II) is selected from the group consisting of

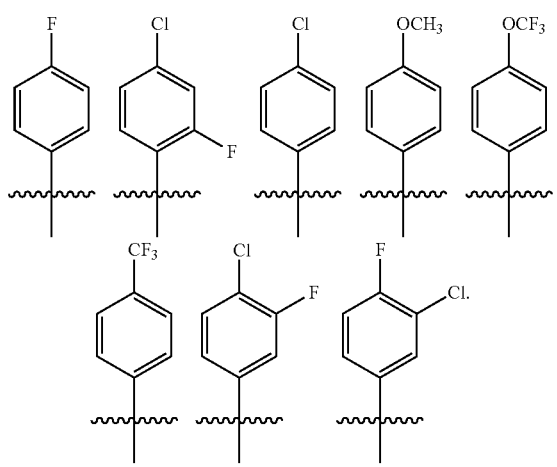

In another preferred embodiment of the compound according to the present invention,
$R^9$ represents H, a $C_{1-10}$ aliphatic residue, branched or unbranched, unsubstituted or mono- or poly-substituted; a $C_{3-10}$ cycloaliphatic residue or a 3 to 10 membered heterocycloaliphatic residue, in each case unsubstituted or mono- or poly-substituted and in each case optionally connected via a $C_{1-8}$ alkylene group, branched or unbranched, which in turn may be unsubstituted or mono- or polysubstituted;

Preferably,
$R^9$ represents H or
a $C_{1-6}$ aliphatic residue, branched or unbranched, unsubstituted or substituted with 1, 2, 3, 4 or 5 substituents independently from one another selected from the group consisting of OH, =O, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—NH$_2$, O(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; or a $C_{3-6}$ cycloaliphatic residue, unsubstituted or substituted with 1, 2, 3, 4 or 5 substituents independently from one another selected from the group consisting of F, Cl, CF$_3$, =O, OCF$_3$; $C_{1-6}$-alkylen-OH, $C_{1-6}$-alkyl, OH, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said $C_{3-6}$ cycloaliphatic residue is optionally connected via a $C_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—$C_{1-6}$-alkyl and $C_{1-6}$-alkylen-OH; or a 3-7-membered heterocycloaliphatic residue, which is unsubstituted or substituted with 1, 2, 3, 4 or 5 substituents independently from one another selected from the group consisting of F, Cl, CF$_3$, =O, OCF$_3$; $C_{1-6}$-alkylen-OH, $C_{1-6}$-alkyl, OH, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, wherein said 3-7-membered heterocycloaliphatic residue is optionally connected via a $C_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—$C_{1-6}$-alkyl and $C_{1-6}$-alkylen-OH.

More preferably,
$R^9$ represents H or
a $C_{1-6}$ aliphatic residue, branched or unbranched, unsubstituted or substituted with 1, 2, 3, 4 or 5 substituents independently from one another selected from the group consisting of OH, =O, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl.

Even more preferably,
$R^9$ represents H or
a $C_{1-6}$ aliphatic residue, branched or unbranched, unsubstituted or substituted with 1, 2, 3, 4 or 5 substituents independently from one another selected from the group consisting of OH, =O, O—$C_{1-6}$-alkyl, S(=O)$_2$—$C_{1-6}$-alkyl, N(H)—S(=O)$_2$—$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl and N(H)—C(=O)—$C_{1-6}$-alkyl.

Still more preferably, $R^9$ represents H or a $C_{1-6}$ unsubstituted aliphatic residue, branched or unbranched.

Particularly preferred, $R^9$ represents H or is selected from the group consisting of methyl, ethyl, isopropyl and n-propyl.

In a preferred embodiment of the compound according to the present invention, $R^9$ denotes H.

In another preferred embodiment of the compound according to the present invention, $R^9$ represents methyl.

In another preferred embodiment of the compound according to the present invention, $R^{10}$ represents H, a $C_{1-10}$ aliphatic residue, branched or unbranched, unsubstituted or mono- or poly-substituted; a $C_{3-10}$ cycloaliphatic residue or a 3 to 10 membered heterocycloaliphatic residue, in each case unsubstituted or mono- or poly-substituted and in each case optionally connected via a $C_{1-8}$ alkylene group, branched or unbranched, which in turn may be unsubstituted or mono- or polysubstituted;

Preferably, $R^{10}$ represents

H or a $C_{1-6}$ aliphatic residue, branched or unbranched, unsubstituted or substituted with 1, 2, 3, 4 or 5 substituents independently from one another selected from the group consisting of F, Cl, CF$_3$, CN, OH, =O, OCF$_3$, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$, N(H)—C(=O)—O—$C_{1-6}$-alkyl; O—C(=O)—NH$_2$, O—C(=O)—N(H)($C_{1-6}$-alkyl), O—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; or a $C_{3-6}$ cycloaliphatic residue, unsubstituted or substituted with 1, 2, 3, 4 or 5 substituents independently from one another selected from the group consisting of F, Cl, CN, CF$_3$, =O, OCF$_3$, $C_{1-6}$-alkylen-OH, $C_{1-6}$ alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—NH$_2$, O—C(=O)—N(H)($C_{1-6}$-alkyl), O—C(=O)—N($C_{1-6}$-alkyl)$_2$, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said $C_{3-6}$ cycloaliphatic residue is optionally connected via a $C_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—$C_{1-6}$-alkyl and $C_{1-6}$-alkylen-OH; or a 3-7-membered heterocycloaliphatic residue, which is unsubstituted or substituted with 1, 2, 3, 4 or 5 substituents independently from one another selected from the group consisting of F, Cl, CN, CF$_3$, =O, OCF$_3$, $C_{1-6}$-alkylen-OH, $C_{1-6}$ alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—NH$_2$, O—C(=O)—N(H)($C_{1-6}$-alkyl), O—C(=O)—N($C_{1-6}$-alkyl)$_2$, N(H)—C(=O)—NH$_2$, N(H)—C(=O)—N(H)($C_{1-6}$-alkyl), N(H)—C(=O)—N($C_{1-6}$-alkyl)$_2$, (C=O)$C_{1-6}$-alkyl, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said 3-7-membered heterocycloaliphatic residue is optionally connected via a $C_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—$C_{1-6}$-alkyl and $C_{1-6}$-alkylen-OH;

or a heteroaryl residue, which is unsubstituted or substituted with 1, 2, 3, 4 or 5 substituents independently from one another selected from the group consisting of F, Cl, CN, CF$_3$, OCF$_3$, $C_{1-6}$-alkylen-OH, $C_{1-6}$-alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—NH$_2$, O—C(=O)—N(H)($C_{1-6}$-alkyl), O—C(=O)—N($C_{1-6}$-alkyl)$_2$, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, wherein said heteroaryl residue is optionally connected via a $C_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—$C_{1-6}$-alkyl and $C_{1-6}$-alkylen-OH.

In another embodiment, $R^{10}$ represents a $C_{3-6}$ cycloaliphatic residue, which is unsubstituted or substituted with 1, 2, 3, 4 or 5 substituents independently from one another selected from the group consisting of F, Cl, CF$_3$, =O, OCF$_3$, OH, O—$C_{1-6}$-alkyl, $C_{1-6}$-alkylen-OH and $C_{1-6}$-alkyl;

or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, and which is unsubstituted or substituted with 1, 2, 3, 4 or 5 substituents independently from one another selected from the group consisting of F, Cl, CF$_3$, OCF$_3$, CN, $C_{1-6}$-alkyl, $C_{1-6}$-alkylen-OH and O—$C_{1-6}$-alkyl;

a heteroaryl residue, which contains at least one nitrogen atom and which is unsubstituted or substituted with 1, 2 or 3 substituents independently from one another selected from the group consisting of F, Cl, CN, CF$_3$, OCF$_3$, $C_{1-6}$- alkylen-OH, $C_{1-6}$-alkyl, OH, O—$C_{1-6}$-alkyl, S(=O)$_2$—$C_{1-6}$-alkyl, S(=O)$_2$—NH$_2$, NH$_2$, NH($C_{1-6}$-alkyl), N($C_{1-6}$-alkyl)$_2$, O—C(=O)—NH$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl;
or a part structure of general formula SF-III

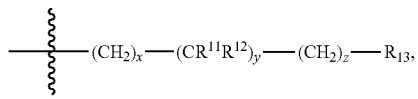
SF-III wherein
x represents 0, 1 or 2; y represents 0, 1 or 2; z represents 0, 1 or 2;
on the condition that the sum of x, y and z is 1, 2, 3, 4, 5 or 6;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF$_3$, OCF$_3$, CN, $C_{1-6}$-alkyl and O—$C_{1-6}$-alkyl;
$R^{13}$ is selected from the group consisting of
H, F, Cl, CN, CF$_3$, OCF$_3$, $C_{1-6}$-alkylen-OH, $C_{1-6}$ alkyl, OH, O—$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and N($C_{1-6}$-alkyl)-C(=O)—$C_{1-6}$-alkyl, or represents
a $C_{3-6}$ cycloaliphatic residue, which is unsubstituted or substituted with 1, 2, 3, 4, or 5 substituents independently from one another selected from the group consisting of F, Cl, CF$_3$, =O, OCF$_3$, OH, O—$C_{1-6}$ alkyl, $C_{1-6}$-alkylen-OH and $C_{1-6}$-alkyl; or
a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, and which is unsubstituted or substituted with 1, 2, 3, 4 or 5 substituents independently from one another selected from the group consisting of F, Cl, CF$_3$, OCF$_3$, CN, $C_{1-6}$-alkyl and O—$C_{1-6}$-alkyl; or
a heteroaryl residue, which contains at least one nitrogen atom and which is unsubstituted or substituted with 1, 2 or 3 substituents independently from one another selected from the group consisting of F, Cl, CN, CF$_3$, OCF$_3$, $C_{1-6}$-alkylen-OH, $C_{1-6}$-alkyl, OH, O—$C_{1-6}$-alkyl, S(=O)$_2$—$C_{1-6}$-alkyl, S(=O)$_2$—NH$_2$, NH$_2$, NH($C_{1-6}$-alkyl), N($C_{1-6}$-alkyl)$_2$, O—C(=O)—NH$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl.

Preferred heteroaryl residues, which contain at least one nitrogen atom, are selected from pyridine, pyrimidine, pyrazine, pyridazine, triazine, quinoline, isoquinoline, phthalazine, naphtheridine, quinoxaline, quinazoline, indole, isoindole, pyrrole, imidazole, pyrazole, 1,2,3-triazole, 1,2,4-triazole, oxazole, isoxazole, thiazole, isothiazole, oxadiazole and thiadiazole.

More preferably, $R^{10}$ represents
a part structure of general formula SF-III

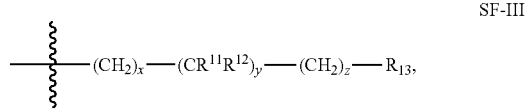
SF-III wherein
x represents 0, 1 or 2; y represents 0, 1 or 2; z represents 0, 1 or 2;
on the condition that the sum of x, y and z is 1, 2, 3, 4, 5 or 6;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF$_3$, OCF$_3$, CN, $C_{1-6}$-alkyl and O—$C_{1-6}$-alkyl;
$R^{13}$ is selected from the group consisting of
H, F, Cl, CN, CF$_3$, OCF$_3$, O—$C_{1-6}$-alkylen-OH, $C_{1-6}$-alkylen-OH, $C_{1-6}$ alkyl, OH, O—$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and N($C_{1-6}$-alkyl)-C(=O)—$C_{1-6}$-alkyl.

Still more preferably, $R^{10}$ represents a part structure of general formula SF-III

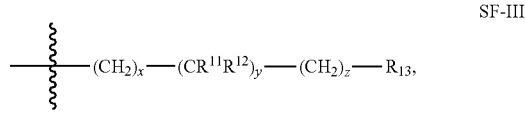
SF-III wherein
x represents 0, 1 or 2; y represents 0, 1 or 2; z represents 0, 1 or 2;

on the condition that the sum of x, y and z is 1, 2, 3, 4, 5 or 6;

R$^{11}$ and R$^{12}$ are independently from one another selected from H or C$_{1-6}$-alkyl; or R$^{11}$ and R$^{12}$ together with the carbon atom connecting them form a C$_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—C$_{1-6}$-alkyl, wherein said C$_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF$_3$, OCF$_3$, CN, C$_{1-6}$-alkyl and O—C$_{1-6}$-alkyl;

R$^{13}$ is selected from the group consisting of
H, OH, F, Cl, CN, S(=O)$_2$—C$_{1-6}$-alkyl, NH$_2$, N(H)—C(=O)—C$_{1-6}$-alkyl, N(H)—S(=O)$_2$—C$_{1-6}$-alkyl, O—C$_{1-6}$-alkyl, C(=O)—NH$_2$, C(=O)—N(H)(C$_{1-6}$-alkyl) and C(=O)—O—C$_{1-6}$-alkyl.

In a preferred embodiment of the invention, the general formula SF-III is selected from formulae SF-IIIa to SF-IIIo SF-IIIa SF-IIIb SF-IIIc SF-IIId SF-IIIe SF-IIIf SF-IIIg SF-IIIh SF-IIIi SF-IIIj SF-IIIk SF-IIIm SF-IIIn SF-IIIo wherein
x represents 0, 1 or 2; y represents 0 or 1; z represents 0, 1 or 2;
on the condition that the sum of x, y and z is 1, 2, 3, 4, 5 or 6.

Preferred are compounds according formula (I), that are characterized that R$^{10}$ is represented by any part structure the general formulae SF-IIIa to SF-IIIo, wherein
x represents 1, y represents 0 and z represents 0.

Preferred are compounds according formula (I), that are characterized that R$^{10}$ is represented by any part structure the general formulae SF-IIIa to SF-IIIo, wherein
x represents 1, y represents 0 and z represents 1.

Also preferred are compounds according formula (I), that are characterized that R$^{10}$ is represented by any part structure the general formulae SF-IIIa to SF-IIIo, wherein
x represents 1, y represents 1 and z represents 0.

Also preferred are compounds according formula (I), that are characterized that R$^{10}$ is represented by any part structure the general formulae SF-IIIa to SF-IIIo, wherein
x represents 0, y represents 1 and z represents 0.

Also preferred are compounds according formula (I), that are characterized that R$^{10}$ is represented by any part structure the general formulae SF-IIIa to SF-IIIo, wherein
x represents 0, y represents 1 and z represents 1.

In a particularly preferred embodiment of the compound according to the present invention, R$^{10}$ is selected from the group consisting of
methyl, ethyl, 2-propyl (iso-propyl), 1-propyl (n-propyl), 1-butyl, 2-butyl, 2-methyl-propyl, 1,1-dimethyl-ethyl (tert-butyl), 1-pentyl, 2-pentyl, 3-pentyl, 2-methyl-butyl, 2,2-dimethyl-propyl (neo-pentyl), 1-hexyl, 2-hexyl, 3-hexyl, 3,3-dimethyl-butyl, cyclopropyl, cyclopropylmethyl, 2-cyclopropyl-ethyl, 1-cyclopropyl-ethyl
and residues according the following substructures:
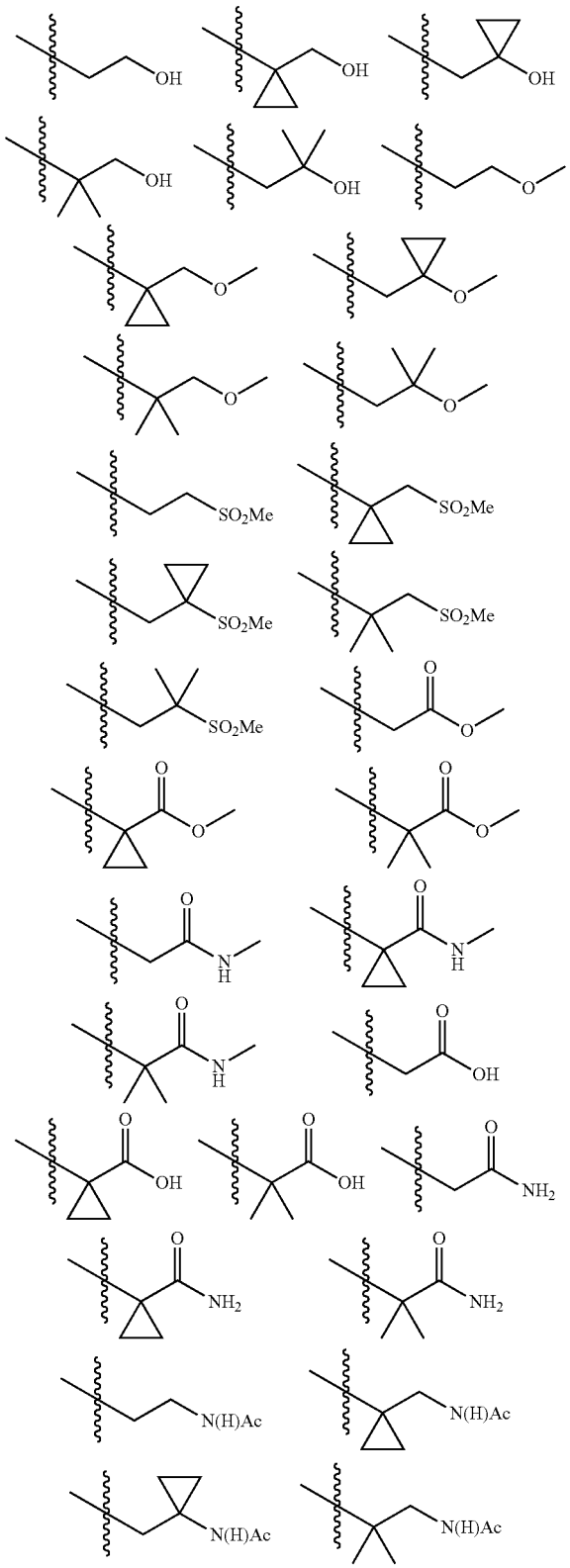
-continued
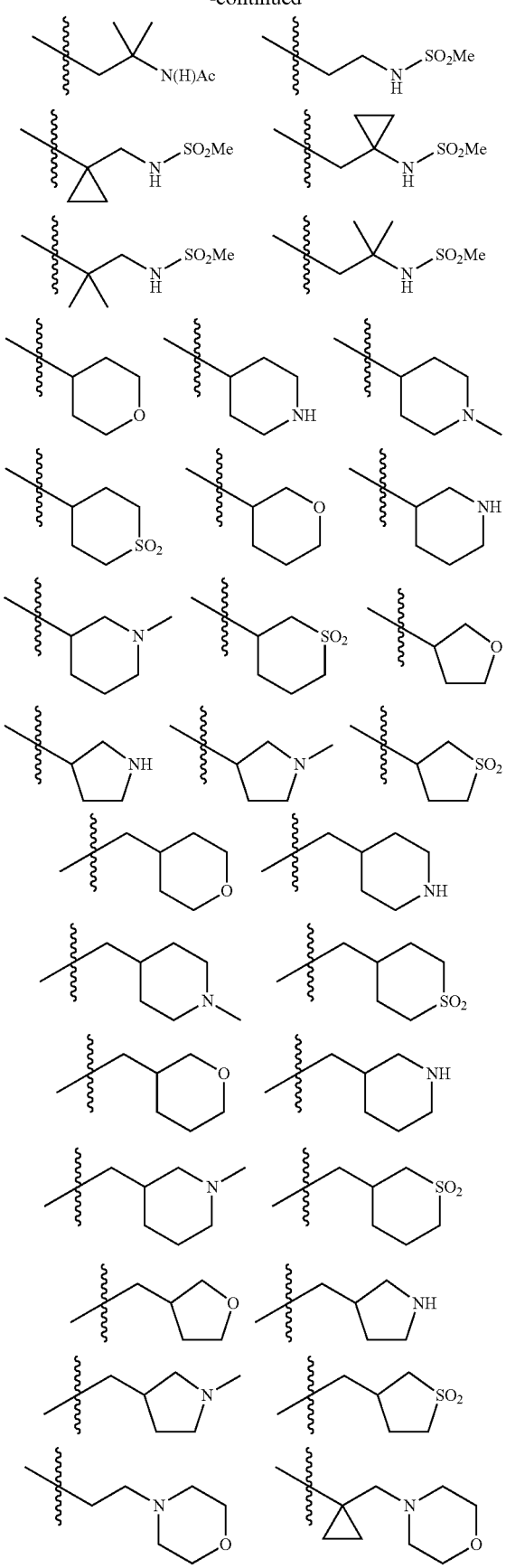

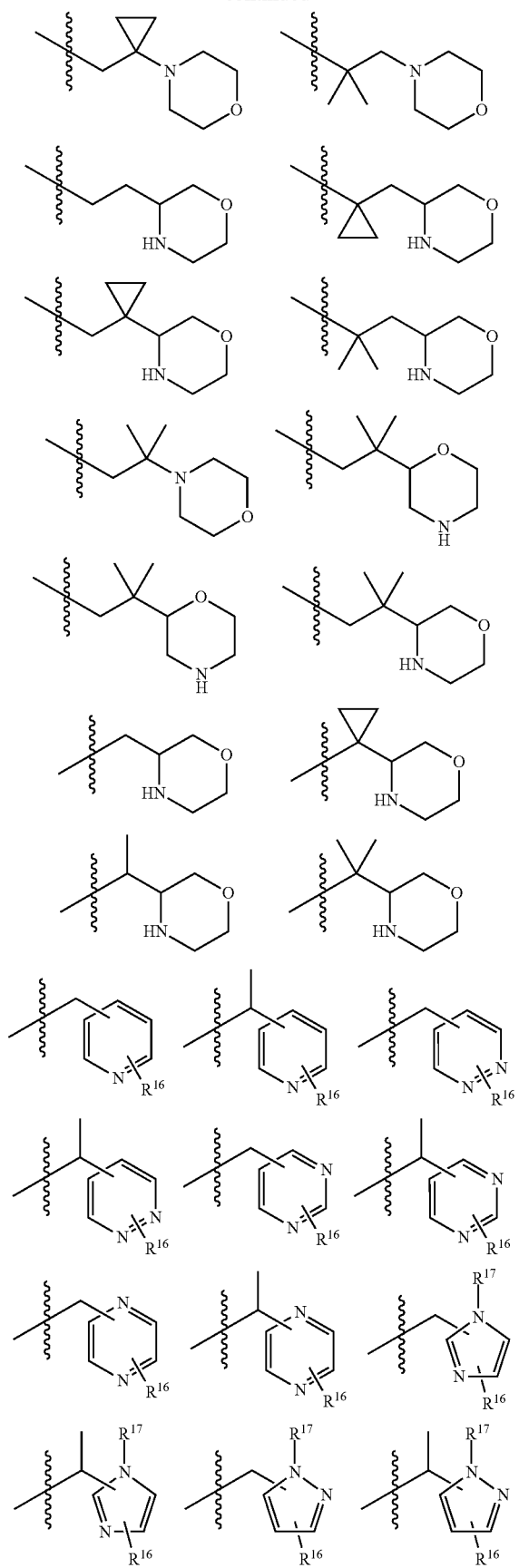
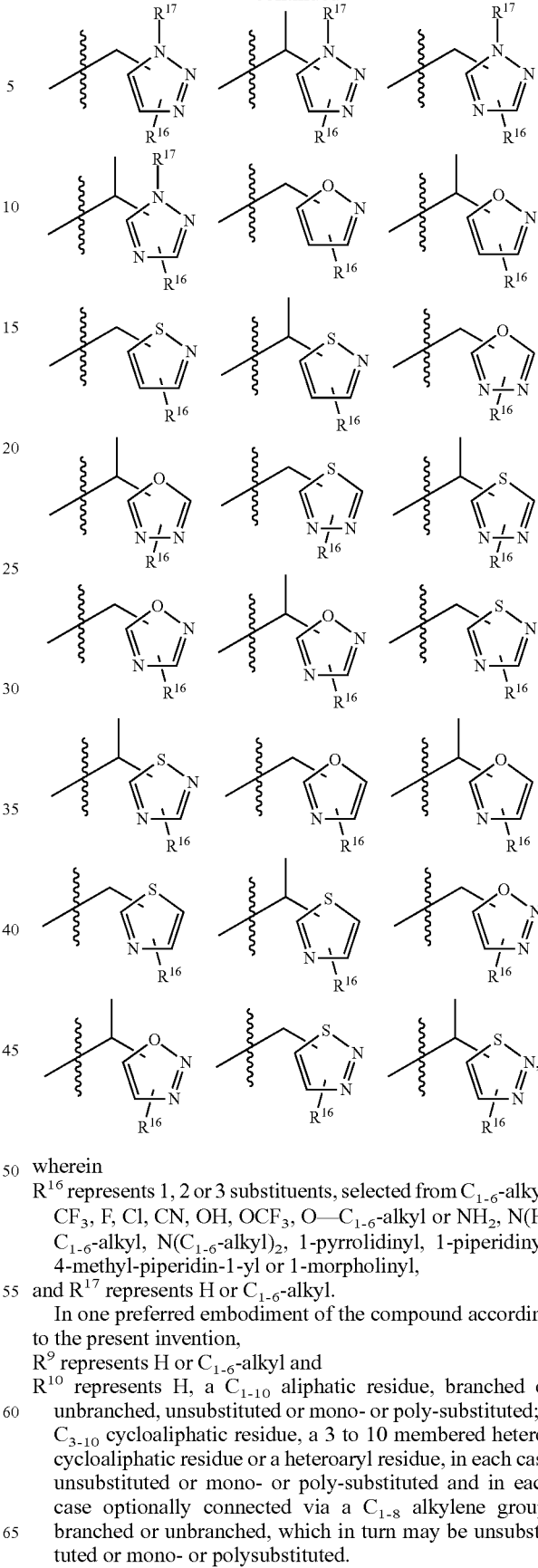

wherein
R[16] represents 1, 2 or 3 substituents, selected from $C_{1-6}$-alkyl, $CF_3$, F, Cl, CN, OH, $OCF_3$, O—$C_{1-6}$-alkyl or $NH_2$, N(H)$C_{1-6}$-alkyl, N($C_{1-6}$-alkyl)$_2$, 1-pyrrolidinyl, 1-piperidinyl, 4-methyl-piperidin-1-yl or 1-morpholinyl,
and R[17] represents H or $C_{1-6}$-alkyl.

In one preferred embodiment of the compound according to the present invention,
R[9] represents H or $C_{1-6}$-alkyl and
R[10] represents H, a $C_{1-10}$ aliphatic residue, branched or unbranched, unsubstituted or mono- or poly-substituted; a $C_{3-10}$ cycloaliphatic residue, a 3 to 10 membered heterocycloaliphatic residue or a heteroaryl residue, in each case unsubstituted or mono- or poly-substituted and in each case optionally connected via a $C_{1-8}$ alkylene group, branched or unbranched, which in turn may be unsubstituted or mono- or polysubstituted.
Preferably, at least one of R[9] and R[10] does not denote H.

Preferably,

R$^9$ represents H or C$_{1-6}$-alkyl and

R$^{10}$ represents

H or a C$_{1-6}$ aliphatic residue, branched or unbranched, unsubstituted or substituted with 1, 2, 3, 4 or 5 substituents independently from one another selected from the group consisting of F, Cl, CF$_3$, CN, OH, =O, OCF$_3$, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl, and N(C$_{1-6}$-alkyl)-C(=O)—C$_{1-6}$-alkyl; or a C$_{3-6}$ cycloaliphatic residue, unsubstituted or substituted with 1, 2, 3, 4 or 5 substituents independently from one another selected from the group consisting of F, Cl, CN, CF$_3$, =O, OCF$_3$, C$_{1-6}$-alkylen-OH, C$_{1-6}$ alkyl, OH, O—C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl, and N(C$_{1-6}$-alkyl)-C(=O)—C$_{1-6}$-alkyl; wherein said C$_{3-6}$ cycloaliphatic residue is optionally connected via a C$_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—C$_{1-6}$-alkyl and C$_{1-6}$-alkylen-OH; or a 3-7-membered heterocycloaliphatic residue, which is unsubstituted or substituted with 1, 2, 3, 4 or 5 substituents independently from one another selected from the group consisting of F, Cl, CN, CF$_3$, =O, OCF$_3$, C$_{1-6}$-alkylen-OH, C$_{1-6}$ alkyl, OH, O—C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, (C=O)C$_{1-6}$-alkyl, C(=O)—O—C$_{1-6}$-alkyl; N(H)—C(=O)—C$_{1-6}$-alkyl, and N(C$_{1-6}$-alkyl)-C(=O)—C$_{1-6}$-alkyl, wherein said 3-7-membered heterocycloaliphatic residue is optionally connected via a C$_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—C$_{1-6}$-alkyl and C$_{1-6}$-alkylen-OH; or a heteroaryl residue, which is unsubstituted or substituted with 1, 2, 3, 4 or 5 substituents independently from one another selected from the group consisting of F, Cl, CN, CF$_3$, OCF$_3$, C$_{1-6}$-alkylen-OH, C$_{1-6}$-alkyl, OH, O—C$_{1-6}$-alkyl, O—(C=O)C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—O—C$_{1-6}$-alkyl; O—C(=O)—NH$_2$, O—C(=O)—N(H)(C$_{1-6}$-alkyl), O—C(=O)—N(C$_{1-6}$-alkyl)$_2$, N(H)—C(=O)—NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl, and N(C$_{1-6}$-alkyl)-C(=O)—C$_{1-6}$-alkyl, wherein said heteroaryl residue is optionally connected via a C$_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—C$_{1-6}$-alkyl and C$_{1-6}$-alkylen-OH.

More preferably,

R$^9$ represents H or C$_{1-6}$-alkyl and

R$^{10}$ represents a C$_{3-6}$ cycloaliphatic residue, which is unsubstituted or substituted with 1, 2, 3, 4 or 5 substituents independently from one another selected from the group consisting of F, Cl, CF$_3$, =O, OCF$_3$, OH, O—C$_{1-6}$-alkyl, C$_{1-6}$-alkylen-OH and C$_{1-6}$-alkyl; or a 3-7-membered heterocycloaliphatic residue, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, =O, OCF$_3$, CN, C$_{1-6}$-alkyl, C$_{1-6}$-alkylen-OH and O—C$_{1-6}$-alkyl; or a heteroaryl residue, which contains at least one nitrogen atom and which is unsubstituted or substituted with 1, 2 or 3 substituents independently from one another selected from the group consisting of F, Cl, CN, CF$_3$, OCF$_3$, C$_{1-6}$-alkylen-OH, C$_{1-6}$-alkyl, OH, O—C$_{1-6}$-alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; or a part structure of general formula SF-III

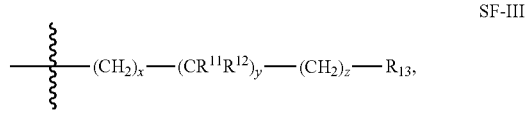

SF-III wherein x represents 0, 1 or 2; y represents 0, 1 or 2; z represents 0, 1 or 2;

on the condition that the sum of x, y and z is 1, 2, 3, 4, 5 or 6;

R$^{11}$ and R$^{12}$ are independently from one another selected from H or C$_{1-6}$-alkyl; or R$^{11}$ and R$^{12}$ together with the carbon atom connecting them form a C$_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—C$_{1-6}$-alkyl, wherein said C$_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;

$R^{13}$ is selected from the group consisting of
H, F, Cl, CN, $CF_3$, $OCF_3$, $C_{1-6}$-alkylen-OH, $C_{1-6}$ alkyl, OH, O—$C_{1-6}$-alkyl, S(=O)—$C_{1-6}$-alkyl, $S(=O)_2$—$C_{1-6}$-alkyl, $S(=O)_2$—$NH_2$, $S(=O)_2$—N(H)$C_{1-6}$-alkyl, $S(=O)_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—$S(=O)_2$—$C_{1-6}$-alkyl, N($C_{1-6}$-alkyl)-$S(=O)_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and N($C_{1-6}$-alkyl)-C(=O)—$C_{1-6}$-alkyl, or represents a $C_{3-6}$ cycloaliphatic residue, which is unsubstituted or substituted with 1, 2, 3, 4, or 5 substituents independently from one another selected from the group consisting of F, Cl, $CF_3$, =O, $OCF_3$, OH, O—$C_{1-6}$ alkyl, $C_{1-6}$-alkylen-OH and $C_{1-6}$-alkyl; or a 3-7-membered heterocycloaliphatic residue, which contains 1 or 2 heteroatoms or heteroatom groups independently from one another selected from the group consisting of O, S, S(=O), $S(=O)_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl; or a heteroaryl residue, which contains at least one nitrogen atom and which is unsubstituted or substituted with 1, 2 or 3 substituents independently from one another selected from the group consisting of F, Cl, CN, $CF_3$, $OCF_3$, $C_{1-6}$-alkylen-OH, $C_{1-6}$-alkyl, OH, O—$C_{1-6}$-alkyl, $S(=O)_2$—$C_{1-6}$-alkyl, $S(=O)_2$—$NH_2$, $NH_2$, NH($C_{1-6}$-alkyl), N($C_{1-6}$-alkyl)$_2$, O—C(=O)—$NH_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl.

More preferably,
$R^9$ represents H or $C_{1-6}$-alkyl and
$R^{10}$ represents
a part structure of general formula SF-III

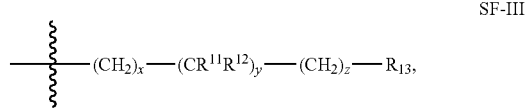

wherein
x represents 0, 1 or 2; y represents 0, 1 or 2; z represents 0, 1 or 2;
on the condition that the sum of x, y and z is 1, 2, 3, 4, 5 or 6;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), $S(=O)_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;

$R^{13}$ is selected from the group consisting of
H, F, Cl, CN, $CF_3$, $OCF_3$, O—$C_{1-6}$-alkylen-OH, $C_{1-6}$-alkylen-OH, $C_{1-6}$ alkyl, OH, O—$C_{1-6}$-alkyl, S(=O)—$S(=O)_2$—$C_{1-6}$-alkyl, $S(=O)_2$—$NH_2$, $S(=O)_2$—N(H)$C_{1-6}$-alkyl, $S(=O)_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—$S(=O)_2$—$C_{1-6}$-alkyl, N($C_{1-6}$-alkyl)-$S(=O)_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and N($C_{1-6}$-alkyl)-C(=O)—$C_{1-6}$-alkyl.

Still more preferably,
$R^9$ represents H or $C_{1-6}$-alkyl and
$R^{10}$ represents
a part structure of general formula SF-III

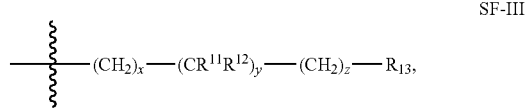

wherein
x represents 0, 1 or 2; y represents 0, 1 or 2; z represents 0, 1 or 2;
on the condition that the sum of x, y and z is 1, 2, 3, 4, 5 or 6;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), $S(=O)_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;

$R^{13}$ is selected from the group consisting of
H, OH, F, Cl, CN, $S(=O)_2$—$C_{1-6}$-alkyl, $NH_2$, N(H)—C(=O)—$C_{1-6}$-alkyl, N(H)—$S(=O)_2$—$C_{1-6}$-alkyl, alkyl, C(=O)—$NH_2$, C(=O)—N(H)($C_{1-6}$-alkyl) and C(=O)—O—$C_{1-6}$-alkyl.

In a particularily preferred embodiment of the compound according to the present invention,
$R^9$ represents H or $C_{1-6}$-alkyl and
$R^{10}$ is selected from the group consisting of
methyl, ethyl, 2-propyl (iso-propyl), 1-propyl (n-propyl), 1-butyl, 2-butyl, 2-methyl-propyl, 1,1-dimethyl-ethyl (tert-butyl), 1-pentyl, 2-pentyl, 3-pentyl, 2-methyl-butyl, 2,2-dimethyl-propyl (neo-pentyl), 1-hexyl, 2-hexyl, 3-hexyl, 3,3-dimethyl-butyl, cyclopropyl, cyclopropylmethyl, 2-cyclopropyl-ethyl, 1-cyclopropyl-ethyl and residues according the following substructures:

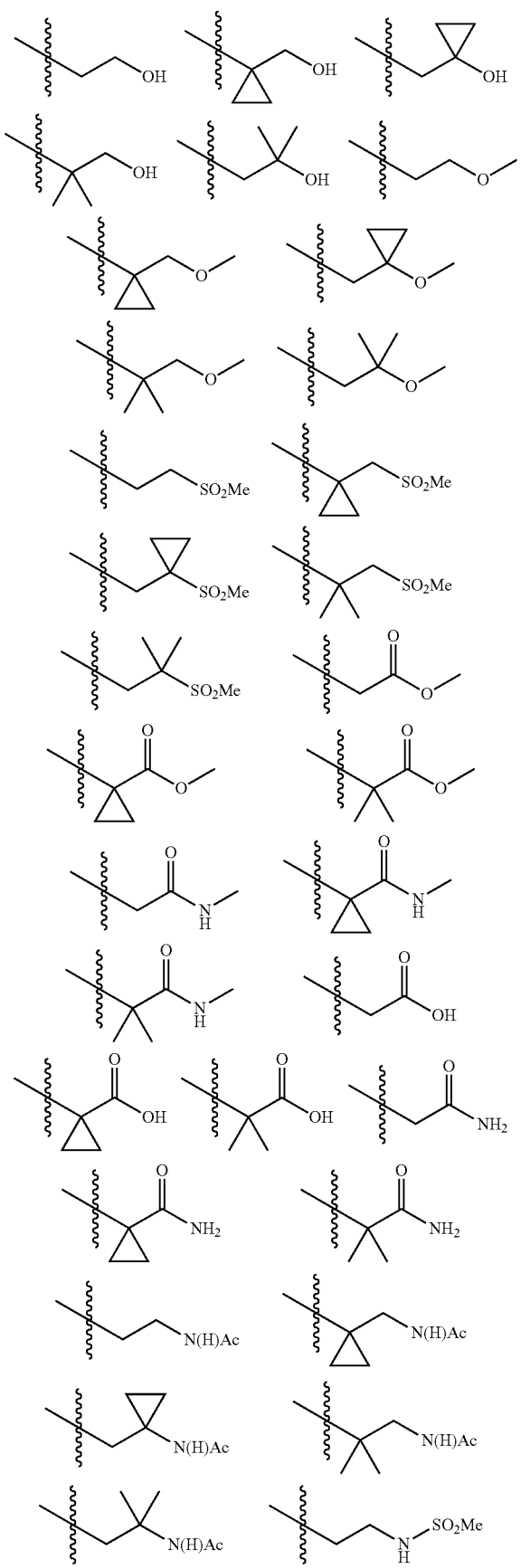
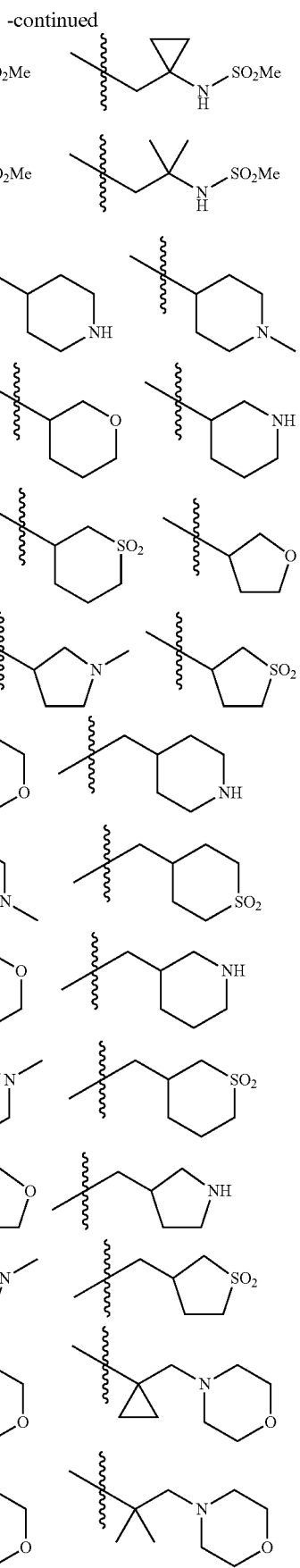

-continued

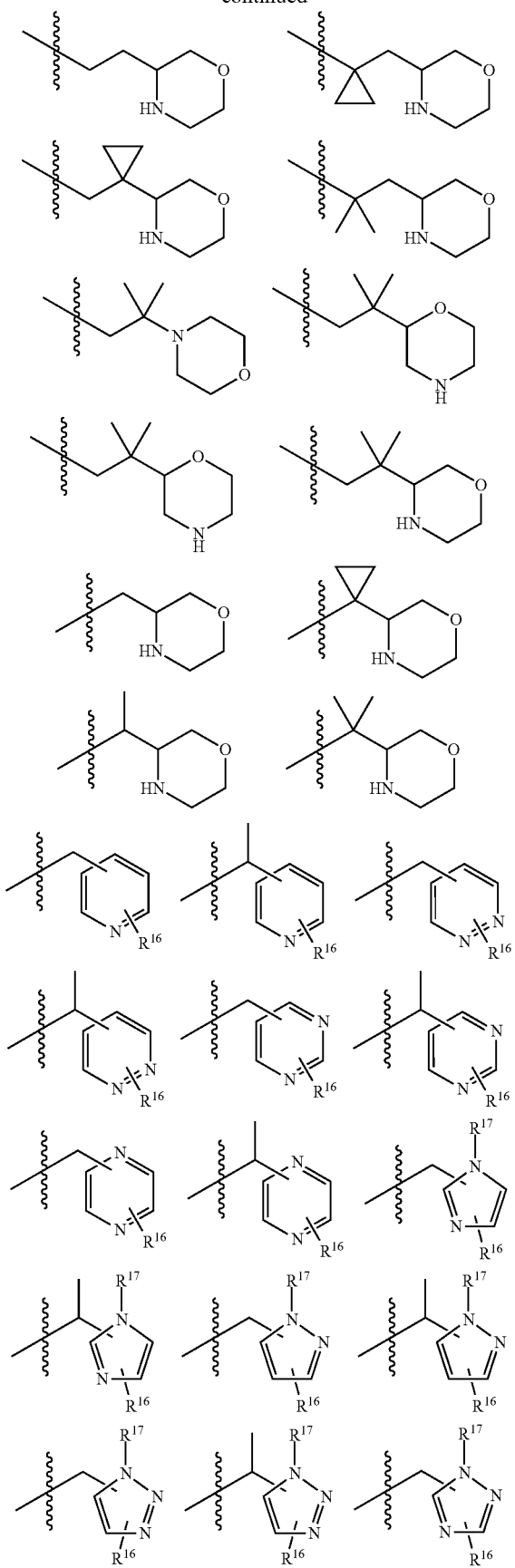
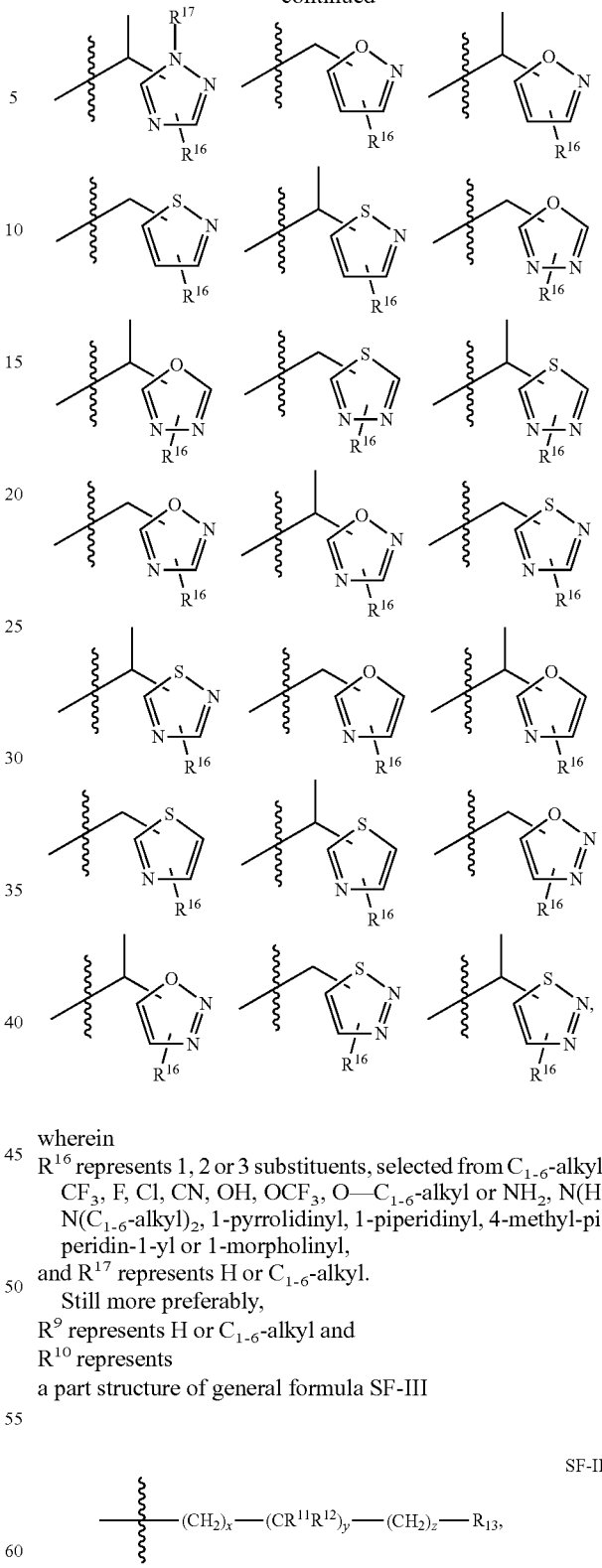

wherein
R$^{16}$ represents 1, 2 or 3 substituents, selected from C$_{1-6}$-alkyl, CF$_3$, F, Cl, CN, OH, OCF$_3$, O—C$_{1-6}$-alkyl or NH$_2$, N(H) N(C$_{1-6}$-alkyl)$_2$, 1-pyrrolidinyl, 1-piperidinyl, 4-methyl-piperidin-1-yl or 1-morpholinyl,
and R$^{17}$ represents H or C$_{1-6}$-alkyl.

Still more preferably,
R$^9$ represents H or C$_{1-6}$-alkyl and
R$^{10}$ represents
a part structure of general formula SF-III $$\text{\{---}(CH_2)_x\text{---}(CR^{11}R^{12})_y\text{---}(CH_2)_z\text{---}R_{13},\quad\text{SF-III}$$

wherein
x represents 0, 1 or 2; y represents 0, 1 or 2; z represents 0, 1 or 2;
on the condition that the sum of x, y and z is 1, 2, 3, 4, 5 or 6;

$R^{11}$ and $R^{12}$ are independently from one another selected from H or $C_{1-6}$-alkyl; or $R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF$_3$, OCF$_3$, CN, $C_{1-6}$-alkyl and O—$C_{1-6}$-alkyl;

$R^{13}$ is selected from the group consisting of

H, OH, F, Cl, CN, S(=O)$_2$—$C_{1-6}$-alkyl, NH$_2$, N(H)—C(=O)—$C_{1-6}$-alkyl, N(H)—S(=O)$_2$—$C_{1-6}$-alkyl, O—$C_{1-6}$-alkyl, C(=O)—NH$_2$, C(=O)—N(H)($C_{1-6}$-alkyl) and C(=O)—O—$C_{1-6}$-alkyl.

In another particularily preferred embodiment of the compound according to the present invention, $R^9$ represents methyl and $R^{10}$ represents H, a $C_{1-10}$ aliphatic residue, branched or unbranched, unsubstituted or mono- or poly-substituted; a $C_{3-10}$ cycloaliphatic residue, a 3 to 10 membered heterocycloaliphatic residue or a heteroaryl residue, in each case unsubstituted or mono- or poly-substituted and in each case optionally connected via a $C_{1-8}$ alkylene group, branched or unbranched, which in turn may be unsubstituted or mono- or polysubstituted.

Preferably, $R^9$ represents methyl and $R^{10}$ represents

H or a $C_{1-6}$ aliphatic residue, branched or unbranched, unsubstituted or substituted with 1, 2, 3, 4 or 5 substituents independently from one another selected from the group consisting of F, Cl, CF$_3$, CN, OH, =O, OCF$_3$, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; or a $C_{3-6}$ cycloaliphatic residue, unsubstituted or substituted with 1, 2, 3, 4 or 5 substituents independently from one another selected from the group consisting of F, Cl, CN, CF$_3$, =O, OCF$_3$, $C_{1-6}$-alkylen-OH, $C_{1-6}$ alkyl, OH, O—$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said $C_{3-6}$ cycloaliphatic residue is optionally connected via a $C_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—$C_{1-6}$-alkyl and $C_{1-6}$-alkylen-OH; or a 3-7-membered heterocycloaliphatic residue, which is unsubstituted or substituted with 1, 2, 3, 4 or 5 substituents independently from one another selected from the group consisting of F, Cl, CN, CF$_3$, =O, OCF$_3$, $C_{1-6}$-alkylen-OH, $C_{1-6}$-alkyl, OH, O—$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$, C(=O)—$C_{1-6}$-alkyl; C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, whereinsaid 3-7-membered heterocycloaliphatic residue is optionally connected via a $C_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—$C_{1-6}$-alkyl and $C_{1-6}$-alkylen-OH; or or a heteroaryl residue, which is unsubstituted or substituted with 1, 2, 3, 4 or 5 substituents independently from one another selected from the group consisting of F, Cl, CN, CF$_3$, OCF$_3$, $C_{1-6}$-alkylen-OH, $C_{1-6}$-alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—NH$_2$, O—C(=O)—N(H)($C_{1-6}$-alkyl), O—C(=O)—N($C_{1-6}$-alkyl)$_2$, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, wherein said heteroaryl residue is optionally connected via a $C_{1-6}$-alkylene group, branched or unbranched, which in turn may be unsubstituted or substituted with 1, 2, 3, 4 or 5 substituents independently from one another selected from the group consisting of F, Cl, CF$_3$, =O, OCF$_3$, OH, O—$C_{1-6}$-alkyl and $C_{1-6}$-alkylen-OH.

More preferably, $R^9$ represents methyl and $R^{10}$ represents a $C_{3-6}$ cycloaliphatic residue, which is unsubstituted or substituted with 1, 2, 3, 4 or 5 substituents independently from one another selected from the group consisting of F, Cl, CF$_3$, =O, OCF$_3$, OH, O—$C_{1-6}$-alkyl, $C_{1-6}$-alkylen-OH and $C_{1-6}$-alkyl; or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, and which is unsubstituted or substituted with 1, 2, 3, 4 or 5 substituents independently from one another selected from the group consisting of F, Cl, CF$_3$, OCF$_3$, CN, $C_{1-6}$-alkylen-OH and O—$C_{1-6}$-alkyl; or a heteroaryl residue, which contains at least one nitrogen atom and which is unsubstituted or substituted with 1, 2 or 3 substituents independently from one another selected from the group consisting of F, Cl, CN, $CF_3$, $OCF_3$, $C_{1-6}$-alkylen-OH, $C_{1-6}$-alkyl, OH, O—$C_{1-6}$-alkyl, $S(=O)_2$—$C_{1-6}$-alkyl, $S(=O)_2$—$NH_2$, $NH_2$, $NH(C_{1-6}$-alkyl), $N(C_{1-6}$-alkyl)$_2$, O—C(=O)—$NH_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; or a part structure of general formula SF-III

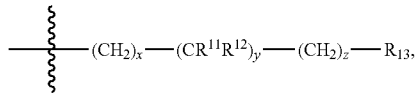

SF-III wherein
x represents 0, 1 or 2; y represents 0, 1 or 2; z represents 0, 1 or 2;
on the condition that the sum of x, y and z is 1, 2, 3, 4, 5 or 6;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), $S(=O)_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;
$R^{13}$ is selected from the group consisting of
H, F, Cl, CN, $CF_3$, $OCF_3$, $C_{1-6}$-alkylen-OH, $C_{1-6}$ alkyl, OH, O—$C_{1-6}$-alkyl, S(=O)—$C_{1-6}$-alkyl, $S(=O)_2$—$C_{1-6}$-alkyl, $S(=O)_2$—$NH_2$, $S(=O)_2$—N(H)$C_{1-6}$-alkyl, $S(=O)_2$—N($C_{1-6}$-alkyl)$_2$, $NH_2$, $NH(C_{1-6}$-alkyl), $N(C_{1-6}$-alkyl)$_2$, N(H)—S(=O)—$C_{1-6}$-alkyl, $N(C_{1-6}$-alkyl)-S(=O)—$C_{1-6}$-alkyl, N(H)—$S(=O)_2$—$C_{1-6}$-alkyl, $N(C_{1-6}$-alkyl)-$S(=O)_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and $N(C_{1-6}$-alkyl)-C(=O)—$C_{1-6}$-alkyl, or represents
a $C_{3-6}$ cycloaliphatic residue, which is unsubstituted or substituted with 1, 2, 3, 4, or 5 substituents independently from one another selected from the group consisting of F, Cl, $CF_3$, =O, $OCF_3$, OH, O—$C_{1-6}$ alkyl, $C_{1-6}$-alkylen-OH and $C_{1-6}$-alkyl; or
a 3-7-membered heterocycloaliphatic residue, which contains 1 or 2 heteroatoms or heteroatom groups independently from one another selected from the group consisting of O, S, S(=O), $S(=O)_2$, NH and N—$C_{1-6}$-alkyl, and which is unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl; or
a heteroaryl residue, which contains at least one nitrogen atom and which is unsubstituted or substituted with 1, 2 or 3 substituents independently from one another selected from the group consisting of F, Cl, CN, $CF_3$, $OCF_3$, $C_{1-6}$-alkylen-OH, $C_{1-6}$-alkyl, OH, O—$C_{1-6}$-alkyl, $S(=O)_2$—$C_{1-6}$-alkyl, $S(=O)_2$—$NH_2$, $NH_2$, $NH(C_{1-6}$-alkyl), $N(C_{1-6}$-alkyl)$_2$, O—C(=O)—$NH_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl.

More preferably,
$R^9$ represents methyl and
$R^{10}$ represents
a part structure of general formula SF-III

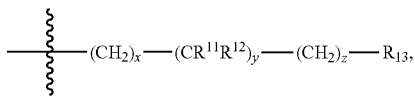

SF-III wherein
x represents 0, 1 or 2; y represents 0, 1 or 2; z represents 0, 1 or 2;
on the condition that the sum of x, y and z is 1, 2, 3, 4, 5 or 6;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), $S(=O)_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;
$R^{13}$ is selected from the group consisting of
H, F, Cl, CN, $CF_3$, $OCF_3$, O—$C_{1-6}$-alkylen-OH, $C_{1-6}$-alkylen-OH, $C_{1-6}$ alkyl, OH, O—$C_{1-6}$-alkyl, S(=O)—$C_{1-6}$-alkyl, $S(=O)_2$—$C_{1-6}$-alkyl, $S(=O)_2$—$NH_2$, $S(=O)_2$—N(H)$C_{1-6}$-alkyl, $S(=O)_2$—N($C_{1-6}$-alkyl)$_2$, $NH_2$, $NH(C_{1-6}$-alkyl), $N(C_{1-6}$-alkyl)$_2$, N(H)—S(=O)—$C_{1-6}$-alkyl, $N(C_{1-6}$-alkyl)-S(=O)—$C_{1-6}$-alkyl, N(H)—$S(=O)_2$—$C_{1-6}$-alkyl, $N(C_{1-6}$-alkyl)-$S(=O)_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and $N(C_{1-6}$-alkyl)-C(=O)—$C_{1-6}$-alkyl.

Still more preferably,
$R^9$ represents methyl and
$R^{10}$ represents
a part structure of general formula SF-III

SF-III wherein
x represents 0, 1 or 2; y represents 0, 1 or 2; z represents 0, 1 or 2;
on the condition that the sum of x, y and z is 1, 2, 3, 4, 5 or 6;
$R^{11}$ and $R^{12}$ are independently from one another selected from H or $C_{1-6}$-alkyl; or $R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF$_3$, OCF$_3$, CN, $C_{1-6}$-alkyl and O—$C_{1-6}$-alkyl;

$R^{13}$ is selected from the group consisting of

H, OH, F, Cl, CN, S(=O)$_2$—$C_{1-6}$-alkyl, NH$_2$, N(H)—C(=O)—$C_{1-6}$-alkyl, N(H)—S(=O)$_2$—$C_{1-6}$-alkyl, C(=O)—NH$_2$, C(=O)—N(H)($C_{1-6}$-alkyl) and C(=O)—O—$C_{1-6}$-alkyl.

In a particularly preferred embodiment of the compound according to the present invention, $R^9$ represents methyl and $R^{10}$ is selected from the group consisting of methyl, ethyl, 2-propyl (iso-propyl), 1-propyl (n-propyl), 1-butyl, 2-butyl, 2-methyl-propyl, 1,1-dimethyl-ethyl (tert-butyl), 1-pentyl, 2-pentyl, 3-pentyl, 2-methyl-butyl, 2,2-dimethyl-propyl (neo-pentyl), 1-hexyl, 2-hexyl, 3-hexyl, 3,3-dimethyl-butyl, cyclopropyl, cyclopropylmethyl, 2-cyclopropyl-ethyl, 1-cyclopropyl-ethyl and residues according the following substructures:

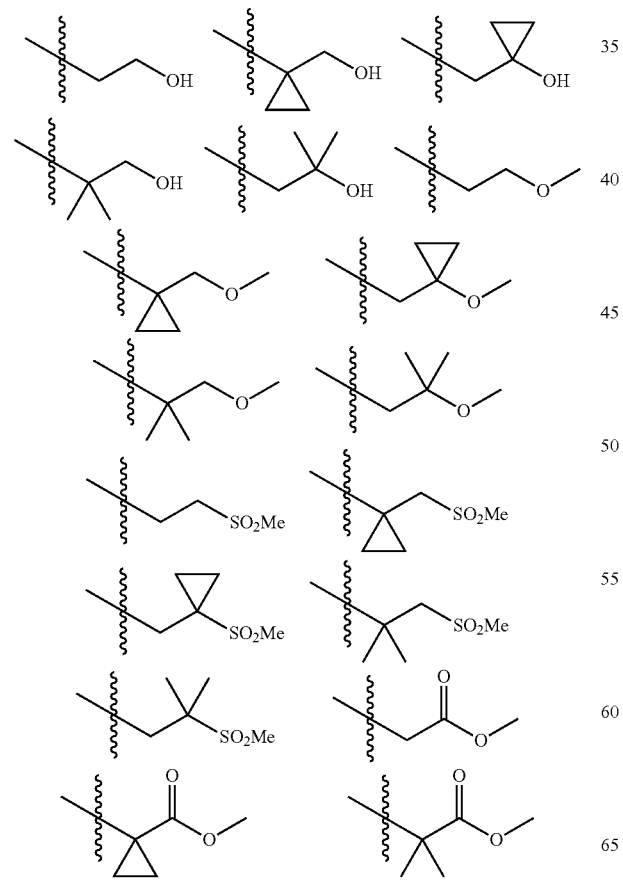

-continued

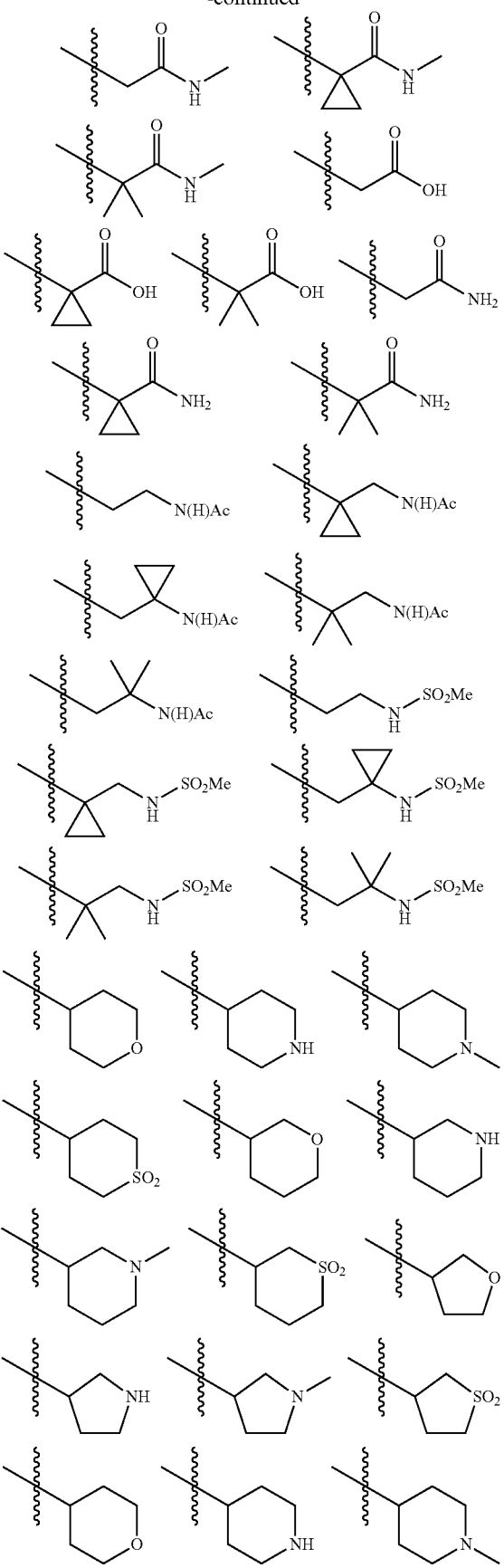

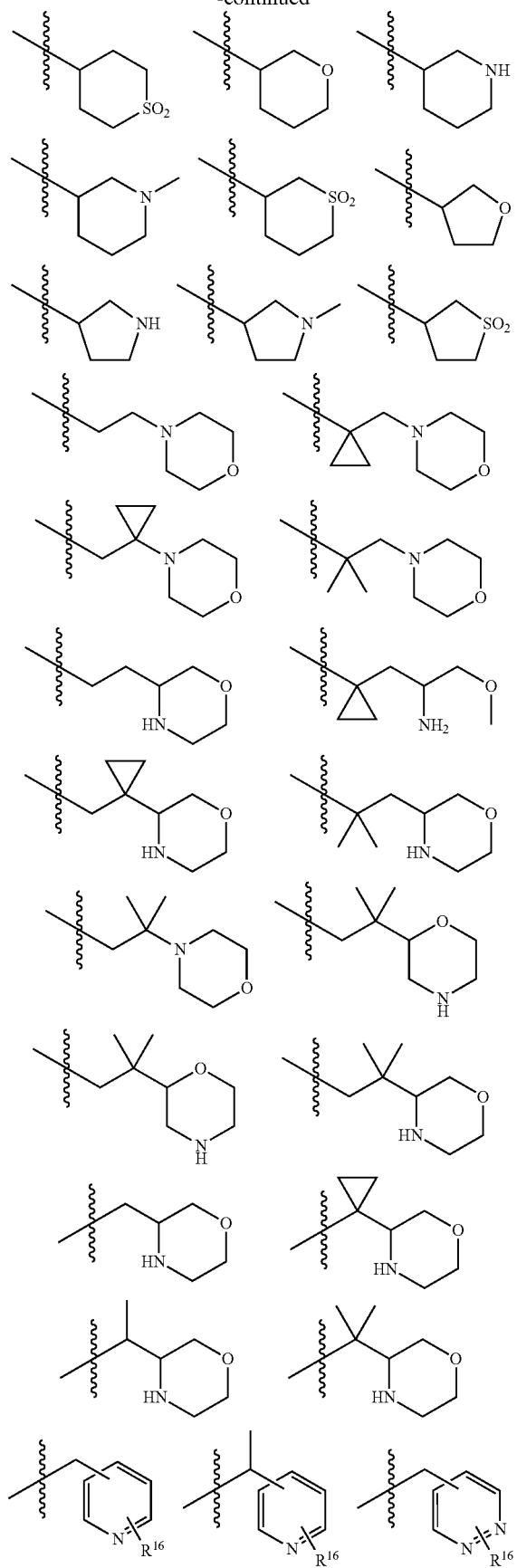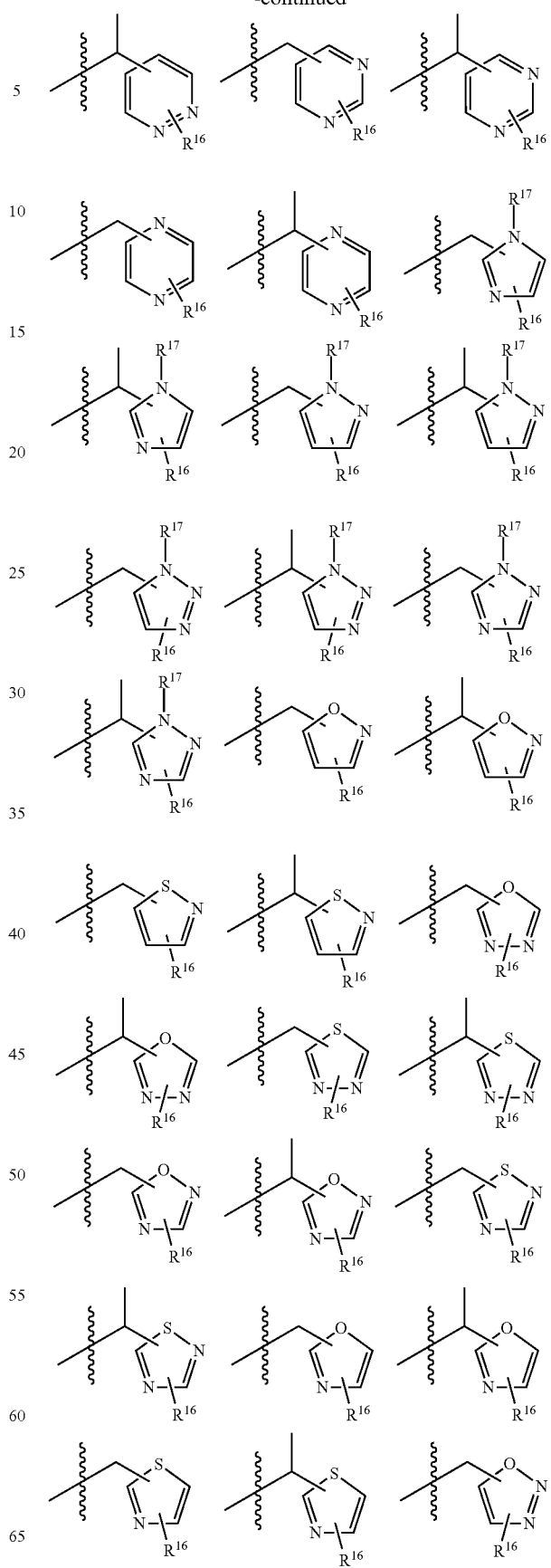

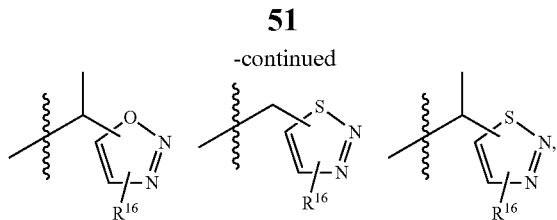

wherein

R$^{16}$ represents 1, 2 or 3 substituents, selected from C$_{1-6}$-alkyl, CF$_3$, F, Cl, CN, OH, OCF$_3$, O—C$_{1-6}$-alkyl or NH$_2$, N(H)C$_{1-6}$-alkyl, N(C$_{1-6}$-alkyl)$_2$, 1-pyrrolidinyl, 1-piperidinyl, 4-methyl-piperidin-1-yl or 1-morpholinyl, and R$^{17}$ represents H or C$_{1-6}$-alkyl.

In another preferred embodiment of the compound according to the present invention, R$^9$ and R$^{10}$ together with the nitrogen atom connecting them form a 3-7-membered heterocycloaliphatic residue, unsubstituted or substituted with 1, 2, 3, 4 or 5 substituents selected from the group consisting of F, Cl, CN, CF$_3$, =O, OH, C$_{1-6}$-alkyl, C$_{1-6}$-alkylen-OH, OCF$_3$, SO$_2$(C$_{1-6}$-alkyl), SO$_2$NH$_2$, SO$_2$N(H)C$_{1-6}$-alkyl, SO$_2$N(C$_{1-6}$-alkyl)$_2$, NH$_2$, NH(C$_{1-6}$-alkyl), N(C$_{1-6}$-alkyl)$_2$, a C$_{3-6}$ cycloaliphatic residue or a 3 to 7 membered heterocycloaliphatic residue, in each case unsubstituted or mono- or polysubstituted.

Preferably,

R$^9$ and R$^{10}$ together with the nitrogen atom connecting them form a heterocycloaliphatic residue selected from the group consisting of

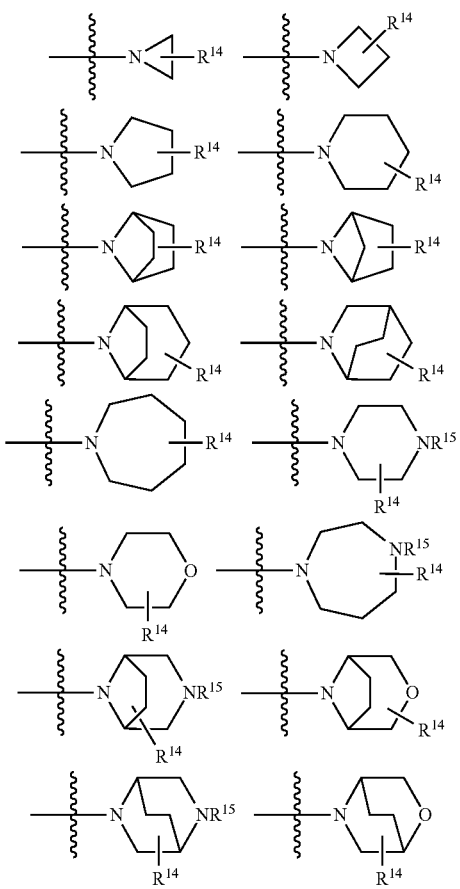

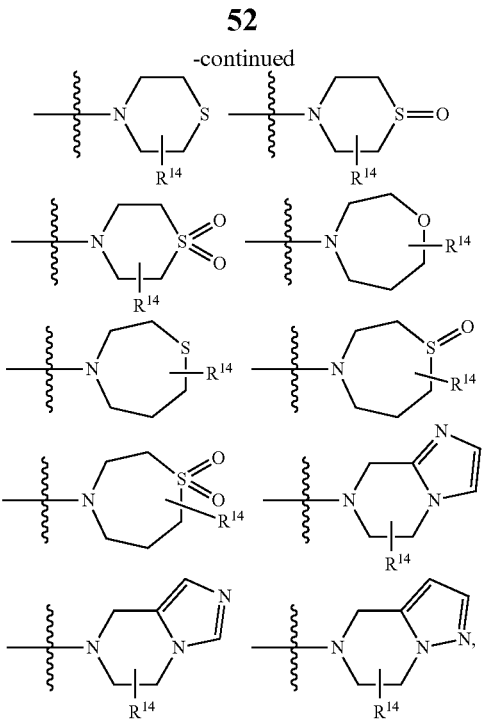

wherein

R$^{14}$ denotes 0, 1, 2, 3 or 4 substituents which are in each case independently of each other selected from the group consisting of F, Cl, CF$_3$, =O, OCF$_3$, OH, O—C$_{1-6}$-alkyl, C$_{1-6}$-alkylen-OH, SO$_2$(C$_{1-6}$-alkyl), C$_{1-6}$-alkylen-SO$_2$(C$_{1-6}$-alkyl), and C$_{1-6}$ alkyl; or R$^{14}$ denotes at least two substituents, wherein two substituents R$^{14}$ stand together for a C$_{1-6}$-alkylen-group, substituted or unsubstituted, wherein optionally one or more C-atoms of the C$_{1-6}$-alkylen-group is replaced by a heteroatom or heteroatom group, selected of O, N—R$^{15}$, S, S(O) and S(O)$_2$, and wherein these two substituents R$^{14}$ are positioned at different carbon atoms of the heterocycloaliphatic residue, so the C$_{1-6}$-alkylen-group represents a bridge to form a bicyclic heterocycloaliphatic residue;

or

R$^{14}$ denotes at least two substituents, wherein two substituents R$^{14}$ stand together for a C$_{2-6}$-alkylen-group, substituted or unsubstituted, wherein optionally one or more C-atoms of the C$_{2-6}$-alkylen-group is replaced by a heteroatom or heteroatom group, selected of O, N—R$^{15}$, S, S(O) and S(O)$_2$, and wherein these two substituents R$^{14}$ are positioned at the same carbon atom of the heterocycloaliphatic residue, so the C$_{2-6}$-alkylen-group forms a spiro-heterocycloaliphatic residue;

and

R$^{15}$ represents H, C$_{1-6}$-alkyl or (C=O)C$_{1-6}$-alkyl.

More preferably,

R$^9$ and R$^{10}$ together with the nitrogen atom connecting them form a heterocycloaliphatic residue selected from the group consisting of

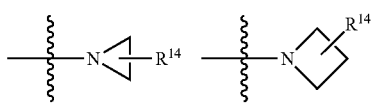

-continued

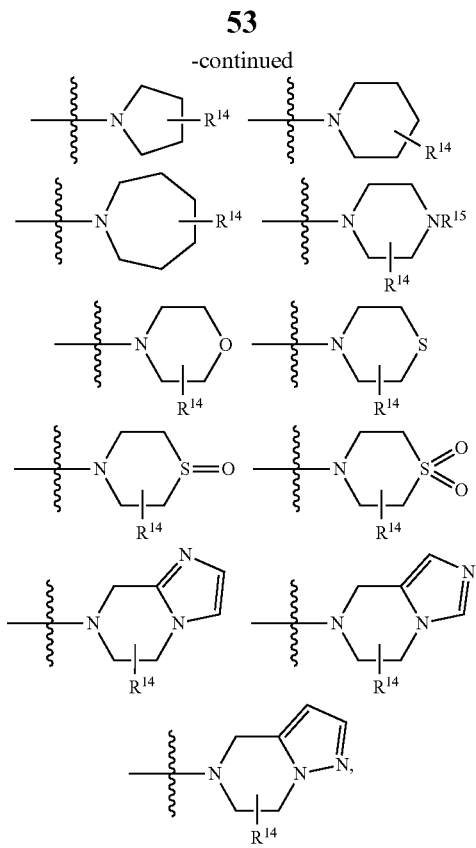

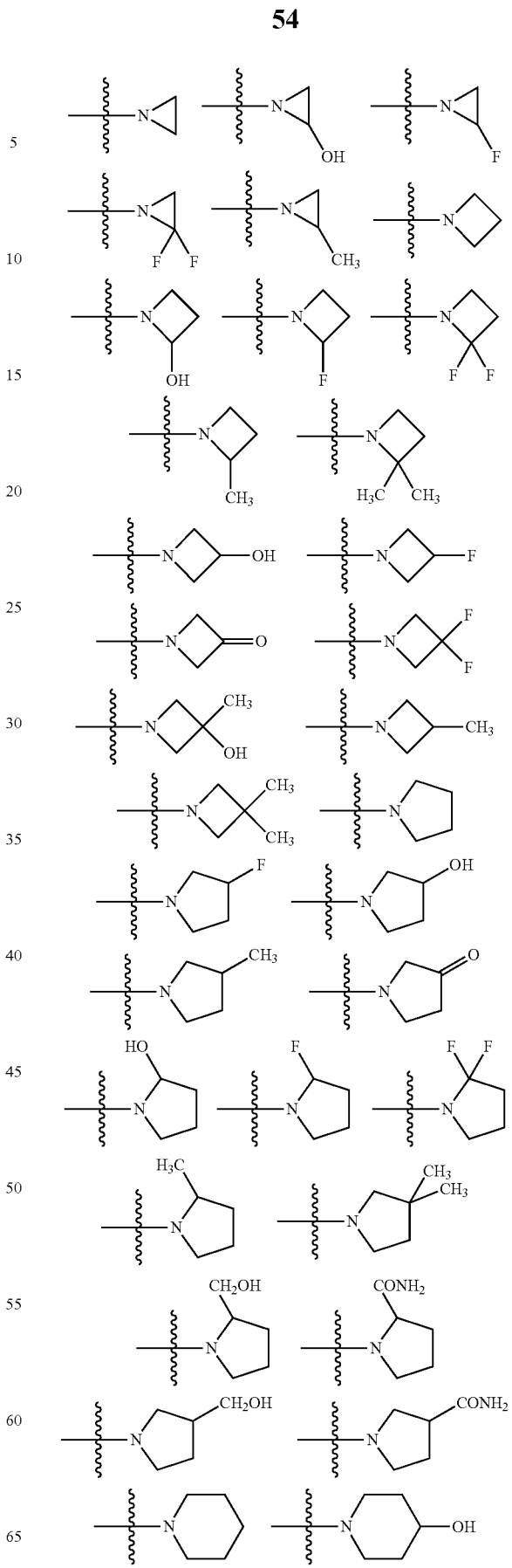

wherein

R[14] denotes 0, 1, 2, 3 or 4 substituents which are in each case independently of each other selected from the group consisting of F, Cl, CF$_3$, =O, OCF$_3$, OH, O—C$_{1-6}$-alkyl, C$_{1-6}$-alkylen-OH, SO$_2$(C$_{1-6}$-alkyl), C$_{1-6}$-alkylen-SO$_2$(C$_{1-6}$-alkyl), and C$_{1-6}$ alkyl; or R[14] denotes at least two substituents, wherein two substituents R[14] stand together for a C$_{1-6}$-alkylen-group, substituted or unsubstituted, wherein optionally one or more C-atoms of the C$_{1-6}$-alkylen-group is replaced by a heteroatom or heteroatom group, selected of O, N—R[15], S, S(O) and S(O)$_2$, and wherein these two substituents R[14] are positioned at different carbon atoms of the heterocycloaliphatic residue, so the C$_{1-6}$-alkylen-group represents a bridge to form a bicyclic heterocycloaliphatic residue;

or

R[14] denotes at least two substituents, wherein two substituents R[14] stand together for a C$_{2-6}$-alkylen-group, substituted or unsubstituted, wherein optionally one or more C-atoms of the C$_{2-6}$-alkylen-group is replaced by a heteroatom or heteroatom group, selected of O, N—R[15], S, S(O) and S(O)$_2$, and wherein these two substituents R[14] are positioned at the same carbon atom of the heterocycloaliphatic residue, so the C$_{2-6}$-alkylen-group forms a spiro-heterocycloaliphatic residue; and R[15] represents H, C$_{1-6}$-alkyl or (C=O)C$_{1-6}$-alkyl.

Still more preferably,

R[9] and R[10] together with the nitrogen atom connecting them form a heterocycloaliphatic residue selected from the group consisting of

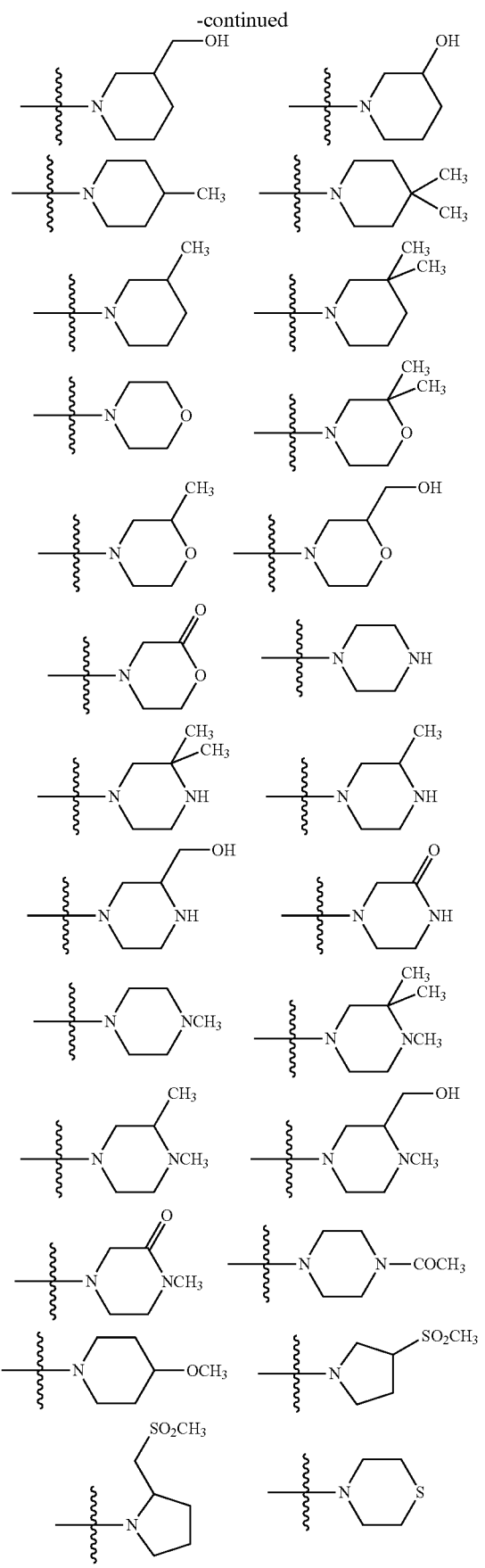
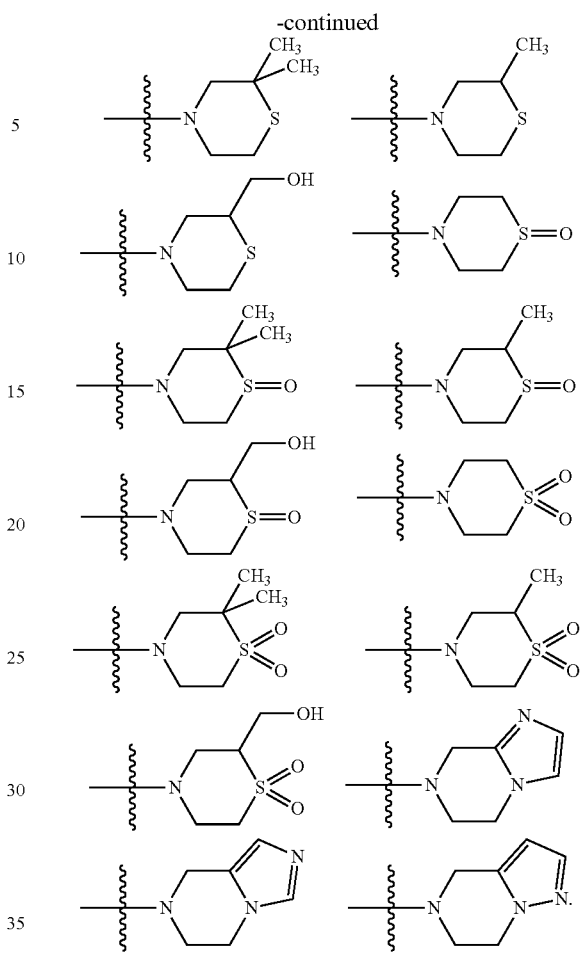
Most preferred, $R^9$ and $R^{10}$ together with the nitrogen atom connecting them form a heterocycloaliphatic residue selected from the group consisting of
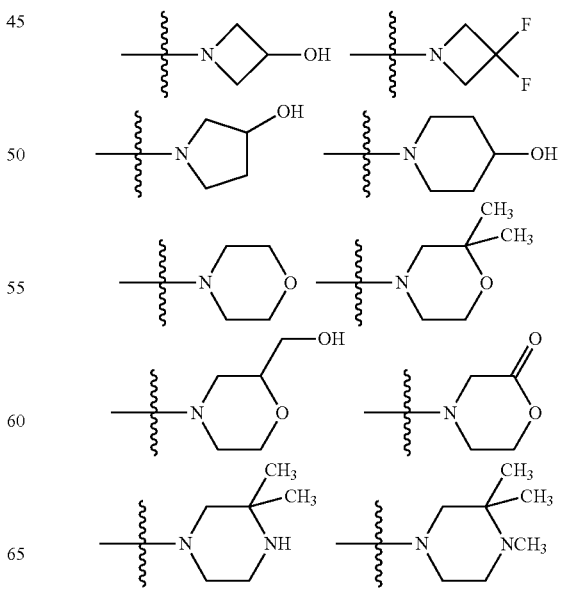

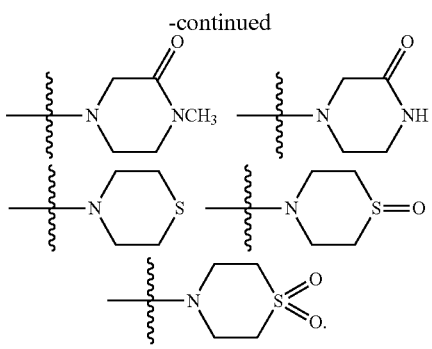

In a particular preferred embodiment according to the present invention, the compound of general formula (I) is selected from the group consisting of compounds according general formula (I), wherein n represents 0 and m represents 0 and $R^4$ represents $CHF_2$ and $R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or poly-substituted;

compounds according general formula (I), wherein n represents 0 and m represents 0 and $R^4$ represents $CF_3$ and $R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or poly-substituted compounds according general formula (I), wherein n represents 1 and m represents 0 and $R^4$ represents $CHF_2$ and $R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or poly-substituted;

compounds according general formula (I), wherein n represents 1 and m represents 0 and $R^4$ represents $CF_3$ and $R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or poly-substituted;

compounds according general formula (I), wherein n represents 2 and m represents 0 and $R^4$ represents $CHF_2$ and $R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or poly-substituted;

compounds according general formula (I), wherein n represents 2 and m represents 0 and $R^4$ represents $CF_3$ and $R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or poly-substituted;

compounds according general formula (I), wherein n represents 2 and m represents 1 and X represents O and $R^4$ represents $CHF_2$ and $R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or poly-substituted;

compounds according general formula (I), wherein n represents 2 and m represents 1 and X represents O and $R^4$ represents $CF_3$ and $R^5$ represents H, $C_{1-6}$-alkyl, branched or unbranched, unsubstituted or mono- or poly-substituted, a $C_{3-6}$ cycloaliphatic residue or a 3 to 7 membered heterocycloaliphatic residue, in each case unsubstituted or mono- or polysubstituted; OH; O—$C_{1-6}$-alkyl; $NH_2$; N(H)—$C_{1-6}$-alkyl; N(—$C_{1-6}$-alkyl)$_2$ or $SO_2$(—$C_{1-6}$-alkyl), whereby in each case $C_{1-6}$-alkyl may be branched or unbranched; unsubstituted or mono- or poly-substituted.

Preferred embodiments of the compound according to the invention of general formula (I) have general formulae (Ia) or (Ib) or (Ic) or (Id):

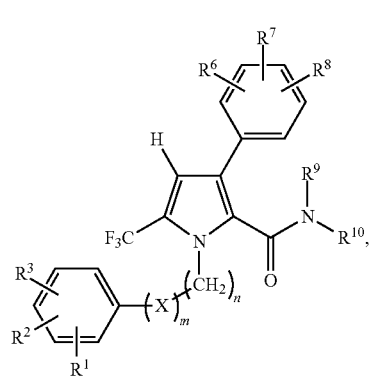
(Ia)
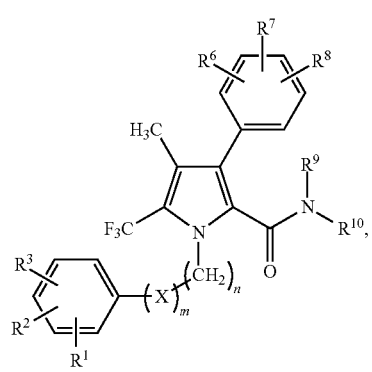
(Ib)
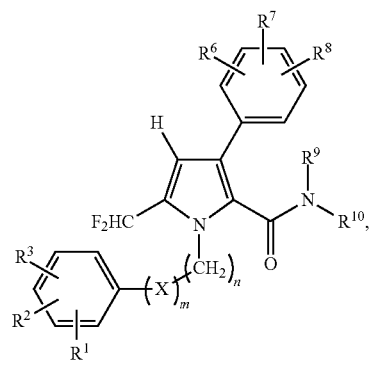
(Ic)
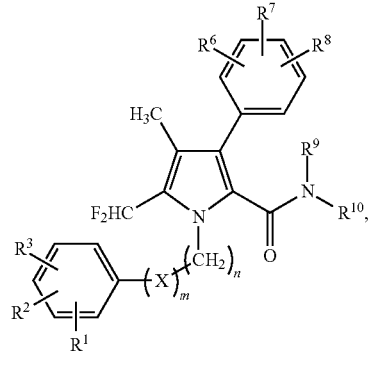
(Id)
wherein the particular radicals, variables and indices have the meanings described herein in connection with the compounds according to the invention and preferred embodiments thereof.
Further preferred embodiments of the compound according to the invention of general formula (I) have general formulae (Ia-1) or (Ia-2) or (Ia-3) or (Ia-4):
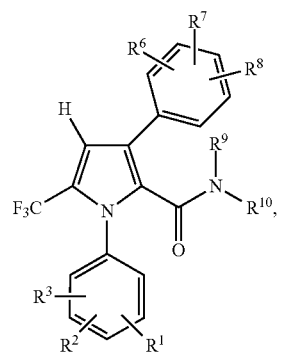
(Ia-1)
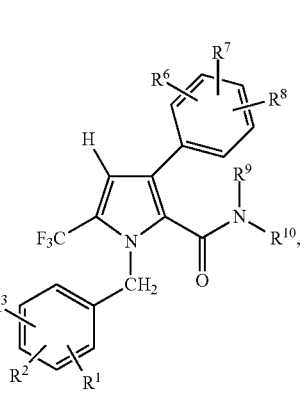
(Ia-2)
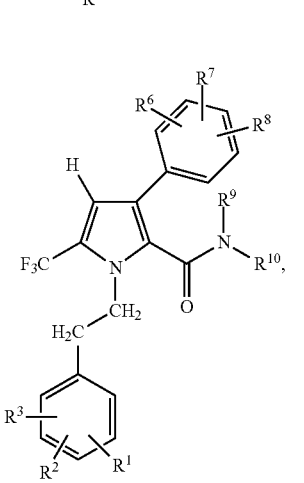
(Ia-3)
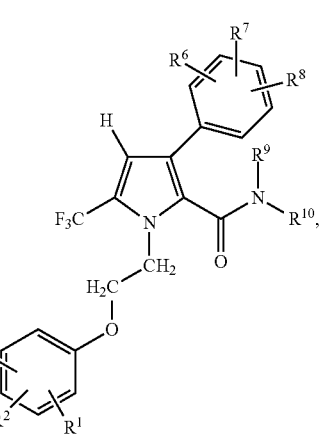
(Ia-4)

wherein the particular radicals, variables and indices have the meanings described herein in connection with the compounds according to the invention and preferred embodiments thereof.

Further preferred embodiments of the compound according to the invention of general formula (I) have general formulae (Ib-1) or (Ib-2) or (Ib-3) or (Ib-4):

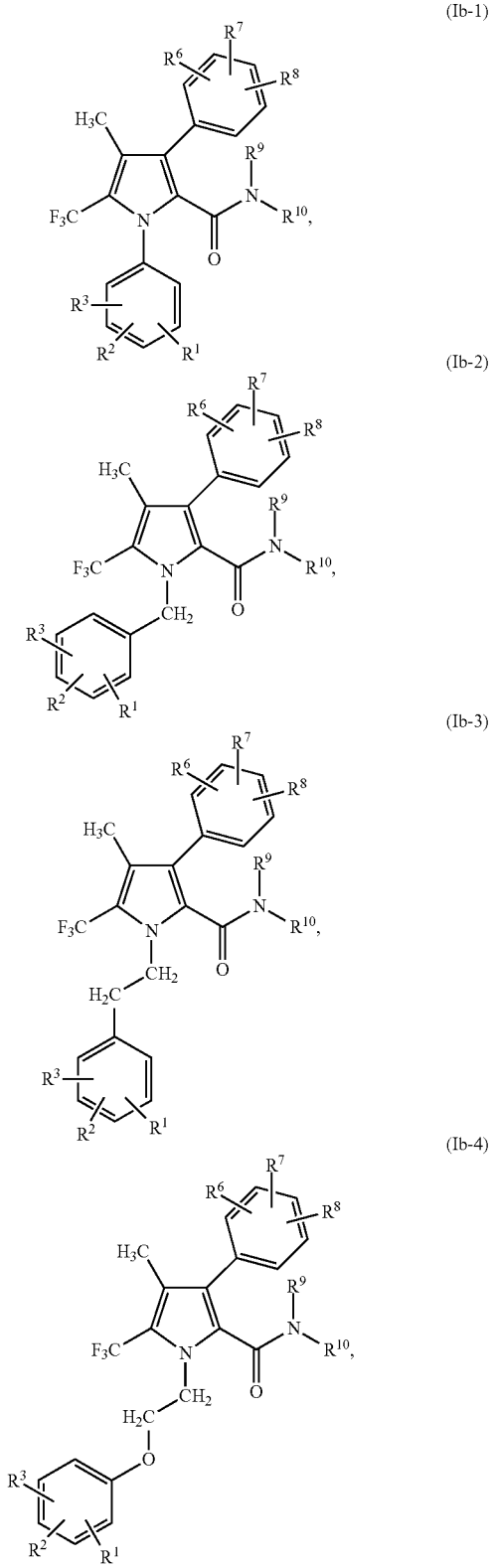

wherein the particular radicals, variables and indices have the meanings described herein in connection with the compounds according to the invention and preferred embodiments thereof.

Further preferred embodiments of the compound according to the invention of general formula (I) have general formulae (Ic-1) or (I-2) or (I-3) or (I-4):

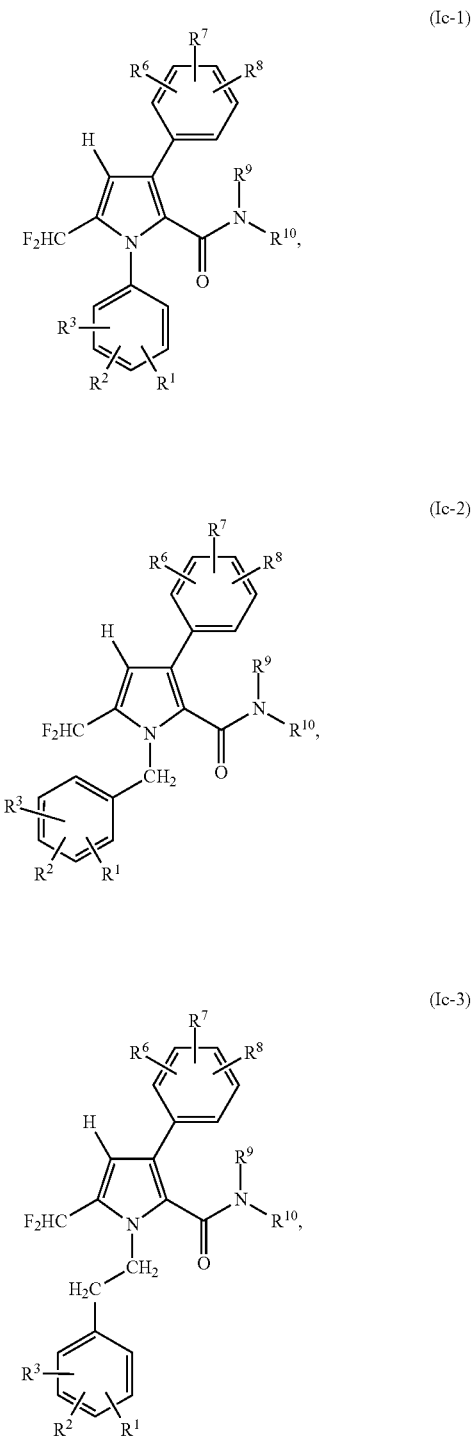

-continued

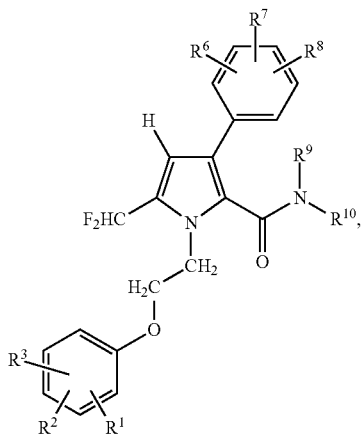
(Ic-4)

wherein the particular radicals, variables and indices have the meanings described herein in connection with the compounds according to the invention and preferred embodiments thereof.

Further preferred embodiments of the compound according to the invention of general formula (I) have general formulae (Id-1) or (Id-2) or (Id-3) or (Id-4):

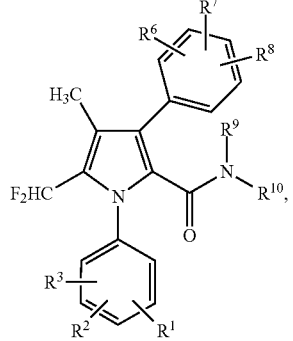
(Id-1)

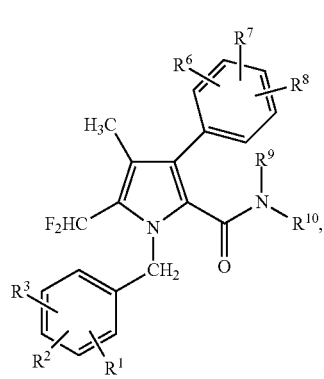
(Id-2)

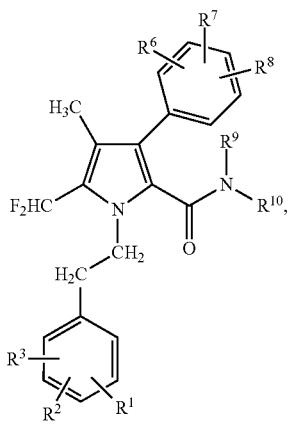
(Id-3)

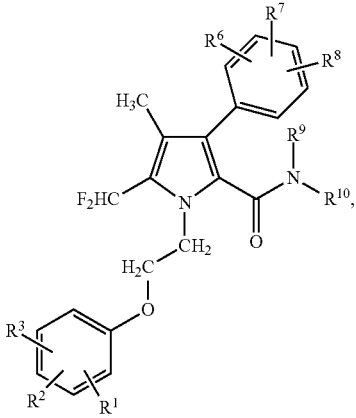
(Id-4)

wherein the particular radicals, variables and indices have the meanings described herein in connection with the compounds according to the invention and preferred embodiments thereof.

In another preferred embodiment of the present invention, the compounds of general formula (I) have general formulae (Ia-1) or (Ia-2) or (Ib-1) or (Ib-2) or (Ic-1) or (I-2) or (Id-1) or (Id-2), particularly (Ia-2) or (Ib-2) or (I-2) or (Id-2).

In another particularly preferred embodiment of the present invention, the compounds of general formula (I) have general formulae (Ia-1-a) or (Ia-2-a) or (Ib-1-a) or (Ib-2-a) or (Ic-1-a) or (I-2-a) or (Id-1-a) or (Id-2-a)

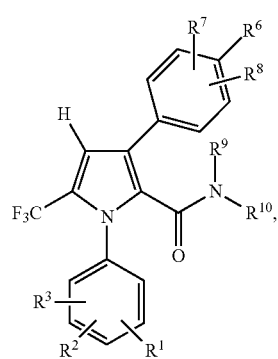
(Ia-1-a)

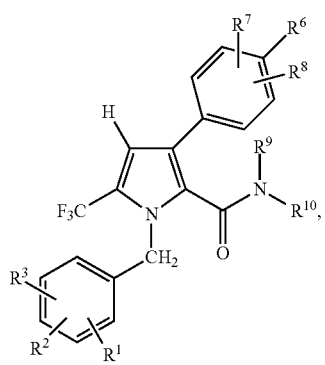
(Ia-2-a)

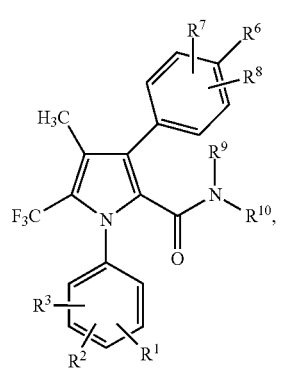
(Ib-1-a)

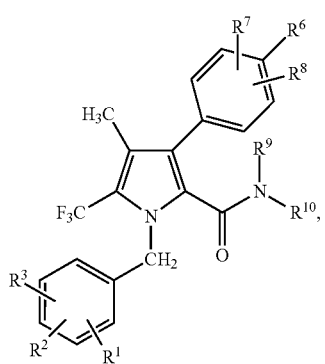
(Ib-2-a)

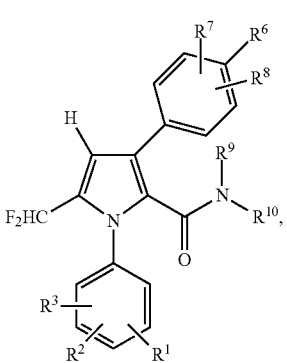
(Ic-1-a)

(Ic-2-a)

(Id-1-a)

(Id-2-a)

wherein $R^6$ denotes $CH_3$ and
wherein the remaining particular radicals, variables and indices have the meanings described herein in connection with the compounds according to the invention and preferred embodiments thereof.

In another particularly preferred embodiment of the present invention, the compounds of general formula (I) have general formulae (Ia-1-a) or (Ia-2-a) or (Ib-1-a) or (Ib-2-a) or (Ic-1-a) or (I-2-a) or (Id-1-a) or (Id-2-a),
wherein $R^6$ denotes Cl and
wherein the remaining particular radicals, variables and indices have the meanings described herein in connection with the compounds according to the invention and preferred embodiments thereof.

In another particularly preferred embodiment of the present invention, the compounds of general formula (I) have general formulae (Ia-1-a) or (Ia-2-a) or (Ib-1-a) or (Ib-2-a) or (Ic-1-a) or (I-2-a) or (Id-1-a) or (Id-2-a),
wherein $R^6$ denotes F and
wherein the remaining particular radicals, variables and indices have the meanings described herein in connection with the compounds according to the invention and preferred embodiments thereof.

In a particularly preferred embodiment of the present invention, the compounds of general formula (I) have general formula (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a),
wherein,
$R^9$ represents methyl or H and $R^{10}$ represents a part structure of general formula SF-III

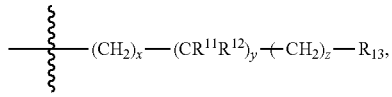

SF-III wherein
x represents 0, 1 or 2; y represents 0, 1 or 2; z represents 0, 1 or 2;
on the condition that the sum of x, y and z is 1, 2, 3 or 4;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF$_3$, OCF$_3$, CN, $C_{1-6}$-alkyl and O—$C_{1-6}$-alkyl;
$R^{13}$ is selected from the group consisting of
H, F, Cl, CN, CF$_3$, OCF$_3$, $C_{1-6}$-alkylen-OH, $C_{1-6}$ alkyl, OH, O—$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)C$_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and N($C_{1-6}$-alkyl)-C(=O)—$C_{1-6}$-alkyl,
or
a $C_{3-6}$ cycloaliphatic residue, selected from cyclopropyl, cyclobutyl, cyclopentyl or cyclohexyl, each unsubstituted or substituted with 1, 2, 3, 4 or 5 substituents independently from one another selected from the group consisting of F, Cl, CF$_3$, OH, OCF$_3$, CN, $C_{1-6}$-alkyl and O—$C_{1-6}$-alkyl;
or
a 3-7-membered heterocycloaliphatic residue, selected from oxetanyl, tetrahydrofuranyl, tetrahydropyranyl, morpholinyl, azetidinyl, pyrrolidinyl, piperidinyl, piperazinyl, thiolanyl, 1-oxo-thiolanyl, 1,1-dioxo-thiolanyl, thianyl, 1-oxo-thianyl, 1,1-dioxo-thianyl, [1,4]thiazinanyl, 1-oxo-[1,4]thiazinanyl or 1,1-dioxo-[1,4]thiazinanyl, each unsubstituted or substituted with 1, 2, 3, 4 or 5 substituents independently from one another selected from the group consisting of F, Cl, CF$_3$, OH, OCF$_3$, CN, $C_{1-6}$-alkyl and O—$C_{1-6}$-alkyl;
or
$R^9$ and $R^{10}$ together with the nitrogen atom connecting them form a 3-7-membered heterocycloaliphatic residue, unsubstituted or substituted with 1, 2, 3, 4 or 5 substituents selected from the group consisting of F, Cl, CN, CF$_3$, =O, OH, $C_{1-6}$-alkyl, O—$C_{1-6}$-alkyl, $C_{1-6}$-alkylen-OH, OCF$_3$, SO$_2$($C_{1-6}$-alkyl), SO$_2$NH$_2$, SO$_2$N(H)$C_{1-6}$-alkyl, SO$_2$N($C_{1-6}$-alkyl)$_2$, NH$_2$, NH($C_{1-6}$-alkyl), N($C_{1-6}$-alkyl)$_2$, a $C_{3-6}$ cycloaliphatic residue or a 3 to 7 membered heterocycloaliphatic residue, in each case unsubstituted or mono- or polysubstituted,
wherein the particular radicals, variables and indices have the meanings described herein in connection with the compounds according to the invention and preferred embodiments thereof.
Preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein
$R^9$ represents H and $R^{10}$ represents a part structure of general formula SF-III

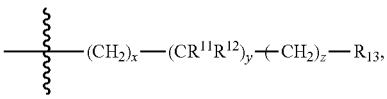

SF-III wherein
x represents 0, 1 or 2; y represents 0, 1 or 2; z represents 0, 1 or 2;
on the condition that the sum of x, y and z is 1, 2, 3 or 4;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF$_3$, OCF$_3$, CN, $C_{1-6}$-alkyl and O—$C_{1-6}$-alkyl;
$R^{13}$ is selected from the group consisting of
H, F, Cl, CN, CF$_3$, OCF$_3$, $C_{1-6}$-alkylen-OH, $C_{1-6}$ alkyl, OH, O—$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and N($C_{1-6}$-alkyl)-C(=O)—$C_{1-6}$-alkyl
or
a $C_{3-6}$ cycloaliphatic residue, selected from cyclopropyl, cyclobutyl, cyclopentyl or cyclohexyl, each unsubstituted or substituted with 1, 2, 3, 4 or 5 substituents independently from one another selected from the group consisting of F, Cl, CF$_3$, OH, OCF$_3$, CN, $C_{1-6}$-alkyl and O—$C_{1-6}$-alkyl;
or
a 3-7-membered heterocycloaliphatic residue, selected from oxetanyl, tetrahydrofuranyl, tetrahydropyranyl, morpholinyl, azetidinyl, pyrrolidinyl, piperidinyl, piperazinyl, thiolanyl, 1-oxo-thiolanyl, 1,1-dioxo-thiolanyl, thianyl, 1-oxo-thianyl, 1,1-dioxo-thianyl, [1,4]thiazinanyl, 1-oxo-[1,4]thiazinanyl or 1,1-dioxo-[1,4]thiazinanyl, each unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl.

Preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein
$R^9$ represents methyl and $R^{10}$ represents a part structure of general formula SF-III

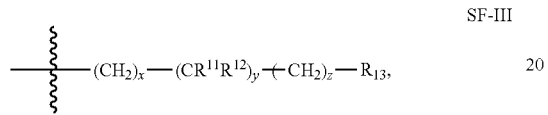

wherein
x represents 0, 1 or 2; y represents 0, 1 or 2; z represents 0, 1 or 2;
on the condition that the sum of x, y and z is 1, 2, 3 or 4;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(═O), S(═O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;
$R^{13}$ is selected from the group consisting of
H, F, Cl, CN, $CF_3$, $OCF_3$, $C_{1-6}$-alkylen-OH, $C_{1-6}$ alkyl, OH, O—$C_{1-6}$-alkyl, S(═O)—$C_{1-6}$-alkyl, S(═O)$_2$—$C_{1-6}$-alkyl, S(═O)$_2$—NH$_2$, S(═O)$_2$—N(H)C$_{1-6}$-alkyl, S(═O)$_2$—N($C_{1-6}$-alkyl)$_2$, NH$_2$, NH($C_{1-6}$-alkyl), N($C_{1-6}$-alkyl)$_2$, N(H)—S(═O)—$C_{1-6}$-alkyl, N($C_{1-6}$-alkyl)-S(═O)—$C_{1-6}$-alkyl, N(H)—S(═O)$_2$—$C_{1-6}$-alkyl, N($C_{1-6}$-alkyl)-S(═O)$_2$—$C_{1-6}$-alkyl, N(H)—C(═O)—NH$_2$, N(H)—C(═O)—N(H)($C_{1-6}$-alkyl), N(H)—C(═O)—N($C_{1-6}$-alkyl)$_2$, C(═O)—NH$_2$, C(═O)—N(H)($C_{1-6}$-alkyl), C(═O)—N($C_{1-6}$-alkyl)$_2$, C(═O)—O—$C_{1-6}$-alkyl; N(H)—C(═O)—$C_{1-6}$-alkyl and N($C_{1-6}$-alkyl)-C(═O)—$C_{1-6}$-alkyl or
a $C_{3-6}$ cycloaliphatic residue, selected from cyclopropyl, cyclobutyl, cyclopentyl or cyclohexyl, each unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl;
or
a 3-7-membered heterocycloaliphatic residue, selected from oxetanyl, tetrahydrofuranyl, tetrahydropyranyl, morpholinyl, azetidinyl, pyrrolidinyl, piperidinyl, piperazinyl, thiolanyl, 1-oxo-thiolanyl, 1,1-dioxo-thiolanyl, thianyl, 1-oxo-thianyl, 1,1-dioxo-thianyl, [1,4]thiazinanyl, 1-oxo-[1,4]thiazinanyl or 1,1-dioxo-[1,4]thiazinanyl, each unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl.

Still preferably,
the compounds of general formula (I) have general formulae (Ia-1), (Ia-2), (Ib-1), (Ib-2), (Ic-1), (Id-1), (Id-2), (Ia-1-a), (Ia-2-a), (Ib-1-a), (Ib-2-a), (Ic-1-a), (I-2-a), (Id-1-a) or (Id-2-a), wherein
$R^9$ and $R^{10}$ together with the nitrogen atom connecting them form a heterocycloaliphatic residue selected from the group consisting of

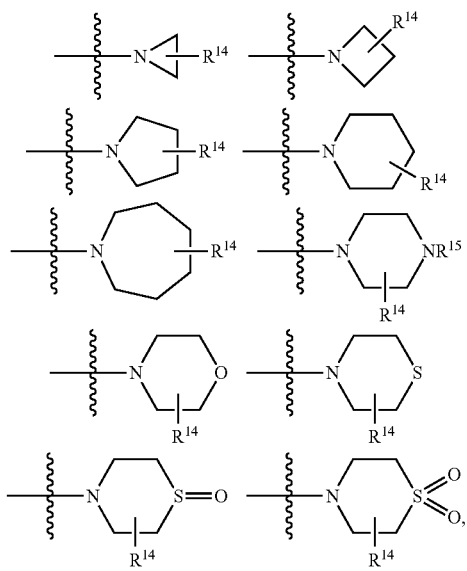

wherein
$R^{14}$ denotes 0, 1, 2, 3 or 4 substituents which are in each case independently of each other selected from the group consisting of F, Cl, $CF_3$, ═O, $OCF_3$, OH, O—$C_{1-6}$-alkyl, $C_{1-6}$-alkylen-OH, SO$_2$($C_{1-6}$-alkyl), $C_{1-6}$-alkylen-SO$_2$ ($C_{1-6}$-alkyl) and $C_{1-6}$ alkyl; or
$R^{14}$ denotes at least two substituents, wherein two substituents $R^{14}$ stand together for a $C_{1-6}$-alkylen-group, substituted or unsubstituted, wherein optionally one or more C-atoms of the $C_{1-6}$-alkylen-group is replaced by a heteroatom or heteroatom group, selected of O, N—$R^{15}$, S, S(O) and S(O)$_2$, and wherein these two substituents $R^{14}$ are positioned at different carbon atoms of the heterocycloaliphatic residue, so the $C_{1-6}$-alkylen-group represents a bridge to form a bicyclic heterocycloaliphatic residue;
or
$R^{14}$ denotes at least two substituents, wherein two substituents $R^{14}$ stand together for a $C_{2-6}$-alkylen-group, substituted or unsubstituted, wherein optionally one or more C-atoms of the $C_{2-6}$-alkylen-group is replaced by a heteroatom or heteroatom group, selected of O, N—$R^{15}$, S, S(O) and S(O)$_2$, and
wherein these two substituents $R^{14}$ are positioned at the same carbon atom of the heterocycloaliphatic residue, so the $C_{2-6}$-alkylen-group forms a spiro-heterocycloaliphatic residue; and
$R^{15}$ represents H, $C_{1-6}$-alkyl or C(═O)$C_{1-6}$-alkyl.

Preferably,
the compounds of general formula (I) have general formulae (Ia-1) and/or (Ia-2) and/or (Ib-1) and/or (Ib-2) and/or (Ic-1) and/or (I-2) and/or (Id-1) and/or (Id-2) and/or (Ia-1-a) and/or (Ia-2-a) and/or (Ib-1-a) and/or (Ib-2-a) and/or (Ic-1-a) and/or (I-2-a) and/or (Id-1-a) and/or (Id-2-a), wherein
$R^6$ denotes $CH_3$,
$R^9$ represents H and $R^{10}$ represents a part structure of general formula SF-III

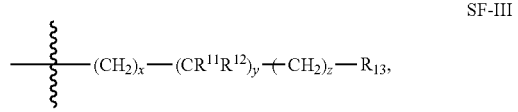

SF-III wherein
x represents 0, 1 or 2; y represents 0, 1 or 2; z represents 0, 1 or 2;
on the condition that the sum of x, y and z is 1, 2, 3 or 4;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;
$R^{13}$ is selected from the group consisting of
H, F, Cl, CN, $CF_3$, $OCF_3$, $C_{1-6}$-alkylen-OH, $C_{1-6}$ alkyl, OH, O—$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and N($C_{1-6}$-alkyl)-C(=O)—$C_{1-6}$-alkyl;
or
a $C_{3-6}$ cycloaliphatic residue, selected from cyclopropyl, cyclobutyl, cyclopentyl or cyclohexyl, each unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl;
or
a 3-7-membered heterocycloaliphatic residue, selected from oxetanyl, tetrahydrofuranyl, tetrahydropyranyl, morpholinyl, azetidinyl, pyrrolidinyl, piperidinyl, piperazinyl, thiolanyl, 1-oxo-thiolanyl, 1,1-dioxo-thiolanyl, thianyl, 1-oxo-thianyl, 1,1-dioxo-thianyl, [1,4]thiazinanyl, 1-oxo-[1,4]thiazinanyl or 1,1-dioxo-[1,4]thiazinanyl, each unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl.

Still preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein
$R^6$ denotes $CH_3$,
$R^9$ represents methyl and $R^{10}$ represents a part structure of general formula SF-III

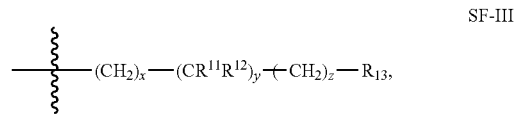

SF-III wherein
x represents 0, 1 or 2; y represents 0, 1 or 2; z represents 0, 1 or 2;
on the condition that the sum of x, y and z is 1, 2, 3 or 4;
$R^{11}$ and $R^{12}$ are independently from one another selected from H or $C_{1-6}$-alkyl; or
$R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;
$R^{13}$ is selected from the group consisting of
H, F, Cl, CN, $CF_3$, $OCF_3$, $C_{1-6}$-alkylen-OH, $C_{1-6}$ alkyl, OH, O—$C_{1-6}$-alkyl, S(=O)—$C_{1-6}$-alkyl, S(=O)$_2$—S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and N($C_{1-6}$-alkyl)-C(=O)—$C_{1-6}$-alkyl;
or
a $C_{3-6}$ cycloaliphatic residue, selected from cyclopropyl, cyclobutyl, cyclopentyl or cyclohexyl, each unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl;
or
a 3-7-membered heterocycloaliphatic residue, selected from oxetanyl, tetrahydrofuranyl, tetrahydropyranyl, morpholinyl, azetidinyl, pyrrolidinyl, piperidinyl, piperazinyl, thiolanyl, 1-oxo-thiolanyl, 1,1-dioxo-thiolanyl, thianyl, 1-oxo-thianyl, 1,1-dioxo-thianyl, [1,4]thiazinanyl, 1-oxo-[1,4]thiazinanyl or 1,1-dioxo-[1,4]thiazinanyl, each unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl.

Still preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein $R^6$ denotes $CH_3$ and $R^9$ and $R^{10}$ together with the nitrogen atom connecting them form a heterocycloaliphatic residue selected from the group consisting of

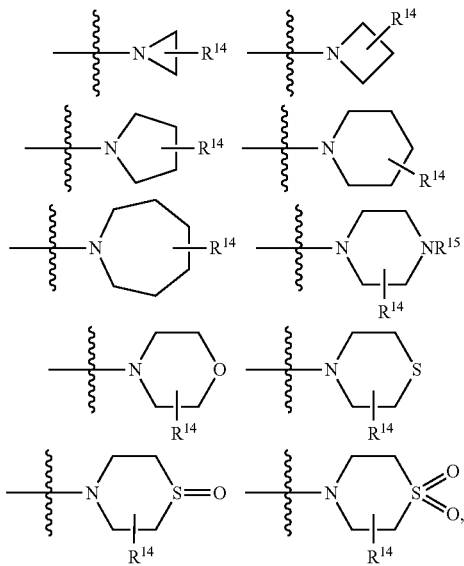

wherein
$R^{14}$ denotes 0, 1, 2, 3 or 4 substituents which are in each case independently of each other selected from the group consisting of F, Cl, $CF_3$, =O, $OCF_3$, OH, O—$C_{1-6}$-alkyl, $SO_2(C_{1-6}$-alkyl), $C_{1-6}$-alkylen-$SO_2(C_{1-6}$-alkyl), $C_{1-6}$-alkylen-OH and $C_{1-6}$ alkyl; or $R^{14}$ denotes at least two substituents, wherein two substituents $R^{14}$ stand together for a $C_{1-6}$-alkylen-group, substituted or unsubstituted, wherein optionally one or more C-atoms of the $C_{1-6}$-alkylen-group is replaced by a heteroatom or heteroatom group, selected of O, N—$R^{15}$, S, S(O) and $S(O)_2$, and wherein these two substituents $R^{14}$ are positioned at different carbon atoms of the heterocycloaliphatic residue, so the $C_{1-6}$-alkylen-group represents a bridge to form a bicyclic heterocycloaliphatic residue;

or $R^{14}$ denotes at least two substituents, wherein two substituents $R^{14}$ stand together for a $C_{2-6}$-alkylen-group, substituted or unsubstituted, wherein optionally one or more C-atoms of the $C_{2-6}$-alkylen-group is replaced by a heteroatom or heteroatom group, selected of O, N—$R^{15}$, S, S(O) and $S(O)_2$, and wherein these two substituents $R^{14}$ are positioned at the same carbon atom of the heterocycloaliphatic residue, so the $C_{2-6}$-alkylen-group forms a spiro-heterocycloaliphatic residue; and $R^{15}$ represents H, $C_{1-6}$-alkyl or $C(=O)C_{1-6}$-alkyl.

Preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein $R^6$ denotes Cl, $R^9$ represents H and $R^{10}$ represents a part structure of general formula SF-III

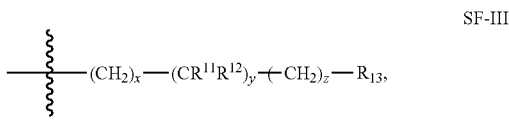

wherein
x represents 0, 1 or 2; y represents 0, 1 or 2; z represents 0, 1 or 2;
on the condition that the sum of x, y and z is 1, 2, 3 or 4;
$R^{11}$ and $R^{12}$ are independently from one another selected from H or $C_{1-6}$-alkyl; or $R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), $S(=O)_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;

$R^{13}$ is selected from the group consisting of
H, F, Cl, CN, $CF_3$, $OCF_3$, $C_{1-6}$-alkylen-OH, $C_{1-6}$ alkyl, OH, O—$C_{1-6}$-alkyl, S(=O)—$C_{1-6}$-alkyl, $S(=O)_2$—$C_{1-6}$-alkyl, $S(=O)_2$—$NH_2$, $S(=O)_2$—N(H)$C_{1-6}$-alkyl, $S(=O)_2$—$N(C_{1-6}$-alkyl)$_2$, $NH_2$, NH($C_{1-6}$-alkyl), $N(C_{1-6}$-alkyl)$_2$, N(H)—S(=O)—$C_{1-6}$-alkyl, $N(C_{1-6}$-alkyl)-S(=O)—$C_{1-6}$-alkyl, $N(H)$—$S(=O)_2$—$C_{1-6}$-alkyl, $N(C_{1-6}$-alkyl)-$S(=O)_2$—$C_{1-6}$-alkyl, N(H)—C(=O)—$NH_2$, N(H)—C(=O)—N(H)($C_{1-6}$-alkyl), N(H)—C(=O)—$N(C_{1-6}$-alkyl)$_2$, C(=O)—$NH_2$, C(=O)—N(H)($C_{1-6}$-alkyl), C(=O)—$N(C_{1-6}$-alkyl)$_2$, C(=O)—O—$C_{1-6}$-alkyl; N(H)—C(=O)—$C_{1-6}$-alkyl and $N(C_{1-6}$-alkyl)-C(=O)—$C_{1-6}$-alkyl or a $C_{3-6}$ cycloaliphatic residue, selected from cyclopropyl, cyclobutyl, cyclopentyl or cyclohexyl, each unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl;

or a 3-7-membered heterocycloaliphatic residue, selected from oxetanyl, tetrahydrofuranyl, tetrahydropyranyl, morpholinyl, azetidinyl, pyrrolidinyl, piperidinyl, piperazinyl, thiolanyl, 1-oxo-thiolanyl, 1,1-dioxo-thiolanyl, thianyl, 1-oxo-thianyl, 1,1-dioxo-thianyl, [1,4]thiazinanyl, 1-oxo-[1,4]thiazinanyl or 1,1-dioxo-[1,4]thiazinanyl, each unsubstituted or substituted with 1, 2, 3, 4 or 5 substituents independently from one another selected from the group consisting of F, Cl, $CF_3$, OH, $OCF_3$, CN, $C_{1-6}$-alkyl and O—$C_{1-6}$-alkyl.

Still preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein $R^6$ denotes Cl,
$R^9$ represents methyl and $R^{10}$ represents a part structure of general formula SF-III $$\text{—}(CH_2)_x\text{—}(CR^{11}R^{12})_y\text{—}(CH_2)_z\text{—}R_{13},\quad \text{SF-III}$$

wherein
  x represents 0, 1 or 2; y represents 0, 1 or 2; z represents 0, 1 or 2;
    on the condition that the sum of x, y and z is 1, 2, 3 or 4;
  $R^{11}$ and $R^{12}$ are independently from one another selected from H or $C_{1-6}$-alkyl; or
    $R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF$_3$, OCF$_3$, CN, $C_{1-6}$-alkyl and O—$C_{1-6}$-alkyl;
  $R^{13}$ is selected from the group consisting of
    H, F, Cl, CN, CF$_3$, OCF$_3$, $C_{1-6}$-alkylen-OH, $C_{1-6}$ alkyl, OH, O—$C_{1-6}$-alkyl, S(=O)—$C_{1-6}$-alkyl, S(=O)$_2$—$C_{1-6}$-alkyl, S(=O)$_2$—NH$_2$, S(=O)$_2$—N(H)$C_{1-6}$-alkyl, S(=O)$_2$—N($C_{1-6}$-alkyl)$_2$, NH$_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—NH$_2$, N(H)—C(=O)—N(H)($C_{1-6}$-alkyl), N(H)—C(=O)—N($C_{1-6}$-alkyl)$_2$, C(=O)—NH$_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl and N($C_{1-6}$-alkyl)-C(=O)—$C_{1-6}$-alkyl;
    or
    a $C_{3-6}$ cycloaliphatic residue, selected from cyclopropyl, cyclobutyl, cyclopentyl or cyclohexyl, each unsubstituted or substituted with 1, 2, 3, 4 or 5 substituents independently from one another selected from the group consisting of F, Cl, CF$_3$, OH, OCF$_3$, CN, $C_{1-6}$-alkyl and O—$C_{1-6}$-alkyl;
    or
    a 3-7-membered heterocycloaliphatic residue, selected from oxetanyl, tetrahydrofuranyl, tetrahydropyranyl, morpholinyl, azetidinyl, pyrrolidinyl, piperidinyl, piperazinyl, thiolanyl, 1-oxo-thiolanyl, 1,1-dioxo-thiolanyl, thianyl, 1-oxo-thianyl, 1,1-dioxo-thianyl, [1,4]thiazinanyl, 1-oxo-[1,4]thiazinanyl or 1,1-dioxo-[1,4]thiazinanyl, each unsubstituted or substituted with 1, 2, 3, 4 or 5 substituents independently from one another selected from the group consisting of F, Cl, CF$_3$, OH, OCF$_3$, CN, $C_{1-6}$-alkyl and O—$C_{1-6}$-alkyl.

Still preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein $R^6$ denotes Cl and
$R^9$ and $R^{10}$ together with the nitrogen atom connecting them form a heterocycloaliphatic residue selected from the group consisting of

[structures showing N-containing rings: aziridine-R$^{14}$, azetidine-R$^{14}$, pyrrolidine-R$^{14}$, piperidine-R$^{14}$, azepane-R$^{14}$, piperazine-NR$^{15}$/R$^{14}$, morpholine-R$^{14}$, thiomorpholine-R$^{14}$, thiomorpholine-S-oxide-R$^{14}$, thiomorpholine-S,S-dioxide-R$^{14}$]

wherein
  $R^{14}$ denotes 0, 1, 2, 3 or 4 substituents which are in each case independently of each other selected from the group consisting of F, Cl, CF$_3$, =O, OCF$_3$, OH, O—$C_{1-6}$-alkyl, SO$_2$($C_{1-6}$-alkyl), $C_{1-6}$-alkylen-SO$_2$($C_{1-6}$-alkyl), $C_{1-6}$-alkylen-OH and $C_{1-6}$ alkyl; or
  $R^{14}$ denotes at least two substituents, wherein two substituents $R^{14}$ stand together for a $C_{1-6}$-alkylen-group, substituted or unsubstituted, wherein optionally one or more C-atoms of the $C_{1-6}$-alkylen-group is replaced by a heteroatom or heteroatom group, selected of O, N—$R^{15}$, S, S(O) and S(O)$_2$, and wherein these two substituents $R^{14}$ are positioned at different carbon atoms of the heterocycloaliphatic residue, so the $C_{1-6}$-alkylen-group represents a bridge to form a bicyclic heterocycloaliphatic residue;
  or
  $R^{14}$ denotes at least two substituents, wherein two substituents $R^{14}$ stand together for a $C_{2-6}$-alkylen-group, substituted or unsubstituted, wherein optionally one or more C-atoms of the $C_{2-6}$-alkylen-group is replaced by a heteroatom or heteroatom group, selected of O, N—$R^{15}$, S, S(O) and S(O)$_2$, and wherein these two substituents $R^{14}$ are positioned at the same carbon atom of the heterocycloaliphatic residue, so the $C_{2-6}$-alkylen-group forms a spiro-heterocycloaliphatic residue; and
  $R^{15}$ represents H, $C_{1-6}$-alkyl or C(=O)$C_{1-6}$-alkyl.

Preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein R⁶ denotes F,
R⁹ represents H and R¹⁰ represents a part structure of general formula SF-III

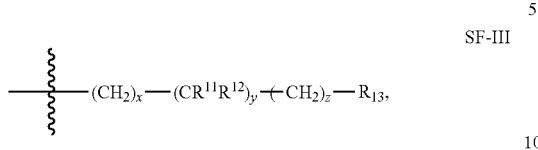

wherein
  x represents 0, 1 or 2; y represents 0, 1 or 2; z represents 0, 1 or 2;
    on the condition that the sum of x, y and z is 1, 2, 3 or 4;
  $R^{11}$ and $R^{12}$ are independently from one another selected from H or $C_{1-6}$-alkyl; or
    $R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)₂, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF₃, OCF₃, CN, $C_{1-6}$-alkyl and O—$C_{1-6}$-alkyl;
  $R^{13}$ is selected from the group consisting of
    H, F, Cl, CN, CF₃, OCF₃, $C_{1-6}$-alkylen-OH, $C_{1-6}$ alkyl, OH, O—$C_{1-6}$-alkyl, S(=O)—$C_{1-6}$-alkyl, S(=O)₂—$C_{1-6}$-alkyl, S(=O)₂—NH₂, S(=O)₂—N(H)$C_{1-6}$-alkyl, S(=O)₂—N($C_{1-6}$-alkyl)₂, NH₂, NH($C_{1-6}$-alkyl), N($C_{1-6}$-alkyl)₂, N(H)—S(=O)—$C_{1-6}$-alkyl, N($C_{1-6}$-alkyl)-S(=O)—$C_{1-6}$-alkyl, N(H)—S(=O)₂—$C_{1-6}$-alkyl, N($C_{1-6}$-alkyl)-S(=O)₂—$C_{1-6}$-alkyl, N(H)—C(=O)—NH₂, N(H)—C(=O)—N(H)($C_{1-6}$-alkyl), N(H)—C(=O)—N($C_{1-6}$-alkyl)₂, C(=O)—NH₂, C(=O)—N(H)($C_{1-6}$-alkyl), C(=O)—N($C_{1-6}$-alkyl)₂, C(=O)—O—$C_{1-6}$-alkyl; N(H)—C(=O)—$C_{1-6}$-alkyl and N($C_{1-6}$-alkyl)-C(=O)—$C_{1-6}$-alkyl;
    or
    a $C_{3-6}$ cycloaliphatic residue, selected from cyclopropyl, cyclobutyl, cyclopentyl or cyclohexyl, each unsubstituted or substituted with 1, 2, 3, 4 or 5 substituents independently from one another selected from the group consisting of F, Cl, CF₃, OH, OCF₃, CN, $C_{1-6}$-alkyl and O—$C_{1-6}$-alkyl;
    or
    a 3-7-membered heterocycloaliphatic residue, selected from oxetanyl, tetrahydrofuranyl, tetrahydropyranyl, morpholinyl, azetidinyl, pyrrolidinyl, piperidinyl, piperazinyl, thiolanyl, 1-oxo-thiolanyl, 1,1-dioxo-thiolanyl, thianyl, 1-oxo-thianyl, 1,1-dioxo-thianyl, [1,4]thiazinanyl, 1-oxo-[1,4]thiazinanyl or 1,1-dioxo-[1,4]thiazinanyl, each unsubstituted or substituted with 1, 2, 3, 4 or 5 substituents independently from one another selected from the group consisting of F, Cl, CF₃, OH, OCF₃, CN, $C_{1-6}$-alkyl and O—$C_{1-6}$-alkyl.

Still preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein R⁶ denotes F,
R⁹ represents methyl and R¹⁰ represents a part structure of general formula SF-III

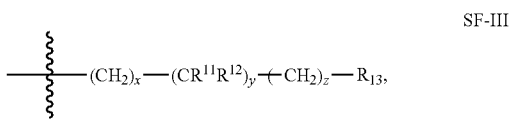

wherein
  x represents 0, 1 or 2; y represents 0, 1 or 2; z represents 0, 1 or 2;
    on the condition that the sum of x, y and z is 1, 2, 3 or 4;
  $R^{11}$ and $R^{12}$ are independently from one another selected from H or $C_{1-6}$-alkyl; or
    $R^{11}$ and $R^{12}$ together with the carbon atom connecting them form a $C_{3-6}$ cycloaliphatic residue or a 3-7-membered heterocycloaliphatic residue, which contains 1 or 2 heteroatoms or heteroatom groups independently from one another selected from the group consisting of O, S, S(=O), S(=O)₂, NH and N—$C_{1-6}$-alkyl, wherein said $C_{3-6}$-cycloaliphatic residue or 3-7-membered heterocycloaliphatic residue may be unsubstituted or substituted with 1, 2, 3, 4 or 5 substituents independently from one another selected from the group consisting of F, Cl, CF₃, OCF₃, CN, $C_{1-6}$-alkyl and O—$C_{1-6}$-alkyl;
  $R^{13}$ is selected from the group consisting of
    H, F, Cl, CN, CF₃, OCF₃, $C_{1-6}$-alkylen-OH, $C_{1-6}$ alkyl, OH, O—$C_{1-6}$-alkyl, S(=O)—$C_{1-6}$-alkyl, S(=O)₂—$C_{1-6}$-alkyl, S(=O)₂—NH₂, S(=O)₂—N(H)$C_{1-6}$-alkyl, S(=O)₂—N($C_{1-6}$-alkyl)₂, NH₂, NH($C_{1-6}$-alkyl), N($C_{1-6}$-alkyl)₂, N(H)—S(=O)—$C_{1-6}$-alkyl, N($C_{1-6}$-alkyl)-S(=O)—$C_{1-6}$-alkyl, N(H)—S(=O)₂—$C_{1-6}$-alkyl, N($C_{1-6}$-alkyl)-S(=O)₂—$C_{1-6}$-alkyl, N(H)—C(=O)—NH₂, N(H)—C(=O)—N(H)($C_{1-6}$-alkyl), N(H)—C(=O)—N($C_{1-6}$-alkyl)₂, C(=O)—NH₂, C(=O)—N(H)($C_{1-6}$-alkyl), C(=O)—N($C_{1-6}$-alkyl)₂, C(=O)—O—$C_{1-6}$-alkyl; N(H)—C(=O)—$C_{1-6}$-alkyl and N($C_{1-6}$-alkyl)-C(=O)—$C_{1-6}$-alkyl;
    or
    a $C_{3-6}$ cycloaliphatic residue, selected from cyclopropyl, cyclobutyl, cyclopentyl or cyclohexyl, each unsubstituted or substituted with 1, 2, 3, 4 or 5 substituents independently from one another selected from the group consisting of F, Cl, CF₃, OH, OCF₃, CN, $C_{1-6}$-alkyl and O—$C_{1-6}$-alkyl;
    or
    a 3-7-membered heterocycloaliphatic residue, selected from oxetanyl, tetrahydrofuranyl, tetrahydropyranyl, morpholinyl, azetidinyl, pyrrolidinyl, piperidinyl, piperazinyl, thiolanyl, 1-oxo-thiolanyl, 1,1-dioxo-thiolanyl, thianyl, 1-oxo-thianyl, 1,1-dioxo-thianyl, [1,4]thiazinanyl, 1-oxo-[1,4]thiazinanyl or 1,1-dioxo-[1,4]thiazinanyl, each unsubstituted or substituted with 1, 2, 3, 4 or 5 substituents independently from one another selected from the group consisting of F, Cl, CF₃, OH, OCF₃, CN, $C_{1-6}$-alkyl and O—$C_{1-6}$-alkyl.

Still preferably,
the compounds of general formula (I) have general formulae (Ia-1), (Ia-2), (Ib-1), (Ib-2), (Ic-1), (I-2), (Id-1), (Id-2), (Ia-1-a), (Ia-2-a), (Ib-1-a), (Ib-2-a), (Ic-1-a), (I-2-a), (Id-1-a) or (Id-2-a), wherein R⁶ denotes F and R⁹ and R¹⁰ together with the nitrogen atom connecting them form a heterocycloaliphatic residue selected from the group consisting of

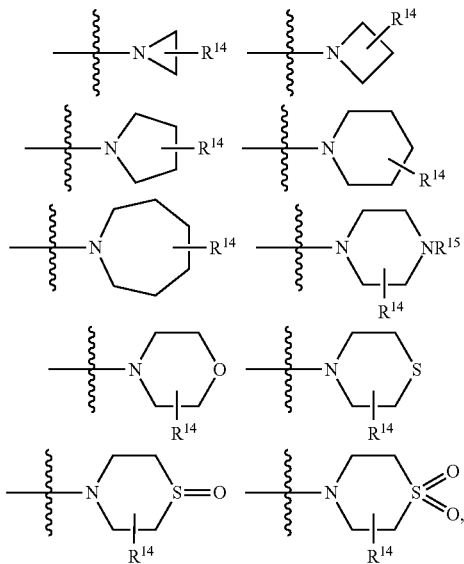

wherein $R^{14}$ denotes 0, 1, 2, 3 or 4 substituents which are in each case independently of each other selected from the group consisting of F, Cl, CF₃, =O, OCF₃, OH, O—$C_{1-6}$-alkyl, $SO_2(C_{1-6}$-alkyl), $C_{1-6}$-alkylen-$SO_2(C_{1-6}$-alkyl), $C_{1-6}$-alkylen-OH and $C_{1-6}$ alkyl; or $R^{14}$ denotes at least two substituents, wherein two substituents $R^{14}$ stand together for a $C_{1-6}$-alkylen-group, substituted or unsubstituted, wherein optionally one or more C-atoms of the $C_{1-6}$-alkylen-group is replaced by a heteroatom or heteroatom group, selected of O, N—$R^{15}$, S, S(O) and S(O)₂, and wherein these two substituents $R^{14}$ are positioned at different carbon atoms of the heterocycloaliphatic residue, so the $C_{1-6}$-alkylen-group represents a bridge to form a bicyclic heterocycloaliphatic residue; or $R^{14}$ denotes at least two substituents, wherein two substituents $R^{14}$ stand together for a $C_{2-6}$-alkylen-group, substituted or unsubstituted, wherein optionally one or more C-atoms of the $C_{2-6}$-alkylen-group is replaced by a heteroatom or heteroatom group, selected of O, N—$R^{15}$, S, S(O) and S(O)₂, and wherein these two substituents $R^{14}$ are positioned at the same carbon atom of the heterocycloaliphatic residue, so the $C_{2-6}$-alkylen-group forms a spiro-heterocycloaliphatic residue; and $R^{15}$ represents H, $C_{1-6}$-alkyl or C(=O)$C_{1-6}$-alkyl.

Particularly preferred are compounds according to the invention from the group consisting of SC-01 [1-Benzyl-3-(4-chlorophenyl)-5-(trifluoromethyl)-1H-pyrrol-2-yl]-morpholin-4-yl-methanone SC-02 1-Benzyl-3-(4-chlorophenyl)-N-(2,2-dimethyl-propyl)-N-methyl-5-(trifluoromethyl)-1H-pyrrole-2-carboxylic acid amide SC-03 [1-Benzyl-3-(4-chlorophenyl)-4-methyl-5-(trifluoromethyl)-1H-pyrrol-2-yl]-morpholin-4-yl-methanone SC-04 1-Benzyl-3-(4-chlorophenyl)-N-(2,2-dimethyl-propyl)-N,4-dimethyl-5-(trifluoromethyl)-1 H-pyrrole-2-carboxylic acid amide SC-05 [1-Benzyl-3-(4-chlorophenyl)-4-methyl-5-(trifluoromethyl)-1H-pyrrol-2-yl]-(3-hydroxy-azetidin-1-yl)-methanone SC-06 1-Benzyl-3-(4-chlorophenyl)-N,4-dimethyl-N-(2-methylsulfonyl-ethyl)-5-(trifluoromethyl)-1H-pyrrole-2-carboxylic acid amide SC-08 4-[1-Benzyl-3-(4-chlorophenyl)-4-methyl-5-(trifluoromethyl)-1H-pyrrole-2-carbonyl]-piperazin-2-one SC-09 4-[1-Benzyl-3-(4-chlorophenyl)-4-methyl-5-(trifluoromethyl)-1H-pyrrole-2-carbonyl]-1-methyl-piperazin-2-one SC-10 1-Benzyl-3-(4-chlorophenyl)-4-methyl-N-tetrahydro-pyran-4-yl-5-(trifluoromethyl)-1H-pyrrole-2-carboxylic acid amide SC-11 1-Benzyl-3-(4-chlorophenyl)-N,4-dimethyl-N-tetrahydro-pyran-4-yl-5-(trifluoromethyl)-1H-pyrrole-2-carboxylic acid amide SC-16 1-Benzyl-3-(4-chlorophenyl)-N-[1-(hydroxymethyl)-cyclopropyl]-4-methyl-5-(trifluoromethyl)-1H-pyrrole-2-carboxylic acid amide SC-17 [1-Benzyl-3-(4-chlorophenyl)-4-methyl-5-(trifluoromethyl)-1H-pyrrol-2-yl]-(4-hydroxy-piperidin-1-yl)-methanone SC-18 1-Benzyl-3-(4-chlorophenyl)-N,N,4-trimethyl-5-(trifluoromethyl)-1H-pyrrole-2-carboxylic acid amide SC-19 [1-Benzyl-3-(4-chlorophenyl)-4-methyl-5-(trifluoromethyl)-1H-pyrrol-2-yl]-(1-oxo-[1,4]thiazinan-4-yl)-methanone SC-20 [1-Benzyl-3-(4-chlorophenyl)-4-methyl-5-(trifluoromethyl)-1H-pyrrol-2-yl]-[2-(hydroxymethyl)-morpholin-4-yl]-methanone SC-21 1-Benzyl-3-(4-chlorophenyl)-N,4-dimethyl-N-(tetrahydro-pyran-4-yl-methyl)-5-(trifluoromethyl)-1H-pyrrole-2-carboxylic acid amide SC-22 1-Benzyl-3-(4-chlorophenyl)-N,4-dimethyl-5-(trifluoromethyl)-1H-pyrrole-2-carboxylic acid amide SC-23 [1-Benzyl-3-(4-chlorophenyl)-4-methyl-5-(trifluoromethyl)-1H-pyrrol-2-yl]-(3-hydroxy-pyrrolidin-1-yl)-methanone SC-24 1-Benzyl-3-(4-chlorophenyl)-N-(2-hydroxy-ethyl)-N,4-dimethyl-5-(trifluoromethyl)-1H-pyrrole-2-carboxylic acid amide SC-25 [3-(4-Chlorophenyl)-1-[(3-chlorophenyl)-methyl]-4-methyl-5-(trifluoromethyl)-1H-pyrrol-2-yl]-morpholin-4-yl-methanone SC-26 [1-Benzyl-3-(4-chlorophenyl)-4-methyl-5-(trifluoromethyl)-1H-pyrrol-2-yl]-(1,1-dioxo-[1,4]thiazinan-4-yl)-methanone SC-29 [1-Benzyl-3-(4-chlorophenyl)-4-methyl-5-(trifluoromethyl)-1H-pyrrol-2-yl]-(3,3-dimethyl-piperazin-1-yl)-methanone SC-32 [3-(4-Chlorophenyl)-1-(3-methoxyphenyl)-4-methyl-5-(trifluoromethyl)-1H-pyrrol-2-yl]-(3,3-difluoro-azetidin-1-yl)-methanone SC-33 [1-(3-Chlorophenyl)-3-(4-chlorophenyl)-4-methyl-5-(trifluoromethyl)-1H-pyrrol-2-yl]-(3,3-difluoro-azetidin-1-yl)-methanone SC-34 1-Benzyl-3-(4-chlorophenyl)-N-cyclopropyl-N,4-dimethyl-5-(trifluoromethyl)-1H-pyrrole-2-carboxylic acid amide SC-35 1-Benzyl-3-(4-chlorophenyl)-N-cyclopropyl-4-methyl-5-(trifluoromethyl)-1H-pyrrole-2-carboxylic acid amide SC-36 1-Benzyl-3-(4-chlorophenyl)-N-[(1-methoxy-cyclopropyl)-methyl]-4-methyl-5-(trifluoromethyl)-1H-pyrrole-2-carboxylic acid amide SC-37 N-(2-Acetylamino-ethyl)-1-benzyl-3-(4-chlorophenyl)-N,4-dimethyl-5-(trifluoromethyl)-1H-pyrrole-2-carboxylic acid amide SC-38 1-Benzyl-3-(4-chlorophenyl)-N-[2-(methanesulfonamido)-ethyl]-N,4-dimethyl-5-(trifluoromethyl)-1H-pyrrole-2-carboxylic acid amide SC-39 1-Benzyl-3-(4-chlorophenyl)-N,4-dimethyl-N-(1-methyl-piperidin-4-yl)-5-(trifluoromethyl)-1H-pyrrole-2-carboxylic acid amide SC-40 [1-Benzyl-3-(4-chlorophenyl)-4-methyl-5-(trifluoromethyl)-1H-pyrrol-2-yl]-(2,2-dimethyl-morpholin-4-yl)-methanone SC-41 [1-Benzyl-3-(4-chlorophenyl)-5-(difluoro-methyl)-4-methyl-1H-pyrrol-2-yl]-morpholin-4-yl-methanone SC-42 1-Benzyl-3-(4-chlorophenyl)-5-(difluoro-methyl)-N-(2,2-dimethyl-propyl)-N,4-dimethyl-1H-pyrrole-2-carboxylic acid amide SC-44 [1,3-Bis(4-chlorophenyl)-4-methyl-5-(trifluoromethyl)-1H-pyrrol-2-yl]-(3,3-difluoro-azetidin-1-yl)-methanone SC-48 1-Benzyl-3-(4-chlorophenyl)-N-[1-(hydroxymethyl)-cyclopropyl]-N,4-dimethyl-5-(trifluoromethyl)-1H-pyrrole-2-carboxylic acid amide SC-49 1-Benzyl-N-(1-carbamoyl-cyclopropyl)-3-(4-chlorophenyl)-N,4-dimethyl-5-(trifluoromethyl)-1H-pyrrole-2-carboxylic acid amide SC-50 4-[1-Benzyl-3-(4-chlorophenyl)-4-methyl-5-(trifluoromethyl)-1H-pyrrole-2-carbonyl]-morpholin-2-one SC-51 [3-(4-Chlorophenyl)-1-[2-(4-fluoro-phenoxy)-ethyl]-4-methyl-5-(trifluoromethyl)-1H-pyrrol-2-yl]-morpholin-4-yl-methanone SC-52 1[[1-Benzyl-3-(4-chlorophenyl)-4-methyl-5-(trifluoromethyl)-1H-pyrrole-2-carbonyl]-methyl-amino]-cyclopropane-1-carboxylic acid ethyl ester SC-53 3-(4-Chlorophenyl)-1-[(3-chlorophenyl)-methyl]-N-(2,2-dimethyl-propyl)-N,4-dimethyl-5-(trifluoromethyl)-1H-pyrrole-2-carboxylic acid amide SC-54 1-Benzyl-3-(4-chlorophenyl)-N-(2-hydroxy-2-methyl-propyl)-N,4-dimethyl-5-(trifluoromethyl)-1H-pyrrole-2-carboxylic acid amide SC-55 4-[3-(4-Chlorophenyl)-1-[(3-chlorophenyl)-methyl]-4-methyl-5-(trifluoromethyl)-1H-pyrrole-2-carbonyl]-piperazin-2-one SC-56 3-(4-Chlorophenyl)-1-[(3-chlorophenyl)-methyl]-N,4-dimethyl-N-(2-methylsulfonyl-ethyl)-5-(trifluoromethyl)-1H-pyrrole-2-carboxylic acid amide SC-57 3-(4-Chlorophenyl)-1-[(3-chlorophenyl)-methyl]-N-(2-hydroxy-2-methyl-propyl)-N,4-dimethyl-5-(trifluoromethyl)-1H-pyrrole-2-carboxylic acid amide SC-58 1-Benzyl-3-(4-chloro-2-fluoro-phenyl)-N-(2-hydroxy-2-methyl-propyl)-N,4-dimethyl-5-(trifluoromethyl)-1H-pyrrole-2-carboxylic acid amide SC-59 1-Benzyl-3-(4-chloro-2-fluoro-phenyl)-N-(2,2-dimethyl-propyl)-N,4-dimethyl-5-(trifluoromethyl)-1H-pyrrole-2-carboxylic acid amide SC-60 1-Benzyl-3-(4-chlorophenyl)-N,4-dimethyl-N-[(3-methyl-oxetan-3-yl)-methyl]-5-(trifluoromethyl)-1H-pyrrole-2-carboxylic acid amide SC-61 4-[1-Benzyl-3-(4-chloro-2-fluoro-phenyl)-4-methyl-5-(trifluoromethyl)-1H-pyrrole-2-carbonyl]-piperazin-2-one SC-62 [1-Benzyl-3-(4-chloro-2-fluoro-phenyl)-4-methyl-5-(trifluoromethyl)-1H-pyrrol-2-yl]-morpholin-4-yl-methanone SC-63 1-Benzyl-3-(4-chlorophenyl)-N-(1,1-dioxo-thiolan-3-yl)-N,4-dimethyl-5-(trifluoromethyl)-1H-pyrrole-2-carboxylic acid amide SC-64 1-Benzyl-3-(4-chloro-2-fluoro-phenyl)-N,4-dimethyl-N-(2-methylsulfonyl-ethyl)-5-(trifluoromethyl)-1H-pyrrole-2-carboxylic acid amide SC-65 1-Benzyl-3-(4-chlorophenyl)-N-[(1-hydroxy-cyclopropyl)-methyl]-N,4-dimethyl-5-(trifluoromethyl)-1H-pyrrole-2-carboxylic acid amide SC-66 4-[1-Benzyl-3-(4-chlorophenyl)-5-(trifluoromethyl)-1H-pyrrole-2-carbonyl]-piperazin-2-one SC-67 1-Benzyl-3-(4-chlorophenyl)-N-methyl-N-(2-methylsulfonyl-ethyl)-5-(trifluoromethyl)-1H-pyrrole-2-carboxylic acid amide SC-68 1-Benzyl-3-(4-chlorophenyl)-N-(2-hydroxy-2-methyl-propyl)-N-methyl-5-(trifluoromethyl)-1H-pyrrole-2-carboxylic acid amide SC-69 3-(4-Chlorophenyl)-1-[(3-chlorophenyl)-methyl]-N-methyl-N-(2-methylsulfonyl-ethyl)-5-(trifluoromethyl)-1H-pyrrole-2-carboxylic acid amide SC-70 3-(4-Chlorophenyl)-1-[(3-chlorophenyl)-methyl]-N-(2-hydroxy-2-methyl-propyl)-N-methyl-5-(trifluoromethyl)-1H-pyrrole-2-carboxylic acid amide SC-71 3-(4-Chlorophenyl)-1-[(3-chlorophenyl)-methyl]-N-(2,2-dimethyl-propyl)-N-methyl-5-(trifluoromethyl)-1H-pyrrole-2-carboxylic acid amide SC-72 [1-Benzyl-3-(4-chlorophenyl)-5-(trifluoromethyl)-1H-pyrrol-2-yl]-(3-hydroxy-azetidin-1-yl)-methanone SC-73 1-Benzyl-3-(4-chlorophenyl)-N-methyl-N-tetrahydro-pyran-4-yl-5-(trifluoromethyl)-1H-pyrrole-2-carboxylic acid amide SC-74 [3-(4-Chlorophenyl)-1-[(3-chlorophenyl)-methyl]-5-(trifluoromethyl)-1H-pyrrol-2-yl]-morpholin-4-yl-methanone SC-75 [1-Benzyl-3-(4-chlorophenyl)-5-(trifluoromethyl)-1H-pyrrol-2-yl]-(2,2-dimethyl-morpholin-4-yl)-methanone SC-76 1-Benzyl-3-(4-chlorophenyl)-N-(cyclopropyl-methyl)-N-methyl-5-(trifluoromethyl)-1H-pyrrole-2-carboxylic acid amide SC-77 1-Benzyl-N-tert-butyl-3-(4-chlorophenyl)-N-methyl-5-(trifluoromethyl)-1H-pyrrole-2-carboxylic acid amide SC-78 1-Benzyl-3-(4-chlorophenyl)-N-methyl-N-[(3-methyl-oxetan-3-yl)-methyl]-5-(trifluoromethyl)-1H-pyrrole-2-carboxylic acid amide SC-79 1-Benzyl-3-(4-chlorophenyl)-N-(3-hydroxy-2,2-dimethyl-propyl)-N-methyl-5-(trifluoromethyl)-1H-pyrrole-2-carboxylic acid amide SC-80 1-Benzyl-3-(4-chlorophenyl)-N,N-dimethyl-5-(trifluoromethyl)-1H-pyrrole-2-carboxylic acid amide SC-81 4-[3-(4-Chlorophenyl)-1-[(3-chlorophenyl)-methyl]-5-(trifluoromethyl)-1H-pyrrole-2-carbonyl]-piperazin-2-one SC-82 [1-Benzyl-3-(4-chlorophenyl)-5-(trifluoromethyl)-1H-pyrrol-2-yl]-(3,3-dimethyl-piperazin-1-yl)-methanone SC-83 1-Benzyl-3-(4-chlorophenyl)-N-(1,1-dioxo-thiolan-3-yl)-N-methyl-5-(trifluoromethyl)-1H-pyrrole-2-carboxylic acid amide SC-84 1-Benzyl-3-(4-chlorophenyl)-N-(3,3-dimethyl-butyl)-N-methyl-5-(trifluoromethyl)-1H-pyrrole-2-carboxylic acid amide SC-85 1-Benzyl-3-(4-chlorophenyl)-N-methyl-N-(2-methyl-2-morpholin-4-yl-propyl)-5-(trifluoromethyl)-1H-pyrrole-2-carboxylic acid amide SC-86 [1-Benzyl-3-(4-chloro-2-fluoro-phenyl)-5-(trifluoromethyl)-1H-pyrrol-2-yl]-morpholin-4-yl-methanone SC-87 1-Benzyl-3-(4-chloro-2-fluoro-phenyl)-N-(2-hydroxy-2-methyl-propyl)-N-methyl-5-(trifluoromethyl)-1H-pyrrole-2-carboxylic acid amide SC-88 1-Benzyl-3-(4-chloro-2-fluoro-phenyl)-N-(2,2-dimethyl-propyl)-N-methyl-5-(trifluoromethyl)-1H-pyrrole-2-carboxylic acid amide SC-89 4-[1-Benzyl-3-(4-chloro-2-fluoro-phenyl)-5-(trifluoromethyl)-1H-pyrrole-2-carbonyl]-piperazin-2-one SC-90 1-Benzyl-3-(4-chloro-2-fluoro-phenyl)-N-methyl-N-(2-methylsulfonyl-ethyl)-5-(trifluoromethyl)-1H-pyrrole-2-carboxylic acid amide SC-92 1-Benzyl-3-(4-chlorophenyl)-N-methyl-N-(2-methyl-2-methylsulfonyl-propyl)-5-(trifluoromethyl)-1H-pyrrole-2-carboxylic acid amide SC-93 [1-Benzyl-3-(4-chlorophenyl)-4-methyl-5-(trifluoromethyl)-1H-pyrrol-2-yl]-(3,3-difluoro-azetidin-1-yl)-methanone SC-94 [1-Benzyl-3-(4-chlorophenyl)-5-(trifluoromethyl)-1H-pyrrol-2-yl]-(3,3-difluoro-azetidin-1-yl)-methanone SC-95 [1-Benzyl-3-(4-fluorophenyl)-4-methyl-5-(trifluoromethyl)-1H-pyrrol-2-yl]-(3,3-difluoro-azetidin-1-yl)-methanone SC-96 [1-Benzyl-4-methyl-5-(trifluoromethyl)-3-[4-(trifluoromethyl)-phenyl]-1H-pyrrol-2-yl]-(3,3-difluoro-azetidin-1-yl)-methanone SC-97 [1-Benzyl-4-methyl-5-(trifluoromethyl)-3-[4-(trifluoromethyloxy)-phenyl]-1H-pyrrol-2-yl]-(3,3-difluoro-azetidin-1-yl)-methanone SC-98 [1-Benzyl-3-(4-chloro-3-fluoro-phenyl)-4-methyl-5-(trifluoromethyl)-1H-pyrrol-2-yl]-(3,3-difluoro-azetidin-1-yl)-methanone SC-99 [1-Benzyl-3-(3-chloro-4-fluoro-phenyl)-4-methyl-5-(trifluoromethyl)-1H-pyrrol-2-yl]-(3,3-difluoro-azetidin-1-yl)-methanone SC-100 [1-Benzyl-3-(4-chloro-2-fluoro-phenyl)-4-methyl-5-(trifluoromethyl)-1H-pyrrol-2-yl]-(3,3-difluoro-azetidin-1-yl)-methanone SC-101 [1-Benzyl-3-(4-fluorophenyl)-4-methyl-5-(trifluoromethyl)-1H-pyrrol-2-yl]-morpholin-4-yl-methanone SC-102 [1-Benzyl-4-methyl-5-(trifluoromethyl)-3-[4-(trifluoromethyl)-phenyl]-1H-pyrrol-2-yl]-morpholin-4-yl-methanone SC-103 [1-Benzyl-3-(4-chloro-3-fluoro-phenyl)-4-methyl-5-(trifluoromethyl)-1H-pyrrol-2-yl]-morpholin-4-yl-methanone SC-104 [1-Benzyl-3-(3-chloro-4-fluoro-phenyl)-4-methyl-5-(trifluoromethyl)-1H-pyrrol-2-yl]-morpholin-4-yl-methanone SC-105 [1-Benzyl-4-methyl-5-(trifluoromethyl)-3-[4-(trifluoromethyloxy)-phenyl]-1H-pyrrol-2-yl]-morpholin-4-yl-methanone SC-106 1-Benzyl-3-(4-chlorophenyl)-N-(3-hydroxy-2,2-dimethyl-propyl)-N,4-dimethyl-5-(trifluoromethyl)-1H-pyrrole-2-carboxylic acid amide SC-107 1-Benzyl-3-(4-chloro-2-fluoro-phenyl)-N-(3-hydroxy-2,2-dimethyl-propyl)-N,4-dimethyl-5-(trifluoromethyl)-1H-pyrrole-2-carboxylic acid amide SC-108 1-Benzyl-3-(4-fluorophenyl)-N-(2-hydroxy-2-methyl-propyl)-N,4-dimethyl-5-(trifluoromethyl)-1H-pyrrole-2-carboxylic acid amide SC-109 1-Benzyl-N-(2-hydroxy-2-methyl-propyl)-N,4-dimethyl-5-(trifluoromethyl)-3-[4-(trifluoromethyl)-phenyl]-1H-pyrrole-2-carboxylic acid amide SC-110 1-Benzyl-N-(2-hydroxy-2-methyl-propyl)-N,4-dimethyl-5-(trifluoromethyl)-3-[4-(trifluoromethyloxy)-phenyl]-1H-pyrrole-2-carboxylic acid amide SC-111 1-Benzyl-3-(4-chloro-3-fluoro-phenyl)-N-(2-hydroxy-2-methyl-propyl)-N,4-dimethyl-5-(trifluoromethyl)-1H-pyrrole-2-carboxylic acid amide SC-112 1-Benzyl-3-(3-chloro-4-fluoro-phenyl)-N-(2-hydroxy-2-methyl-propyl)-N,4-dimethyl-5-(trifluoromethyl)-1H-pyrrole-2-carboxylic acid amide, SC-113 1-Benzyl-3-(4-chlorophenyl)-N-(3-hydroxy-3-methyl-butyl)-N,4-dimethyl-5-(trifluoromethyl)-1H-pyrrole-2-carboxylic acid amide SC-114 1-Benzyl-3-(4-chlorophenyl)-N-(3-hydroxy-2,2-dimethyl-propyl)-4-methyl-5-(trifluoromethyl)-1H-pyrrole-2-carboxylic acid amide SC-115 1-Benzyl-3-(4-chlorophenyl)-N-[[1-(hydroxymethyl)-cyclopropyl]-methyl]-N,4-dimethyl-5-(trifluoromethyl)-1H-pyrrole-2-carboxylic acid amide SC-116 1-Benzyl-3-(4-chlorophenyl)-N-[[1-(hydroxymethyl)-cyclobutyl]-methyl]-N,4-dimethyl-5-(trifluoromethyl)-1H-pyrrole-2-carboxylic acid amide SC-117 [1-Benzyl-3-(4-chlorophenyl)-4-methyl-5-(trifluoromethyl)-1H-pyrrol-2-yl]-[3-(hydroxymethyl)-pyrrolidin-1-yl]-methanone SC-118 1-Benzyl-3-(4-chlorophenyl)-N-(2,2-dimethyl-3-morpholin-4-yl-propyl)-N,4-dimethyl-5-(trifluoromethyl)-1H-pyrrole-2-carboxylic acid amide SC-119 1-Benzyl-3-(4-chlorophenyl)-N-(2,2-dimethyl-propyl)-4-ethyl-N-methyl-5-(trifluoromethyl)-1H-pyrrole-2-carboxylic acid amide SC-120 1-Benzyl-3-(4-chlorophenyl)-4-cyclopropyl-N-(2,2-dimethyl-propyl)-N-methyl-5-(trifluoromethyl)-1H-pyrrole-2-carboxylic acid amide SC-121 1-Benzyl-3-(4-chlorophenyl)-N,4-dimethyl-N-(tetrahydro-furan-3-yl-methyl)-5-(trifluoromethyl)-1H-pyrrole-2-carboxylic acid amide SC-122 1-Benzyl-3-(4-chlorophenyl)-N-(3-hydroxy-1,1-dimethyl-propyl)-N,4-dimethyl-5-(trifluoromethyl)-1H-pyrrole-2-carboxylic acid amide SC-123 [1-Benzyl-3-(4-chlorophenyl)-4-methyl-5-(trifluoromethyl)-1H-pyrrol-2-yl]-(3-methylsulfonyl-pyrrolidin-1-yl)-methanone SC-124 1-Benzyl-3-(4-chlorophenyl)-N-[1-(hydroxymethyl)-2,2-dimethyl-propyl]-N,4-dimethyl-5-(trifluoromethyl)-1H-pyrrole-2-carboxylic acid amide SC-125 1-Benzyl-3-(4-chlorophenyl)-N-[3-hydroxy-2-(hydroxymethyl)-2-methyl-propyl]-N,4-dimethyl-5-(trifluoromethyl)-1H-pyrrole-2-carboxylic acid amide SC-126 1-Benzyl-3-(4-chlorophenyl)-N-(2-hydroxy-1,1-dimethyl-ethyl)-N,4-dimethyl-5-(trifluoromethyl)-1H-pyrrole-2-carboxylic acid amide SC-127 1-Benzyl-3-(4-chlorophenyl)-N,4-dimethyl-N-(3-methylsulfonyl-propyl)-5-(trifluoromethyl)-1H-pyrrole-2-carboxylic acid amide SC-128 1-Benzyl-3-(4-chlorophenyl)-N-ethyl-4-methyl-N-(2-methylsulfonyl-ethyl)-5-(trifluoromethyl)-1H-pyrrole-2-carboxylic acid amide SC-129 1-Benzyl-3-(4-chlorophenyl)-4-methyl-N-(2-methylsulfonyl-ethyl)-5-(trifluoromethyl)-1H-pyrrole-2-carboxylic acid amide SC-130 1-Benzyl-3-(4-chlorophenyl)-N-[2-(isopropylsulfonyl)-ethyl]-N,4-dimethyl-5-(trifluoromethyl)-1H-pyrrole-2-carboxylic acid amide SC-131 1-Benzyl-3-(4-chlorophenyl)-N-(1,1-dioxo-thian-4-yl)-N,4-dimethyl-5-(trifluoromethyl)-1H-pyrrole-2-carboxylic acid amide SC-132 1-Benzyl-3-(4-chlorophenyl)-N-[2-(ethylsulfonyl)-ethyl]-N,4-dimethyl-5-(trifluoromethyl)-1H-pyrrole-2-carboxylic acid amide SC-133 1-Benzyl-3-(4-chlorophenyl)-N,4-dimethyl-N-(2-tetrahydro-furan-2-yl-ethyl)-5-(trifluoromethyl)-1H-pyrrole-2-carboxylic acid amide SC-134 1-Benzyl-3-(4-chlorophenyl)-N,4-dimethyl-N-(tetrahydro-furan-2-yl-methyl)-5-(trifluoromethyl)-1H-pyrrole-2-carboxylic acid amide SC-135 1-Benzyl-3-(4-chlorophenyl)-N-[[(2S)-2-hydroxy-cyclopentyl]-methyl]-N,4-dimethyl-5-(trifluoromethyl)-1H-pyrrole-2-carboxylic acid amide SC-136 1-Benzyl-3-(4-chlorophenyl)-N-[[(2R)-2-hydroxy-cyclopentyl]-methyl]-N,4-dimethyl-5-(trifluoromethyl)-1H-pyrrole-2-carboxylic acid amide SC-137 [1-Benzyl-3-(4-chlorophenyl)-4-methyl-5-(trifluoromethyl)-1H-pyrrol-2-yl]-(3-methylsulfonyl-azetidin-1-yl)-methanone SC-138 1-Benzyl-3-(4-chlorophenyl)-N,4-dimethyl-N-(tetrahydro-pyran-2-yl-methyl)-5-(trifluoromethyl)-1H-pyrrole-2-carboxylic acid amide SC-139 1-Benzyl-3-(4-chlorophenyl)-N-[2,2-dimethyl-3-[methyl-(2-pyrrolidin-1-yl-ethyl)-amino]-propyl]-N,4-dimethyl-5-(trifluoromethyl)-1H-pyrrole-2-carboxylic acid amide SC-140 1-Benzyl-3-(4-chlorophenyl)-N,4-dimethyl-N-[(3-methyl-isoxazol-5-yl)-methyl]-5-(trifluoromethyl)-1H-pyrrole-2-carboxylic acid amide SC-141 1-Benzyl-3-(4-chlorophenyl)-N,4-dimethyl-N-(1-methyl-2-methylsulfonyl-ethyl)-5-(trifluoromethyl)-1H-pyrrole-2-carboxylic acid amide SC-142 1-Benzyl-3-(4-chlorophenyl)-N,4-dimethyl-N-[(5-methyl-isoxazol-3-yl)-methyl]-5-(trifluoromethyl)-1H-pyrrole-2-carboxylic acid amide SC-143 1-Benzyl-3-(4-chlorophenyl)-N,4-dimethyl-N-[(5-methyl-[1,3,4]oxadiazol-2-yl)-methyl]-5-(trifluoromethyl)-1H-pyrrole-2-carboxylic acid amide SC-144 1-Benzyl-3-(4-chlorophenyl)-N,4-dimethyl-N-(pyrimidin-4-yl-methyl)-5-(trifluoromethyl)-1H-pyrrole-2-carboxylic acid amide SC-145 [1-Benzyl-3-(4-chlorophenyl)-4-methyl-5-(trifluoromethyl)-1H-pyrrol-2-yl]-(4-methoxy-piperidin-1-yl)-methanone SC-146 1-Benzyl-3-(4-chlorophenyl)-N,4-dimethyl-N-(pyrazin-2-yl-methyl)-5-(trifluoromethyl)-1H-pyrrole-2-carboxylic acid amide SC-147 1-Benzyl-3-(4-chlorophenyl)-N-[(2-dimethylamino-pyrimidin-4-yl)-methyl]-N,4-dimethyl-5-(trifluoromethyl)-1H-pyrrole-2-carboxylic acid amide SC-148 1-Benzyl-3-(4-chlorophenyl)-N,4-dimethyl-N-[(1-methyl-1H-imidazol-2-yl)-methyl]-5-(trifluoromethyl)-1H-pyrrole-2-carboxylic acid amide SC-149 1-Benzyl-3-(4-chlorophenyl)-N-isopropyl-N,4-dimethyl-5-(trifluoromethyl)-1H-pyrrole-2-carboxylic acid amide SC-150 1-Benzyl-3-(4-chlorophenyl)-N-isopropyl-4-methyl-5-(trifluoromethyl)-1H-pyrrole-2-carboxylic acid amide SC-151 1-Benzyl-3-(4-chlorophenyl)-N,4-dimethyl-N-[(5-methyl-pyrazin-2-yl)-methyl]-5-(trifluoromethyl)-1H-pyrrole-2-carboxylic acid amide SC-152 1-Benzyl-3-(4-chlorophenyl)-N-[(2-dimethylamino-pyrimidin-5-yl)-methyl]-N,4-dimethyl-5-(trifluoromethyl)-1H-pyrrole-2-carboxylic acid amide SC-153 1-[4-[1-Benzyl-3-(4-chlorophenyl)-4-methyl-5-(trifluoromethyl)-1H-pyrrole-2-carbonyl]-piperazin-1-yl]-ethanone SC-154 [1-Benzyl-3-(4-chloro-2-fluoro-phenyl)-4-methyl-5-(trifluoromethyl)-1H-pyrrol-2-yl]-(3-hydroxy-azetidin-1-yl)-methanone SC-155 [1-Benzyl-3-(4-chloro-2-fluoro-phenyl)-4-methyl-5-(trifluoromethyl)-1H-pyrrol-2-yl]-(2,2-dimethyl-morpholin-4-yl)-methanone SC-156 1-Benzyl-3-(4-chloro-2-fluoro-phenyl)-N,4-dimethyl-N-tetrahydro-pyran-4-yl-5-(trifluoromethyl)-1H-pyrrole-2-carboxylic acid amide SC-158 1-Benzyl-3-(4-chloro-2-fluoro-phenyl)-4-methyl-5-(trifluoromethyl)-N-[(1R)-1,2,2-trimethyl-propyl]-1H-pyrrole-2-carboxylic acid amide SC-159 1-Benzyl-3-(4-chloro-2-fluoro-phenyl)-N-cyclopropyl-N,4-dimethyl-5-(trifluoromethyl)-1H-pyrrole-2-carboxylic acid amide SC-160 1-Benzyl-3-(4-chloro-2-fluoro-phenyl)-N-(1,1-dioxo-thian-4-yl)-N,4-dimethyl-5-(trifluoromethyl)-1H-pyrrole-2-carboxylic acid amide SC-161 1-Benzyl-3-(4-chloro-2-fluoro-phenyl)-N,4-dimethyl-N-(3-methylsulfonyl-propyl)-5-(trifluoromethyl)-1H-pyrrole-2-carboxylic acid amide SC-162 [1-Benzyl-3-(4-chloro-2-fluoro-phenyl)-4-methyl-5-(trifluoromethyl)-1H-pyrrol-2-yl]-[2-(methylsulfonyl-methyl)-pyrrolidin-1-yl]-methanone SC-163 1-Benzyl-3-(4-chloro-2-fluoro-phenyl)-4-methyl-N-(2-methylsulfonyl-ethyl)-5-(trifluoromethyl)-1H-pyrrole-2-carboxylic acid amide SC-164 1-Benzyl-3-(4-chloro-2-fluoro-phenyl)-N,4-dimethyl-N-(2-tetrahydro-furan-2-yl-ethyl)-5-(trifluoromethyl)-1H-pyrrole-2-carboxylic acid amide SC-165 1-Benzyl-3-(4-chloro-2-fluoro-phenyl)-N,4-dimethyl-N-(tetrahydro-furan-2-yl-methyl)-5-(trifluoromethyl)-1H-pyrrole-2-carboxylic acid amide SC-166 [1-Benzyl-3-(4-chloro-2-fluoro-phenyl)-4-methyl-5-(trifluoromethyl)-1H-pyrrol-2-yl]-[3-(hydroxymethyl)-pyrrolidin-1-yl]-methanone SC-167 1-Benzyl-3-(4-chloro-2-fluoro-phenyl)-N,4-dimethyl-N-(tetrahydro-furan-3-yl-methyl)-5-(trifluoromethyl)-1H-pyrrole-2-carboxylic acid amide SC-168 1-Benzyl-3-(4-chloro-2-fluoro-phenyl)-N,4-dimethyl-N-(2-methyl-2-methylsulfonyl-propyl)-5-(trifluoromethyl)-1H-pyrrole-2-carboxylic acid amide SC-169 1-Benzyl-3-(4-chloro-2-fluoro-phenyl)-N-isopropyl-4-methyl-N-(2-methylsulfonyl-ethyl)-5-(trifluoromethyl)-1H-pyrrole-2-carboxylic acid amide SC-170 [1-Benzyl-3-(4-chloro-2-fluoro-phenyl)-4-methyl-5-(trifluoromethyl)-1H-pyrrol-2-yl]-(2,2-dimethyl-1,1-dioxo-[1,4]thiazinan-4-yl)-methanone SC-171 1-Benzyl-3-(4-chloro-2-fluoro-phenyl)-N-(1,1-dioxo-thiolan-3-yl)-N,4-dimethyl-5-(trifluoromethyl)-1H-pyrrole-2-carboxylic acid amide SC-172 1-Benzyl-3-(4-chloro-2-fluoro-phenyl)-N-cyclopropyl-4-methyl-5-(trifluoromethyl)-1H-pyrrole-2-carboxylic acid amide SC-173 [1-Benzyl-3-(4-chloro-2-fluoro-phenyl)-4-methyl-5-(trifluoromethyl)-1H-pyrrol-2-yl]-(1,1-dioxo-[1,4]thiazinan-4-yl)-methanone SC-174 1-Benzyl-N-(2-carbamoyl-2-methyl-propyl)-3-(4-chlorophenyl)-N-methyl-5-(trifluoromethyl)-1H-pyrrole-2-carboxylic acid amide SC-175 N-(2-Amino-2-methyl-propyl)-1-benzyl-3-(4-chlorophenyl)-N-methyl-5-(trifluoromethyl)-1H-pyrrole-2-carboxylic acid amide SC-176 1-Benzyl-3-(4-chlorophenyl)-N-(3-hydroxy-3-methyl-butyl)-N-methyl-5-(trifluoromethyl)-1H-pyrrole-2-carboxylic acid amide SC-177 1-Benzyl-3-(4-chlorophenyl)-N-(3-hydroxy-2,2-dimethyl-propyl)-5-(trifluoromethyl)-1H-pyrrole-2-carboxylic acid amide SC-178 1-Benzyl-3-(4-chlorophenyl)-N-[[1-(hydroxymethyl)-cyclopropyl]-methyl]-N-methyl-5-(trifluoromethyl)-1H-pyrrole-2-carboxylic acid amide SC-179 1-Benzyl-3-(4-chlorophenyl)-N-[[1-(hydroxymethyl)-cyclobutyl]-methyl]-N-methyl-5-(trifluoromethyl)-1H-pyrrole-2-carboxylic acid amide
SC-180 1-Benzyl-3-(4-chlorophenyl)-N-(2,2-dimethyl-3-morpholin-4-yl-propyl)-N-methyl-5-(trifluoromethyl)-1H-pyrrole-2-carboxylic acid amide
SC-181 [1-Benzyl-3-(4-chlorophenyl)-5-(trifluoromethyl)-1H-pyrrol-2-yl]-[3-(hydroxymethyl)-pyrrolidin-1-yl]-methanone
SC-182 1-Benzyl-3-(4-chlorophenyl)-N-methyl-N-(tetrahydro-furan-3-yl-methyl)-5-(trifluoromethyl)-1H-pyrrole-2-carboxylic acid amide
SC-183 1-Benzyl-3-(4-chlorophenyl)-N-[3-hydroxy-2-(hydroxymethyl)-2-methyl-propyl]-N-methyl-5-(trifluoromethyl)-1H-pyrrole-2-carboxylic acid amide
SC-184 1-Benzyl-3-(4-chlorophenyl)-N-(3-hydroxy-1,1-dimethyl-propyl)-N-methyl-5-(trifluoromethyl)-1H-pyrrole-2-carboxylic acid amide
SC-185 [1-Benzyl-3-(4-chlorophenyl)-5-(trifluoromethyl)-1H-pyrrol-2-yl]-(3-methylsulfonyl-pyrrolidin-1-yl)-methanone
SC-186 1-Benzyl-3-(4-chlorophenyl)-N-[1-(hydroxymethyl)-2,2-dimethyl-propyl]-N-methyl-5-(trifluoromethyl)-1H-pyrrole-2-carboxylic acid amide
SC-187 1-Benzyl-3-(4-chlorophenyl)-N-(2-cyano-2-methylpropyl)-N-methyl-5-(trifluoromethyl)-1H-pyrrole-2-carboxylic acid amide
SC-188 N-(3-Amino-2,2-dimethyl-propyl)-1-benzyl-3-(4-chlorophenyl)-N-methyl-5-(trifluoromethyl)-1H-pyrrole-2-carboxylic acid amide
SC-189 1-Benzyl-3-(4-chlorophenyl)-N-methyl-N-(3-methylsulfonyl-propyl)-5-(trifluoromethyl)-1H-pyrrole-2-carboxylic acid amide
SC-190 1-Benzyl-3-(4-chlorophenyl)-N-ethyl-N-(2-methylsulfonyl-ethyl)-5-(trifluoromethyl)-1H-pyrrole-2-carboxylic acid amide
SC-191 1-Benzyl-3-(4-chlorophenyl)-N-(2-methylsulfonyl-ethyl)-5-(trifluoromethyl)-1H-pyrrole-2-carboxylic acid amide
SC-192 1-Benzyl-3-(4-chlorophenyl)-N-[2-(ethylsulfonyl)-ethyl]-N-methyl-5-(trifluoromethyl)-1H-pyrrole-2-carboxylic acid amide
SC-193 1-Benzyl-3-(4-chlorophenyl)-N-(1,1-dioxo-thian-4-yl)-N-methyl-5-(trifluoromethyl)-1H-pyrrole-2-carboxylic acid amide
SC-194 1-Benzyl-3-(4-chlorophenyl)-N-[2-(isopropylsulfonyl)-ethyl]-N-methyl-5-(trifluoromethyl)-1H-pyrrole-2-carboxylic acid amide
SC-195 1-Benzyl-3-(4-chlorophenyl)-N-methyl-N-(2-tetrahydro-furan-2-yl-ethyl)-5-(trifluoromethyl)-1H-pyrrole-2-carboxylic acid amide
SC-196 [1-Benzyl-3-(4-chlorophenyl)-5-(trifluoromethyl)-1H-pyrrol-2-yl]-(1,1-dioxo-[1,4]thiazinan-4-yl)-methanone
SC-197 1-Benzyl-3-(4-chlorophenyl)-N-methyl-N-(tetrahydro-furan-2-yl-methyl)-5-(trifluoromethyl)-1H-pyrrole-2-carboxylic acid amide
SC-198 1-Benzyl-3-(4-chlorophenyl)-N-methyl-N-(1-methyl-2-methylsulfonyl-ethyl)-5-(trifluoromethyl)-1H-pyrrole-2-carboxylic acid amide
SC-199 1-Benzyl-3-(4-chlorophenyl)-N-[[(2S)-2-hydroxycyclopentyl]-methyl]-N-methyl-5-(trifluoromethyl)-1H-pyrrole-2-carboxylic acid amide
SC-200 1-Benzyl-3-(4-chlorophenyl)-N-[[(2R)-2-hydroxycyclopentyl]-methyl]-N-methyl-5-(trifluoromethyl)-1H-pyrrole-2-carboxylic acid amide
SC-201 [1-Benzyl-3-(4-chlorophenyl)-5-(trifluoromethyl)-1H-pyrrol-2-yl]-(3-methylsulfonyl-azetidin-1-yl)-methanone
SC-202 1-Benzyl-3-(4-chlorophenyl)-N-methyl-N-(tetrahydro-pyran-2-yl-methyl)-5-(trifluoromethyl)-1H-pyrrole-2-carboxylic acid amide
SC-203 1-Benzyl-3-(4-chlorophenyl)-N-[2,2-dimethyl-3-[methyl-(2-pyrrolidin-1-yl-ethyl)-amino]-propyl]-N-methyl-5-(trifluoromethyl)-1H-pyrrole-2-carboxylic acid amide
SC-204 1-Benzyl-3-(4-chlorophenyl)-N-methyl-N-[(3-methyl-isoxazol-5-yl)-methyl]-5-(trifluoromethyl)-1H-pyrrole-2-carboxylic acid amide
SC-205 1-Benzyl-3-(4-chlorophenyl)-N-methyl-N-[(5-methyl-isoxazol-3-yl)-methyl]-5-(trifluoromethyl)-1H-pyrrole-2-carboxylic acid amide
SC-206 1-Benzyl-3-(4-chlorophenyl)-N-methyl-N-[(5-methyl-[1,3,4]oxadiazol-2-yl)-methyl]-5-(trifluoromethyl)-1H-pyrrole-2-carboxylic acid amide
SC-207 1-Benzyl-3-(4-chlorophenyl)-N-methyl-N-(pyrimidin-4-yl-methyl)-5-(trifluoromethyl)-1H-pyrrole-2-carboxylic acid amide
SC-208 [1-Benzyl-3-(4-chlorophenyl)-5-(trifluoromethyl)-1H-pyrrol-2-yl]-(4-methoxy-piperidin-1-yl)-methanone
SC-209 1-[4-[1-Benzyl-3-(4-chlorophenyl)-5-(trifluoromethyl)-1H-pyrrole-2-carbonyl]-piperazin-1-yl]-ethanone
SC-210 1-Benzyl-3-(4-chlorophenyl)-N-methyl-N-(pyrazin-2-yl-methyl)-5-(trifluoromethyl)-1H-pyrrole-2-carboxylic acid amide
SC-211 1-Benzyl-3-(4-chlorophenyl)-N-[(2-dimethylamino-pyrimidin-4-yl)-methyl]-N-methyl-5-(trifluoromethyl)-1H-pyrrole-2-carboxylic acid amide
SC-212 1-Benzyl-3-(4-chlorophenyl)-N-methyl-N-[(1-methyl-1H-imidazol-2-yl)-methyl]-5-(trifluoromethyl)-1H-pyrrole-2-carboxylic acid amide
SC-213 1-Benzyl-3-(4-chlorophenyl)-N-isopropyl-N-methyl-5-(trifluoromethyl)-1H-pyrrole-2-carboxylic acid amide
SC-214 1-Benzyl-3-(4-chlorophenyl)-N-isopropyl-5-(trifluoromethyl)-1H-pyrrole-2-carboxylic acid amide
SC-215 1-Benzyl-3-(4-chlorophenyl)-N-methyl-N-[(5-methyl-pyrazin-2-yl)-methyl]-5-(trifluoromethyl)-1H-pyrrole-2-carboxylic acid amide
SC-216 1-Benzyl-3-(4-chlorophenyl)-N-[(2-dimethylamino-pyrimidin-5-yl)-methyl]-N-methyl-5-(trifluoromethyl)-1H-pyrrole-2-carboxylic acid amide
SC-217 [1-Benzyl-3-(4-chlorophenyl)-5-(trifluoromethyl)-1H-pyrrol-2-yl]-(5,6,7,8-tetrahydro-imidazo[1,2-a]pyrazin-7-yl)-methanone
SC-218 1-Benzyl-3-(4-fluorophenyl)-N-(3-hydroxy-2,2-dimethyl-propyl)-N,4-dimethyl-5-(trifluoromethyl)-1H-pyrrole-2-carboxylic acid amide
SC-219 1-Benzyl-3-(4-fluorophenyl)-N,4-dimethyl-N-(2-methylsulfonyl-ethyl)-5-(trifluoromethyl)-1H-pyrrole-2-carboxylic acid amide
SC-220 1-Benzyl-3-(4-fluorophenyl)-N,4-dimethyl-N-tetrahydro-pyran-4-yl-5-(trifluoromethyl)-1H-pyrrole-2-carboxylic acid amide
SC-221 1-Benzyl-N-cyclopropyl-3-(4-fluorophenyl)-N,4-dimethyl-5-(trifluoromethyl)-1H-pyrrole-2-carboxylic acid amide
SC-222 1-Benzyl-3-(4-fluorophenyl)-N-(2-hydroxy-1,1-dimethyl-ethyl)-N,4-dimethyl-5-(trifluoromethyl)-1H-pyrrole-2-carboxylic acid amide
SC-223 [1-Benzyl-3-(4-fluorophenyl)-4-methyl-5-(trifluoromethyl)-1H-pyrrol-2-yl]-(3-hydroxy-azetidin-1-yl)-methanone SC-224 1-Benzyl-N-(2,2-dimethyl-propyl)-3-(4-fluorophenyl)-N,4-dimethyl-5-(trifluoromethyl)-1H-pyrrole-2-carboxylic acid amide SC-225 [1-Benzyl-3-(4-fluorophenyl)-4-methyl-5-(trifluoromethyl)-1H-pyrrol-2-yl]-(2,2-dimethyl-morpholin-4-yl)-methanone SC-226 1-Benzyl-3-(4-fluorophenyl)-N,4-dimethyl-N-(tetrahydro-furan-3-yl-methyl)-5-(trifluoromethyl)-1H-pyrrole-2-carboxylic acid amide SC-227 1-Benzyl-N-(3-hydroxy-2,2-dimethyl-propyl)-N,4-dimethyl-5-(trifluoromethyl)-3-[4-(trifluoromethyl)-phenyl]-1H-pyrrole-2-carboxylic acid amide SC-228 1-Benzyl-N,4-dimethyl-N-(2-methylsulfonyl-ethyl)-5-(trifluoromethyl)-3-[4-(trifluoromethyl)-phenyl]-1H-pyrrole-2-carboxylic acid amide SC-229 1-Benzyl-N,4-dimethyl-N-tetrahydro-pyran-4-yl-5-(trifluoromethyl)-3-[4-(trifluoromethyl)-phenyl]-1H-pyrrole-2-carboxylic acid amide SC-230 1-Benzyl-N-cyclopropyl-N,4-dimethyl-5-(trifluoromethyl)-3-[4-(trifluoromethyl)-phenyl]-1H-pyrrole-2-carboxylic acid amide SC-231 1-Benzyl-N-(2-hydroxy-1,1-dimethyl-ethyl)-N,4-dimethyl-5-(trifluoromethyl)-3-[4-(trifluoromethyl)-phenyl]-1H-pyrrole-2-carboxylic acid amide SC-232 [1-Benzyl-4-methyl-5-(trifluoromethyl)-3-[4-(trifluoromethyl)-phenyl]-1H-pyrrol-2-yl]-(3-hydroxy-azetidin-1-yl)-methanone SC-233 1-Benzyl-N-(2,2-dimethyl-propyl)-N,4-dimethyl-5-(trifluoromethyl)-3-[4-(trifluoromethyl)-phenyl]-1H-pyrrole-2-carboxylic acid amide SC-234 [1-Benzyl-4-methyl-5-(trifluoromethyl)-3-[4-(trifluoromethyl)-phenyl]-1H-pyrrol-2-yl]-(2,2-dimethyl-morpholin-4-yl)-methanone SC-235 1-Benzyl-N-(3-hydroxy-2,2-dimethyl-propyl)-N,4-dimethyl-5-(trifluoromethyl)-3-[4-(trifluoromethyloxy)-phenyl]-1H-pyrrole-2-carboxylic acid amide SC-236 1-Benzyl-N,4-dimethyl-N-(2-methylsulfonyl-ethyl)-5-(trifluoromethyl)-3-[4-(trifluoromethyloxy)-phenyl]-1H-pyrrole-2-carboxylic acid amide SC-237 1-Benzyl-N,4-dimethyl-N-tetrahydro-pyran-4-yl-5-(trifluoromethyl)-3-[4-(trifluoromethyloxy)-phenyl]-1H-pyrrole-2-carboxylic acid amide SC-238 1-Benzyl-N-cyclopropyl-N,4-dimethyl-5-(trifluoromethyl)-3-[4-(trifluoromethyloxy)-phenyl]-1H-pyrrole-2-carboxylic acid amide SC-239 [1-Benzyl-4-methyl-5-(trifluoromethyl)-3-[4-(trifluoromethyloxy)-phenyl]-1H-pyrrol-2-yl]-(3-hydroxy-azetidin-1-yl)-methanone SC-240 1-Benzyl-N-(2,2-dimethyl-propyl)-N,4-dimethyl-5-(trifluoromethyl)-3-[4-(trifluoromethyloxy)-phenyl]-1H-pyrrole-2-carboxylic acid amide SC-241 1-Benzyl-N-(2-hydroxy-1,1-dimethyl-ethyl)-N,4-dimethyl-5-(trifluoromethyl)-3-[4-(trifluoromethyloxy)-phenyl]-1H-pyrrole-2-carboxylic acid amide SC-242 [1-Benzyl-4-methyl-5-(trifluoromethyl)-3-[4-(trifluoromethyloxy)-phenyl]-1H-pyrrol-2-yl]-(2,2-dimethyl-morpholin-4-yl)-methanone SC-243 1-Benzyl-3-(4-chloro-3-fluoro-phenyl)-N-(3-hydroxy-2,2-dimethyl-propyl)-N,4-dimethyl-5-(trifluoromethyl)-1H-pyrrole-2-carboxylic acid amide SC-244 1-Benzyl-3-(4-chloro-3-fluoro-phenyl)-N,4-dimethyl-N-(2-methylsulfonyl-ethyl)-5-(trifluoromethyl)-1H-pyrrole-2-carboxylic acid amide SC-245 1-Benzyl-3-(4-chloro-3-fluoro-phenyl)-N,4-dimethyl-N-tetrahydro-pyran-4-yl-5-(trifluoromethyl)-1H-pyrrole-2-carboxylic acid amide SC-246 1-Benzyl-3-(4-chloro-3-fluoro-phenyl)-N-cyclopropyl-N,4-dimethyl-5-(trifluoromethyl)-1H-pyrrole-2-carboxylic acid amide SC-247 [1-Benzyl-3-(4-chloro-3-fluoro-phenyl)-4-methyl-5-(trifluoromethyl)-1H-pyrrol-2-yl]-(3-hydroxy-azetidin-1-yl)-methanone SC-248 1-Benzyl-3-(4-chloro-3-fluoro-phenyl)-N-(2-hydroxy-1,1-dimethyl-ethyl)-N,4-dimethyl-5-(trifluoromethyl)-1H-pyrrole-2-carboxylic acid amide SC-249 [1-Benzyl-3-(4-chloro-3-fluoro-phenyl)-4-methyl-5-(trifluoromethyl)-1H-pyrrol-2-yl]-(2,2-dimethyl-morpholin-4-yl)-methanone SC-250 1-Benzyl-3-(4-chloro-3-fluoro-phenyl)-N-(2,2-dimethyl-propyl)-N,4-dimethyl-5-(trifluoromethyl)-1H-pyrrole-2-carboxylic acid amide SC-251 1-Benzyl-3-(3-chloro-4-fluoro-phenyl)-N-(3-hydroxy-2,2-dimethyl-propyl)-N,4-dimethyl-5-(trifluoromethyl)-1H-pyrrole-2-carboxylic acid amide SC-252 1-Benzyl-3-(3-chloro-4-fluoro-phenyl)-N,4-dimethyl-N-(2-methylsulfonyl-ethyl)-5-(trifluoromethyl)-1H-pyrrole-2-carboxylic acid amide SC-253 1-Benzyl-3-(3-chloro-4-fluoro-phenyl)-N,4-dimethyl-N-tetrahydro-pyran-4-yl-5-(trifluoromethyl)-1H-pyrrole-2-carboxylic acid amide SC-254 1-Benzyl-3-(3-chloro-4-fluoro-phenyl)-N-cyclopropyl-N,4-dimethyl-5-(trifluoromethyl)-1H-pyrrole-2-carboxylic acid amide SC-255 [1-Benzyl-3-(3-chloro-4-fluoro-phenyl)-4-methyl-5-(trifluoromethyl)-1H-pyrrol-2-yl]-(3-hydroxy-azetidin-1-yl)-methanone SC-256 1-Benzyl-3-(3-chloro-4-fluoro-phenyl)-N-(2,2-dimethyl-propyl)-N,4-dimethyl-5-(trifluoromethyl)-1H-pyrrole-2-carboxylic acid amide SC-257 1-Benzyl-3-(3-chloro-4-fluoro-phenyl)-N-(2-hydroxy-1,1-dimethyl-ethyl)-N,4-dimethyl-5-(trifluoromethyl)-1H-pyrrole-2-carboxylic acid amide SC-258 [1-Benzyl-3-(3-chloro-4-fluoro-phenyl)-4-methyl-5-(trifluoromethyl)-1H-pyrrol-2-yl]-(2,2-dimethyl-morpholin-4-yl)-methanone SC-259 1-Benzyl-3-(4-chlorophenyl)-N-(2,2-dimethyl-propyl)-N-methyl-4-methylsulfonyl-5-(trifluoromethyl)-1H-pyrrole-2-carboxylic acid amide SC-260 1-Benzyl-N-(2,2-dimethyl-propyl)-N,4-dimethyl-3-[4-(2,2,2-trifluoro-ethoxy)-phenyl]-5-(trifluoromethyl)-1H-pyrrole-2-carboxylic acid amide SC-261 3-(4-Chlorophenyl)-N-(2,2-dimethyl-propyl)-1-[(4-fluorophenyl)-methyl]-N-methyl-5-(trifluoromethyl)-1H-pyrrole-2-carboxylic acid amide SC-262 [1-Benzyl-3-[2-fluoro-4-(trifluoromethyloxy)-phenyl]-4-methyl-5-(trifluoromethyl)-1H-pyrrol-2-yl]-morpholin-4-yl-methanone SC-263 [1-Benzyl-4-methyl-3-[4-(2,2,2-trifluoro-ethoxy)-phenyl]-5-(trifluoromethyl)-1H-pyrrol-2-yl]-morpholin-4-yl-methanone SC-264 4-[1-Benzyl-4-methyl-2-(morpholine-4-carbonyl)-5-(trifluoromethyl)-1H-pyrrol-3-yl]-3-fluoro-benzonitrile SC-265 [3-(4-Chlorophenyl)-4-methyl-1-[(3-methylsulfonyl-phenyl)-methyl]-5-(trifluoromethyl)-1H-pyrrol-2-yl]-morpholin-4-yl-methanone SC-266 3-(4-Chlorophenyl)-N-(2,2-dimethyl-propyl)-N-methyl-1-[(3-methylsulfonyl-phenyl)-methyl]-5-(trifluoromethyl)-1H-pyrrole-2-carboxylic acid amide, optionally in the form of a single stereoisomer or a mixture of stereoisomers, in the form of the free compound and/or a physiologically acceptable salt or solvate thereof.

Furthermore, preference may be given to compounds according to the invention that cause at least a 50% inhibition, which is present at a concentration of 3 μM, in a fluorescent assay for CaV2.2 channels with HEK293 cells in which human CaV2.2 channels were stably expressed at a concentration of less 3 μM, preferably less than 1000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR 3, Molecular Devices, Sunnyvale, USA), as described hereinafter.

The compounds according to the invention and corresponding stereoisomers and also the respective corresponding acids, bases, salts and solvates are suitable for the treatment and/or prophylaxis of one or more disorders and/or diseases selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

The present invention further relates to a compound according to the present invention for CaV2.2 calcium channel regulation, preferably for use in CaV2.2 calcium channel blockage.

The present invention therefore further relates to a compound according to the present invention for the prophylaxis and/or treatment of disorders and/or diseases which are mediated, at least in part, at least in part, by CaV2.2 channels.

The term "disorders and/or diseases which are mediated, at least in part, by CaV2.2 channels", is intended to include each of or all of the disease states.

The substances according to the invention hence act, for example, on CaV2.2 channels relevant in connection with various diseases, so that they are suitable as a pharmacologically active compound in pharmaceutical compositions.

The compounds according to the first aspect of the present invention and the corresponding stereoisomers and the respective salts and solvates are toxicologically safe and are therefore suitable as pharmacologically active ingredients in pharmaceutical compositions.

In another sepcet of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art, such as are described for example in "Remington's Pharmaceutical Sciences", A.R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

CaV2.2 channels are believed to be involved in a variety of diseases or disorders in mammals such as humans. These include pain (e.g.; acute pain, chronic pain, visceral pain, headache pain, inflammatory pain, mixed pain), stroke (the neuronal damage resulting from head trauma), epilepsy, mood disorders, schizophrenia, neurodegenerative disorders.

Another embodiment of the present invention is at least one compound according the present invention for the treatment and/or prophylaxis of one or more disorders selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Another embodiment of the present invention is at least one compound according to the present invention for the treatment and/or prophylaxis of pain, in particular acute pain and/or chronic pain and/or visceral pain and/or headache pain and/or inflammatory pain and/or mixed pain.

Acute pain according to the invention might include nociceptive pain and post-operative or surgical pain.

Chronic pain according to the invention might include peripheral neuropathic pain such as post-herpetic neuralgia, traumatic nerve injury, nerve compression or entrapment, small fibre neuropathy, diabetic neuropathy, neuropathic cancer pain, failed back surgery Syndrome, trigeminal neuralgia, phantom limb pain; neuroma pain, complex regional pain syndrome, chronic arthritic pain and related neuralgias, and pain associated with cancer, chemotherapy, HIV and HIV treatment-induced neuropathy; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome. In treating osteoarthritic pain, joint mobility will also improve as the underlying chronic pain is reduced. Thus, at least one compound for treatment of osteoarthritic pain inherently will also improve joint mobility in patients suffering from osteoarthritis.

Visceral pain according to the invention might include interstitial cystitis, irritable bowel syndrome, Crohn's disease and chronic pelvic pain syndrome.

Inflammatory pain according to the invention might include rheumatoid arthritis and endometriosis.

Headachepain according to the invention might include migraine, cluster headache, tension headache syndrome, facial pain and headache caused by other diseases.

Mixed pain according to the invention might include lower back pain, neck and shoulder pain, burning mouth syndrome and complex regional pain syndrome.

In another embodiment of the invention, at least one compound according to the present invention is particularly suitable for the treatment and/or prophylaxis of mood disorders.

Mood disorders according to the invention might include anxiety disorder, social anxiety disorder, panic disorder, specific phobias, for example, specific animal phobias, social phobias, obsessive-compulsive disorder, agoraphobia, post-traumatic stress syndrome, addiction (including dependence, withdrawal and/or relapse of medication, including opioids, but also drugs such as cocaine, opioids, alcohol and nicotine), generalised anxiety disorders, single episodic or recurrent major depressive disorders and dysthymic disorders, or bipolar disorders, for example, bipolar I disorder, bipolar II disorder and cyclothymic disorder.

In another embodiment of the invention, at least one compound according to the present invention is particularly suitable for the treatment and/or prophylaxis of epilepsy.

Epilepsy according to the invention might include partial seizures such as temporal lobe epilepsy, absence seizures generalized seizures, and tonic/clonic seizures.

In yet another embodiment of the invention, at least one compound according to the present invention is particularly suitable for the treatment and/or prophylaxis of neurodegenerative disorders.

Neurodegenerative disorders according to the invention might include Parkinson's disease, Alzheimer's disease, multiple sclerosis, neuropathies, Huntington's disease, presbycusis and amyotrophic lateral sclerosis (ALS).

Particularly preferably, at least one compound according to the present invention is suitable for the treatment and/or prophylaxis of one or more disorders and/or diseases selected from the group consisting of pain, preferably of pain selected from the group consisting of acute pain, chronic pain, visceral pain, headache pain, inflammatory pain and mixed pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Most particularly preferably, at least one compound according to the present invention according to the invention is suitable for the treatment and/or prophylaxis of pain, preferably of pain selected from the group consisting of acute pain, chronic pain, visceral pain, headache pain, inflammatory pain and mixed pain.

The present invention further relates to a compound according to the present invention and one or more additional pharmaceutically active agents for use in the prophylaxis and/or treatment of disorders and/or diseases which are mediated, at least in part, at least in part, by CaV2.2 channels.

In particular, the present invention therefore further relates to a compound according to the present invention and one or more additional pharmaceutically active agents for the prophylaxis and/or treatment of disorders and/or diseases selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Most particularly preferred is a compound according to the present invention one or more additional pharmaceutically active agents for the prophylaxis and/or treatment of pain, preferably of pain selected from the group consisting of acute pain, chronic pain, visceral pain, headache pain, inflammatory pain and mixed pain.

Additional pharmaceutically active agents in the treatment of pain may include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NKI antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, xiv) neurontin (gabapentin), xv) pregabalin.

Additional pharmaceutically active agents in the treatment of depression or anxiety can include other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), adrenoreceptor antagonists, atypical anti-depressants, benzodiazepines, 5-HT1 A agonists or antagonists, especially 5-HT1A partial agonists, neurokinin 1 receptor antagonists, corticotropin releasing factor (CRF) antagonists, and pharmaceutically acceptable salts thereof.

Another embodiment of the present invention therefore relates to use of at least one compound according to the present invention for the preparation of a pharmaceutical composition for the treatment and/or prophylaxis of one or more disorders or diseases, particularly selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders.

Another aspect of the present invention is a method of treatment and/or prophylaxis of disorders and/or diseases in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

Another embodiment of the present invention is a method for CaV2.2 calcium channel regulation, preferably for use in CaV2.2 calcium channel blockage, and, further, a method of treatment and/or prophylaxis of disorders and/or diseases, which are mediated, at least in part, by CaV2.2 channels, in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

All preferred embodiments of the first aspect of the invention are preferred vice versa for the other aspects and embodiments.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74 79 (1941)) or by the formalin test (e.g. according to D. Dubuisson et al., Pain 1977, 4, 161-174).

Preparation

The present invention further relates to processes for preparing compounds according to the invention. The compounds (I) according the present invention may be prepared by various methods. Several exemplified syntheses are outlined in following synthetic schemes 1 to 7. The methods mentioned therein are known to those skilled in the art and the specific reaction conditions may readily adjusted to different substrates.

For sake of clarity, the residues R' and R" in schemes 1 to 7 represent the following substructures

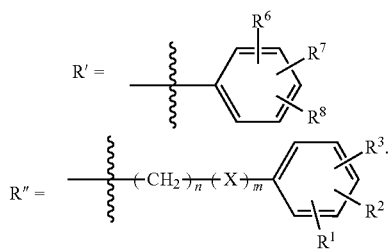

Compounds according to the present invention may be prepared in particular from aryl aldehydes that are commercially available or easily prepared according to standard procedures known in the art. Suitable syntheses involve general intermediates IN-1 which are accessible from the respective aryl aldehydes (Scheme 1).

Scheme 1: Preparation of general intermediate IN-1 from aryl aldehydes R'CHO.

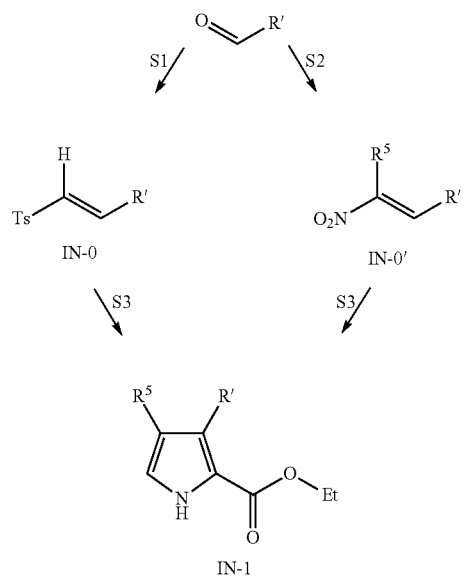

S1: (i) MePPh$_3$Hal, base; (ii) NaI, NaTs, CAN; (iii) NEt$_3$.
S2: R$^5$—CH$_2$NO$_2$, base.
S3: CN—CH$_2$CO$_2$Et.

Such intermediates IN-1 are readily converted into the compounds according to the present invention as outlined in Scheme 2.

Scheme 2: Preparation of compounds according to formula (I) from general intermediate IN-1.

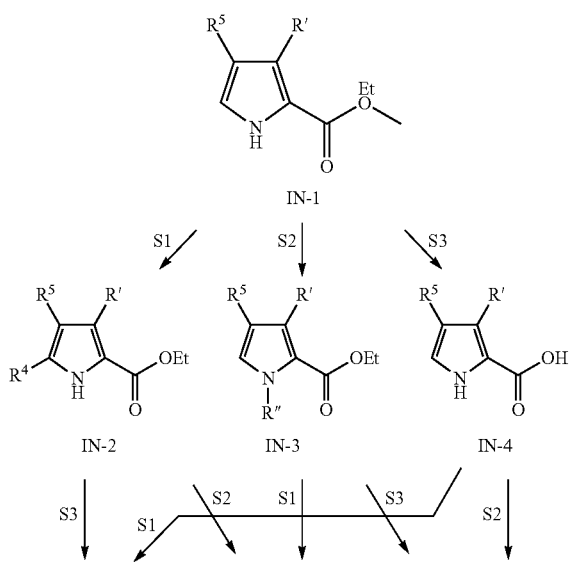

-continued

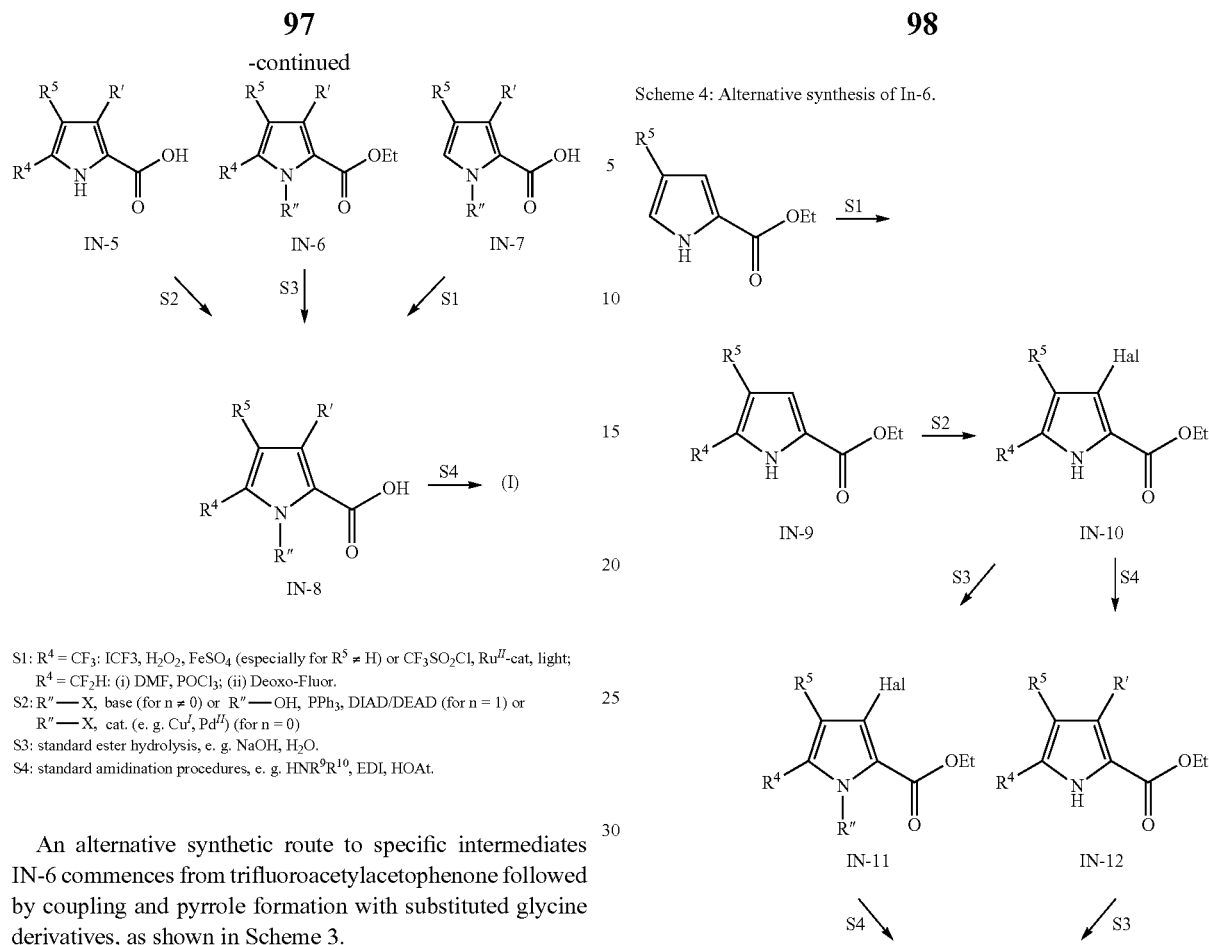

S1: R⁴ = CF₃: ICF3, H₂O₂, FeSO₄ (especially for R⁵ ≠ H) or CF₃SO₂Cl, Ru^II-cat, light; R⁴ = CF₂H: (i) DMF, POCl₃; (ii) Deoxo-Fluor.
S2: R″—X, base (for n ≠ 0) or R″—OH, PPh₃, DIAD/DEAD (for n = 1) or R″—X, cat. (e. g. Cu^I, Pd^II) (for n = 0)
S3: standard ester hydrolysis, e. g. NaOH, H₂O.
S4: standard amidination procedures, e. g. HNR⁹R¹⁰, EDI, HOAt.

An alternative synthetic route to specific intermediates IN-6 commences from trifluoroacetylacetophenone followed by coupling and pyrrole formation with substituted glycine derivatives, as shown in Scheme 3.

Scheme 3: Alternative synthesis of In-6 (with R⁵ = H, and R⁴ = CF₃).

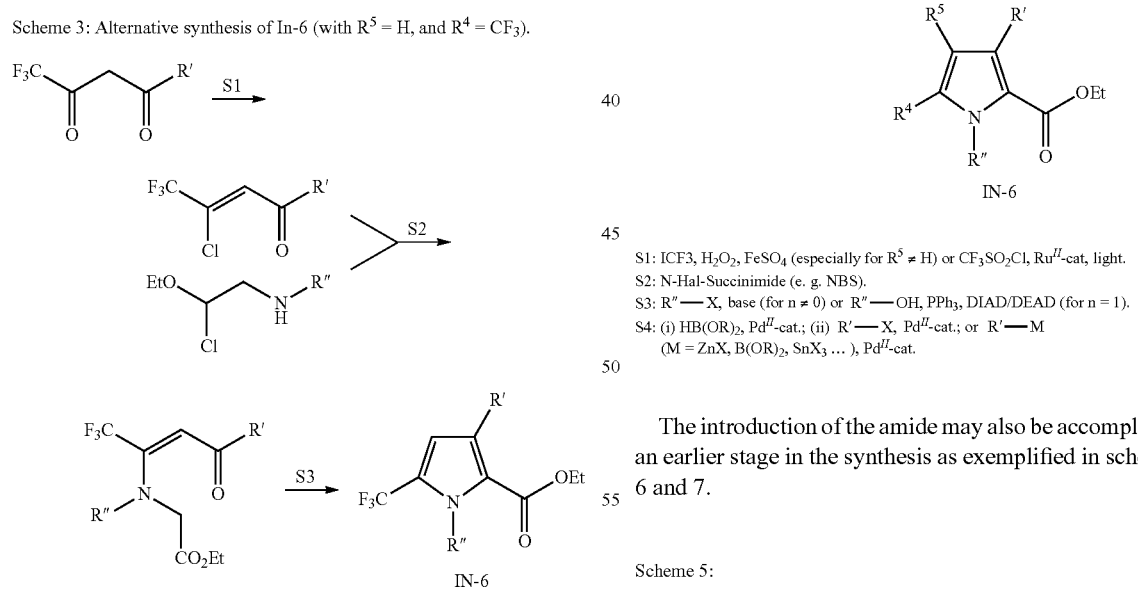

S1: (COCl)₂, DMF.
S2: base.
S3: base, H₂O.

Yet another alternative synthesis to intermediates of type IN-6 involves transition metal catalyzed coupling between pyrroles and aryl compounds, as shown in scheme 4.

Scheme 4: Alternative synthesis of In-6.

(scheme showing IN-9 → IN-10, IN-11, IN-12 → IN-6)

S1: ICF3, H₂O₂, FeSO₄ (especially for R⁵ ≠ H) or CF₃SO₂Cl, Ru^II-cat, light.
S2: N-Hal-Succinimide (e. g. NBS).
S3: R″—X, base (for n ≠ 0) or R″—OH, PPh₃, DIAD/DEAD (for n = 1).
S4: (i) HB(OR)₂, Pd^II-cat.; (ii) R′—X, Pd^II-cat.; or R′—M (M = ZnX, B(OR)₂, SnX₃ ... ), Pd^II-cat.

The introduction of the amide may also be accomplished at an earlier stage in the synthesis as exemplified in schemes 5, 6 and 7.

Scheme 5:

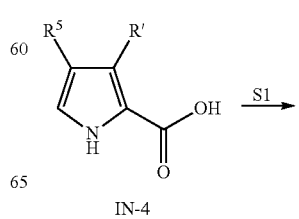

IN-4

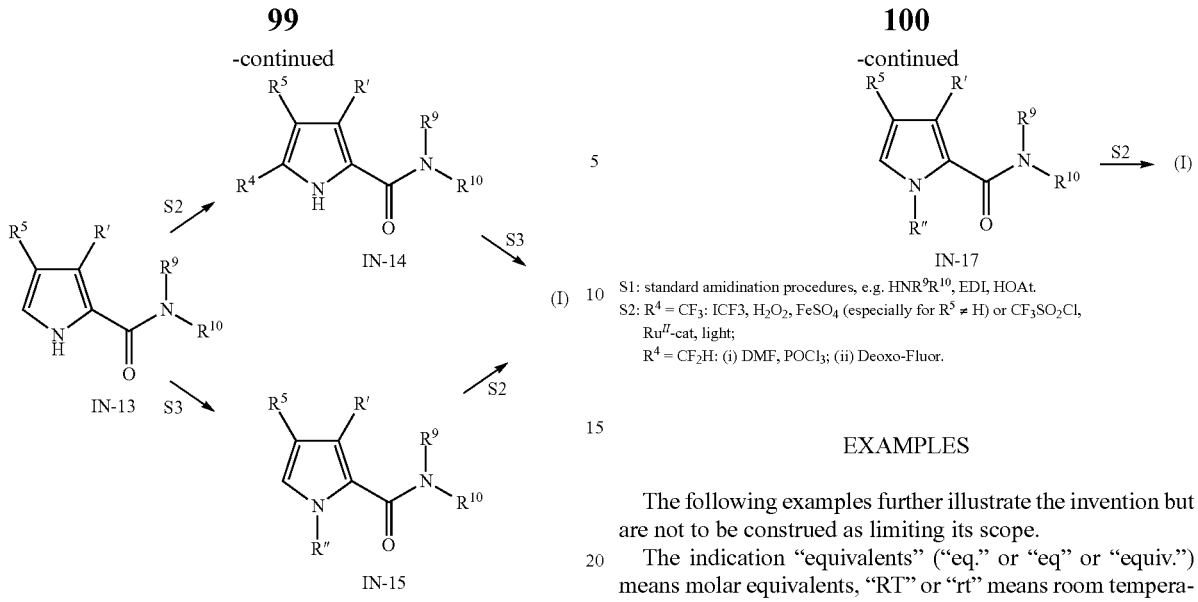

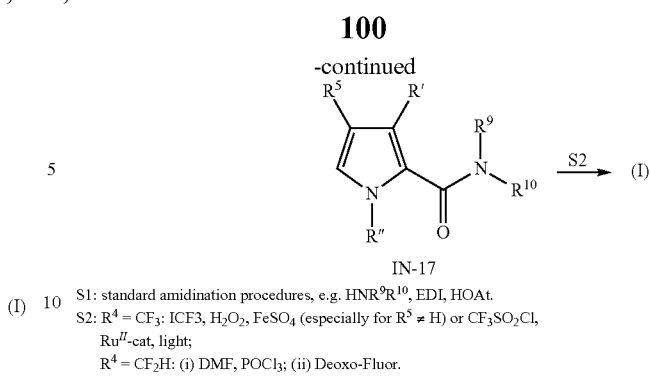

S1: standard amidination procedures, e.g. HNR⁹R¹⁰, EDI, HOAt.
S2: R⁴ = CF₃: ICF3, H₂O₂, FeSO₄ (especially for R⁵ ≠ H) or CF₃SO₂Cl, Ru^II-cat, light;
R⁴ = CF₂H: (i) DMF, POCl₃; (ii) Deoxo-Fluor.

Scheme 6:

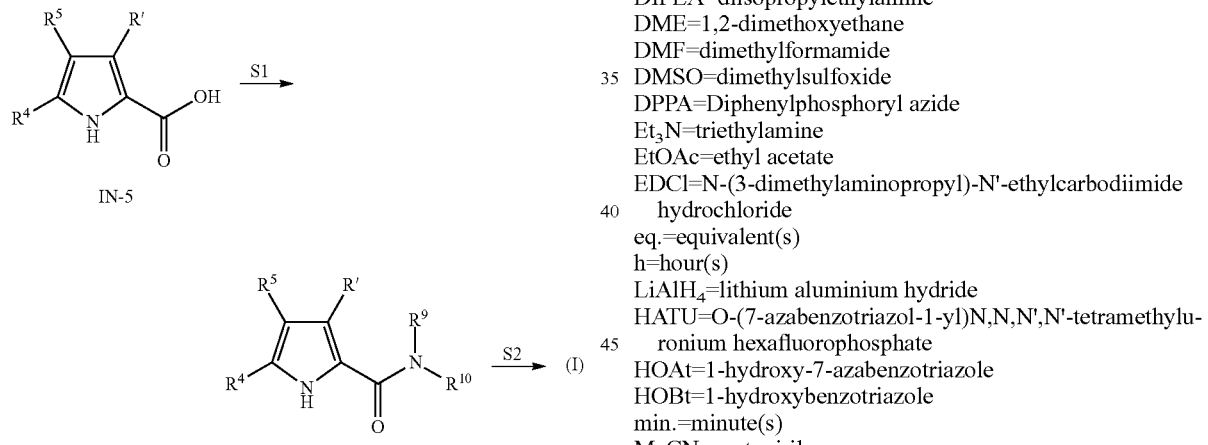

S1: standard amidination procedures, e.g. HNR⁹R¹⁰, EDI, HOAt.
S2: R″—X, base (for n ≠ 0) or R″—OH, PPh₃, DIAD/DEAD (for n = 1) or
R″—X, cat. (e.g. Cu^I, Pd^II) (for n = 0).

Scheme 7:

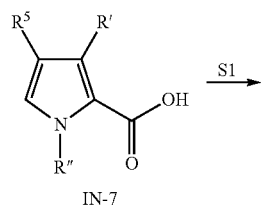

EXAMPLES

The following examples further illustrate the invention but are not to be construed as limiting its scope.

The indication "equivalents" ("eq." or "eq" or "equiv.") means molar equivalents, "RT" or "rt" means room temperature (23±7° C.), "M" are indications of concentration in mol/l, "aq." means aqueous, "sat." means saturated, "sol." means solution, "conc." means concentrated.

Boc=tert-butoxycarbonyl
BOP-Cl=bis(2-oxo-3-oxazolidinyl)phosphonic chloride
conc.=concentrated
d=day(s)
DCM=dichloromethane
deoxo-Fluor=bis(2-methoxyethyl)aminosulfur trifluoride
DIAD=diisopropyl azodicarboxylate
DIPEA=diisopropylethylamine
DME=1,2-dimethoxyethane
DMF=dimethylformamide
DMSO=dimethylsulfoxide
DPPA=Diphenylphosphoryl azide
Et₃N=triethylamine
EtOAc=ethyl acetate
EDCl=N-(3-dimethylaminopropyl)-N'-ethylcarbodiimide hydrochloride
eq.=equivalent(s)
h=hour(s)
LiAlH₄=lithium aluminium hydride
HATU=O-(7-azabenzotriazol-1-yl)N,N,N',N'-tetramethyluronium hexafluorophosphate
HOAt=1-hydroxy-7-azabenzotriazole
HOBt=1-hydroxybenzotriazole
min.=minute(s)
MeCN=acetonirile
MeI=methyl iodide
MeOH=methanol
Oxone=potassium monopersulfate
iPrOH=iso-propanol
TBD on polystyrene=1,5,7-triazabicyclo[4.4.0]dec-5-ene polystyrene
TFA=trifluoroacetic acid
TFAA=trifluoroacetic acid anhydride
THF=tetrahydrofuran
TLC=thin layer chromatography
Ts=para-toluenesulfonyl
T3P=propylphosphonic anhydride All starting materials which are not explicitly described were either commercially available (the details of suppliers such as for example Acros, Avocado, Aldrich, Apollo, Bachem, Fluke, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, repspectively, for example) or can be prepared using the conventional methods known to the person skilled in the art.

The stationary phase used for the column chromatography was silica gel 60 (0.04-0.063 mm) from E. Merck, Darmstadt. The reactions were, if necessary, carried out under an inert amosphere (mostly nitrogen).

The yields of the compounds prepared are not optimized.

The mixing ratios of solvents are usually stated in the volume/volume ratio.

The reactions were, if necessary, carried out under an inert amosphere (mostly nitrogen). The number of equivalents of reagents and the amounts of solvents employed as well as the reaction temperatures and times can vary slightly between different reactions carried out by the same (general) method. The work-up and purification methods were adapted according to the characteristic properties of each compound and can vary slightly for analogous/general methods.

All the intermediate products and exemplary compounds were analytically characterized by means of $^1$H-NMR spectroscopy. In addition, mass spectrometry tests (MS, m/z for [M+H]$^+$) were carried out for all the exemplary compounds and selected intermediate products.

1. Synthesis of Example Compounds 1.1 Synthesis of Carboxylic Acid Building Blocks (ACI)

Synthesis of 1-Benzyl-3-(4-chlorophenyl)-1H-pyrrole-2-carboxylic acid (ACI-01)

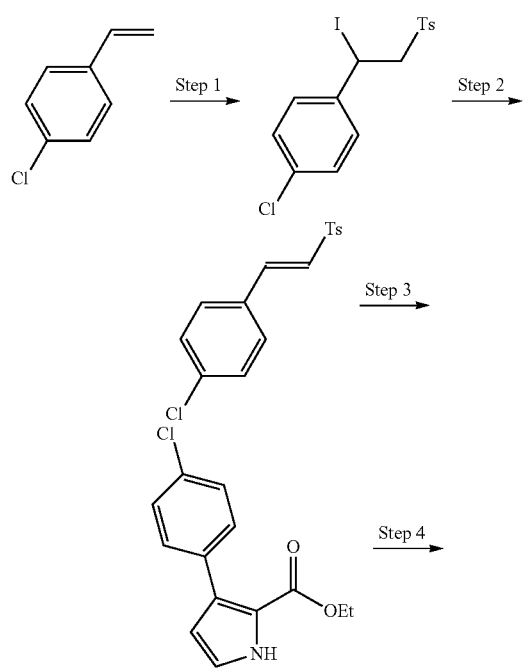

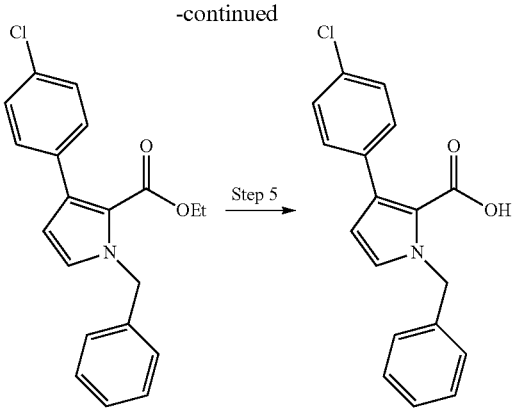

Step 1: 1-Chloro-4-(1-iodo-2-tosylethyl)benzene

A flask was charged with sodium p-toluenesulfinate (19.28 g, 108 mmol) and NaI (16.22 g, 108 mmol) in dry MeCN (360 mL). The reaction mixture was bubbled through with argon for 15 min followed by addition of 4-chlorostyrene (9.09 mL, 72.2 mmol) and $(NH_4)_2Ce(NO_3)_6$ (79 g, 144 mmol). The reaction mixture was stirred for 18 h under argon atmosphere at room temperature. Then the solvent was evaporated under reduced pressure and the residue was partitioned between $H_2O$ (400 mL) and DCM (500 mL). The layers were separated and the aqueous phase was extracted with DCM (200 mL). The organic layer was washed with saturated aqueous $Na_2S_2O_3$ (150 mL), brine (150 mL), dried over $Na_2SO_4$, filtered and evaporate to dryness to afford 28.5 g (94%) of the desired product.

Step 2: (E)-1-Chloro-4-(2-tosylvinyl)benzene

1-Chloro-4-(1-iodo-2-tosylethyl)benzene (28.5 g, 67.7 mmol) was dissolved in dry MeCN (376 mL) followed by addition of $Et_3N$ (18.83 mL, 135 mmol) and the mixture was stirred at room temperature for 1 h. Then the solvent was evaporated under reduced pressure and the residue partitioned between DCM (400 mL) and 1M aqueous $KHSO_4$ (300 mL). The layers were separated and the organic phase was dried over $Na_2SO_4$, filtered and evaporated to dryness under reduced pressure to afford 19 g (96%) of the desired product.

Step 3: Ethyl 3-(4-chlorophenyl)-1H-pyrrole-2-carboxylate

Under $N_2$, at 0° C. 60% NaH in mineral oil (3.11 g, 78 mmol) was added to a solution of (E)-1-chloro-4-(2-tosylvinyl)benzene (19 g, 64.9 mmol) in dry THF (300 mL). After 5 minutes ethyl 2-isocyanoacetate (7.76 mL, 71.4 mmol) was added and the reaction mixture stirred at room temperature. After 18 h EtOH (50 mL) was added and the solvents were evaporated under reduced pressure. The residue was partitioned between EtOAc (400 mL) and $H_2O$ (400 mL). The organic phase was washed with (100 mL), dried over $Na_2SO_4$, filtered and evaporated to dryness under reduced pressure. The crude product (16.55 g, "102%") was used in the next step.

Step 4: Ethyl 1-benzyl-3-(4-chlorophenyl)-1H-pyrrole-2-carboxylate

Under $N_2$ ethyl 3-(4-chlorophenyl)-1H-pyrrole-2-carboxylate (16.5 g, 66.1 mmol) was dissolved in DMF (132 mL) and 60% NaH in mineral oil (2.91 g, 72.7 mmol) was added while cooling the solution in an ice-bath and the reaction mixture was then stirred at room temperature. After 20 min benzyl bromide (9.48 mL, 79 mmol) was added and stirring was continued for 24 h. The reaction mixture was poured into $H_2O$ (200 mL) and the product was extracted with EtOAc (300 mL). The organic phase was washed with saturated aqueous $NaH_4Cl$ (2×200 mL), brine (150 mL), dried over $Na_2SO_4$, filtered and evaporated to dryness under reduced pressure. The crude mixture was purified by gravity chromatography (silica, heptane/EtOAc, 9:1), to yield 8 g (36%) of the desired product.

Step 5: 1-Benzyl-3-(4-chlorophenyl)-1H-pyrrole-2-carboxylic acid (ACI-01)

Ethyl 1-benzyl-3-(4-chlorophenyl)-1H-pyrrole-2-carboxylate (8 g, 23.54 mmol) was dissolved in MeOH (33.4 mL) and THF (33.4 mL) followed by addition of aqueous 6M NaOH (33.4 mL, 200 mmol) and the reaction mixture was stirred at reflux for 18 h. The volatile solvents were evaporated under reduced pressure. The remaining aqueous phase was acidified with aqueous 1M HCl until pH=4 and a solid precipitated. The solid was filtered off and washed with cold $H_2O$. The collected solid was dissolved in EtOAc, dried over $Na_2SO_4$, filtered and the solution evaporated to dryness to give 6.69 g (91%) of ACI-01.

Synthesis of 1-Benzyl-3-(4-chlorophenyl)-4-methyl-1H-pyrrole-2-carboxylic acid (ACI-02)

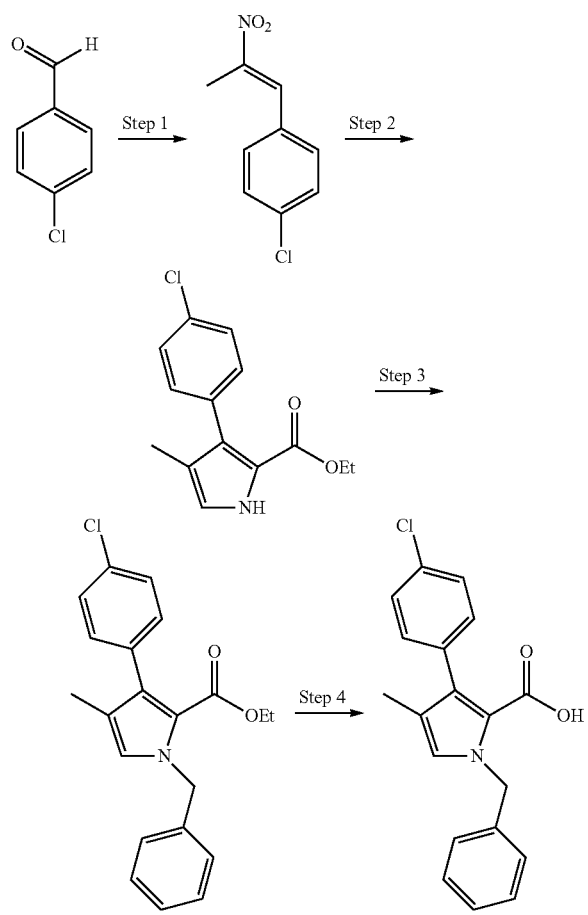

Step 1: (E)-1-Chloro-4-(2-nitroprop-1-enyl)benzene

A solution of 4-chlorobenzaldehyde (28.57 g, 203 mmol), nitroethane (44.0 mL, 610 mmol) and piperidine (4.01 mL, 40.6 mmol) in toluene (200 mL) was stirred at reflux (Dean-Stark) for 6 h and the mixture was stored at room temperature overnight. The solvent was removed under reduced pressure and the product was recrystallised from absolute EtOH. The crystals were filtered off, washed with a small amount of absolute EtOH and dried to give 23.25 g of the desired product. The mother liquor was concentrated, heated, cooled. Another batch of crystals was filtered off, washed with a small amount of absolute EtOH and dried in vacuo, to afford 3.95 g of the desired product. Total yield: 27.20 g (68%).

Step 2: Ethyl 3-(4-chlorophenyl)-4-methyl-1H-pyrrole-2-carboxylate 2.6 mmol TBD/g polystyrene (21.4 g, 55.7 mmol) was added to a suspension of (E)-1-chloro-4-(2-nitroprop-1-enyl)benzene (10 g, 50.6 mmol) and ethyl 2-isocyanoacetate (6.01 g, 53.1 mmol) in i-PrOH (40 mL) and dry THF (40 mL). The reaction mixture was stirred at room temperature overnight. The suspension was filtered, washed with i-PrOH/THF (1/1, v/v, 40 mL). The combined filtrate was evaporated under reduced pressure to furnish 11.0 g (82%) of the desired product.

Step 3: Ethyl 1-benzyl-3-(4-chlorophenyl)-4-methyl-1H-pyrrole-2-carboxylate

Ethyl 3-(4-chlorophenyl)-4-methyl-1H-pyrrole-2-carboxylate (9 g, 34.1 mmol) was dissolved in dry DMF (20 mL). At 0° C., 60% NaH in mineral oil (1.365 g, 34.1 mmol) was added. After 20 min gas evolution had ceased and benzyl bromide (4.08 mL, 34.1 mmol) was added. The reaction mixture was stirred at room temperature overnight. Brine (400 mL) was added, followed by EtOAc (400 mL). The organic layer was washed with $H_2O$ (2×400 mL), brine (400 mL), dried ($Na_2SO_4$) and evaporated under reduced pressure. The product was purified by column chromatography (silica, heptane/EtOAc, 9:1), to yield 8.40 g (70%) of the desired product.

Step 4: 1-Benzyl-3-(4-chlorophenyl)-4-methyl-1H-pyrrole-2-carboxylic acid (ACI-02)

To a suspension of ethyl 1-benzyl-3-(4-chlorophenyl)-4-methyl-1H-pyrrole-2-carboxylate (8.50 g, 24.0 mmol) in THF (15 mL), EtOH (15 mL) and $H_2O$ (15 mL) was added $LiOH·H_2O$ (10.1 g, 240 mmol). The reaction mixture was stirred at reflux temperature for 2 h. To the reaction mixture were added extra $H_2O$ (45 mL) and EtOH (30 mL) and the reaction mixture was stirred at reflux temperature overnight. The reaction mixture was allowed to cool to room temperature and was almost completely concentrated. Aqueous 1 M $KHSO_4$ (~240 mL) was added to the reaction mixture while cooling with an ice-bath (pH reached 1), followed by the addition of EtOAc (500 mL). The organic layer was separated, washed with brine (2×400 mL), dried ($Na_2SO_4$) and concentrated. The residue was washed with a minimal amount of i-$Pr_2O$ and dried on a filter for 1 h to give ACI-02 (7.26 g, 93%).

Synthesis of 1-Benzyl-3-(4-chlorophenyl)-4-methyl-5-(trifluoromethyl)-1H-pyrrole-2-carboxylic acid (ACI-03)

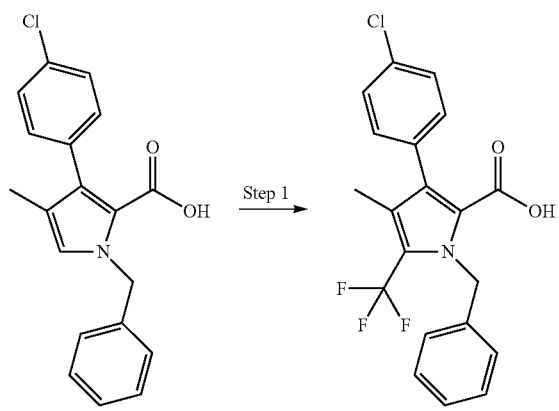 [SMILES: Cc1cn(Cc2ccccc2)c(C(=O)O)c1-c1ccc(Cl)cc1 ; Cc1c(-c2ccc(Cl)cc2)c(C(=O)O)n(Cc2ccccc2)c1C(F)(F)F]

Step 1: 1-Benzyl-3-(4-chlorophenyl)-4-methyl-5-(trifluoromethyl)-1H-pyrrole-2-carboxylic acid ACI-02

(250 mg, 0.767 mmol) and FeSO$_4$·7H$_2$O (128 mg, 0.460 mmol) were dissolved in DMSO (5 mL) to give a dark yellow solution. Trifluoromethyl iodide (gas) was bubbled through for 2 minutes via a syringe, giving a red solution. Subsequently, 35% aqueous H$_2$O$_2$ (0.403 mL, 4.60 mmol) was added, giving an exothermic reaction which was cooled using an ice bath. The very dark brown mixture was stirred 1 h at room temperature. The reaction mixture was partitioned between brine (25 mL) and EtOAc (25 mL) and the layers were separated. The aqueous layer was extracted with EtOAc (2×15 mL) and the combined organic layers were washed with brine (2×25 mL), dried on Na$_2$SO$_4$ and concentrated in vacuo to give an off-white solid. The product was triturated with heptane and filtered off to give ACI-03 (170 mg, 56%) as a white solid.

Synthesis of 1-Benzyl-3-(4-chloro-2-fluorophenyl)-4-methyl-5-(trifluoromethyl)-1H-pyrrole-2-carboxylic acid (ACI-04)

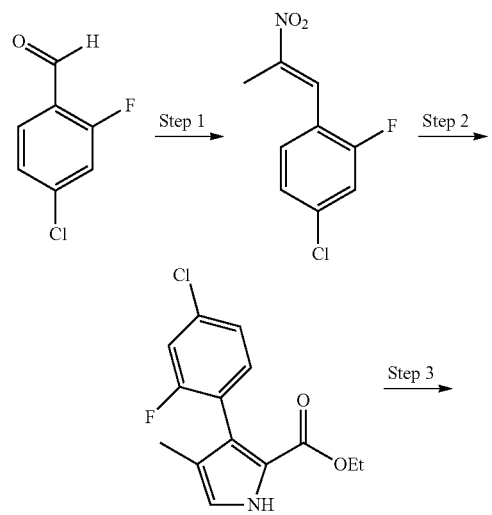

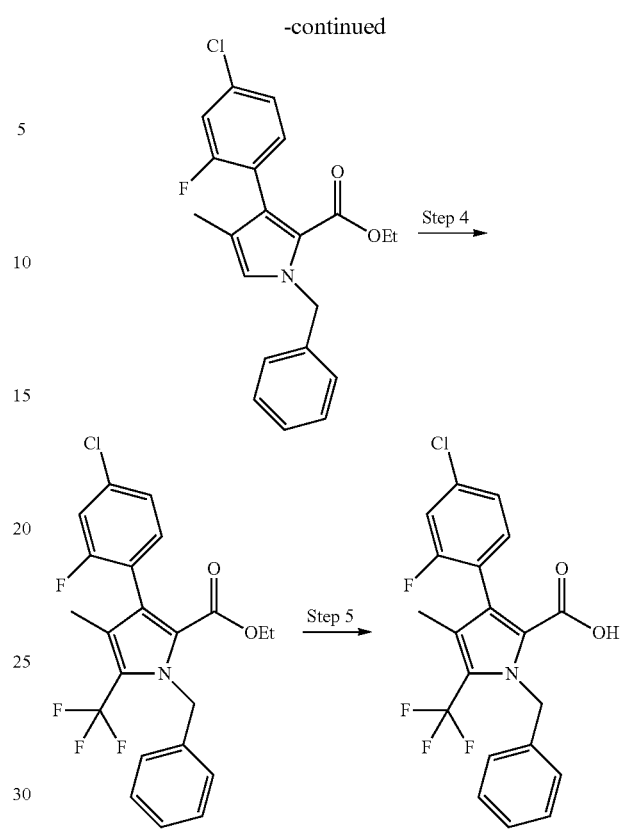

Step 1: (E)-4-Chloro-2-fluoro-1-(2-nitroprop-1-enyl)benzene

4-Chloro-2-fluorobenzaldehyde (10 g, 63.1 mmol), nitroethane (54.6 mL, 757 mmol) and piperidine (1.869 mL, 18.92 mmol) were dissolved in toluene (150 mL) and refluxed under Dean Stark conditions overnight. The reaction mixture was cooled to room temperature and the solvents were evaporated. The crude product was purified by column chromatography (silica, heptane/EtOAc 98:2) to give the desired product (10.4 g, 76%) as a yellow solid.

Step 2: Ethyl 3-(4-chloro-2-fluorophenyl)-4-methyl-1H-pyrrole-2-carboxylate

To a suspension of (E)-4-Chloro-2-fluoro-1-(2-nitroprop-1-enyl)benzene (5 g, 23.2 mmol) and ethyl 2-isocyanoacetate (2.65 mL, 24.4 mmol) in a mixture of dry THF (20 mL) and i-PrOH (20 mL) was added 2.6 mmol TBD/g polymer (9.8 g, 25.5 mmol). The suspension was stirred at room temperature for 5 d. The reaction mixture was filtered off and the residue was washed with i-PrOH/THF (1:1, 30 mL). The filtrate was concentrated to give the desired product (5.7 g, 87%) as a yellow oil.

Step 3: Ethyl 1-benzyl-3-(4-chloro-2-fluorophenyl)-4-methyl-1H-pyrrole-2-carboxylate A solution of ethyl 3-(4-chloro-2-fluorophenyl)-4-methyl-1H-pyrrole-2-carboxylate (5.7 g, 20.2 mmol) in dry DMF (25 mL) was added dropwise to a cooled suspension of 60% NaH in mineral oil (0.89 g, 22.3 mmol) in dry DMF (25 mL). The mixture was stirred at 0° C. for 20 min, then benzylbromide (2.54 mL, 21.3 mmol) was added dropwise. The mixture was stirred for 10 min at 0° C., the cooling was removed and stirring was continued for 2 h at room temperature. The reaction was quenched by addition of saturated aqueous NH$_4$Cl/ ice (1:1, 150 mL) and the product was extracted with EtOAc (150 mL). The combined organic layers were dried on Na$_2$SO$_4$ and evaporated. The residual crude product purified using column chromatography (silica, heptane/EtOAc 2:1) to give the desired product (6.6 g, 88%) as an orange oil.

Step 4: Ethyl 1-benzyl-3-(4-chloro-2-fluorophenyl)-4-methyl-5-(trifluoromethyl)-1H-pyrrole-2-carboxylate To a solution of ethyl 1-benzyl-3-(4-chloro-2-fluorophenyl)-4-methyl-1H-pyrrole-2-carboxylate (3 g, 8.74 mmol) in DMSO (45 mL) was added FeSO$_4$.7H$_2$O (0.67 g, 2.42 mmol) and H$_2$SO$_4$ (0.43 mL, 8.07 mmol). Subsequently, CF$_3$I was bubbled through for 5 min and the dark brown mixture became slightly warm. Aqueous 35% H$_2$O$_2$ (1.41 mL, 16.1 mmol) was carefully added. The reaction mixture was stirred for 30 min, then diluted carefully with saturated aqueous Na$_2$CO$_3$ and the product was extracted with EtOAc. The combined organic layers were dried on Na$_2$SO$_4$ and concentrated. The product was purified using flash column chromatograph (silica, heptane/EtOAc 95:5) and reversed phase chromatography (MeCN/H$_2$O) to give the desired product (1.55 g, 44%) as a yellow oil.

Step 5: 1-Benzyl-3-(4-chloro-2-fluorophenyl)-4-methyl-5-(trifluoromethyl)-1H-pyrrole-2-carboxylic acid (ACI-04)

To a mixture of ethyl 1-benzyl-3-(4-chloro-2-fluorophenyl)-4-methyl-5-(trifluoromethyl)-1H-pyrrole-2-carboxylate (1.55 g, 3.5 mmol) in H$_2$O (20 mL) and EtOH (20 mL) was added NaOH (2.82 g, 71 mmol) and the mixture stirred at reflux for 2 h. The reaction mixture cooled to room temperature and concentrated. The reaction mixture was acidified using aqueous 5N HCl and the solids which had been formed were filtered off to give 1.45 g (100%) of ACI-04 as an off white solid.

Synthesis of 1-(3-chlorobenzyl)-3-(4-chlorophenyl)-4-methyl-5-(trifluoromethyl)-1H-pyrrole-2-carboxylic acid (ACI-05)

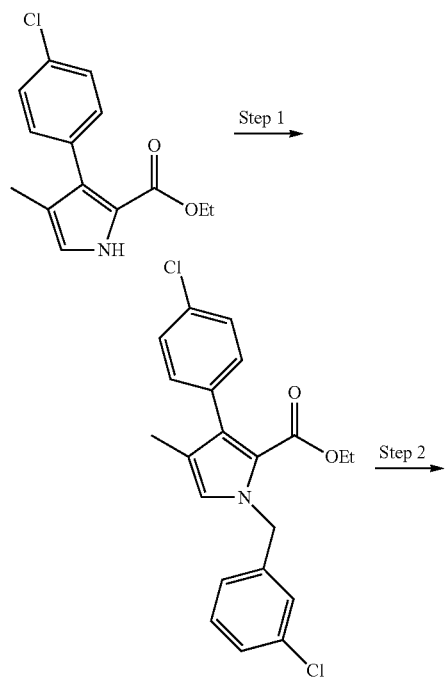

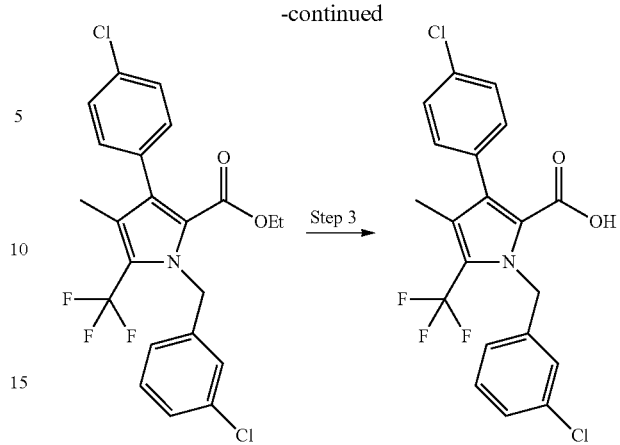

Step 1: Ethyl 3-(4-chlorophenyl)-4-methyl-1H-pyrrole-2-carboxylate

A solution of ethyl 1-(3-chlorobenzyl)-3-(4-chlorophenyl)-4-methyl-1H-pyrrole-2-carboxylate (1 g, 3.79 mmol) in dry DMF (5 mL) was added dropwise to a cooled suspension of 60% NaH in mineral oil (0.167 g, 4.17 mmol) in dry DMF (5 mL). The mixture was stirred at 0° C. for 20 min, then 3-chlorobenzyl bromide (0.524 mL, 3.98 mmol) was added dropwise over 5 min. The mixture was stirred for 10 min at 0° C., then the cooling was removed and the stirring was continued for 2.5 h at room temperature. The reaction was quenched by the addition of saturated aqueous NH$_4$Cl/ice (1:1, 50 mL) and the product was extracted with EtOAc (50 mL). The combined organic layers were dried on Na$_2$SO$_4$ and evaporated and the residual crude product purified using gravity column chromatography (silica, heptane/EtOAc 9:1) to give the desired product (1.18 g, 80%).

Step 2: Ethyl 1-(3-chlorobenzyl)-3-(4-chlorophenyl)-4-methyl-5-(trifluoromethyl)-1H-pyrrole-2-carboxylate To a solution of ethyl 1-(3-chlorobenzyl)-3-(4-chlorophenyl)-4-methyl-1H-pyrrole-2-carboxylate (1.18 g, 3.04 mmol) in DMSO (15 mL) was added FeSO$_4$.7H$_2$O (0.253 g, 0.912 mmol) and H$_2$SO$_4$ (0.162 mL, 3.04 mmol). Subsequently, CF$_3$I was bubbled through for 5 min and the dark brown mixture became slightly warm. The reaction mixture was cooled in an ice-bath until the first solid particles were visible. The cooling bath was removed and aqueous 35% H$_2$O$_2$ (0.53 mL, 6.08 mmol) was carefully added. The reaction mixture was stirred for 10 min, then diluted carefully with saturated aqueous Na$_2$CO$_3$ (15 mL) and the product was extracted with EtOAc (100 mL). The combined organic layers were dried on Na$_2$SO$_4$ and concentration. The product was purified using reversed phase chromatography (MeCN/H$_2$O) to give the desired product (737 mg, 53%) as a yellow oil.

Step 3: 1-(3-chlorobenzyl)-3-(4-chlorophenyl)-4-methyl-5-(trifluoromethyl)-1H-pyrrole-2-carboxylic acid (ACI-05)

To a mixture of ethyl 1-(3-chlorobenzyl)-3-(4-chlorophenyl)-4-methyl-5-(trifluoromethyl)-1H-pyrrole-2-carboxylate (737 mg, 1.6 mmol) in H₂O (10 mL) and EtOH (10 mL) was added NaOH (1.29 g, 32 mmol) and the mixture stirred at reflux for 3 h. The reaction mixture cooled to room temperature and concentrated the next day. Aqueous 5N HCl was added and the solids which had been formed were filtered off and dried on air for 5 d to give 768 mg of compound ACI-05 as a yellow solid.

Synthesis of 1-Benzyl-3-(4-chlorophenyl)-5-(trifluoromethyl)-1H-pyrrole-2-carboxylic acid (ACI-06)

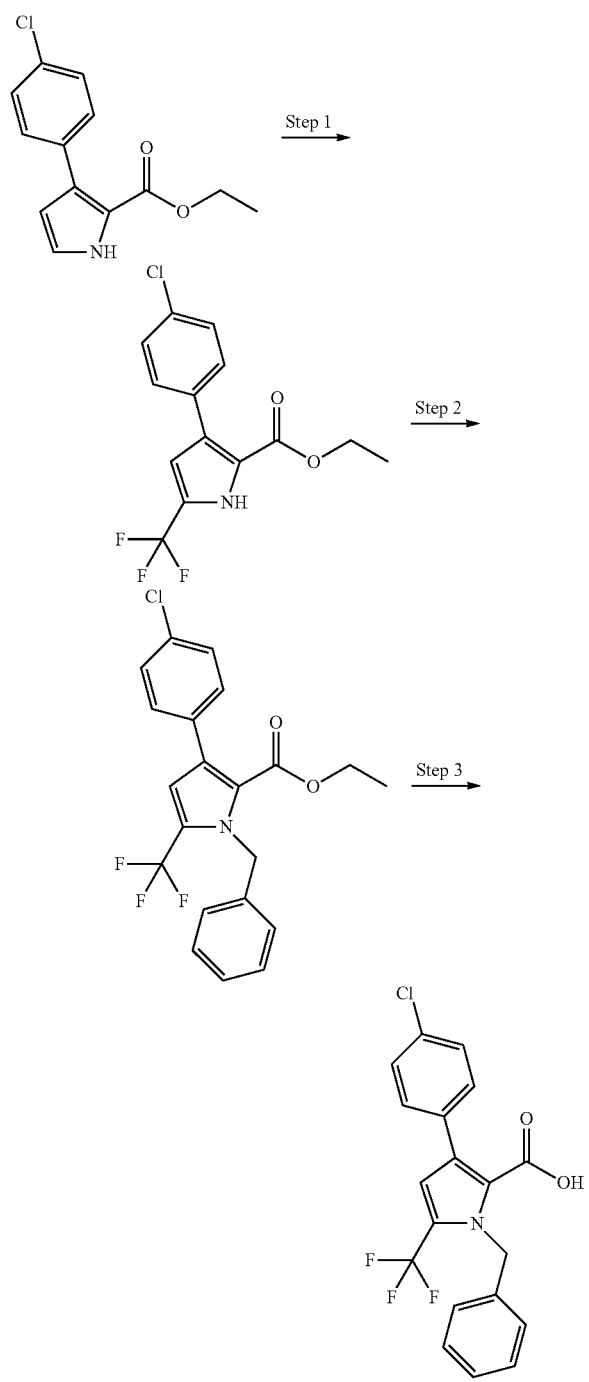

Step 1: Ethyl 3-(4-chlorophenyl)-5-(trifluoromethyl)-1H-pyrrole-2-carboxylate

This reaction was carried out in 5 batches using the same procedure. To a mixture of ethyl 3-(4-chlorophenyl)-1H-pyrrole-2-carboxylate [for synthesis see ACI-01] (1.25 g, 5.01 mmol), K₂HPO₄ (2.62 g, 15 mmol) and dichlortris(1,10-phenanthroline)-ruthenium(II) hydrate (71 mg, 0.10 mmol) in argon degassed dry MeCN (35 mL) was added CF₃SO₂Cl (1.60 mL, 15 mmol). The reaction mixture was stirred for 16 h at room temperature adjacent to a fluorescent light bulb (E27-32W, 4000K, 65 mA). After 16 h, an additional amount of CF₃SO₂Cl (0.20 mL, 1.88 mmol) was added and the reaction mixture was stirred overnight at room temperature adjacent to a fluorescent light bulb. All reaction mixtures were combined and diluted with EtOAc (150 mL) and H₂O was added. The aqueous layer was extracted with EtOAc (150 mL). The organic layers were combined and the solvent was evaporated to give an oil. The crude product was purified by flash chromatography (silica, gradient heptane/EtOAc, 1:0→1:1) to furnish the desired product (4.59 g, 58%).

Step 2: Ethyl 1-benzyl-3-(4-chlorophenyl)-5-(trifluoromethyl)-1H-pyrrole-2-carboxylate To a solution of ethyl 3-(4-chlorophenyl)-5-(trifluoromethyl)-1H-pyrrole-2-carboxylate (2.0 g, 6.30 mmol) in dry THF (20 mL) was added triphenylphosphine (1.899 g, 7.24 mmol) and benzyl alcohol (0.720 mL, 6.92 mmol). DIAD (1.373 mL, 6.92 mmol) in dry THF (5 mL) was added dropwise. The reaction mixture was stirred at room temperature for 1 h. THF was removed in vacuo. The crude product was dissolved in EtOAc (20 mL) and saturated NaHCO₃ (40 mL) was added. The layers were separated and the aqueous layer was extracted with EtOAc (20 mL). The combined organic layer was washed with brine (50 mL) and dried over Na₂SO₄ and the solvent was evaporated. The residue was co-evaporated with DCM (10 mL) and then stirred in Et₂O (20 mL) and the solids were filtered off. The filtrate was purified by column chromatography (silica, heptane/EtOAc, 3:1) to give 2.6 g (97%) the desired product as a yellow oil.

Step 3: 1-Benzyl-3-(4-chlorophenyl)-5-(trifluoromethyl)-1H-pyrrole-2-carboxylic acid (ACI-06)

To a solution of ethyl 1-benzyl-3-(4-chlorophenyl)-5-(trifluoromethyl)-1H-pyrrole-2-carboxylate (2.59 g, 6.35 mmol) in dry THF (15 mL) was added a solution of NaOH (3.9 g, 98 mmol) in H₂O (15 mL). The reaction mixture was stirred overnight at 80° C. An additional portion of NaOH (4.25 g, 106 mmol) was added and the reaction mixture was stirred at 100° C. during 7 h. The organic solvent was evaporated and the residue was acidified with aqueous 5 M HCl (55 mL). The product was extracted with EtOAc (3×20 mL). The combined organic layer was washed with brine (3×20 mL) and dried (Na₂SO₄). The remaining oil was triturated with heptane (20 mL). The off-white solids were filtered off to give 1.29 g (51%) ACI-06.

Synthesis of 1-(3-Chlorobenzyl)-3-(4-chlorophenyl)-5-(trifluoromethyl)-1H-pyrrole-2-carboxylic acid (ACI-07)

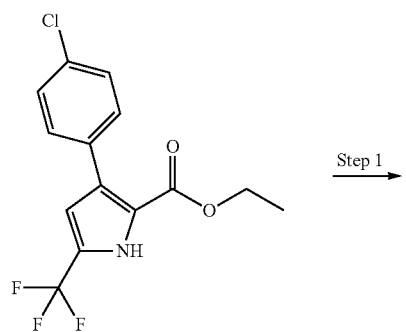

Step 1 →

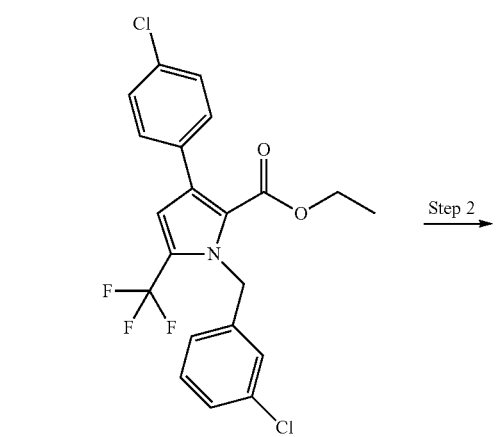

Step 2 →

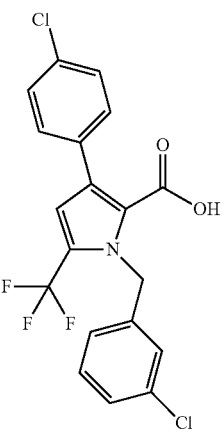

Step 1: Ethyl 1-(3-chlorobenzyl)-3-(4-chlorophenyl)-5-(trifluoromethyl)-1H-pyrrole-2-carboxylate KOt-Bu (265 mg, 2.36 mmol) and 18-crown-6 (catalytic amount) were added to ethyl 3-(4-chlorophenyl)-5-(trifluoromethyl)-1H-pyrrole-2-carboxylate [for synthesis see ACI-06] (500 mg, 1.57 mmol) in dry THF (5 mL). The reaction mixture was stirred for 30 min. and 1-(bromomethyl)-3-chlorobenzene (647 mg, 3.15 mmol) was added to the reaction mixture. The reaction mixture was stirred at reflux temperature overnight. The reaction mixture was acidified with aqueous 1M KHSO₄ (4 mL), diluted with H₂O (4 mL) and extracted with EtOAc (50 mL). The organic layer was washed with brine, dried (Na₂SO₄), and concentrated to give crude product as a colourless oil (732 mg).

Step 2: 1-(3-Chlorobenzyl)-3-(4-chlorophenyl)-5-(trifluoromethyl)-1H-pyrrole-2-carboxylic acid (ACI-07)

To crude ethyl 1-(3-chlorobenzyl)-3-(4-chlorophenyl)-5-(trifluoromethyl)-1H-pyrrole-2-carboxylate (732 mg, max. 1.57 mmol) in EtOH (2 mL) and H₂O (2 mL) was added LiOH.H₂O (347 mg, 8.28 mmol). The reaction mixture was stirred at reflux temperature overnight. The reaction mixture was concentrated, diluted with H₂O (5 mL) and acidified with aqueous 1 M KHSO₄ (10 mL) while cooling with an ice-bath. The precipitate was filtered, washed with H₂O (2×) and dried on filter to give ACI-07 (533 mg, 82% over two steps).

Synthesis of 1-Benzyl-3-(4-chloro-2-fluorophenyl)-5-(trifluoromethyl)-1H-pyrrole-2-carboxylic acid (ACI-08)

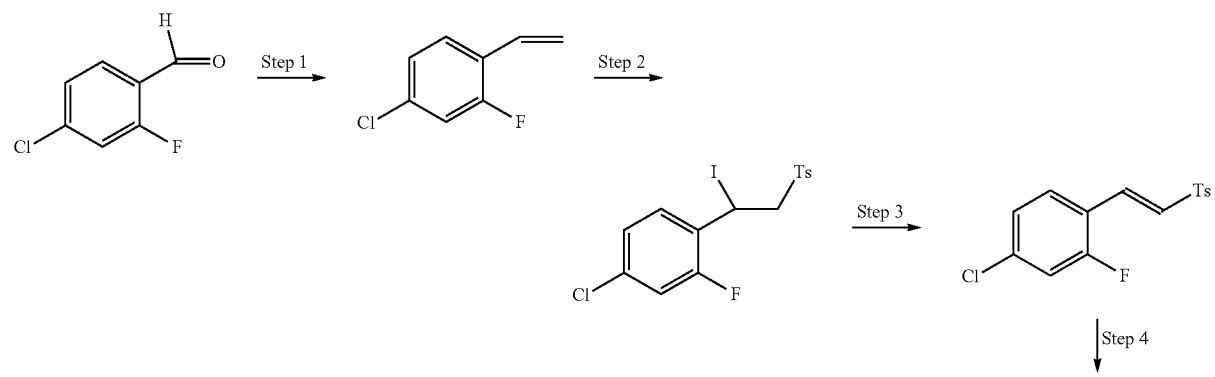

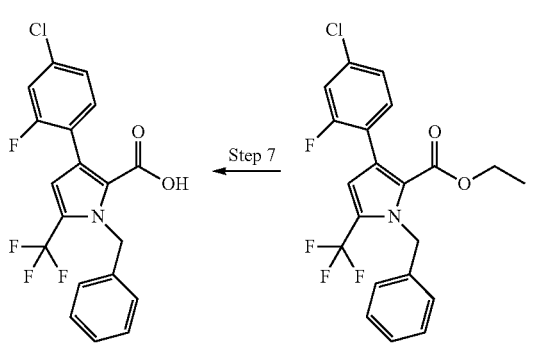 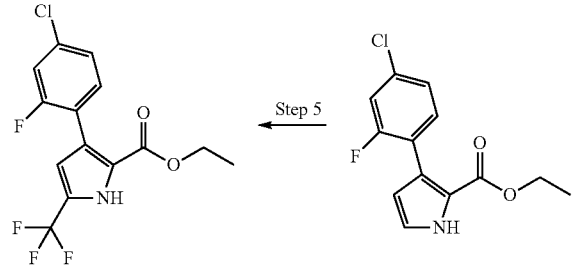

Step 1: 4-Chloro-2-fluoro-1-vinylbenzene

A solution of KOt-Bu (19.5 g, 174 mmol) in dry THF (300 mL) was cooled with an ice/water bath. Portionwise addition of MePPh₃Br (62.2 g, 174 mmol) resulted in a suspension, which was stirred for 5 min at 0° C. and for 1 h at 15° C. Subsequently, the temperature was lowered to 0° C. and a solution of 4-chloro-2-fluorobenzaldehyde (25.1 g, 158 mmol) in dry THF (100 mL) was added dropwise. The temperature was raised to room temperature slowly. The reaction mixture was stirred at room temperature for 20 h. Addition of brine (100 mL) resulted in a clear two phase system and a white solid. The combination of layers was decanted from the solid. The layers were separated, the aqueous layer was combined with the solid residue and Et₂O (200 mL). The combination of layers was decanted from the solid. The layers were separated, the combination of organic layers was dried (Na₂SO₄) and concentrated at a controlled vacuum of 100 mbar. The residual oil was combined with pentane (300 mL) and Na₂SO₄. The suspension was triturated. Filtration and pentane washing provided a filtrate, which was concentrated at a controlled vacuum of 100 mbar to arrive at 26.76 g (97%, 90% purity) of impure title compound as a yellow oil.

Step 2: 4-Chloro-2-fluoro-1-(1-iodo-2-tosylethyl)benzene

To a mechanically stirred mixture of impure 4-chloro-2-fluoro-1-vinylbenzene (26.76 g, 154 mmol), sodium p-toluenesulfinate (28.8 g, 161 mmol) and NaI (34.6 g, 231 mmol) in MeCN (700 mL) was added (NH₄)₂Ce(NO₃)₆ (169 g, 308 mmol) portionwise. The mixture was stirred under a nitrogen atmosphere during 3 h at room temperature. The liquid was separated by decantation and the solids were washed with MeCN (3×100 mL). The solvent was evaporated in vacuo and re-dissolved in EtOAc (500 mL). The organic layer was washed with brine (400 mL), aqueous 10 wt % Na₂S₂O₃ (2×200 mL) and brine (200 mL). The organic layer was dried (Na₂SO₄) and the solvent was evaporated to arrive at 51.86 g of crude title compound as a yellow solid.

Step 3: (E)-4-Chloro-2-fluoro-1-(2-tosylvinyl)benzene

Crude 4-chloro-2-fluoro-1-(1-iodo-2-tosylethyl)benzene (51.8 g, max. 154 mmol) was dissolved in a mixture of Et₂O (250 mL), THF (50 mL) and EtOAc (80 mL) after some warming. Carefully, Et₃N (23.6 mL, 170 mmol) was added in 2 mL portions at room temperature. The mixture was stirred for 90 min at room temperature. Aqueous 1 M NaHSO₄ (200 mL) and H₂O (100 mL) were added and the organic layer was separated. The aqueous layer was extracted with EtOAc (50 mL). The combination of organic layers was washed with saturated aqueous NaHCO₃ and with brine, dried (Na₂SO₄) and filtered. The solvent was evaporated in vacuo to give a yellow solid. The residue was triturated in MeOH (50 mL), filtration and air-drying provided 23.04 g (48% over two steps) of the desired product as a white solid.

Step 4: Ethyl 3-(4-chloro-2-fluorophenyl)-1H-pyrrole-2-carboxylate

A suspension of 60% NaH in mineral oil (0.772 g, 19.3 mmol) in dry THF (30 mL) was prepared and cooled with a water bath. A solution of (E)-4-chloro-2-fluoro-1-(2-tosylvinyl)benzene (5.0 g, 16.1 mmol) and ethyl 2-isocyanoacetate (1.93 mL, 17.7 mmol) in dry THF (30 mL) was prepared and added dropwise at room temperature. The reaction mixture was stirred for 2 h at room temperature. Subsequently, saturated aqueous NH₄Cl (30 mL), ice (ca. 10 g), Et₂O (100 mL) and EtOAc (10 mL) were added to result in a clear two phase system. The layers were separated, the aqueous layer was extracted with Et₂O (30 mL). The combination of organic layers was washed with brine twice, dried (Na₂SO₄), co-evaporated with DCM and with toluene twice. The resulting dark oil was dissolved in DCM (a few mL) and used for filtration over silica (heptane/EtOAc 1:1). This resulted in 3.88 g (90%) of the desired product as a yellow oil, which crystallised on standing.

Step 5: Ethyl 3-(4-chloro-2-fluorophenyl)-5-(trifluoromethyl)-1H-pyrrole-2-carboxylate To a mixture of ethyl 3-(4-chloro-2-fluorophenyl)-1H-pyrrole-2-carboxylate (2.00 g, 7.47 mmol), K₂HPO₄ (3.90 g, 22.4 mmol) and dichlortris(1,10-phenanthroline)-ruthenium (II) hydrate (106 mg, 0.149 mmol) in argon degassed dry MeCN (24 mL) was added CF₃SO₂Cl (1.59 mL, 14.9 mmol). The reaction mixture was stirred for 18 h at a temperature of 25-30° C. adjacent to a fluorescent light bulb (E27-32W, 4000K, 65 mA). The reaction mixture was diluted with argon degassed dry MeCN (24 mL). Extra reagents were added: CF₃SO₂Cl (398 μL, 3.73 mmol) and dichlortris(1,10-phenanthroline)-ruthenium(II) hydrate (106 mg, 0.149 mmol). The reaction mixture was stirred for 3 d at a temperature of 25-30° C. adjacent to a fluorescent light bulb. Subsequently, EtOAc (100 mL) and H₂O (100 mL) were added. The aqueous layer was extracted with EtOAc (50 mL). The combination of organic layers was washed with saturated aqueous NaHCO₃ and with brine, dried (Na₂SO₄) and the solvent was evaporated. The crude product was purified by flash chromatography (silica, gradient heptane/EtOAc, 1:0→4:1) to give a yellow solid, which was crystallised from hot heptane to provide 1.01 g (40%) of the desired product as colourless crystals.

Step 6: Ethyl 1-benzyl-3-(4-chloro-2-fluorophenyl)-5-(trifluoromethyl)-1H-pyrrole-2-carboxylate To a solution of ethyl 3-(4-chloro-2-fluorophenyl)-5-(trifluoromethyl)-1H-pyrrole-2-carboxylate (1.33 g, 3.96 mmol) in dry MeCN (20 mL) was added $K_2CO_3$ (1.10 g, 7.92 mmol) and benzyl bromide (521 µL, 4.36 mmol). The reaction mixture was stirred overnight at 80° C. Addition of silica (ca. 2 g) was followed by filtration; the filtrate was concentrated in vacuo. The product was co-evaporated twice with toluene (30 mL), to result in 1.75 g (99%, 95% purity) of the desired product as a clear oil.

Step 7: 1-Benzyl-3-(4-chloro-2-fluorophenyl)-5-(trifluoromethyl)-1H-pyrrole-2-carboxylic acid (ACI-08)

To a solution of ethyl 1-benzyl-3-(4-chloro-2-fluorophenyl)-5-(trifluoromethyl)-1H-pyrrole-2-carboxylate (1.69 g, 3.77 mmol) in DMSO (10 mL) were added crushed pellets of NaOH (397 mg, 9.92 mmol). The reaction mixture was stirred at room temperature overnight. Subsequently, 0.3 M aqueous HCl (70 mL) and EtOAc (30 mL) were added to result in a clear two phase system. The layers were separated, the organic layer was washed with $H_2O$ (20 mL) twice and with brine twice, dried ($Na_2SO_4$) and concentrated in vacuo. The residue was triturated in heptane, filtration and air-drying provided 1.36 g (91%) of carboxylic acid ACI-08 as a white solid.

Synthesis of 1-Benzyl-3-(4-fluorophenyl)-4-methyl-5-(trifluoromethyl)-1H-pyrrole-2-carboxylic acid (ACI-09)

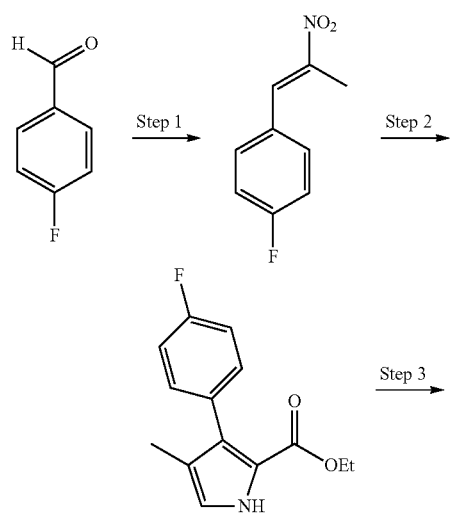

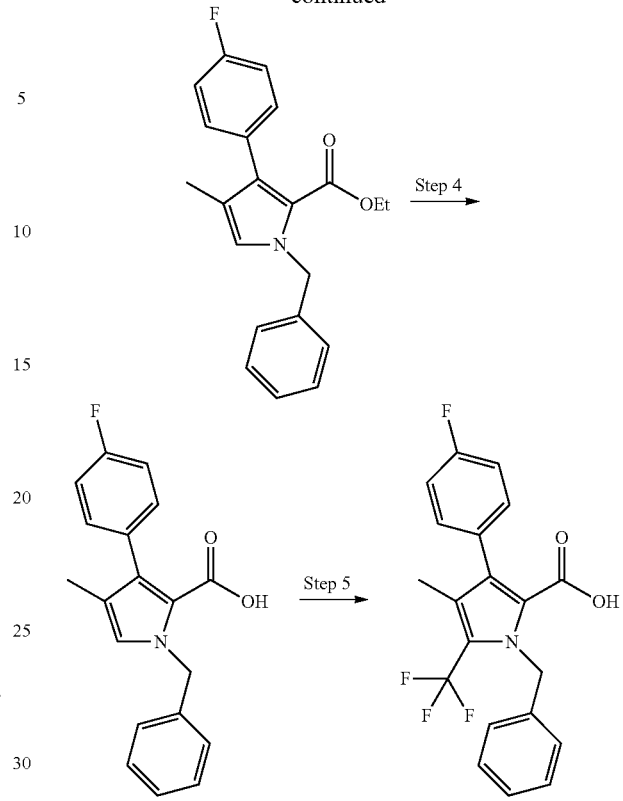

Step 1: (E)-1-Fluoro-4-(2-nitroprop-1-enyl)benzene

A solution of 4-fluorobenzaldehyde (5.0 g, 40.32 mmol), nitro ethane (3.2 mL, 44.35 mmol), trimethyl orthoformate (9.7 mL, 88.70 mmol), methylamine HCl (2.1 g, 31.44 mmol) and potassium acetate (2.76 g, 28.22 mmol) in methanol (50 mL) was refluxed at 80° C. for 18 h. Methanol was evaporated; the residue diluted with water (100 mL), extracted with EtOAc (3×50 mL). The combined organic layer was washed with water (50 mL), brine (50 mL), dried ($Na_2SO_4$) and concentrated. The residue triturated with methanol (10 mL), filtered off and washed with cold methanol (5 mL) to afford the desired product (1.82 g, 25%) as a yellow solid.

Step 2: Ethyl 3-(4-fluorophenyl)-4-methyl-1H-pyrrole-2-carboxylate

Ethyl isocyanoacetate (4.36 mL, 42.09 mmol) and DBU (6.28 mL, 42.09 mmol) was added to a solution of (E)-1-fluoro-4-(2-nitroprop-1-enyl)benzene (6.0 g, 33.14 mmol) in THF (60 mL) at 0° C. The reaction mixture was stirred for 30 min at room temperature; quenched with water (100 mL) and extracted with EtOAc (2×100 mL). The combined organic layers were washed with water (1×100 mL) and brine (75 mL), dried ($Na_2SO_4$) and concentrated under reduced pressure to give the crude product, which was purified by column chromatography (silica gel; 60-120 mesh). The pure product was eluted with 10% EtOAc in petroleum ether to yield the desired compound (6.0 g, 73%) as pale yellow solid.

Step 3: Ethyl 1-benzyl-3-(4-fluorophenyl)-4-methyl-1H-pyrrole-2-carboxylate

A solution of ethyl 3-(4-fluorophenyl)-4-methyl-1H-pyrrole-2-carboxylate (5.5 g, 22.26 mmol) in DMF (12 mL) was added to a mixture of 60% NaH (1.1 g, 33.39 mmol) in dry DMF (20 mL) at 0° C. under a N₂ atmosphere and the mixture was stirred for 15 min. Benzyl bromide (2.9 mL, 24.49 mmol) was added and it was stirred at 80° C. for 12 h. The reaction mixture was cooled to 0° C., quenched with brine (20 mL), diluted with water (50 mL) and extracted with EtOAc (3×50 mL). The combined organic layers were washed with water (75 mL) and brine (75 mL), dried (Na₂SO₄) and concentrated under reduced pressure to afford the desired product (6.5 g, 87%) as brown color solid.

Step 4: 1-Benzyl-3-(4-fluorophenyl)-4-methyl-1H-pyrrole-2-carboxylic acid

Ethyl 1-benzyl-3-(4-fluorophenyl)-4-methyl-1H-pyrrole-2-carboxylate (5.0 g, 14.83 mmol) was added to a solution of 8M NaOH (30 mL) and catalytic amount of TBAF (0.5 mL) at 0° C. The resulting mixture was stirred at 110° C. for 24 h. The reaction mixture was cooled to 0° C., acidified (pH-2) with 6N HCl and extracted with EtOAc (3×50 mL). The combined organic layers were washed with brine (100 mL), dried (Na₂SO₄) and concentrated to afford the desired product (3.8 g, 84%) as a brown solid.

Step 5: 1-Benzyl-3-(4-fluorophenyl)-4-methyl-5-(trifluoromethyl)-1H-pyrrole-2-carboxylic acid (ACI-09)

CF₃I (10 g) gas was bubbled through a solution of 1-benzyl-3-(4-fluorophenyl)-4-methyl-1H-pyrrole-2-carboxylic acid (4.0 g, 12.94 mmol) in DMSO (40 mL) and FeSO₄.7H₂O (2.15 g, 7.76 mmol) at RT for 5 min. 30% Aqueous H₂O₂ (8.7 mL, 77.64 mmol) was then added at 0° C. and stirring was continued at room temperature for 16 h. The reaction mixture was diluted with water (100 mL) and extracted with EtOAc (3×50 mL). The combined organic layers were washed with water (1×100 mL) and brine (50 mL), dried (Na₂SO₄) and concentrated in vacuo. The crude product was purified by column chromatography (silica gel; 60-120 mesh); it eluted with 10-12% EtOAc in petroleum ether to yield ACI-09 (1.7 g, 35%) as a white solid.

1-Benzyl-4-methyl-5-(trifluoromethyl)-3-(4-(trifluoromethyl)phenyl)-1H-pyrrole-2-carboxylic acid (ACI-10), 1-Benzyl-4-methyl-3-(4-(trifluoromethoxy)phenyl)-5-(trifluoromethyl)-1H-pyrrole-2-carboxylic acid (ACI-11), 1-Benzyl-3-(4-chloro-3-fluorophenyl)-4-methyl-5-(trifluoromethyl)-1H-pyrrole-2-carboxylic acid (ACI-12) and 1-Benzyl-3-(3-chloro-4-fluorophenyl)-4-methyl-5-(trifluoromethyl)-1H-pyrrole-2-carboxylic acid (ACI-13) were synthesized in analogy to ACI-09, utilising the appropriate benzaldehyde.

1.2 Synthesis of Non-Commercially Available Amine Building Blocks (AMN)

Synthesis of (1-Methoxycyclopropylmethanamine hydrochloride (AMN-22)

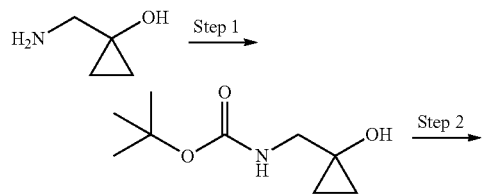

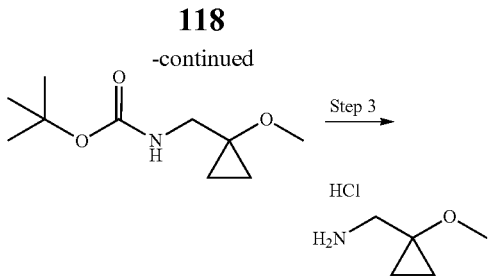

Step 1: tert-Butyl (1-hydroxycyclopropyl)methylcarbamate 1-(Aminomethyl)cyclopropanol (250 mg, 2.87 mmol) was dissolved in DCM (8 mL) with dry DMF (2 mL). Boc₂O (626 mg, 2.87 mmol) was added and the mixture was stirred at room temperature overnight. The reaction mixture was concentrated in vacuo and the residue (still containing DMF) was partitioned between brine (10 mL) and EtOAc (10 mL). The aqueous layer was extracted with EtOAc (2×10 mL) and the combined organic layers were washed with brine (2×10 mL) and dried on Na₂SO₄ before concentration in vacuo to give 505 mg (94%) of a light yellow oil which solidified on standing. According to ¹H-NMR this appeared to be a mixture of the expected product and 40% Boc₂O. The intermediate was dissolved in dry THF (2 mL) and the solution was added dropwise at room temperature to 2.4M LiAlH₄ in THF (6 mL, 14.40 mmol). The mixture was stirred at 70° C. overnight. The reaction mixture was cooled in an ice bath and saturated aqueous Na₂SO₄ (20 mL) was added slowly. The turbid mixture was filtered over Celite and washed with EtOAc and the layers were separated. The organic layer was washed with brine (2×20 mL) and dried over Na₂SO₄ before concentration in vacuo to give the desired product (150 mg) as a yellow solid.

Step 2: tert-Butyl (1-methoxycyclopropyl)methylcarbamate tert-Butyl (1-hydroxycyclopropyl)methylcarbamate (150 mg) was dissolved in dry DMF (2 mL) and Cs₂CO₃ (313 mg, 0.961 mmol) was added, followed by MeI (0.053 mL, 0.841 mmol). The light yellow suspension was stirred in a sealed vessel at room temperature overnight. More MeI (0.050 mL, 0.801 mmol) was added and stirring was continued for 2 d. The reaction mixture was partitioned between aqueous saturated NaHCO₃ (25 mL) and EtOAc (25 mL). The aqueous layer was extracted with EtOAc (2×10 mL) and the combined organic layers were washed with saturated aqueous NaHCO₃ (2×25 mL). The organic layer was washed with brine (2×25 mL) and dried on Na₂SO₄ before concentration in vacuo to give a yellow oil. The product was filtered over a plug of silica (eluent heptane/iPr₂O 1:1) to give the title compound (90 mg, 16% from 1-(aminomethyl)cyclopropanol) as a colorless oil.

Step 3: (1-Methoxycyclopropyl)methanamine hydrochloride (AMN-22)

4M HCl in dioxane (0.447 mL, 1.789 mmol) was added dropwise to a solution of tert-butyl (1-methoxycyclopropyl)methylcarbamate (90 mg, 0.447 mmol) in dry dioxane (1 mL) under a N₂ atmosphere. The mixture was stirred at room temperature overnight. The mixture was evaporated to dryness and the residue was co-evaporated with Et₂O to afford 57 mg (93%) of AMN-22 as a yellow solid.

Synthesis of 1-((Methylamino)methyncyclopropanol hydrochloride (AMN-24)

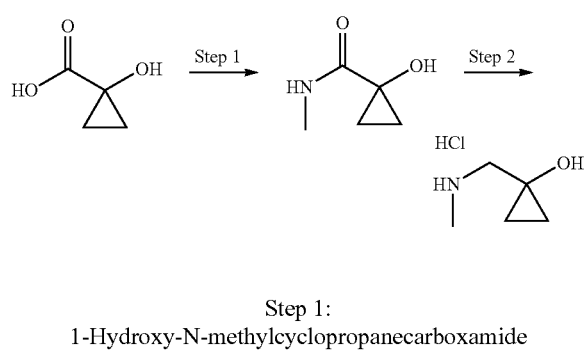

Step 1: 1-Hydroxy-N-methylcyclopropanecarboxamide

To a solution of 1-hydroxycyclopropanecarboxylic acid (250 mg, 2.45 mmol) and Et₃N (0.851 mL, 6.12 mmol) in DCM (5 mL) were added subsequently methylamine HCl (207 mg, 3.06 mmol), EDCI (540 mg, 2.82 mmol) and HOAt (333 mg, 2.45 mmol) at room temperature. After stirring for 5 d, the mixture was concentrated and the crude product was purified by flash chromatography (silica, gradient heptane/EtOAc, 1:1→0:1) to give the desired product (220 mg, 78%) as a white solid.

Step 2: 1-((Methylamino)methyl)cyclopropanol hydrochloride (AMN-24)

To a solution of 1-hydroxy-N-methylcyclopropanecarboxamide (110 mg, 0.955 mmol) in dry Et₂O (2 mL) was added 1M BH₃ in THF (4.78 mL, 4.78 mmol). The reaction mixture was refluxed for 2.5 h, cooled to room temperature and quenched with MeOH (0.5 mL). 1M HCl in Et₂O (9.55 mL, 9.55 mmol) was added dropwise and the mixture stirred for 1.5 h. The solids were filtered off and transferred into a flask and co-evaporated with Et₂O to afford 94 mg (72%) of AMN-24 as a colorless glass like solid.

Synthesis of N,3,3-Trimethylbutan-1-amine hydrochloride (AMN-38)

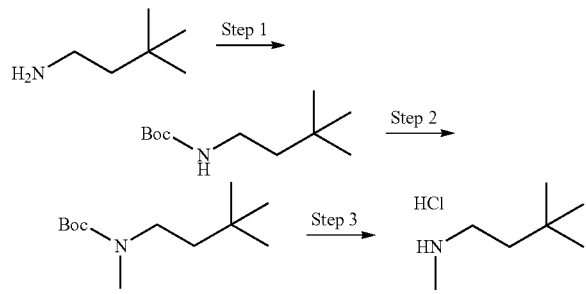

Step 1: tert-Butyl 3,3-dimethylbutylcarbamate

To a cooled (0° C.) solution of 3,3-dimethylbutan-1-amine (866 mg, 8.56 mmol in DCM (9 mL) was added Boc₂O (1.87 g, 8.56 mmol). The reaction mixture was stirred at room temperature overnight. The reaction mixture was concentrated and diluted with saturated aqueous NaHCO₃ (20 mL) and extracted with DCM (10 mL). The combined organic layers were dried (Na₂SO₄) and evaporated to give the desired product (1.72 g, 100%) as a colourless oil.

Step 2: tert-Butyl 3,3-dimethylbutyl(methyl)carbamate

To a solution of tert-butyl 3,3-dimethylbutylcarbamate (1.72 g, 8.56 mmol) in dry DMF (20 mL) was portionwise added 60% NaH in mineral oil (685 mg, 17.12 mmol) under a N₂ atmosphere. After 30 min, MeI (2.68 mL, 42.8 mmol) was added dropwise with ice cooling. The mixture was stirred at room temperature for 2 d, poured in ice-H₂O and extracted with Et₂O (30 mL). The organic layer was dried (Na₂SO₄) and concentrated to yield the desired product (1.43 g, 63%, 80% purity) as a colourless oil.

Step 3: N,3,3-Trimethylbutan-1-amine hydrochloride (AMN-38)

4 M HCl in dioxane (4.05 mL, 16.2 mmol) was added dropwise to a solution of tert-butyl 3,3-dimethylbutyl(methyl)carbamate (436 mg, 1.62 mmol) in dry dioxane (4 mL) under a N₂ atmosphere. The mixture was stirred at room temperature for 3 d. The mixture was evaporated to dryness, co-evaporated with DCM (15 mL) and the residue was stirred in Et₂O for 30 min. The solids were filtered off, rinsed with Et₂O and dried on air to yield AMN-38 (222 mg, 72%) as a white solid.

Synthesis of N,2-Dimethyl-2-morpholinopropan-1-amine hydrochloride (AMN-39)

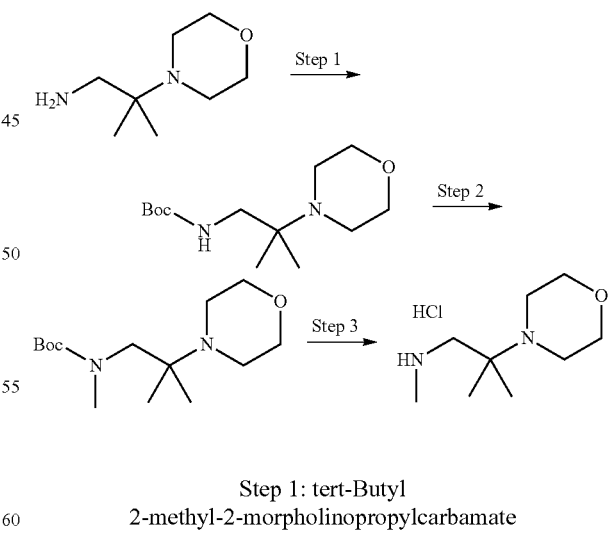

Step 1: tert-Butyl 2-methyl-2-morpholinopropylcarbamate

To a solution of 2-methyl-2-morpholinopropan-1-amine (531 mg, 3.36 mmol) in DCM (5 mL) was added Boc₂O (732 mg, 3.36 mmol). The reaction mixture was stirred at room temperature. After 1.5 h the reaction mixture was concentrated and diluted with aqueous saturated NaHCO₃ and extracted with DCM (30 mL). The combined organic layers were dried (Na$_2$SO$_4$) and evaporated to give the desired product (770 mg, 89%) as a yellow oil.

Step 2: tert-Butyl methyl(2-methyl-2-morpholinopropyl)carbamate

To a suspension of 60% NaH in mineral oil (238 mg, 5.96 mmol) in dry DMF (5 mL) was added dropwise a solution of tert-butyl 2-methyl-2-morpholinopropylcarbamate (770 mg, 2.98 mmol) in dry DMF (5 mL). After 30 min MeI (0.928 mL, 14.9 mmol) was added dropwise. The mixture was stirred at room temperature for 5 d, poured in H$_2$O and extracted with Et$_2$O (30 mL). The organic layer was dried (Na$_2$SO$_4$) and concentrated to yield the desired crude product (970 mg,) as a light yellow oil.

Step 3: N,2-Dimethyl-2-morpholinopropan-1-amine hydrochloride (AMN-39)

4 M HCl in dioxane (0.890 mL, 3.5 mmol) was added dropwise to a solution of tert-butyl methyl(2-methyl-2-morpholinopropyl)carbamate (970 mg, max. 2.98 mmol) in dry dioxane (5 mL) under a N$_2$ atmosphere. The mixture was stirred at room temperature for 6 h. The mixture was evaporated to dryness and the residue was stirred in Et$_2$O overnight. The solids were filtered off, rinsed with Et$_2$O and dried on air to yield a white solid. The solids were dissolved in dry dioxane (2 mL) and 4 M HCl in dioxane (0.890 mL, 3.5 mmol) was added. The reaction mixture was stirred at room temperature overnight. The mixture was diluted with Et$_2$O and the solids were filtered off, which resulted in AMN-39 (453 mg, 73% over 2 steps).

Synthesis of N,2-Dimethyl-2-(methylsulfonyl)propan-1-amine (AMN-43)

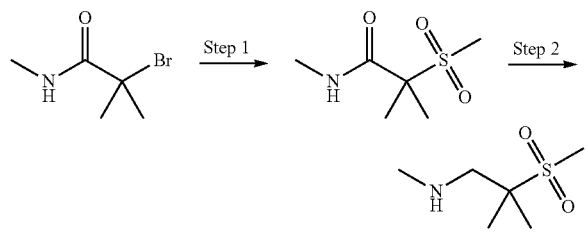

Step 1: N,2-Dimethyl-2-(methylsulfonyl)propanamide

To a suspension of methanesulfinic acid sodium salt (310 mg, 3.04 mmol) in dry DMF (3.5 mL) was added under a nitrogen atmosphere, dry pyridine (0.5 mL) and 2-bromo-N,2-dimethylpropanamide (365 mg, 2.027 mmol). The reaction mixture was stirred at 50° C. overnight, cooled and H$_2$O (5 mL) and EtOAc (10 mL) were added. The aqueous layer was separated and extracted twice with EtOAc (5 mL). The combined organic phase was washed with brine (20 mL) and dried over Na$_2$SO$_4$. The solution was concentrated in vacuo and stirred in heptane (25 mL). The solids were filtered to give the desired product (88 mg, 23%) as a white solid.

Step 1: N,2-Dimethyl-2-(methylsulfonyl)propan-1-amine (AMN-43)

AlCl$_3$ (101 mg, 0.759 mmol) was cooled to 0° C. under an nitrogen atmosphere and Et$_2$O (2 mL) was added. Dry THF (2 mL) was added after 10 min. followed by the addition of 2.4 M LiAlH$_4$ in THF (0.632 mL, 1.518 mmol). After 30 min. a solution of N,2-Dimethyl-2-(methylsulfonyl)propanamide (68 mg, 0.379 mmol) in dry THF (3 mL) was addec dropwise. The temperature was allowed to warm up to room temperature overnight. The mixture was cooled (0° C.) and qeunched with a solution of THF (5 mL) and H$_2$O (5 mL). Aqueous 1N HCl (6 mL) was added, followed by basification with solid NaHCO$_3$. The solvents were removed in vacuo. DCM (10 mL) was added and the suspension was filtered. The residue was washed with DCM (10 mL). The aqueous layer of the filtrate was separated and extracted twice with DCM (10 mL). The combined organic phase was washed with brine (20 mL) and dried over Na$_2$SO$_4$. Concentration in vacuo afforded amine AMN-43 (25 mg, 30%, 72% purity) as a white solid.

1.3 Pyrrole Derivatives (SC)

General Method for Synthesis of Pyrrole Derivatives (SC):

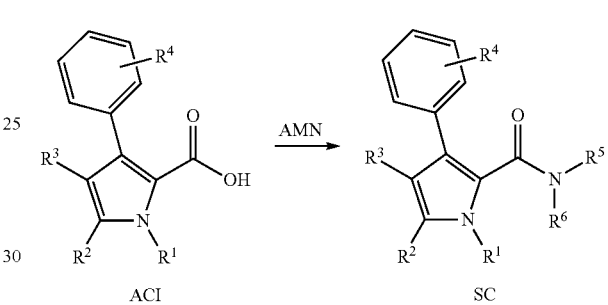

General Procedure 1 (GP-1):
ACI (1 eq.) and AMN (1-1.5 eq.) were dissolved in DME, BOP-CI (1-2.5 eq.) and DIPEA (3-5 eq.) were added. The reaction mixture was stirred at 60° C. for 2-4 h and then cooled to room temperature. Saturated aqueous NaHCO$_3$ and EtOAc were added. The layers were separated and the aqueous layer was extracted with EtOAc. The organic layers were combined, dried over Na$_2$SO$_4$ and evaporated. The product was purified by flash column chromatography.

General Procedure 2 (GP-2):
To a solution of ACI (1 eq.) and AMN (1-1.2 eq.) in DCM was added EDCI (1-1.2 eq.), followed by HOAt (0.1 eq.). The reaction mixture was stirred at room temperature for 4-16 h. The reaction mixture was washed with aqueous 1M KHSO$_4$ and saturated aqueous NaHCO$_3$, dried over Na$_2$SO$_4$ and concentrated. The crude product was purified by flash column chromatography.

General Procedure 3 (GP-3):
To a stirred solution of ACI (1 eq.) and DIPEA (2-4 eq.) in DCM or THF was added HATU (1 eq.) and stirring was continued for 15 min at 0° C. AMN (1 eq.) was added and the solution was stirred at room temperature for 12-48 h. The reaction mixture was washed with saturated aqueous NaHCO$_3$, aqueous NH$_4$Cl and brine, dried over MgSO$_4$ and concentrated. The crude product was purified by flash column chromatography.

General Procedure 4 (GP-4):
To a stirred solution of ACI (1 eq.) and DIPEA (2-4 eq.) in DCM was added EDCI (1.2 eq.), followed by HOBt (0.2 eq.) and stirring was coninued for 15 min 0° C. AMN (1 eq.) was added and the solution was stirred at room temperature for 12-72 h. The reaction mixture was washed with saturated aqueous NaHCO$_3$ and concentrated in vacuo. The crude product was purified by flash column chromatography.

General Procedure 5 (GP-5):

To a stirred solution of ACI (1 eq.) and DIPEA (2-4 eq.) in THF was added HATU (1 eq.) and stirring was continued for 15 min at 0° C. AMN (1 eq.) was added and the solution was stirred at room temperature for 12-48 h. The reaction mixture was washed with saturated aqueous NaHCO$_3$, aqueous HCl solution (pH 5) and brine, dried over MgSO$_4$ and concentrated. The crude product was purified by flash column chromatography.

General Procedure 6 (GP-6):

To a stirred solution of ACI (1 eq.) and DIPEA (2-4 eq.) in DCM or THF was added HATU (1.0 eq.), and stirring was coninued for 15 min 0° C. AMN (1 eq.) was added and the solution was stirred at room temperature for 12-72 h. The reaction mixture was diluted with DCM, washed with saturated aqueous NaHCO$_3$ and concentrated in vacuo. The crude product was purified by flash column chromatography.

Table Synthesis of pyrrole derivatives (SC):

| Example No. | Structure | Name | Synthesis according to | Yield | Comments |
|---|---|---|---|---|---|
| SC-01 | 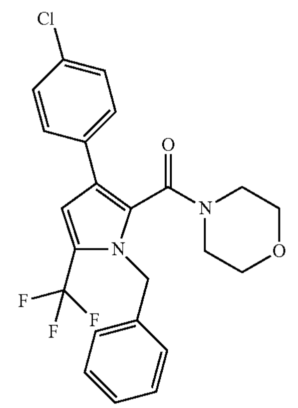 [SMILES: O=C(c1c(-c2ccc(Cl)cc2)cc(C(F)(F)F)n1Cc1ccccc1)N1CCOCC1] | [1-Benzyl-3-(4-chlorophenyl)-5-(trifluoromethyl)-1H-pyrrol-2-yl]-morpholin-4-yl-methanone | | | Prepared in analogy to SC-02 |
| SC-02 | 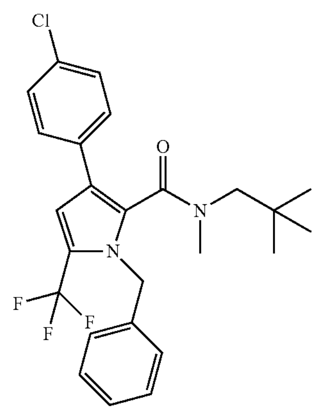 [SMILES: CN(CC(C)(C)C)C(=O)c1c(-c2ccc(Cl)cc2)cc(C(F)(F)F)n1Cc1ccccc1] | 1-Benzyl-3-(4-chlorophenyl)-N-(2,2-dimethyl-propyl)-N-methyl-5-(trifluoromethyl)-1H-pyrrole-2-carboxylic acid amide | see below | | |
| SC-03 | 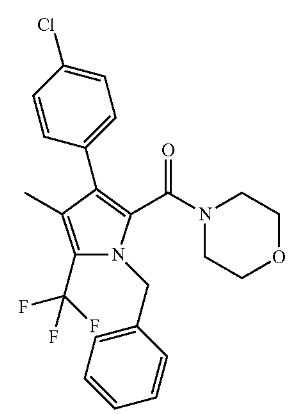 [SMILES: Cc1c(-c2ccc(Cl)cc2)c(C(=O)N2CCOCC2)n(Cc2ccccc2)c1C(F)(F)F] | [1-Benzyl-3-(4-chlorophenyl)-4-methyl-5-(trifluoromethyl)-1H-pyrrol-2-yl]-morpholin-4-yl-methanone | see below | | |

-continued

Table Synthesis of pyrrole derivatives (SC):

| Example No. | Structure | Name | Synthesis according to | Yield | Comments |
|---|---|---|---|---|---|
| SC-04 | 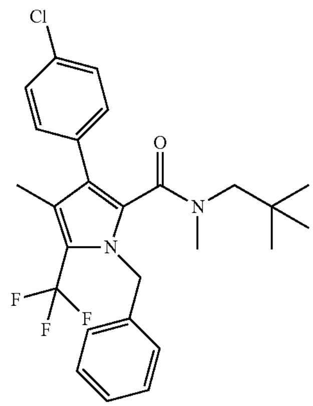 [SMILES: Cc1c(-c2ccc(Cl)cc2)c(C(=O)N(C)CC(C)(C)C)n(Cc2ccccc2)c1C(F)(F)F] | 1-Benzyl-3-(4-chlorophenyl)-N-(2,2-dimethyl-propyl)-N,4-dimethyl-5-(trifluoromethyl)-1H-pyrrole-2-carboxylic acid amide | see below | | |
| SC-05 | 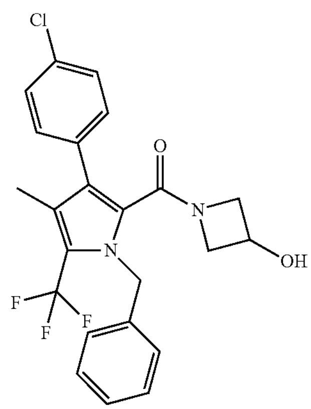 [SMILES: Cc1c(-c2ccc(Cl)cc2)c(C(=O)N2CC(O)C2)n(Cc2ccccc2)c1C(F)(F)F] | [1-Benzyl-3-(4-chlorophenyl)-4-methyl-5-(trifluoromethyl)-1H-pyrrol-2-yl]-(3-hydroxy-azetidin-1-yl)-methanone | GP-1 | 78 mg (40%) | |
| SC-06 | 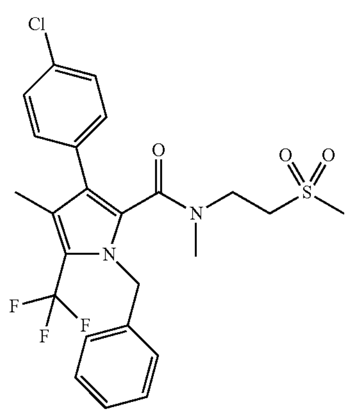 [SMILES: Cc1c(-c2ccc(Cl)cc2)c(C(=O)N(C)CCS(C)(=O)=O)n(Cc2ccccc2)c1C(F)(F)F] | 1-Benzyl-3-(4-chlorophenyl)-N,4-dimethyl-N-(2-methylsulfonyl-ethyl)-5-(trifluoromethyl)-1H-pyrrole-2-carboxylic acid amide | GP-2 | 178 mg (40%) | |

-continued

Table Synthesis of pyrrole derivatives (SC):

| Example No. | Structure | Name | Synthesis according to | Yield | Comments |
|---|---|---|---|---|---|
| SC-08 | 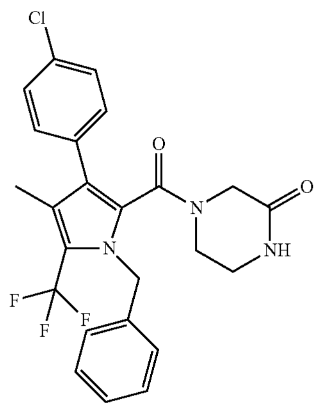 [SMILES: Cc1c(-c2ccc(Cl)cc2)c(C(=O)N2CCNC(=O)C2)n(Cc2ccccc2)c1C(F)(F)F] | 4-[1-Benzyl-3-(4-chlorophenyl)-4-methyl-5-(trifluoromethyl)-1H-pyrrole-2-carbonyl]-piperazin-2-one | GP-2 | 131 mg (40%) | |
| SC-09 | 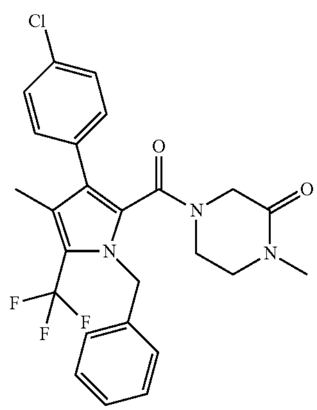 [SMILES: Cc1c(-c2ccc(Cl)cc2)c(C(=O)N2CCN(C)C(=O)C2)n(Cc2ccccc2)c1C(F)(F)F] | 4-[1-Benzyl-3-(4-chlorophenyl)-4-methyl-5-(trifluoromethyl)-1H-pyrrole-2-carbonyl]-1-methyl-piperazin-2-one | see below | | |
| SC-10 | 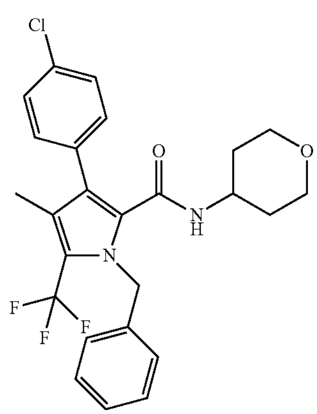 [SMILES: Cc1c(-c2ccc(Cl)cc2)c(C(=O)NC2CCOCC2)n(Cc2ccccc2)c1C(F)(F)F] | 1-Benzyl-3-(4-chlorophenyl)-4-methyl-N-tetrahydro-pyran-4-yl-5-(trifluoromethyl)-1H-pyrrole-2-carboxylic acid amide | GP-1 | 42 mg (34%) | |

Table Synthesis of pyrrole derivatives (SC):

| Example No. | Structure | Name | Synthesis according to | Yield | Comments |
|---|---|---|---|---|---|
| SC-11 | 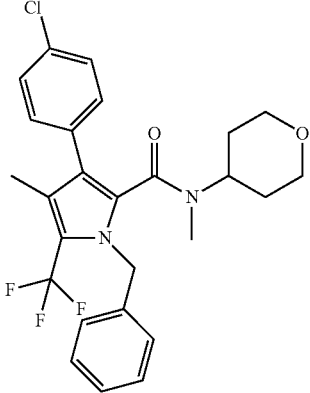 | 1-Benzyl-3-(4-chlorophenyl)-N,4-dimethyl-N-tetrahydro-pyran-4-yl-5-(trifluoromethyl)-1H-pyrrole-2-carboxylic acid amide | GP-1 | 98 mg (39%) | |
| SC-16 | 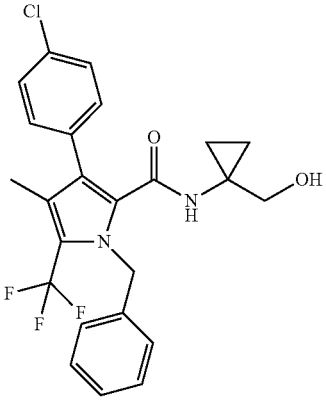 [SMILES: Cc1c(-c2ccc(Cl)cc2)c(C(=O)NC2(CO)CC2)n(Cc2ccccc2)c1C(F)(F)F] | 1-Benzyl-3-(4-chlorophenyl)-N-[1-(hydroxymethyl)-cyclopropyl]-4-methyl-5-(trifluoromethyl)-1H-pyrrole-2-carboxylic acid amide | GP-1 | 23 mg (19%) | |
| SC-17 | 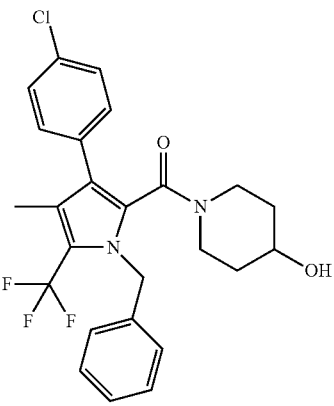 [SMILES: Cc1c(-c2ccc(Cl)cc2)c(C(=O)N2CCC(O)CC2)n(Cc2ccccc2)c1C(F)(F)F] | [1-Benzyl-3-(4-chlorophenyl)-4-methyl-5-(trifluoromethyl)-1H-pyrrol-2-yl]-(4-hydroxy-piperidin-1-yl)-methanone | GP-2 | 88 mg (73%) | |

Table Synthesis of pyrrole derivatives (SC):

| Example No. | Structure | Name | Synthesis according to | Yield | Comments |
|---|---|---|---|---|---|
| SC-18 | 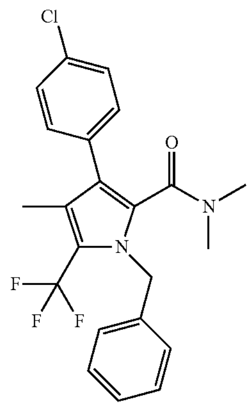 [SMILES: Cc1c(-c2ccc(Cl)cc2)c(C(=O)N(C)C)n(Cc2ccccc2)c1C(F)(F)F] | 1-Benzyl-3-(4-chlorophenyl)-N,N,4-trimethyl-5-(trifluoromethyl)-1H-pyrrole-2-carboxylic acid amide | see below | | |
| SC-19 | 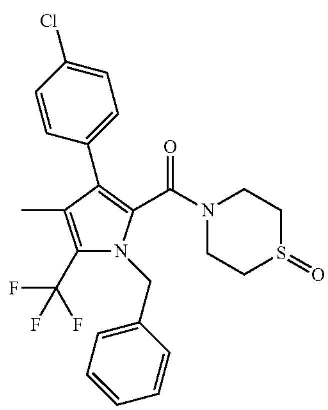 [SMILES: Cc1c(-c2ccc(Cl)cc2)c(C(=O)N2CCS(=O)CC2)n(Cc2ccccc2)c1C(F)(F)F] | [1-Benzyl-3-(4-chlorophenyl)-4-methyl-5-(trifluoromethyl)-1H-pyrrol-2-yl]-(1-oxo-[1,4]thiazinan-4-yl)-methanone | see below | | |
| SC-20 | 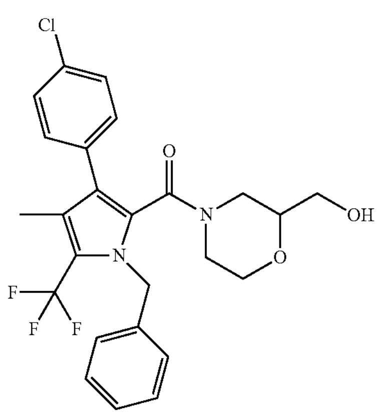 [SMILES: Cc1c(-c2ccc(Cl)cc2)c(C(=O)N2CCOC(CO)C2)n(Cc2ccccc2)c1C(F)(F)F] | [1-Benzyl-3-(4-chlorophenyl)-4-methyl-5-(trifluoromethyl)-1H-pyrrol-2-yl]-[2-(hydroxymethyl)-morpholin-4-yl]-methanone | GP-2 | 37 mg (39%) | |

-continued

Table Synthesis of pyrrole derivatives (SC):

| Example No. | Structure | Name | Synthesis according to | Yield | Comments |
|---|---|---|---|---|---|
| SC-21 | 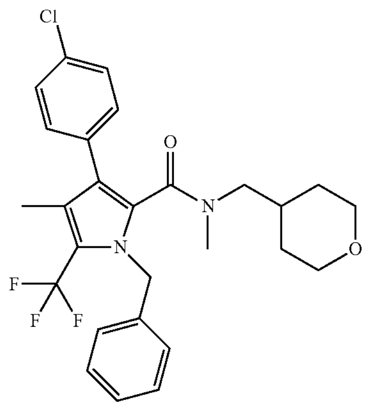 [SMILES: Cc1c(-c2ccc(Cl)cc2)c(C(=O)N(C)CC2CCOCC2)n(Cc2ccccc2)c1C(F)(F)F] | 1-Benzyl-3-(4-chlorophenyl)-N,4-dimethyl-N-(tetrahydro-pyran-4-yl-methyl)-5-(trifluoromethyl)-1H-pyrrole-2-carboxylic acid amide | GP-1 | 50 mg (39%) | |
| SC-22 | 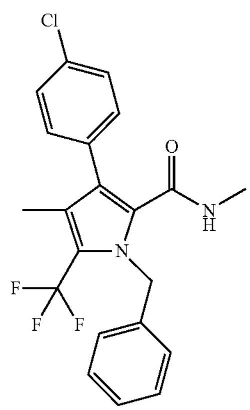 [SMILES: CNC(=O)c1c(-c2ccc(Cl)cc2)c(C)c(C(F)(F)F)n1Cc1ccccc1] | 1-Benzyl-3-(4-chlorophenyl)-N,4-dimethyl-5-(trifluoromethyl)-1H-pyrrole-2-carboxylic acid amide | see below | | |
| SC-23 | 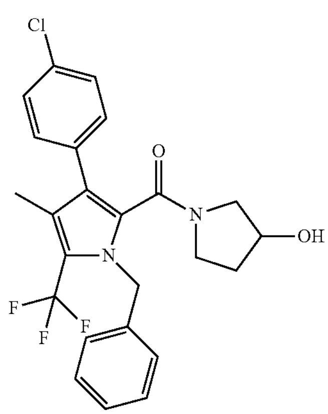 [SMILES: Cc1c(-c2ccc(Cl)cc2)c(C(=O)N2CCC(O)C2)n(Cc2ccccc2)c1C(F)(F)F] | [1-Benzyl-3-(4-chlorophenyl)-4-methyl-5-(trifluoromethyl)-1H-pyrrol-2-yl]-(3-hydroxy-pyrrolidin-1-yl)-methanone | GP-2 | 67 mg (57%) | reaction time & no. of eq of reagents/ educts were adjusted |

-continued

Table Synthesis of pyrrole derivatives (SC):

| Example No. | Structure | Name | Synthesis according to | Yield | Comments |
|---|---|---|---|---|---|
| SC-24 | 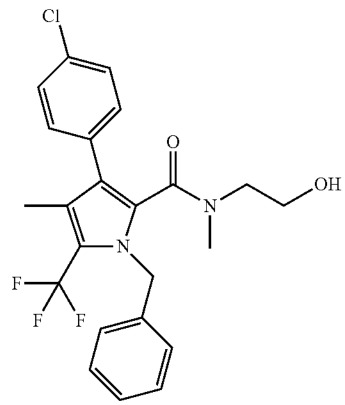 [SMILES: Cc1c(-c2ccc(Cl)cc2)c(C(=O)N(C)CCO)n(Cc2ccccc2)c1C(F)(F)F] | 1-Benzyl-3-(4-chlorophenyl)-N-(2-hydroxy-ethyl)-N,4-dimethyl-5-(trifluoromethyl)-1H-pyrrole-2-carboxylic acid amide | GP-1 | 68 mg (59%) | |
| SC-25 | 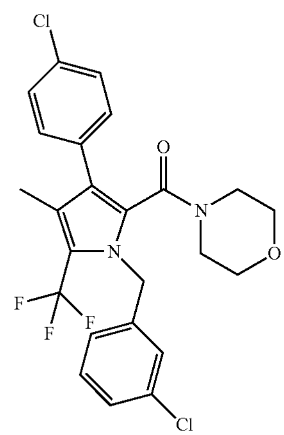 [SMILES: Cc1c(-c2ccc(Cl)cc2)c(C(=O)N2CCOCC2)n(Cc2cccc(Cl)c2)c1C(F)(F)F] | [3-(4-Chlorophenyl)-1-[(3-chlorophenyl)-methyl]-4-methyl-5-(trifluoromethyl)-1H-pyrrol-2-yl]-morpholin-4-yl-methanone | see below | | |
| SC-26 | 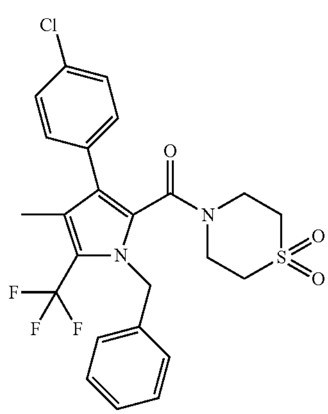 [SMILES: Cc1c(-c2ccc(Cl)cc2)c(C(=O)N2CCS(=O)(=O)CC2)n(Cc2ccccc2)c1C(F)(F)F] | [1-Benzyl-3-(4-chlorophenyl)-4-methyl-5-(trifluoromethyl)-1H-pyrrol-2-yl]-(1,1-dioxo-[1,4]thiazinan-4-yl)-methanone | see below | | |

-continued

Table Synthesis of pyrrole derivatives (SC):

| Example No. | Structure | Name | Synthesis according to | Yield | Comments |
|---|---|---|---|---|---|
| SC-29 | 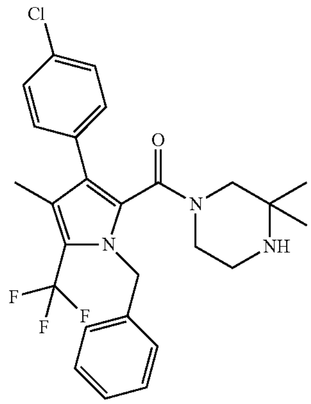 [SMILES: Cc1c(-c2ccc(Cl)cc2)c(C(=O)N2CCNC(C)(C)C2)n(Cc2ccccc2)c1C(F)(F)F] | [1-Benzyl-3-(4-chlorophenyl)-4-methyl-5-(trifluoromethyl)-1H-pyrrol-2-yl]-(3,3-dimethyl-piperazin-1-yl)-methanone | GP-1 | 109 mg (44%) | |
| SC-32 | 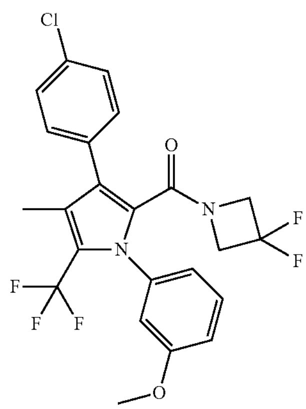 [SMILES: COc1cccc(-n2c(C(=O)N3CC(F)(F)C3)c(-c3ccc(Cl)cc3)c(C)c2C(F)(F)F)c1] | [3-(4-Chlorophenyl)-1-(3-methoxyphenyl)-4-methyl-5-(trifluoromethyl)-1H-pyrrol-2-yl]-(3,3-difluoro-azetidin-1-yl)-methanone | see below | | |
| SC-33 | 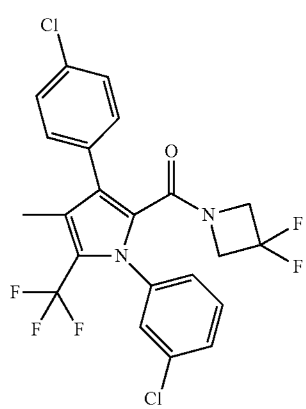 [SMILES: Cc1c(-c2ccc(Cl)cc2)c(C(=O)N2CC(F)(F)C2)n(-c2cccc(Cl)c2)c1C(F)(F)F] | [1-(3-Chlorophenyl)-3-(4-chlorophenyl)-4-methyl-5-(trifluoromethyl)-1H-pyrrol-2-yl]-(3,3-difluoro-azetidin-1-yl)-methanone | see below | | |

-continued

Table Synthesis of pyrrole derivatives (SC):

| Example No. | Structure | Name | Synthesis according to | Yield | Comments |
|---|---|---|---|---|---|
| SC-34 | 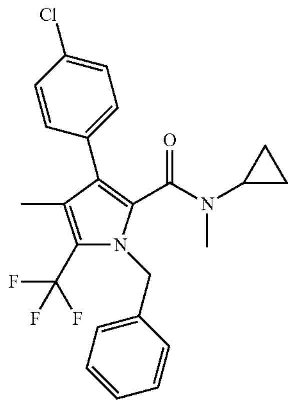 [SMILES: Cc1c(-c2ccc(Cl)cc2)c(C(=O)N(C)C2CC2)n(Cc2ccccc2)c1C(F)(F)F] | 1-Benzyl-3-(4-chlorophenyl)-N-cyclopropyl-N,4-dimethyl-5-(trifluoromethyl)-1H-pyrrole-2-carboxylic acid amide | GP-1 | 51 mg (45%) | |
| SC-35 | 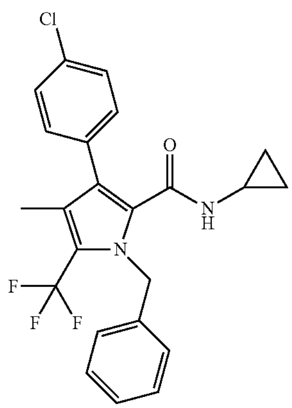 [SMILES: Cc1c(-c2ccc(Cl)cc2)c(C(=O)NC2CC2)n(Cc2ccccc2)c1C(F)(F)F] | 1-Benzyl-3-(4-chlorophenyl)-N-cyclopropyl-4-methyl-5-(trifluoromethyl)-1H-pyrrole-2-carboxylic acid amide | GP-2 | 64 mg (60%) | |
| SC-36 | 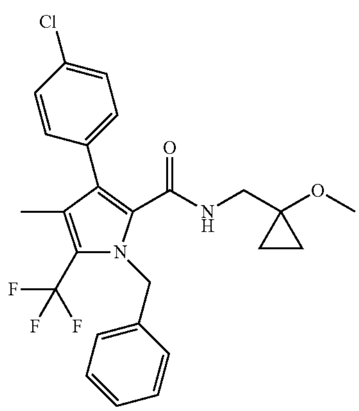 [SMILES: COC1(CNC(=O)c2c(-c3ccc(Cl)cc3)c(C)c(C(F)(F)F)n2Cc2ccccc2)CC1] | 1-benzyl-3-(4-chlorophenyl)-N-((1-methoxycyclopropyl)methyl)-4-methyl-5-(trifluoromethyl)-1H-pyrrole-2-carboxamide | GP-1 | 49 mg (37%) | |

-continued

Table Synthesis of pyrrole derivatives (SC):

| Example No. | Structure | Name | Synthesis according to | Yield | Comments |
|---|---|---|---|---|---|
| SC-37 | 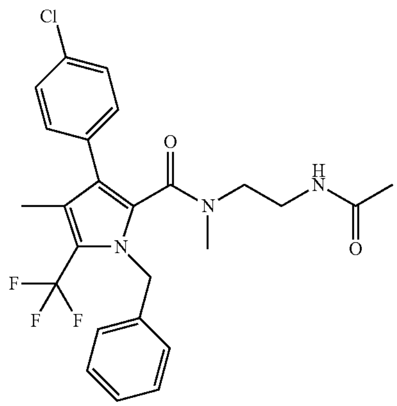 [SMILES: CC(=O)NCCN(C)C(=O)c1c(-c2ccc(Cl)cc2)c(C)c(C(F)(F)F)n1Cc1ccccc1] | N-(2-Acetylamino-ethyl)-1-benzyl-3-(4-chlorophenyl)-N,4-dimethyl-5-(trifluoromethyl)-1H-pyrrole-2-carboxylic acid amide | see below | | |
| SC-38 | 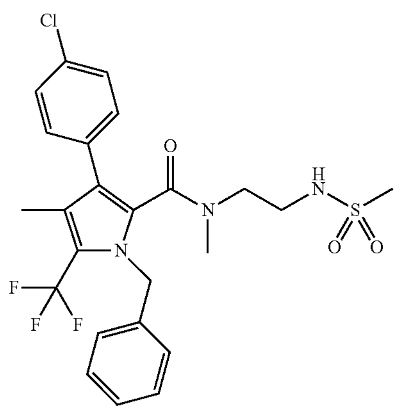 [SMILES: Cc1c(-c2ccc(Cl)cc2)c(C(=O)N(C)CCNS(C)(=O)=O)n(Cc2ccccc2)c1C(F)(F)F] | 1-Benzyl-3-(4-chlorophenyl)-N-[2-(methanesulfonamido)-ethyl]-N,4-dimethyl-5-(trifluoromethyl)-1H-pyrrole-2-carboxylic acid amide | see below | | |
| SC-39 | 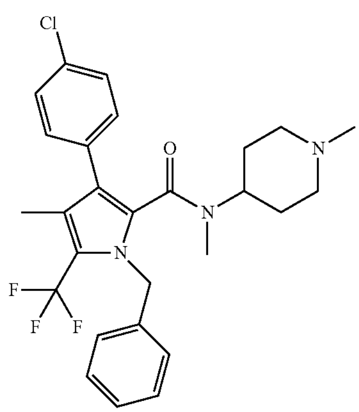 [SMILES: Cc1c(-c2ccc(Cl)cc2)c(C(=O)N(C)C2CCN(C)CC2)n(Cc2ccccc2)c1C(F)(F)F] | 1-Benzyl-3-(4-chlorophenyl)-N,4-dimethyl-N-(1-methyl-piperidin-4-yl)-5-(trifluoromethyl)-1H-pyrrole-2-carboxylic acid amide | GP-1 | 53 mg (36%) | |

-continued

Table Synthesis of pyrrole derivatives (SC):

| Example No. | Structure | Name | Synthesis according to | Yield | Comments |
| --- | --- | --- | --- | --- | --- |
| SC-40 | 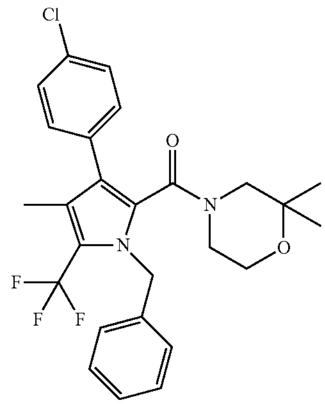 [SMILES: Cc1c(-c2ccc(Cl)cc2)c(C(=O)N2CCOC(C)(C)C2)n(Cc2ccccc2)c1C(F)(F)F] | [1-Benzyl-3-(4-chlorophenyl)-4-methyl-5-(trifluoromethyl)-1H-pyrrol-2-yl]-(2,2-dimethyl-morpholin-4-yl)-methanone | GP-2 | 85 mg (68%) | |
| SC-41 | 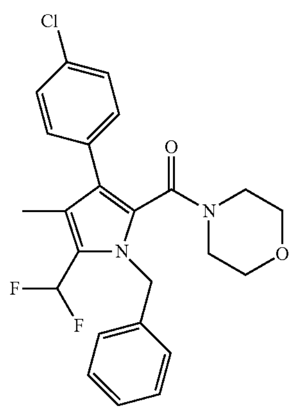 [SMILES: Cc1c(-c2ccc(Cl)cc2)c(C(=O)N2CCOCC2)n(Cc2ccccc2)c1C(F)F] | [1-Benzyl-3-(4-chlorophenyl)-5-(difluoro-methyl)-4-methyl-1H-pyrrol-2-yl]-morpholin-4-yl-methanone | see below | | |
| SC-42 | 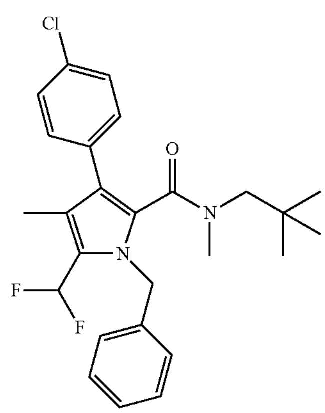 [SMILES: Cc1c(-c2ccc(Cl)cc2)c(C(=O)N(C)CC(C)(C)C)n(Cc2ccccc2)c1C(F)F] | 1-Benzyl-3-(4-chlorophenyl)-5-(difluoro-methyl)-N-(2,2-dimethyl-propyl)-N,4-dimethyl-1H-pyrrole-2-carboxylic acid amide | | | Prepared in analogy to SC-41 |

Table Synthesis of pyrrole derivatives (SC):

| Example No. | Structure | Name | Synthesis according to | Yield | Comments |
|---|---|---|---|---|---|
| SC-44 | 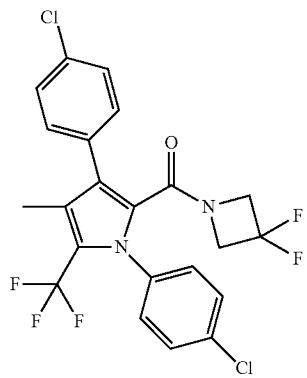 [SMILES: Cc1c(-c2ccc(Cl)cc2)c(C(=O)N2CC(F)(F)C2)n(-c2ccc(Cl)cc2)c1C(F)(F)F] | [1,3-Bis(4-chlorophenyl)-4-methyl-5-(trifluoromethyl)-1H-pyrrol-2-yl]-(3,3-difluoro-azetidin-1-yl)-methanone | see below | | |
| SC-48 | 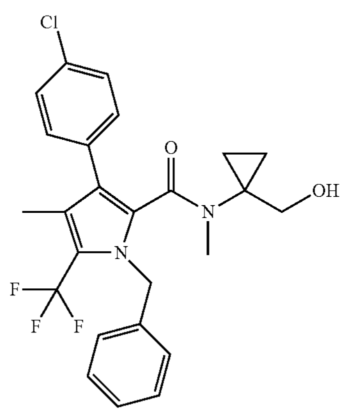 [SMILES: Cc1c(-c2ccc(Cl)cc2)c(C(=O)N(C)C2(CO)CC2)n(Cc2ccccc2)c1C(F)(F)F] | 1-Benzyl-3-(4-chlorophenyl)-N-[1-(hydroxymethyl)-cyclopropyl]-N,4-dimethyl-5-(trifluoromethyl)-1H-pyrrole-2-carboxylic acid amide | see below | | |
| SC-49 | 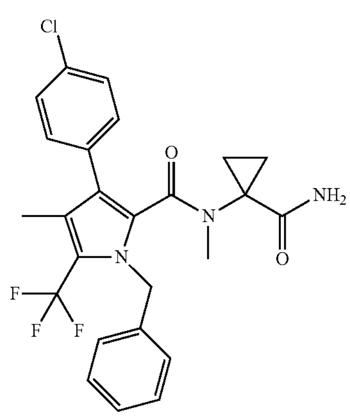 [SMILES: Cc1c(-c2ccc(Cl)cc2)c(C(=O)N(C)C2(C(N)=O)CC2)n(Cc2ccccc2)c1C(F)(F)F] | 1-Benzyl-N-(1-carbamoyl-cyclopropyl)-3-(4-chlorophenyl)-N,4-dimethyl-5-(trifluoromethyl)-1H-pyrrole-2-carboxylic acid amide | see below | | |

-continued

Table Synthesis of pyrrole derivatives (SC):

| Example No. | Structure | Name | Synthesis according to | Yield | Comments |
|---|---|---|---|---|---|
| SC-50 | 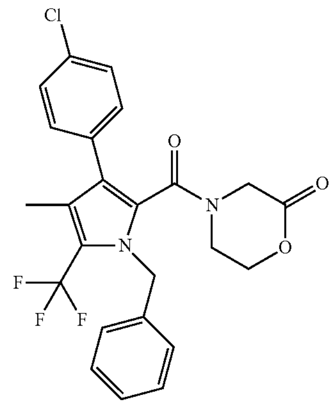 [SMILES: Cc1c(-c2ccc(Cl)cc2)c(C(=O)N2CCOC(=O)C2)n(Cc2ccccc2)c1C(F)(F)F] | 4-[1-Benzyl-3-(4-chlorophenyl)-4-methyl-5-(trifluoromethyl)-1H-pyrrole-2-carbonyl]-morpholin-2-one | see below | | |
| SC-51 | 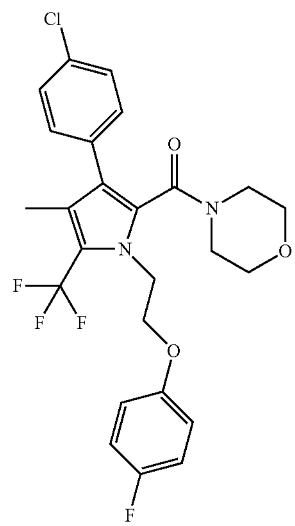 [SMILES: Cc1c(-c2ccc(Cl)cc2)c(C(=O)N2CCOCC2)n(CCOc2ccc(F)cc2)c1C(F)(F)F] | [3-(4-Chlorophenyl)-1-[2-(4-fluoro-phenoxy)-ethyl]-4-methyl-5-(trifluoromethyl)-1H-pyrrol-2-yl]-morpholin-4-yl-methanone | see below | | |
| SC-52 | 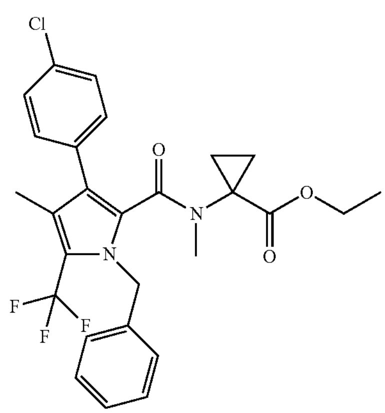 [SMILES: CCOC(=O)C1(N(C)C(=O)c2c(-c3ccc(Cl)cc3)c(C)c(C(F)(F)F)n2Cc2ccccc2)CC1] | 1-[[1-Benzyl-3-(4-chlorophenyl)-4-methyl-5-(trifluoromethyl)-1H-pyrrole-2-carbonyl]-methyl-amino]-cyclopropane-1-carboxylic acid ethyl ester | see below | | |

-continued

Table Synthesis of pyrrole derivatives (SC):

| Example No. | Structure | Name | Synthesis according to | Yield | Comments |
|---|---|---|---|---|---|
| SC-53 | 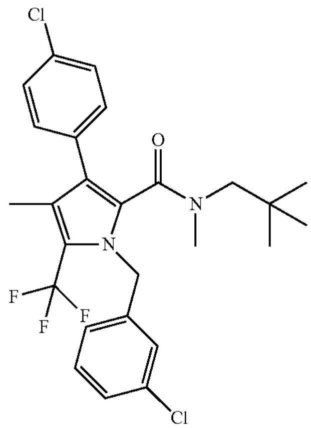 [SMILES: Cc1c(-c2ccc(Cl)cc2)c(C(=O)N(C)CC(C)(C)C)n(Cc2cccc(Cl)c2)c1C(F)(F)F] | 3-(4-Chlorophenyl)-1-[(3-chlorophenyl)-methyl]-N-(2,2-dimethyl-propyl)-N,4-dimethyl-5-(trifluoromethyl)-1H-pyrrole-2-carboxylic acid amide | GP-1 | 130 mg (63%) | |
| SC-54 | 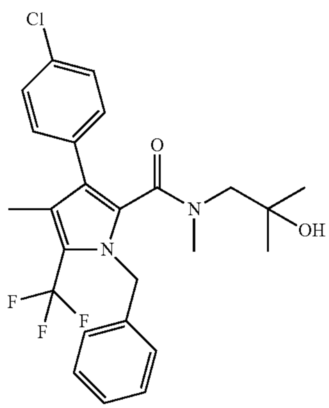 [SMILES: Cc1c(-c2ccc(Cl)cc2)c(C(=O)N(C)CC(C)(C)O)n(Cc2ccccc2)c1C(F)(F)F] | 1-Benzyl-3-(4-chlorophenyl)-N-(2-hydroxy-2-methyl-propyl)-N,4-dimethyl-5-(trifluoromethyl)-1H-pyrrole-2-carboxylic acid amide | GP-2 | 178 mg (73%) | |
| SC-55 | 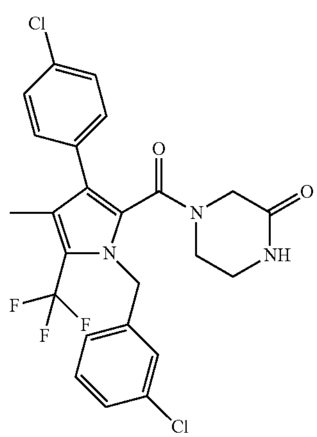 [SMILES: Cc1c(-c2ccc(Cl)cc2)c(C(=O)N2CCNC(=O)C2)n(Cc2cccc(Cl)c2)c1C(F)(F)F] | 4-[3-(4-Chlorophenyl)-1-[(3-chlorophenyl)-methyl]-4-methyl-5-(trifluoromethyl)-1H-pyrrole-2-carbonyl]-piperazin-2-one | GP-2 | 116 mg (57%) | |

-continued

Table Synthesis of pyrrole derivatives (SC):

| Example No. | Structure | Name | Synthesis according to | Yield | Comments |
|---|---|---|---|---|---|
| SC-56 | 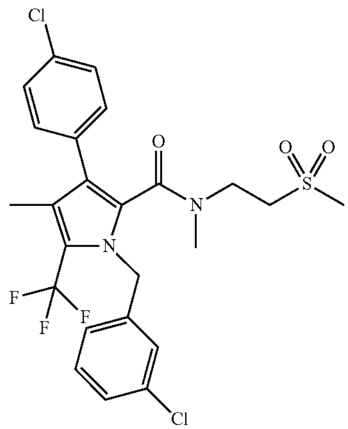 | 3-(4-Chlorophenyl)-1-[(3-chlorophenyl)-methyl]-N,4-dimethyl-N-(2-methylsulfonyl-ethyl)-5-(trifluoromethyl)-1H-pyrrole-2-carboxylic acid amide | GP-2 | 120 mg (55%) | |
| SC-57 | 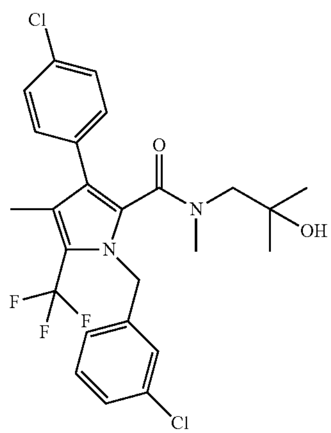 [SMILES: Cc1c(-c2ccc(Cl)cc2)c(C(=O)N(C)CC(C)(C)O)n(Cc2cccc(Cl)c2)c1C(F)(F)F] | 3-(4-Chlorophenyl)-1-[(3-chlorophenyl)-methyl]-N-(2-hydroxy-2-methyl-propyl)-N,4-dimethyl-5-(trifluoromethyl)-1H-pyrrole-2-carboxylic acid amide | GP-1 | 120 mg (58%) | |
| SC-58 | 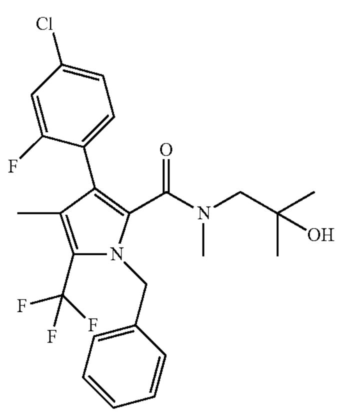 | 1-Benzyl-3-(4-chloro-2-fluoro-phenyl)-N-(2-hydroxy-2-methyl-propyl)-N,4-dimethyl-5-(trifluoromethyl)-1H-pyrrole-2-carboxylic acid amide | GP-1 | 145 mg (60%) | |

-continued

Table Synthesis of pyrrole derivatives (SC):

| Example No. | Structure | Name | Synthesis according to | Yield | Comments |
|---|---|---|---|---|---|
| SC-59 | 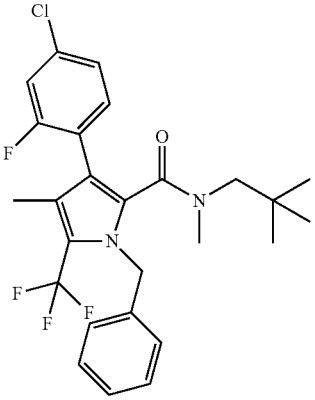 [SMILES: Cc1c(-c2ccc(Cl)cc2F)c(C(=O)N(C)CC(C)(C)C)n(Cc2ccccc2)c1C(F)(F)F] | 1-Benzyl-3-(4-chloro-2-fluoro-phenyl)-N-(2,2-dimethyl-propyl)-N,4-dimethyl-5-(trifluoromethyl)-1H-pyrrole-2-carboxylic acid amide | GP-1 | 104 mg (43%) | |
| SC-60 | 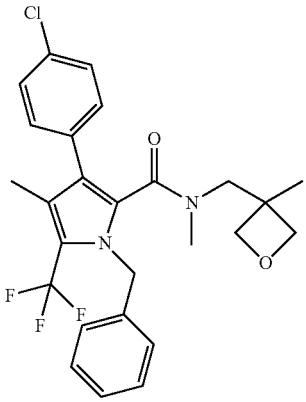 [SMILES: Cc1c(-c2ccc(Cl)cc2)c(C(=O)N(C)CC2(C)COC2)n(Cc2ccccc2)c1C(F)(F)F] | 1-Benzyl-3-(4-chlorophenyl)-N,4-dimethyl-N-[(3-methyl-oxetan-3-yl)-methyl]-5-(trifluoromethyl)-1H-pyrrole-2-carboxylic acid amide | GP-2 | 123 mg (57%) | |
| SC-61 | 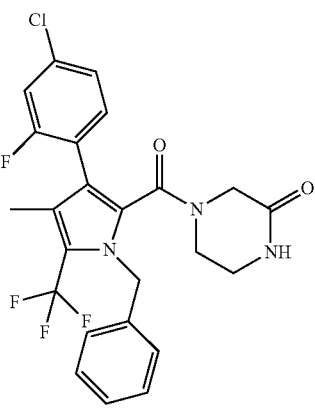 | 4-[1-Benzyl-3-(4-chloro-2-fluoro-phenyl)-4-methyl-5-(trifluoromethyl)-1H-pyrrole-2-carbonyl]-piperazin-2-one | GP-2 | 108 mg (45%) | |

-continued

Table Synthesis of pyrrole derivatives (SC):

| Example No. | Structure | Name | Synthesis according to | Yield | Comments |
|---|---|---|---|---|---|
| SC-62 | 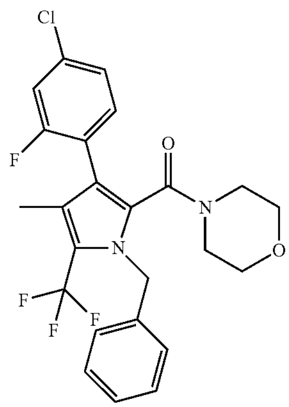 | [1-Benzyl-3-(4-chloro-2-fluoro-phenyl)-4-methyl-5-(trifluoromethyl)-1H-pyrrol-2-yl]-morpholin-4-yl-methanone | GP-2 | 125 mg (54%) | |
| SC-63 | 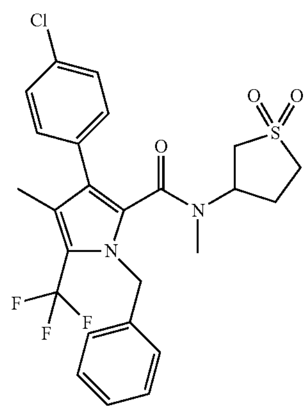 [SMILES: Cc1c(-c2ccc(Cl)cc2)c(C(=O)N(C)C2CCS(=O)(=O)C2)n(Cc2ccccc2)c1C(F)(F)F] | 1-Benzyl-3-(4-chlorophenyl)-N-(1,1-dioxo-thiolan-3-yl)-N,4-dimethyl-5-(trifluoromethyl)-1H-pyrrole-2-carboxylic acid amide | GP-1 | 138 mg (58%) | |
| SC-64 | 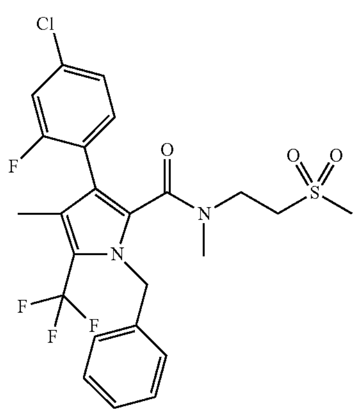 [SMILES: Cc1c(-c2ccc(Cl)cc2F)c(C(=O)N(C)CCS(C)(=O)=O)n(Cc2ccccc2)c1C(F)(F)F] | 1-Benzyl-3-(4-chloro-2-fluoro-phenyl)-N,4-dimethyl-N-(2-methylsulfonyl-ethyl)-5-(trifluoromethyl)-1H-pyrrole-2-carboxylic acid amide | GP-2 | 86 mg (33%) | |

-continued

Table Synthesis of pyrrole derivatives (SC):

| Example No. | Structure | Name | Synthesis according to | Yield | Comments |
|---|---|---|---|---|---|
| SC-65 | 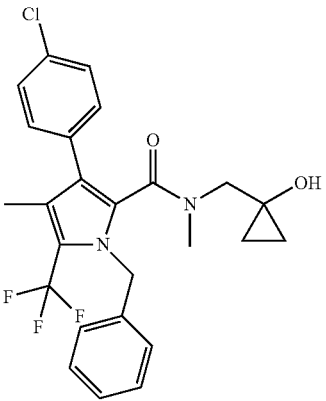 [SMILES: Cc1c(-c2ccc(Cl)cc2)c(C(=O)N(C)CC2(O)CC2)n(Cc2ccccc2)c1C(F)(F)F] | 1-Benzyl-3-(4-chlorophenyl)-N-[(1-hydroxy-cyclopropyl)-methyl]-N,4-dimethyl-5-(trifluoromethyl)-1H-pyrrole-2-carboxylic acid amide | GP-1 | 40 mg (15%) | |
| SC-66 | 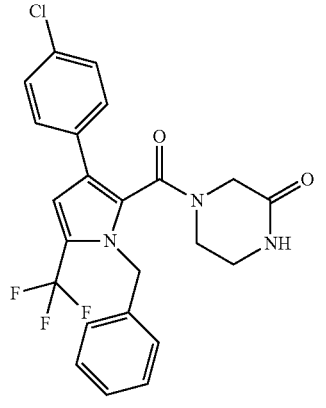 | 4-[1-Benzyl-3-(4-chlorophenyl)-5-(trifluoromethyl)-1H-pyrrole-2-carbonyl]-piperazin-2-one | GP-2 | 88 mg (72%) | |
| SC-67 | 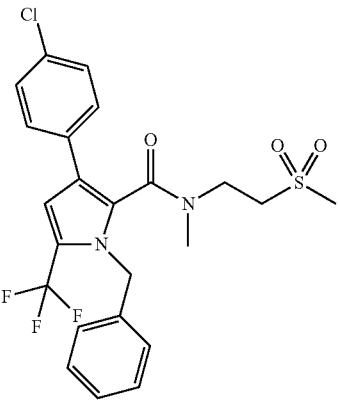 [SMILES: CN(CCS(C)(=O)=O)C(=O)c1c(-c2ccc(Cl)cc2)cc(C(F)(F)F)n1Cc1ccccc1] | 1-Benzyl-3-(4-chlorophenyl)-N-methyl-N-(2-methylsulfonyl-ethyl)-5-(trifluoromethyl)-1H-pyrrole-2-carboxylic acid amide | GP-1 | 108 mg (81%) | |

-continued

Table Synthesis of pyrrole derivatives (SC):

| Example No. | Structure | Name | Synthesis according to | Yield | Comments |
|---|---|---|---|---|---|
| SC-68 | 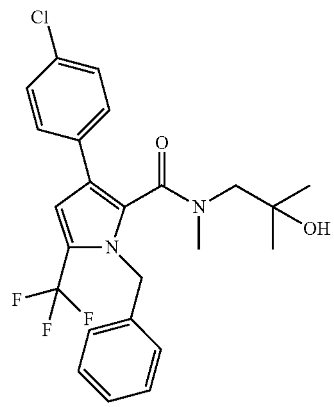 [SMILES: CN(CC(C)(C)O)C(=O)c1c(-c2ccc(Cl)cc2)cc(C(F)(F)F)n1Cc1ccccc1] | 1-Benzyl-3-(4-chlorophenyl)-N-(2-hydroxy-2-methyl-propyl)-N-methyl-5-(trifluoromethyl)-1H-pyrrole-2-carboxylic acid amide | GP-1 | 94 mg (75%) | |
| SC-69 | 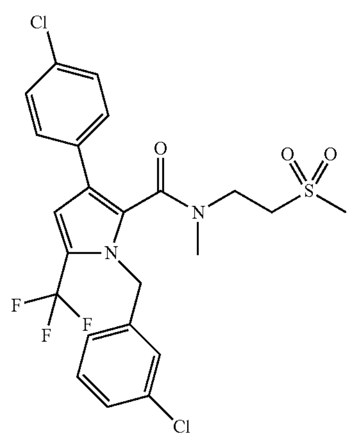 [SMILES: CN(CCS(C)(=O)=O)C(=O)c1c(-c2ccc(Cl)cc2)cc(C(F)(F)F)n1Cc1cccc(Cl)c1] | 3-(4-Chlorophenyl)-1-[(3-chlorophenyl)-methyl]-N-methyl-N-(2-methylsulfonyl-ethyl)-5-(trifluoromethyl)-1H-pyrrole-2-carboxylic acid amide | GP-2 | 51 mg (40%) | |
| SC-70 | 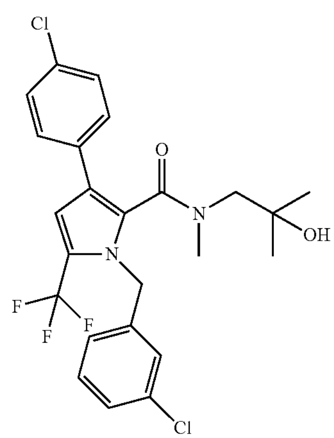 [SMILES: CN(CC(C)(C)O)C(=O)c1c(-c2ccc(Cl)cc2)cc(C(F)(F)F)n1Cc1cccc(Cl)c1] | 3-(4-Chlorophenyl)-1-[(3-chlorophenyl)-methyl]-N-(2-hydroxy-2-methyl-propyl)-N-methyl-5-(trifluoromethyl)-1H-pyrrole-2-carboxylic acid amide | GP-2 | 51 mg (42%) | |

-continued

Table Synthesis of pyrrole derivatives (SC):

| Example No. | Structure | Name | Synthesis according to | Yield | Comments |
|---|---|---|---|---|---|
| SC-71 | 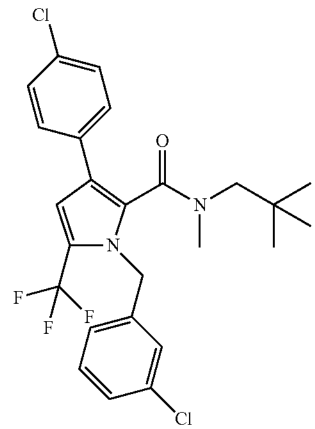 [SMILES: CN(CC(C)(C)C)C(=O)c1c(-c2ccc(Cl)cc2)cc(C(F)(F)F)n1Cc1cccc(Cl)c1] | 3-(4-Chlorophenyl)-1-[(3-chlorophenyl)-methyl]-N-(2,2-dimethyl-propyl)-N-methyl-5-(trifluoromethyl)-1H-pyrrole-2-carboxylic acid amide | GP-2 | 35 mg (29%) | |
| SC-72 | 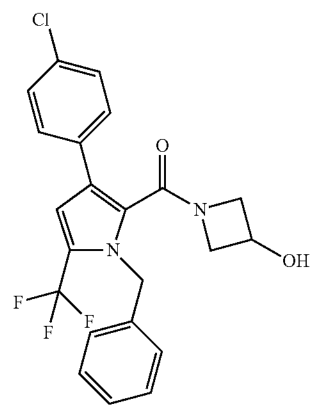 [SMILES: O=C(c1c(-c2ccc(Cl)cc2)cc(C(F)(F)F)n1Cc1ccccc1)N1CC(O)C1] | [1-Benzyl-3-(4-chlorophenyl)-5-(trifluoromethyl)-1H-pyrrol-2-yl]-(3-hydroxy-azetidin-1-yl)-methanone | GP-1 | 82 mg (70%) | |
| SC-73 | 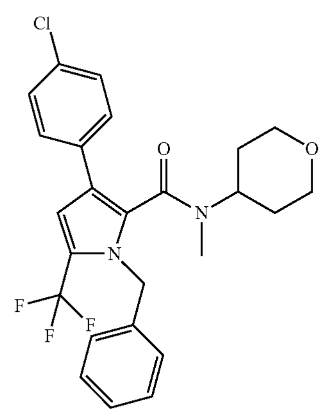 [SMILES: CN(C(=O)c1c(-c2ccc(Cl)cc2)cc(C(F)(F)F)n1Cc1ccccc1)C1CCOCC1] | 1-Benzyl-3-(4-chlorophenyl)-N-methyl-N-tetrahydro-pyran-4-yl-5-(trifluoromethyl)-1H-pyrrole-2-carboxylic acid amide | GP-2 | 65 mg (39%) | |

-continued

Table Synthesis of pyrrole derivatives (SC):

| Example No. | Structure | Name | Synthesis according to | Yield | Comments |
|---|---|---|---|---|---|
| SC-74 | 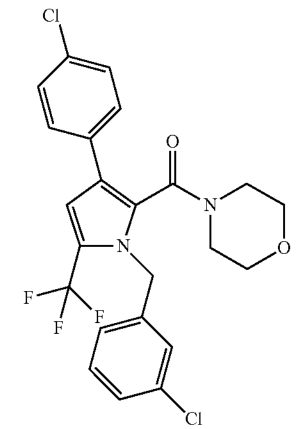 [SMILES: O=C(c1c(-c2ccc(Cl)cc2)cc(C(F)(F)F)n1Cc1cccc(Cl)c1)N1CCOCC1] | [3-(4-Chlorophenyl)-1-[(3-chlorophenyl)-methyl]-5-(trifluoromethyl)-1H-pyrrol-2-yl]-morpholin-4-yl-methanone | GP-2 | 47 mg (40%) | |
| SC-75 | 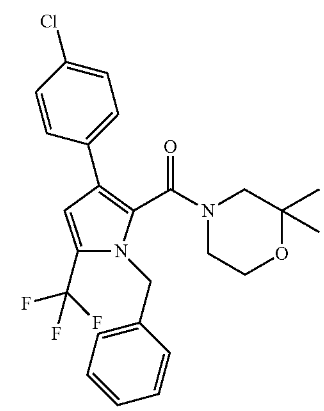 [SMILES: CC1(C)CN(C(=O)c2c(-c3ccc(Cl)cc3)cc(C(F)(F)F)n2Cc2ccccc2)CCO1] | [1-Benzyl-3-(4-chlorophenyl)-5-(trifluoromethyl)-1H-pyrrol-2-yl]-(2,2-dimethyl-morpholin-4-yl)-methanone | GP-2 | 58 mg (66%) | |
| SC-76 | 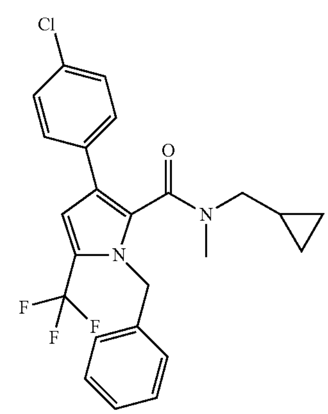 [SMILES: CN(CC1CC1)C(=O)c1c(-c2ccc(Cl)cc2)cc(C(F)(F)F)n1Cc1ccccc1] | 1-Benzyl-3-(4-chlorophenyl)-N-(cyclopropyl-methyl)-N-methyl-5-(trifluoromethyl)-1H-pyrrole-2-carboxylic acid amide | GP-1 | 34 mg (36%) | |

-continued

Table Synthesis of pyrrole derivatives (SC):

| Example No. | Structure | Name | Synthesis according to | Yield | Comments |
|---|---|---|---|---|---|
| SC-77 | 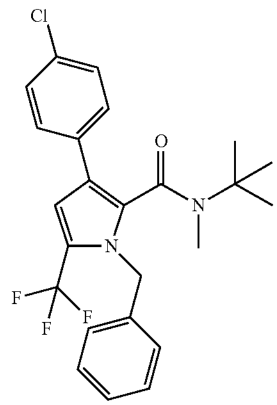 [SMILES: CN(C(=O)c1c(-c2ccc(Cl)cc2)cc(C(F)(F)F)n1Cc1ccccc1)C(C)(C)C] | 1-Benzyl-N-tert-butyl-3-(4-chlorophenyl)-N-methyl-5-(trifluoromethyl)-1H-pyrrole-2-carboxylic acid amide | GP-1 | 31 mg (15%) | |
| SC-78 | 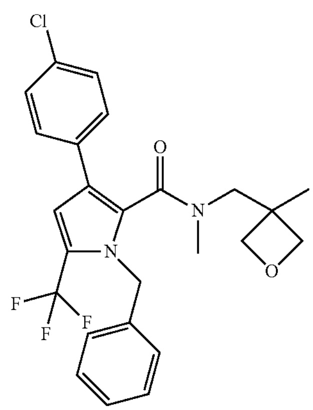 [SMILES: CN(CC1(C)COC1)C(=O)c1c(-c2ccc(Cl)cc2)cc(C(F)(F)F)n1Cc1ccccc1] | 1-Benzyl-3-(4-chlorophenyl)-N-methyl-N-[(3-methyl-oxetan-3-yl)-methyl]-5-(trifluoromethyl)-1H-pyrrole-2-carboxylic acid amide | GP-2 | 117 mg (70%) | |
| SC-79 | 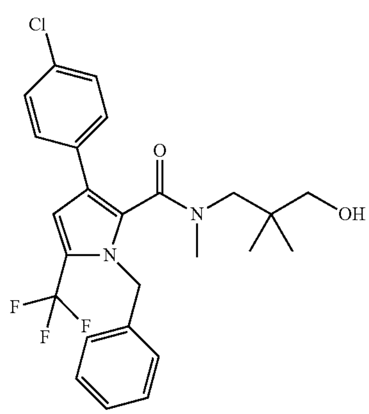 [SMILES: CN(CC(C)(C)CO)C(=O)c1c(-c2ccc(Cl)cc2)cc(C(F)(F)F)n1Cc1ccccc1] | 1-Benzyl-3-(4-chlorophenyl)-N-(3-hydroxy-2,2-dimethyl-propyl)-N-methyl-5-(trifluoromethyl)-1H-pyrrole-2-carboxylic acid amide | GP-2 | 80 mg (63%) | |

-continued

Table Synthesis of pyrrole derivatives (SC):

| Example No. | Structure | Name | Synthesis according to | Yield | Comments |
|---|---|---|---|---|---|
| SC-80 | 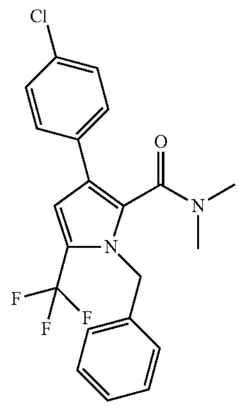 [SMILES: CN(C)C(=O)c1c(-c2ccc(Cl)cc2)cc(C(F)(F)F)n1Cc1ccccc1] | 1-Benzyl-3-(4-chlorophenyl)-N,N-dimethyl-5-(trifluoromethyl)-1H-pyrrole-2-carboxylic acid amide | GP-2 | 89 mg (83%) | |
| SC-81 | 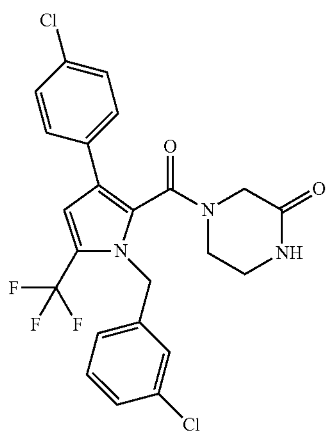 [SMILES: O=C1CN(C(=O)c2c(-c3ccc(Cl)cc3)cc(C(F)(F)F)n2Cc2cccc(Cl)c2)CCN1] | 4-[3-(4-Chlorophenyl)-1-[(3-chlorophenyl)-methyl]-5-(trifluoromethyl)-1H-pyrrole-2-carbonyl]-piperazin-2-one | GP-2 | 67 mg (56%) | |
| SC-82 | 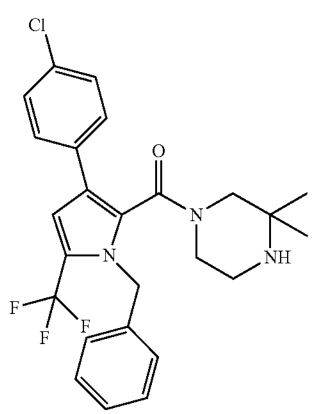 [SMILES: CC1(C)CN(C(=O)c2c(-c3ccc(Cl)cc3)cc(C(F)(F)F)n2Cc2ccccc2)CCN1] | [1-Benzyl-3-(4-chlorophenyl)-5-(trifluoromethyl)-1H-pyrrol-2-yl]-(3,3-dimethyl-piperazin-1-yl)-methanone | see below | | |

-continued

Table Synthesis of pyrrole derivatives (SC):

| Example No. | Structure | Name | Synthesis according to | Yield | Comments |
|---|---|---|---|---|---|
| SC-83 | 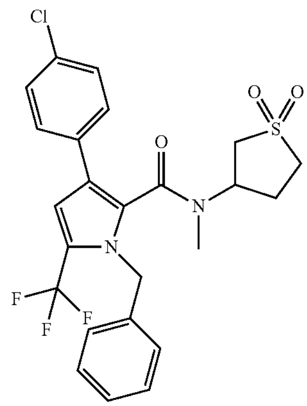 [SMILES: CN(C(=O)c1c(-c2ccc(Cl)cc2)cc(C(F)(F)F)n1Cc1ccccc1)C1CCS(=O)(=O)C1] | 1-Benzyl-3-(4-chlorophenyl)-N-(1,1-dioxo-thiolan-3-yl)-N-methyl-5-(trifluoromethyl)-1H-pyrrole-2-carboxylic acid amide | GP-1 | 45 mg (47%) | |
| SC-84 | 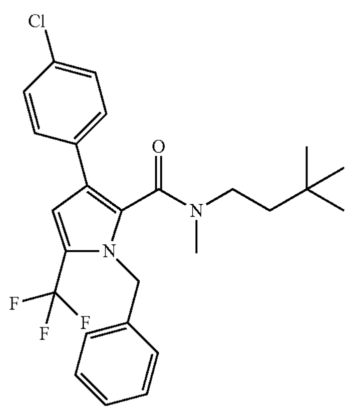 [SMILES: CN(CCC(C)(C)C)C(=O)c1c(-c2ccc(Cl)cc2)cc(C(F)(F)F)n1Cc1ccccc1] | 1-Benzyl-3-(4-chlorophenyl)-N-(3,3-dimethyl-butyl)-N-methyl-5-(trifluoromethyl)-1H-pyrrole-2-carboxylic acid amide | GP-1 | 68 mg (45%) | |
| SC-85 | 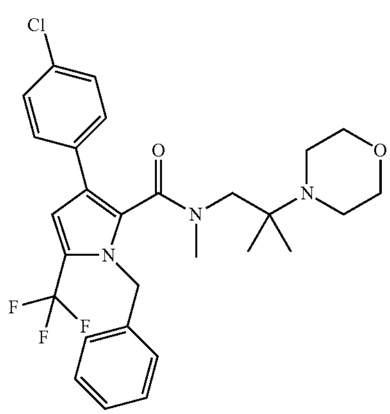 [SMILES: CN(CC(C)(C)N1CCOCC1)C(=O)c1c(-c2ccc(Cl)cc2)cc(C(F)(F)F)n1Cc1ccccc1] | 1-Benzyl-3-(4-chlorophenyl)-N-methyl-N-(2-methyl-2-morpholin-4-yl-propyl)-5-(trifluoromethyl)-1H-pyrrole-2-carboxylic acid amide | GP-1 | 43 mg (26%) | |

-continued

Table Synthesis of pyrrole derivatives (SC):

| Example No. | Structure | Name | Synthesis according to | Yield | Comments |
| --- | --- | --- | --- | --- | --- |
| SC-86 | 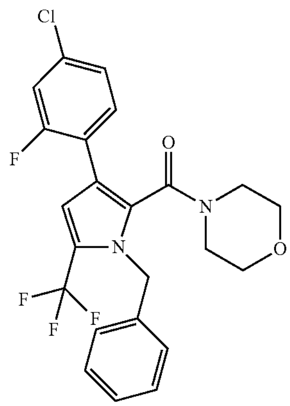 [SMILES: O=C(c1c(-c2ccc(Cl)cc2F)cc(C(F)(F)F)n1Cc1ccccc1)N1CCOCC1] | [1-Benzyl-3-(4-chloro-2-fluorophenyl)-5-(trifluoromethyl)-1H-pyrrol-2-yl]-morpholin-4-yl-methanone | GP-2 | 131 mg (93%) | |
| SC-87 | 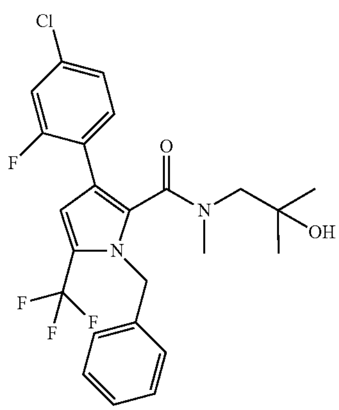 [SMILES: CN(CC(C)(C)O)C(=O)c1c(-c2ccc(Cl)cc2F)cc(C(F)(F)F)n1Cc1ccccc1] | 1-Benzyl-3-(4-chloro-2-fluorophenyl)-N-(2-hydroxy-2-methyl-propyl)-N-methyl-5-(trifluoromethyl)-1H-pyrrole-2-carboxylic acid amide | GP-1 | 155 mg (85%) | |
| SC-88 | 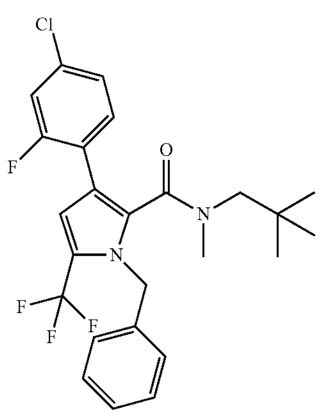 [SMILES: CN(CC(C)(C)C)C(=O)c1c(-c2ccc(Cl)cc2F)cc(C(F)(F)F)n1Cc1ccccc1] | 1-Benzyl-3-(4-chloro-2-fluorophenyl)-N-(2,2-dimethyl-propyl)-N-methyl-5-(trifluoromethyl)-1H-pyrrole-2-carboxylic acid amide | GP-1 | 82 mg (45%) | |

-continued

Table Synthesis of pyrrole derivatives (SC):

| Example No. | Structure | Name | Synthesis according to | Yield | Comments |
|---|---|---|---|---|---|
| SC-89 | 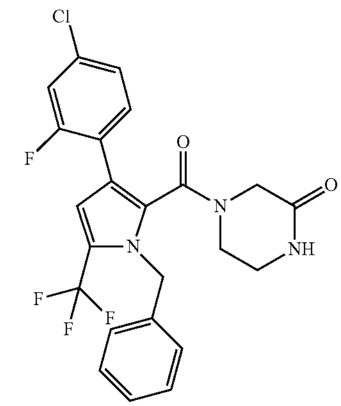 [SMILES: O=C1CN(C(=O)c2c(-c3ccc(Cl)cc3F)cc(C(F)(F)F)n2Cc2ccccc2)CCN1] | 4-[1-Benzyl-3-(4-chloro-2-fluoro-phenyl)-5-(trifluoromethyl)-1H-pyrrole-2-carbonyl]-piperazin-2-one | GP-2 | 60 mg (41%) | |
| SC-90 | 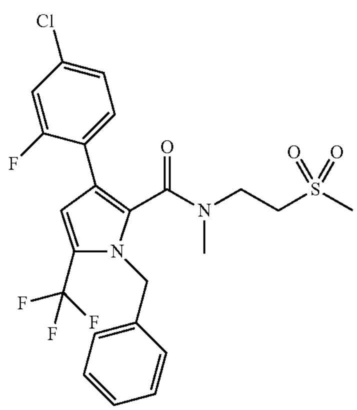 [SMILES: CN(CCS(C)(=O)=O)C(=O)c1c(-c2ccc(Cl)cc2F)cc(C(F)(F)F)n1Cc1ccccc1] | 1-Benzyl-3-(4-chloro-2-fluoro-phenyl)-N-methyl-N-(2-methylsulfonyl-ethyl)-5-(trifluoromethyl)-1H-pyrrole-2-carboxylic acid amide | GP-1 | 146 mg (74%) | |
| SC-92 | 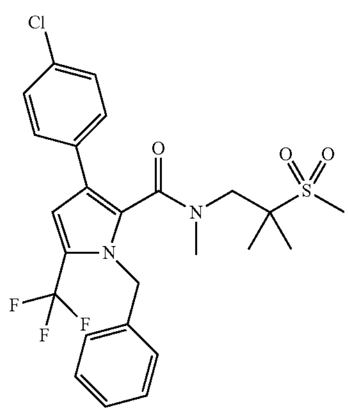 [SMILES: CN(CC(C)(C)S(C)(=O)=O)C(=O)c1c(-c2ccc(Cl)cc2)cc(C(F)(F)F)n1Cc1ccccc1] | 1-Benzyl-3-(4-chlorophenyl)-N-methyl-N-(2-methyl-2-methylsulfonyl-propyl)-5-(trifluoromethyl)-1H-pyrrole-2-carboxylic acid amide | GP-1 | 49 mg (48%) | |

-continued

Table Synthesis of pyrrole derivatives (SC):

| Example No. | Structure | Name | Synthesis according to | Yield | Comments |
|---|---|---|---|---|---|
| SC-93 | 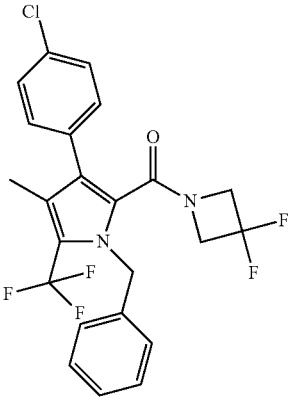 | [1-Benzyl-3-(4-chlorophenyl)-4-methyl-5-(trifluoromethyl)-1H-pyrrol-2-yl]-(3,3-difluoro-azetidin-1-yl)-methanone | GP-3 | 40 mg (67%) | |
| SC-94 | 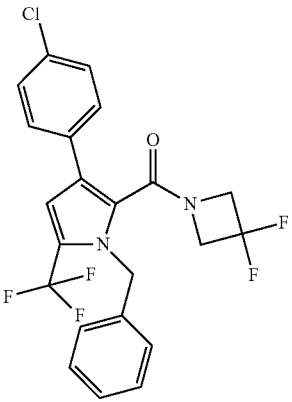 [SMILES: O=C(c1c(-c2ccc(Cl)cc2)cc(C(F)(F)F)n1Cc1ccccc1)N1CC(F)(F)C1] | [1-Benzyl-3-(4-chlorophenyl)-5-(trifluoromethyl)-1H-pyrrol-2-yl]-(3,3-difluoro-azetidin-1-yl)-methanone | GP-4 | 80 mg (67%) | |
| SC-95 | 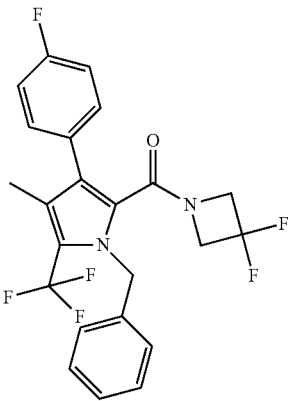 [SMILES: Cc1c(-c2ccc(F)cc2)c(C(=O)N2CC(F)(F)C2)n(Cc2ccccc2)c1C(F)(F)F] | [1-Benzyl-3-(4-fluorophenyl)-4-methyl-5-(trifluoromethyl)-1H-pyrrol-2-yl]-(3,3-difluoro-azetidin-1-yl)-methanone | GP-4 | 80 mg (67%) | |

-continued

Table Synthesis of pyrrole derivatives (SC):

| Example No. | Structure | Name | Synthesis according to | Yield | Comments |
|---|---|---|---|---|---|
| SC-96 | 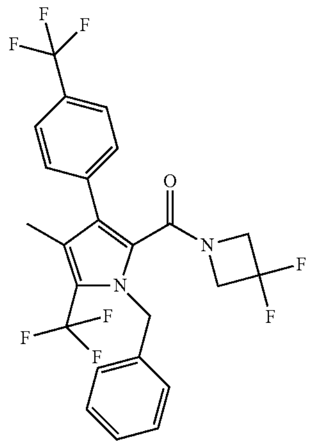 [SMILES: Cc1c(-c2ccc(C(F)(F)F)cc2)c(C(=O)N2CC(F)(F)C2)n(Cc2ccccc2)c1C(F)(F)F] | [1-Benzyl-4-methyl-5-(trifluoromethyl)-3-[4-(trifluoromethyl)-phenyl]-1H-pyrrol-2-yl]-(3,3-difluoro-azetidin-1-yl)-methanone | GP-4 | 90 mg (77%) | |
| SC-97 | 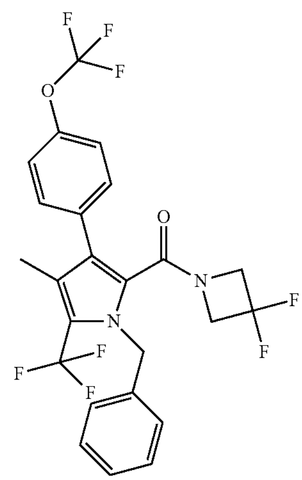 [SMILES: Cc1c(-c2ccc(OC(F)(F)F)cc2)c(C(=O)N2CC(F)(F)C2)n(Cc2ccccc2)c1C(F)(F)F] | [1-Benzyl-4-methyl-5-(trifluoromethyl)-3-[4-(trifluoromethyloxy)-phenyl]-1H-pyrrol-2-yl]-(3,3-difluoro-azetidin-1-yl)-methanone | GP-4 | 100 mg (85%) | |
| SC-98 | 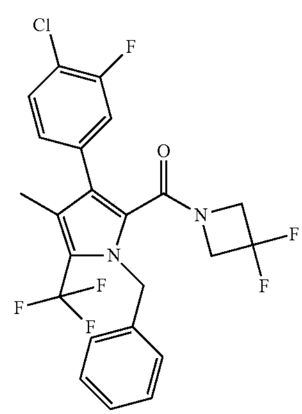 [SMILES: Cc1c(-c2ccc(Cl)c(F)c2)c(C(=O)N2CC(F)(F)C2)n(Cc2ccccc2)c1C(F)(F)F] | [1-Benzyl-3-(4-chloro-3-fluoro-phenyl)-4-methyl-5-(trifluoromethyl)-1H-pyrrol-2-yl]-(3,3-difluoro-azetidin-1-yl)-methanone | GP-4 | 60 mg (51%) | |

-continued

Table Synthesis of pyrrole derivatives (SC):

| Example No. | Structure | Name | Synthesis according to | Yield | Comments |
|---|---|---|---|---|---|
| SC-99 | 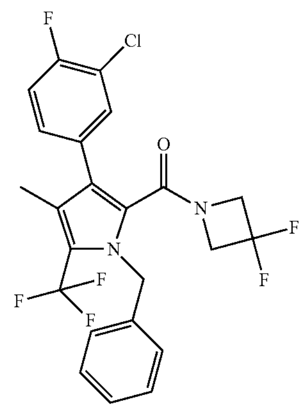 [SMILES: Cc1c(-c2ccc(F)c(Cl)c2)c(C(=O)N2CC(F)(F)C2)n(Cc2ccccc2)c1C(F)(F)F] | [1-Benzyl-3-(3-chloro-4-fluoro-phenyl)-4-methyl-5-(trifluoromethyl)-1H-pyrrol-2-yl]-(3,3-difluoro-azetidin-1-yl)-methanone | GP-4 | 90 mg (76%) | |
| SC-100 | 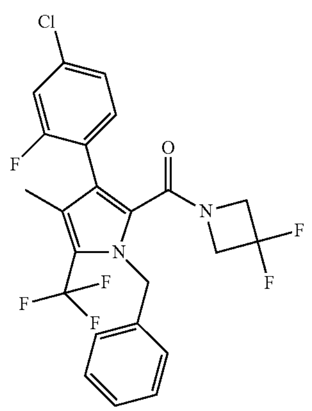 [SMILES: Cc1c(-c2ccc(Cl)cc2F)c(C(=O)N2CC(F)(F)C2)n(Cc2ccccc2)c1C(F)(F)F] | [1-Benzyl-3-(4-chloro-2-fluoro-phenyl)-4-methyl-5-(trifluoromethyl)-1H-pyrrol-2-yl]-(3,3-difluoro-azetidin-1-yl)-methanone | GP-4 | 80 mg (68%) | |
| SC-101 | 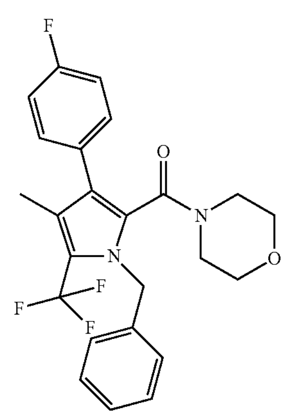 [SMILES: Cc1c(-c2ccc(F)cc2)c(C(=O)N2CCOCC2)n(Cc2ccccc2)c1C(F)(F)F] | [1-Benzyl-3-(4-fluorophenyl)-4-methyl-5-(trifluoromethyl)-1H-pyrrol-2-yl]-morpholin-4-yl-methanone | GP-4 | 90 mg (76%) | |

-continued

Table Synthesis of pyrrole derivatives (SC):

| Example No. | Structure | Name | Synthesis according to | Yield | Comments |
|---|---|---|---|---|---|
| SC-102 | 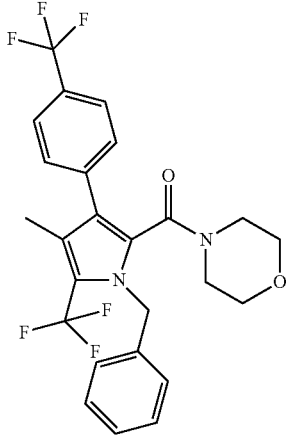 [SMILES: Cc1c(-c2ccc(C(F)(F)F)cc2)c(C(=O)N2CCOCC2)n(Cc2ccccc2)c1C(F)(F)F] | [1-Benzyl-4-methyl-5-(trifluoromethyl)-3-[4-(trifluoromethyl)-phenyl]-1H-pyrrol-2-yl]-morpholin-4-yl-methanone | GP-4 | 90 mg (77%) | |
| SC-103 | 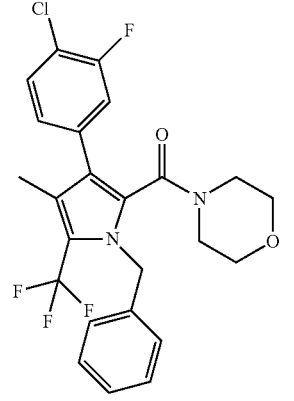 [SMILES: Cc1c(-c2ccc(Cl)c(F)c2)c(C(=O)N2CCOCC2)n(Cc2ccccc2)c1C(F)(F)F] | [1-Benzyl-3-(4-chloro-3-fluoro-phenyl)-4-methyl-5-(trifluoromethyl)-1H-pyrrol-2-yl]-morpholin-4-yl-methanone | GP-4 | 80 mg (68%) | |
| SC-104 | 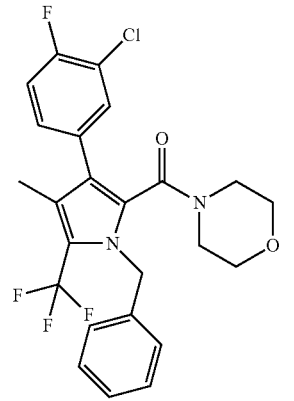 [SMILES: Cc1c(-c2ccc(F)c(Cl)c2)c(C(=O)N2CCOCC2)n(Cc2ccccc2)c1C(F)(F)F] | [1-Benzyl-3-(3-chloro-4-fluoro-phenyl)-4-methyl-5-(trifluoromethyl)-1H-pyrrol-2-yl]-morpholin-4-yl-methanone | GP-4 | 90 mg (77%) | |

-continued

Table Synthesis of pyrrole derivatives (SC):

| Example No. | Structure | Name | Synthesis according to | Yield | Comments |
|---|---|---|---|---|---|
| SC-105 | 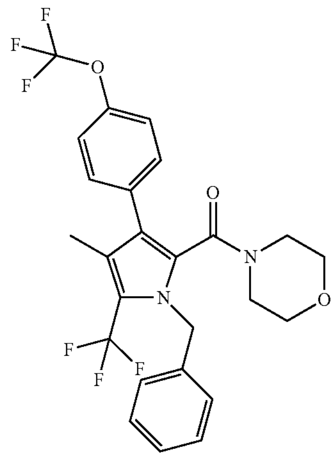 [SMILES: Cc1c(-c2ccc(OC(F)(F)F)cc2)c(C(=O)N2CCOCC2)n(Cc2ccccc2)c1C(F)(F)F] | [1-Benzyl-4-methyl-5-(trifluoromethyl)-3-[4-(trifluoromethyloxy)-phenyl]-1H-pyrrol-2-yl]-morpholin-4-yl-methanone | GP-4 | 70 mg (60%) | |
| SC-106 | 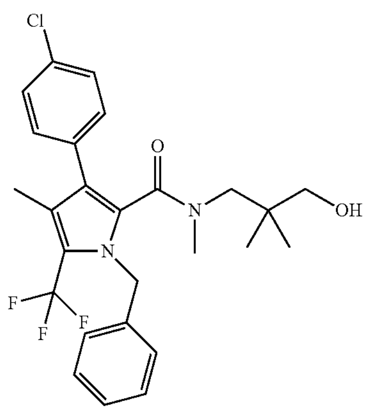 [SMILES: Cc1c(-c2ccc(Cl)cc2)c(C(=O)N(C)CC(C)(C)CO)n(Cc2ccccc2)c1C(F)(F)F] | 1-Benzyl-3-(4-chlorophenyl)-N-(3-hydroxy-2,2-dimethyl-propyl)-N,4-dimethyl-5-(trifluoromethyl)-1H-pyrrole-2-carboxylic acid amide | GP-4 | 110 mg (73%) | |
| SC-107 | 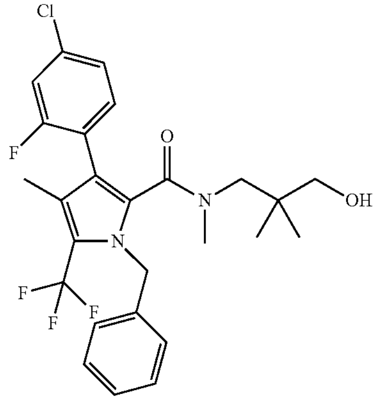 [SMILES: Cc1c(-c2ccc(Cl)cc2F)c(C(=O)N(C)CC(C)(C)CO)n(Cc2ccccc2)c1C(F)(F)F] | 1-Benzyl-3-(4-chloro-2-fluoro-phenyl)-N-(3-hydroxy-2,2-dimethyl-propyl)-N,4-dimethyl-5-(trifluoromethyl)-1H-pyrrole-2-carboxylic acid amide | GP-4 | 40 mg (32%) | |

-continued

Table Synthesis of pyrrole derivatives (SC):

| Example No. | Structure | Name | Synthesis according to | Yield | Comments |
|---|---|---|---|---|---|
| SC-108 | 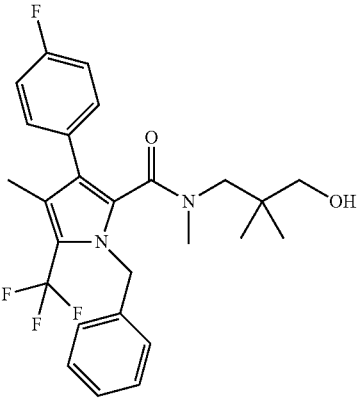 [SMILES: Cc1c(-c2ccc(F)cc2)c(C(=O)N(C)CC(C)(C)CO)n(Cc2ccccc2)c1C(F)(F)F] | 1-Benzyl-3-(4-fluorophenyl)-N-(2-hydroxy-2-methyl-propyl)-N,4-dimethyl-5-(trifluoromethyl)-1H-pyrrole-2-carboxylic acid amide | GP-4 | 130 mg (88%) | |
| SC-109 | 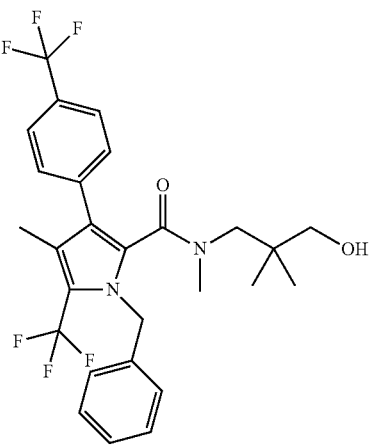 [SMILES: Cc1c(-c2ccc(C(F)(F)F)cc2)c(C(=O)N(C)CC(C)(C)CO)n(Cc2ccccc2)c1C(F)(F)F] | 1-Benzyl-N-(2-hydroxy-2-methyl-propyl)-N,4-dimethyl-5-(trifluoromethyl)-3-[4-(trifluoromethyl)-phenyl]-1H-pyrrole-2-carboxylic acid amide | GP-4 | 110 mg (76%) | |
| SC-110 | 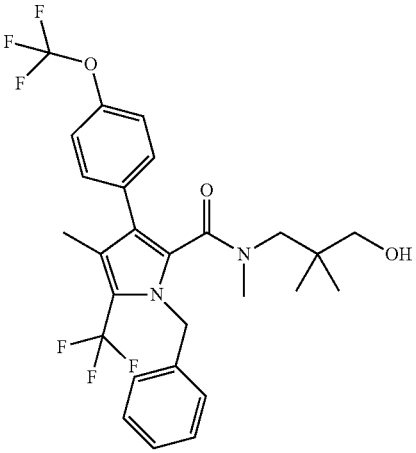 [SMILES: Cc1c(-c2ccc(OC(F)(F)F)cc2)c(C(=O)N(C)CC(C)(C)CO)n(Cc2ccccc2)c1C(F)(F)F] | 1-Benzyl-N-(2-hydroxy-2-methyl-propyl)-N,4-dimethyl-5-(trifluoromethyl)-3-[4-(trifluoromethyloxy)-phenyl]-1H-pyrrole-2-carboxylic acid amide | GP-4 | 110 mg (76%) | |

-continued

Table Synthesis of pyrrole derivatives (SC):

| Example No. | Structure | Name | Synthesis according to | Yield | Comments |
|---|---|---|---|---|---|
| SC-111 | 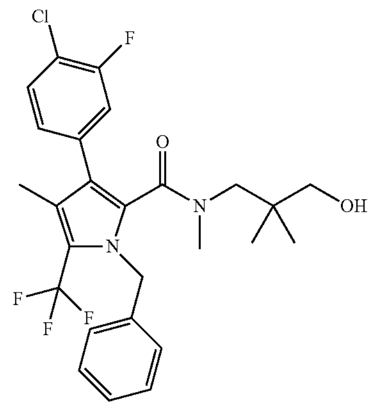 | 1-Benzyl-3-(4-chloro-3-fluoro-phenyl)-N-(2-hydroxy-2-methyl-propyl)-N,4-dimethyl-5-(trifluoromethyl)-1H-pyrrole-2-carboxylic acid amide | GP-4 | 120 mg (83%) | |
| SC-112 | 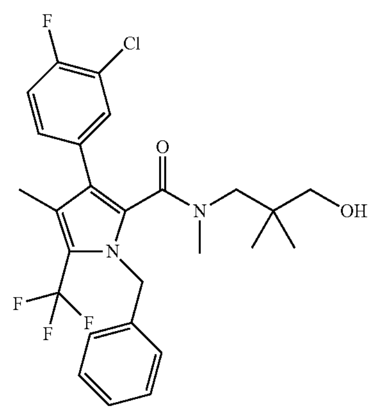 [SMILES: Cc1c(-c2ccc(F)c(Cl)c2)c(C(=O)N(C)CC(C)(C)CO)n(Cc2ccccc2)c1C(F)(F)F] | 1-Benzyl-3-(3-chloro-4-fluoro-phenyl)-N-(2-hydroxy-2-methyl-propyl)-N,4-dimethyl-5-(trifluoromethyl)-1H-pyrrole-2-carboxylic acid amide | GP-4 | 110 mg (76%) | |
| SC-113 | 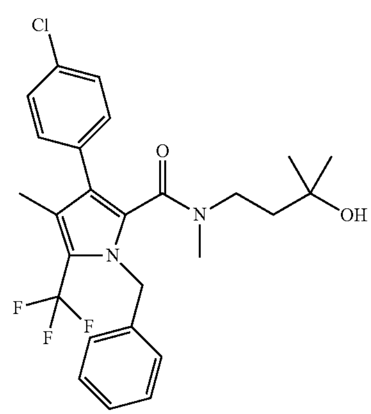 [SMILES: Cc1c(-c2ccc(Cl)cc2)c(C(=O)N(C)CCC(C)(C)O)n(Cc2ccccc2)c1C(F)(F)F] | 1-Benzyl-3-(4-chlorophenyl)-N-(3-hydroxy-3-methyl-butyl)-N,4-dimethyl-5-(trifluoromethyl)-1H-pyrrole-2-carboxylic acid amide | GP-4 | 110 mg (88%) | |

-continued

Table Synthesis of pyrrole derivatives (SC):

| Example No. | Structure | Name | Synthesis according to | Yield | Comments |
|---|---|---|---|---|---|
| SC-114 | 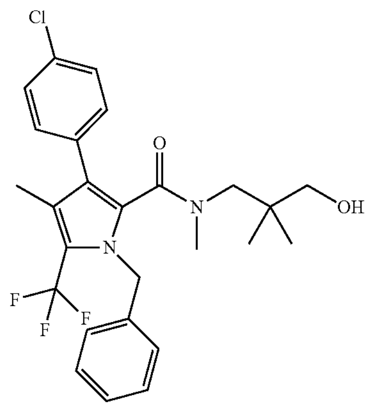 [SMILES: Cc1c(-c2ccc(Cl)cc2)c(C(=O)N(C)CC(C)(C)CO)n(Cc2ccccc2)c1C(F)(F)F] | 1-Benzyl-3-(4-chlorophenyl)-N-(3-hydroxy-2,2-dimethyl-propyl)-4-methyl-5-(trifluoromethyl)-1H-pyrrole-2-carboxylic acid amide | GP-4 | 100 mg (82%) | |
| SC-115 | 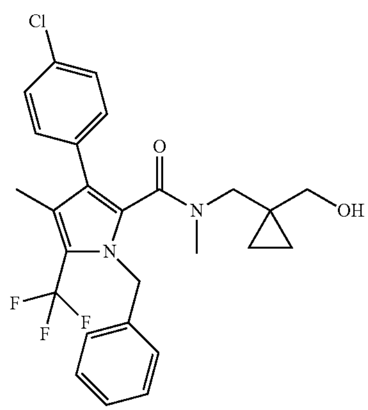 [SMILES: Cc1c(-c2ccc(Cl)cc2)c(C(=O)N(C)CC2(CO)CC2)n(Cc2ccccc2)c1C(F)(F)F] | 1-Benzyl-3-(4-chlorophenyl)-N-[[1-(hydroxymethyl)-cyclopropyl]-methyl]-N,4-dimethyl-5-(trifluoromethyl)-1H-pyrrole-2-carboxylic acid amide | GP-4 | 100 mg (80%) | |
| SC-116 | 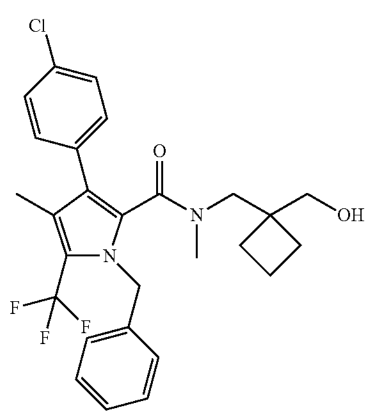 [SMILES: Cc1c(-c2ccc(Cl)cc2)c(C(=O)N(C)CC2(CO)CCC2)n(Cc2ccccc2)c1C(F)(F)F] | 1-Benzyl-3-(4-chlorophenyl)-N-[[1-(hydroxymethyl)-cyclobutyl]-methyl]-N,4-dimethyl-5-(trifluoromethyl)-1H-pyrrole-2-carboxylic acid amide | GP-4 | 80 mg (62%) | |

-continued

Table Synthesis of pyrrole derivatives (SC):

| Example No. | Structure | Name | Synthesis according to | Yield | Comments |
|---|---|---|---|---|---|
| SC-117 | 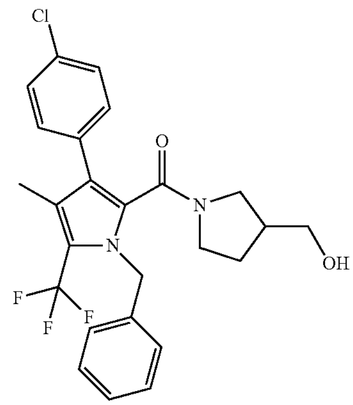 [SMILES: Cc1c(-c2ccc(Cl)cc2)c(C(=O)N2CCC(CO)C2)n(Cc2ccccc2)c1C(F)(F)F] | [1-Benzyl-3-(4-chlorophenyl)-4-methyl-5-(trifluoromethyl)-1H-pyrrol-2-yl]-[3-(hydroxymethyl)-pyrrolidin-1-yl]-methanone | GP-4 | 140 mg (58%) | |
| SC-118 | 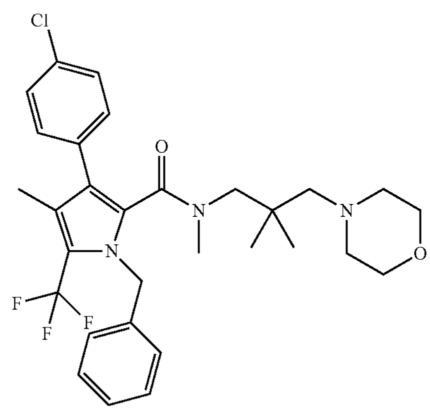 [SMILES: Cc1c(-c2ccc(Cl)cc2)c(C(=O)N(C)CC(C)(C)CN2CCOCC2)n(Cc2ccccc2)c1C(F)(F)F] | 1-Benzyl-3-(4-chlorophenyl)-N-(2,2-dimethyl-3-morpholin-4-yl-propyl)-N,4-dimethyl-5-(trifluoromethyl)-1H-pyrrole-2-carboxylic acid amide | GP-4 | 120 mg (84%) | |
| SC-119 | 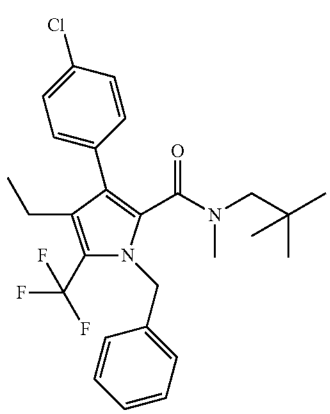 [SMILES: CCc1c(-c2ccc(Cl)cc2)c(C(=O)N(C)CC(C)(C)C)n(Cc2ccccc2)c1C(F)(F)F] | 1-Benzyl-3-(4-chlorophenyl)-N-(2,2-dimethyl-propyl)-4-ethyl-N-methyl-5-(trifluoromethyl)-1H-pyrrole-2-carboxylic acid amide | see below | | |

-continued

Table Synthesis of pyrrole derivatives (SC):

| Example No. | Structure | Name | Synthesis according to | Yield | Comments |
|---|---|---|---|---|---|
| SC-120 | 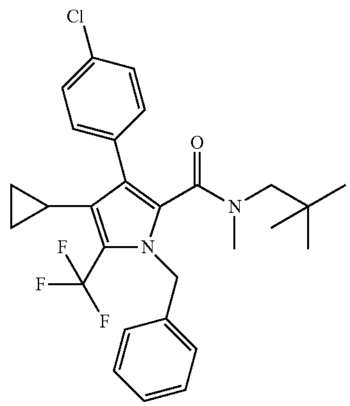 [SMILES: CN(CC(C)(C)C)C(=O)c1c(-c2ccc(Cl)cc2)c(C2CC2)c(C(F)(F)F)n1Cc1ccccc1] | 1-Benzyl-3-(4-chlorophenyl)-4-cyclopropyl-N-(2,2-dimethyl-propyl)-N-methyl-5-(trifluoromethyl)-1H-pyrrole-2-carboxylic acid amide | see below | | |
| SC-121 | 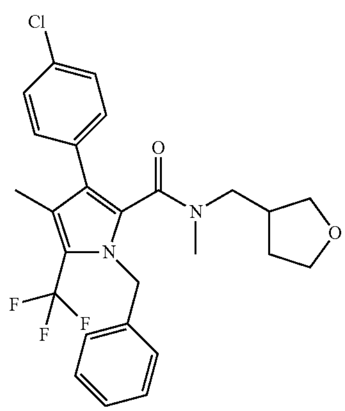 [SMILES: Cc1c(-c2ccc(Cl)cc2)c(C(=O)N(C)CC2CCOC2)n(Cc2ccccc2)c1C(F)(F)F] | 1-Benzyl-3-(4-chlorophenyl)-N,4-dimethyl-N-(tetrahydro-furan-3-yl-methyl)-5-(trifluoromethyl)-1H-pyrrole-2-carboxylic acid amide | GP-4 | 100 mg (80%) | |
| SC-122 | 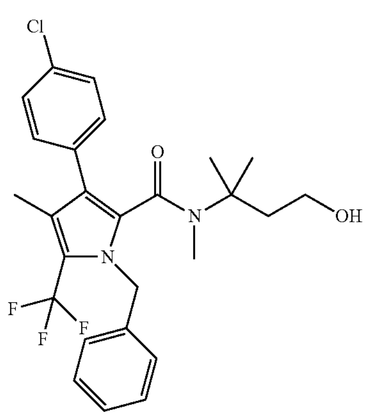 [SMILES: Cc1c(-c2ccc(Cl)cc2)c(C(=O)N(C)C(C)(C)CCO)n(Cc2ccccc2)c1C(F)(F)F] | 1-Benzyl-3-(4-chlorophenyl)-N-(3-hydroxy-1,1-dimethyl-propyl)-N,4-dimethyl-5-(trifluoromethyl)-1H-pyrrole-2-carboxylic acid amide | GP-5 | 110 mg (59%) | |

-continued

Table Synthesis of pyrrole derivatives (SC):

| Example No. | Structure | Name | Synthesis according to | Yield | Comments |
|---|---|---|---|---|---|
| SC-123 | 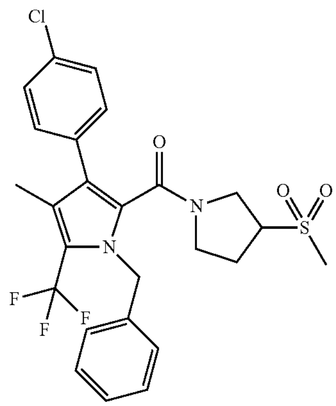 [SMILES: Cc1c(-c2ccc(Cl)cc2)c(C(=O)N2CCC(S(C)(=O)=O)C2)n(Cc2ccccc2)c1C(F)(F)F] | [1-Benzyl-3-(4-chlorophenyl)-4-methyl-5-(trifluoromethyl)-1H-pyrrol-2-yl]-(3-methylsulfonyl-pyrrolidin-1-yl)-methanone | GP-4 | 90 mg (84%) | |
| SC-124 | 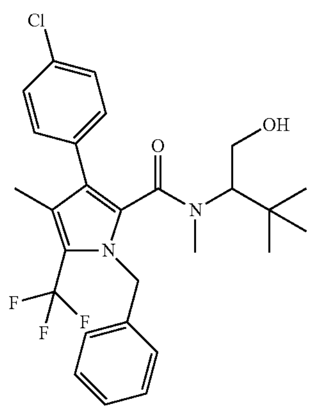 [SMILES: Cc1c(-c2ccc(Cl)cc2)c(C(=O)N(C)C(CO)C(C)(C)C)n(Cc2ccccc2)c1C(F)(F)F] | 1-Benzyl-3-(4-chlorophenyl)-N-[1-(hydroxymethyl)-2,2-dimethyl-propyl]-N,4-dimethyl-5-(trifluoromethyl)-1H-pyrrole-2-carboxylic acid amide | GP-3 | 110 mg (57%) | |
| SC-125 | 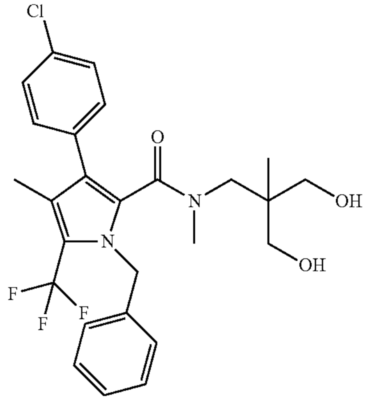 [SMILES: Cc1c(-c2ccc(Cl)cc2)c(C(=O)N(C)CC(C)(CO)CO)n(Cc2ccccc2)c1C(F)(F)F] | 1-Benzyl-3-(4-chlorophenyl)-N-[3-hydroxy-2-(hydroxymethyl)-2-methyl-propyl]-N,4-dimethyl-5-(trifluoromethyl)-1H-pyrrole-2-carboxylic acid amide | GP-3 | 140 mg (72%) | |

-continued

Table Synthesis of pyrrole derivatives (SC):

| Example No. | Structure | Name | Synthesis according to | Yield | Comments |
|---|---|---|---|---|---|
| SC-126 | 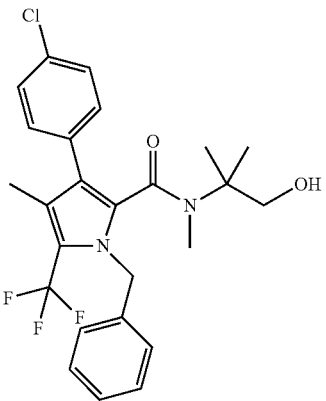 | 1-Benzyl-3-(4-chlorophenyl)-N-(2-hydroxy-1,1-dimethyl-ethyl)-N,4-dimethyl-5-(trifluoromethyl)-1H-pyrrole-2-carboxylic acid amide | GP-3 | 130 mg (71%) | |
| SC-127 | 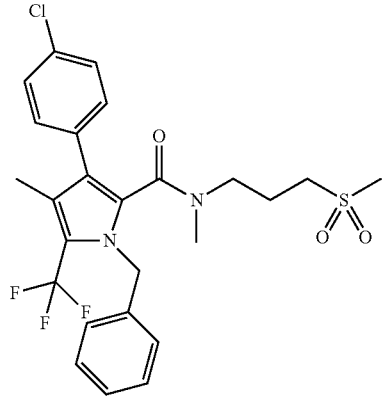 [SMILES: Cc1c(-c2ccc(Cl)cc2)c(C(=O)N(C)CCCS(C)(=O)=O)n(Cc2ccccc2)c1C(F)(F)F] | 1-Benzyl-3-(4-chlorophenyl)-N,4-dimethyl-N-(3-methylsulfonyl-propyl)-5-(trifluoromethyl)-1H-pyrrole-2-carboxylic acid amide | GP-4 | 100 mg (78%) | |
| SC-128 | 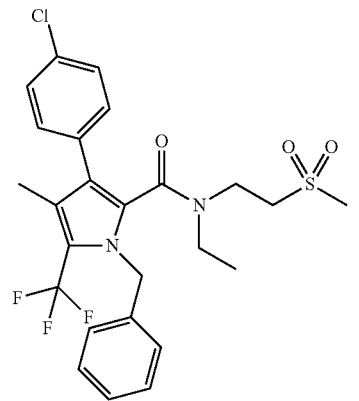 [SMILES: CCN(CCS(C)(=O)=O)C(=O)c1c(-c2ccc(Cl)cc2)c(C)c(C(F)(F)F)n1Cc1ccccc1] | 1-Benzyl-3-(4-chlorophenyl)-N-ethyl-4-methyl-N-(2-methylsulfonyl-ethyl)-5-(trifluoromethyl)-1H-pyrrole-2-carboxylic acid amide | GP-4 | 35 mg (26%) | |

Table Synthesis of pyrrole derivatives (SC):

| Example No. | Structure | Name | Synthesis according to | Yield | Comments |
|---|---|---|---|---|---|
| SC-129 | 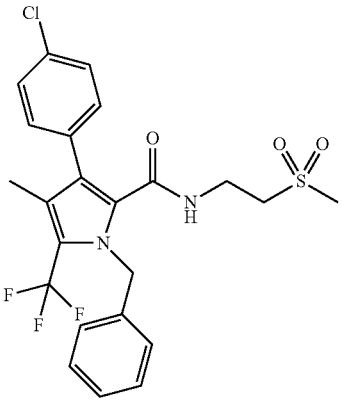 [SMILES: Cc1c(-c2ccc(Cl)cc2)c(C(=O)NCCS(C)(=O)=O)n(Cc2ccccc2)c1C(F)(F)F] | 1-Benzyl-3-(4-chlorophenyl)-4-methyl-N-(2-methylsulfonyl-ethyl)-5-(trifluoromethyl)-1H-pyrrole-2-carboxylic acid amide | GP-4 | 110 mg (88%) | |
| SC-130 | 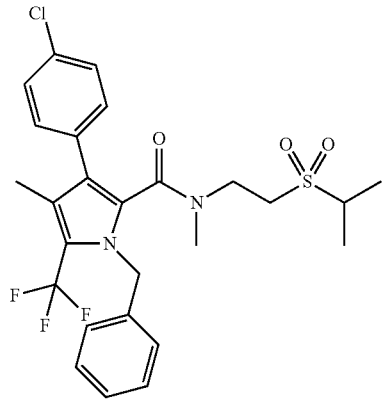 [SMILES: Cc1c(-c2ccc(Cl)cc2)c(C(=O)N(C)CCS(=O)(=O)C(C)C)n(Cc2ccccc2)c1C(F)(F)F] | 1-Benzyl-3-(4-chlorophenyl)-N-[2-(isopropylsulfonyl)-ethyl]-N,4-dimethyl-5-(trifluoromethyl)-1H-pyrrole-2-carboxylic acid amide | GP-4 | 110 mg (78%) | |
| SC-131 | 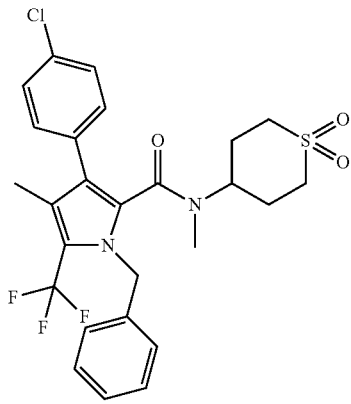 [SMILES: Cc1c(-c2ccc(Cl)cc2)c(C(=O)N(C)C2CCS(=O)(=O)CC2)n(Cc2ccccc2)c1C(F)(F)F] | 1-Benzyl-3-(4-chlorophenyl)-N-(1,1-dioxo-thian-4-yl)-N,4-dimethyl-5-(trifluoromethyl)-1H-pyrrole-2-carboxylic acid amide | GP-4 | 15 mg (11%) | |

-continued

Table Synthesis of pyrrole derivatives (SC):

| Example No. | Structure | Name | Synthesis according to | Yield | Comments |
|---|---|---|---|---|---|
| SC-132 | 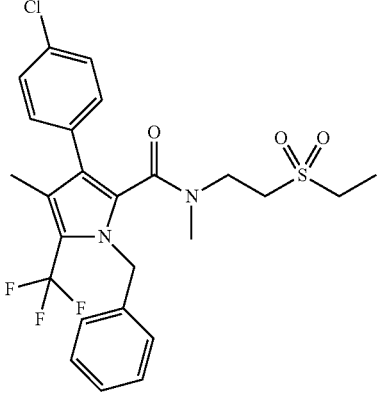 [SMILES: CCS(=O)(=O)CCN(C)C(=O)c1c(-c2ccc(Cl)cc2)c(C)c(C(F)(F)F)n1Cc1ccccc1] | 1-Benzyl-3-(4-chlorophenyl)-N-[2-(ethylsulfonyl)-ethyl]-N,4-dimethyl-5-(trifluoromethyl)-1H-pyrrole-2-carboxylic acid amide | GP-4 | 70 mg (53%) | |
| SC-133 | 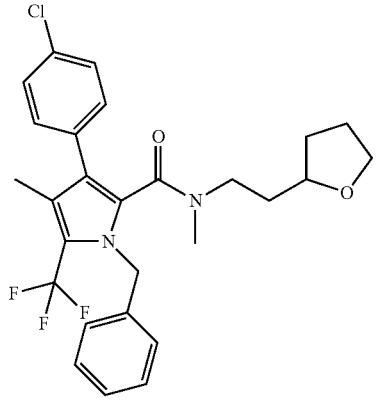 [SMILES: Cc1c(-c2ccc(Cl)cc2)c(C(=O)N(C)CCC2CCCO2)n(Cc2ccccc2)c1C(F)(F)F] | 1-Benzyl-3-(4-chlorophenyl)-N,4-dimethyl-N-(2-tetrahydro-furan-2-yl-ethyl)-5-(trifluoromethyl)-1H-pyrrole-2-carboxylic acid amide | GP-4 | 90 mg (67%) | |
| SC-134 | 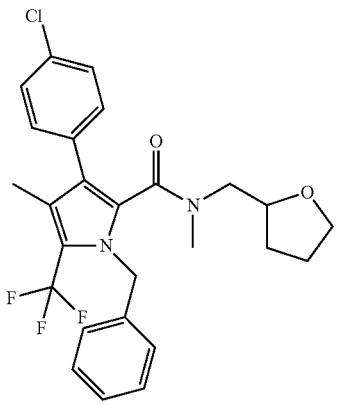 [SMILES: Cc1c(-c2ccc(Cl)cc2)c(C(=O)N(C)CC2CCCO2)n(Cc2ccccc2)c1C(F)(F)F] | 1-Benzyl-3-(4-chlorophenyl)-N,4-dimethyl-N-(tetrahydro-furan-2-yl-methyl)-5-(trifluoromethyl)-1H-pyrrole-2-carboxylic acid amide | GP-4 | 100 mg (78%) | |

Table Synthesis of pyrrole derivatives (SC):

| Example No. | Structure | Name | Synthesis according to | Yield | Comments |
|---|---|---|---|---|---|
| SC-135 | 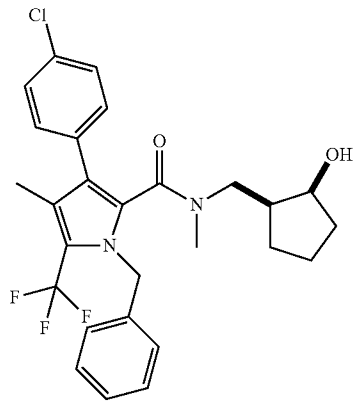 | 1-Benzyl-3-(4-chlorophenyl)-N-[[(1S,2S)-2-hydroxy-cyclopentyl]-methyl]-N,4-dimethyl-5-(trifluoromethyl)-1H-pyrrole-2-carboxylic acid amide and 1-Benzyl-3-(4-chlorophenyl)-N-[[(1R,2R)-2-hydroxy-cyclopentyl]-methyl]-N,4-dimethyl-5-(trifluoromethyl)-1H-pyrrole-2-carboxylic acid amide | GP-4 | 40 mg (31%) | |
| SC-136 | 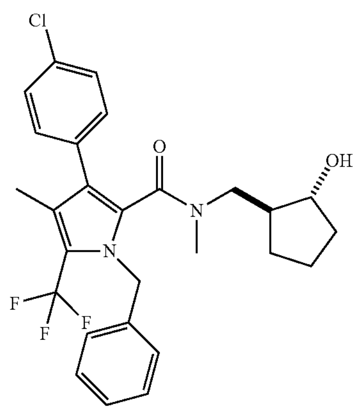 | 1-Benzyl-3-(4-chlorophenyl)-N-[[(1S,2R)-2-hydroxy-cyclopentyl]-methyl]-N,4-dimethyl-5-(trifluoromethyl)-1H-pyrrole-2-carboxylic acid amide and 1-Benzyl-3-(4-chlorophenyl)-N-[[(1R,2S)-2-hydroxy-cyclopentyl]-methyl]-N,4-dimethyl-5-(trifluoromethyl)-1H-pyrrole-2-carboxylic acid amide | GP-4 | 30 mg (23%) | |
| SC-137 | 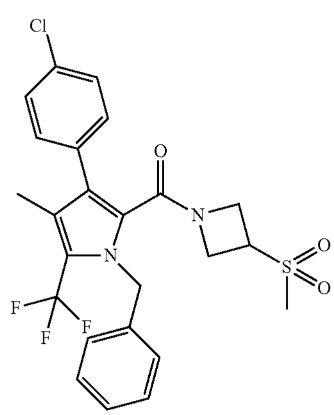 [SMILES: Cc1c(-c2ccc(Cl)cc2)c(C(=O)N2CC(S(C)(=O)=O)C2)n(Cc2ccccc2)c1C(F)(F)F] | [1-Benzyl-3-(4-chlorophenyl)-4-methyl-5-(trifluoromethyl)-1H-pyrrol-2-yl]-(3-methylsulfonyl-azetidin-1-yl)-methanone | GP-4 | 100 mg (74%) | |

-continued

Table Synthesis of pyrrole derivatives (SC):

| Example No. | Structure | Name | Synthesis according to | Yield | Comments |
|---|---|---|---|---|---|
| SC-138 | 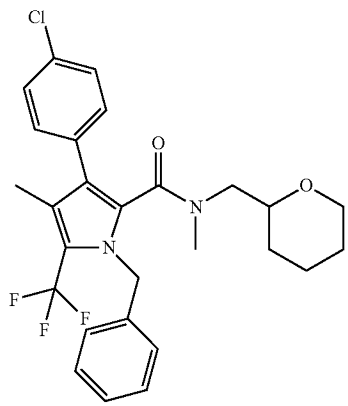 [SMILES: Cc1c(-c2ccc(Cl)cc2)c(C(=O)N(C)CC2CCCCO2)n(Cc2ccccc2)c1C(F)(F)F] | 1-Benzyl-3-(4-chlorophenyl)-N,4-dimethyl-N-(tetrahydro-pyran-2-yl-methyl)-5-(trifluoromethyl)-1H-pyrrole-2-carboxylic acid amide | GP-6 | 100 mg (75%) | |
| SC-139 | 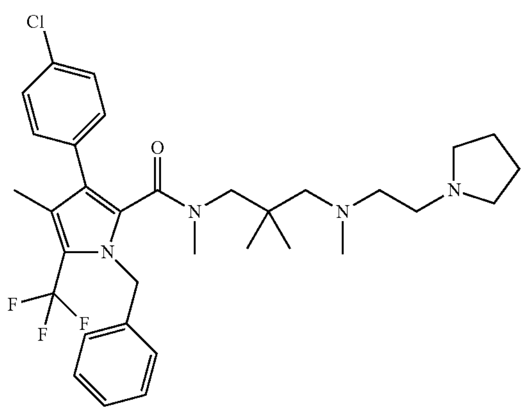 [SMILES: Cc1c(-c2ccc(Cl)cc2)c(C(=O)N(C)CC(C)(C)CN(C)CCN2CCCC2)n(Cc2ccccc2)c1C(F)(F)F] | 1-Benzyl-3-(4-chlorophenyl)-N-[2,2-dimethyl-3-[methyl-(2-pyrrolidin-1-yl-ethyl)-amino]-propyl]-N,4-dimethyl-5-(trifluoromethyl)-1H-pyrrole-2-carboxylic acid amide | GP-4 | 110 mg (72%) | |
| SC-140 | 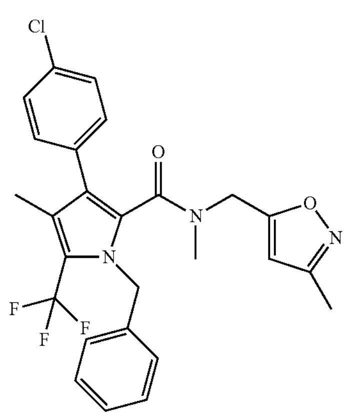 [SMILES: Cc1cc(CN(C)C(=O)c2c(-c3ccc(Cl)cc3)c(C)c(C(F)(F)F)n2Cc2ccccc2)on1] | 1-Benzyl-3-(4-chlorophenyl)-N,4-dimethyl-N-[(3-methyl-isoxazol-5-yl)-methyl]-5-(trifluoromethyl)-1H-pyrrole-2-carboxylic acid amide | GP-6 | 67 mg (53%) | |

-continued

Table Synthesis of pyrrole derivatives (SC):

| Example No. | Structure | Name | Synthesis according to | Yield | Comments |
|---|---|---|---|---|---|
| SC-141 | 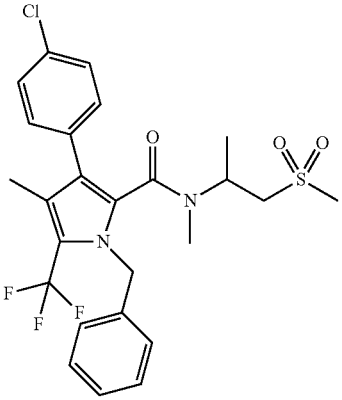 [SMILES: Cc1c(-c2ccc(Cl)cc2)c(C(=O)N(C)C(C)CS(C)(=O)=O)n(Cc2ccccc2)c1C(F)(F)F] | 1-Benzyl-3-(4-chlorophenyl)-N,4-dimethyl-N-(1-methyl-2-methylsulfonyl-ethyl)-5-(trifluoromethyl)-1H-pyrrole-2-carboxylic acid amide | GP-4 | 86 mg (64%) | |
| SC-142 | 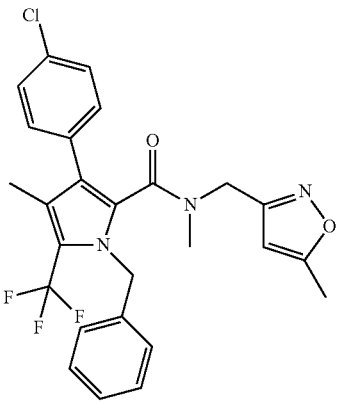 [SMILES: Cc1nnc(CN(C)C(=O)c2c(-c3ccc(Cl)cc3)c(C)c(C(F)(F)F)n2Cc2ccccc2)o1] | 1-Benzyl-3-(4-chlorophenyl)-N,4-dimethyl-N-[(5-methyl-isoxazol-3-yl)-methyl]-5-(trifluoromethyl)-1H-pyrrole-2-carboxylic acid amide | GP-4 | 90 mg (71%) | |
| SC-143 | 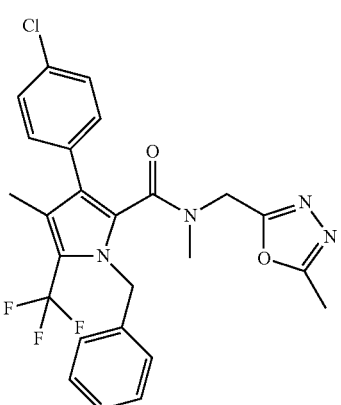 | 1-Benzyl-3-(4-chlorophenyl)-N,4-dimethyl-N-[(5-methyl-[1,3,4]oxadiazol-2-yl)-methyl]-5-(trifluoromethyl)-1H-pyrrole-2-carboxylic acid amide | GP-4 | 55 mg (43%) | |

-continued

Table Synthesis of pyrrole derivatives (SC):

| Example No. | Structure | Name | Synthesis according to | Yield | Comments |
|---|---|---|---|---|---|
| SC-144 | 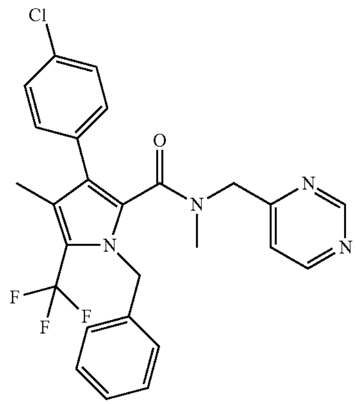 [SMILES: Cc1c(-c2ccc(Cl)cc2)c(C(=O)N(C)Cc2ccncn2)n(Cc2ccccc2)c1C(F)(F)F] | 1-Benzyl-3-(4-chlorophenyl)-N,4-dimethyl-N-(pyrimidin-4-yl-methyl)-5-(trifluoromethyl)-1H-pyrrole-2-carboxylic acid amide | GP-4 | 62 mg (49%) | |
| SC-145 | 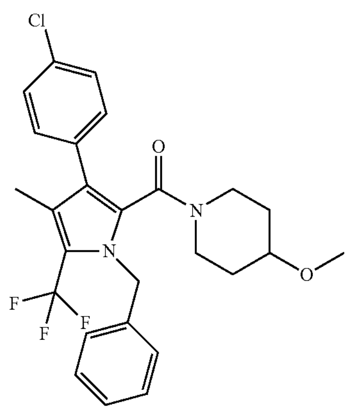 [SMILES: COC1CCN(C(=O)c2c(-c3ccc(Cl)cc3)c(C)c(C(F)(F)F)n2Cc2ccccc2)CC1] | [1-Benzyl-3-(4-chlorophenyl)-4-methyl-5-(trifluoromethyl)-1H-pyrrol-2-yl]-(4-methoxy-piperidin-1-yl)-methanone | GP-4 | 80 mg (64%) | |
| SC-146 | 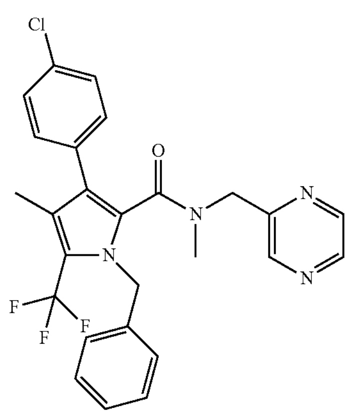 [SMILES: Cc1c(-c2ccc(Cl)cc2)c(C(=O)N(C)Cc2cnccn2)n(Cc2ccccc2)c1C(F)(F)F] | 1-Benzyl-3-(4-chlorophenyl)-N,4-dimethyl-N-(pyrazin-2-yl-methyl)-5-(trifluoromethyl)-1H-pyrrole-2-carboxylic acid amide | GP-4 | 110 mg (85%) | |

-continued

Table Synthesis of pyrrole derivatives (SC):

| Example No. | Structure | Name | Synthesis according to | Yield | Comments |
|---|---|---|---|---|---|
| SC-147 | 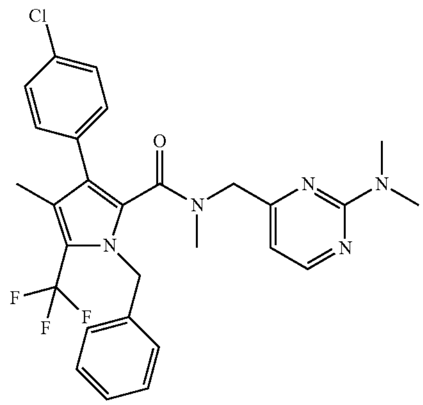 [SMILES: Cc1c(-c2ccc(Cl)cc2)c(C(=O)N(C)Cc2ccnc(N(C)C)n2)n(Cc2ccccc2)c1C(F)(F)F] | 1-Benzyl-3-(4-chlorophenyl)-N-[(2-dimethylamino-pyrimidin-4-yl)-methyl]-N,4-dimethyl-5-(trifluoromethyl)-1H-pyrrole-2-carboxylic acid amide | GP-4 | 110 mg (76%) | |
| SC-148 | 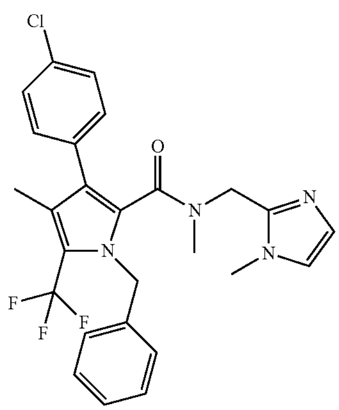 [SMILES: Cc1c(-c2ccc(Cl)cc2)c(C(=O)N(C)Cc2nccn2C)n(Cc2ccccc2)c1C(F)(F)F] | 1-Benzyl-3-(4-chlorophenyl)-N,4-dimethyl-N-[(1-methyl-1H-imidazol-2-yl)-methyl]-5-(trifluoromethyl)-1H-pyrrole-2-carboxylic acid amide | GP-4 | 110 mg (85%) | |
| SC-149 | 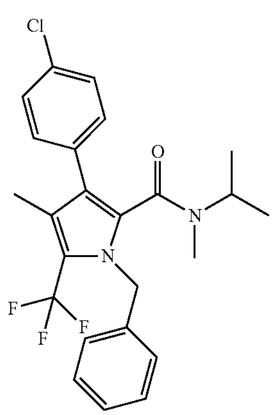 [SMILES: Cc1c(-c2ccc(Cl)cc2)c(C(=O)N(C)C(C)C)n(Cc2ccccc2)c1C(F)(F)F] | 1-Benzyl-3-(4-chlorophenyl)-N-isopropyl-N,4-dimethyl-5-(trifluoromethyl)-1H-pyrrole-2-carboxylic acid amide | GP-4 | 80 mg (47%) | |

-continued

Table Synthesis of pyrrole derivatives (SC):

| Example No. | Structure | Name | Synthesis according to | Yield | Comments |
|---|---|---|---|---|---|
| SC-150 | 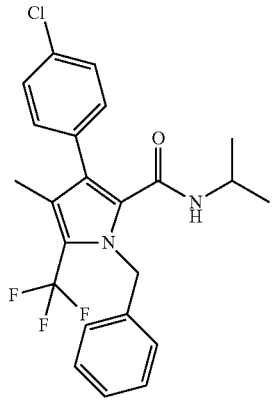 [SMILES: Cc1c(-c2ccc(Cl)cc2)c(C(=O)NC(C)C)n(Cc2ccccc2)c1C(F)(F)F] | 1-Benzyl-3-(4-chlorophenyl)-N-isopropyl-4-methyl-5-(trifluoromethyl)-1H-pyrrole-2-carboxylic acid amide | GP-4 | 70 mg (42%) | |
| SC-151 | 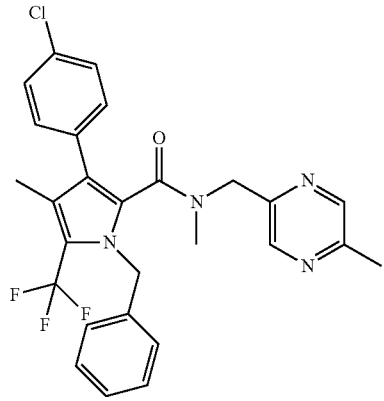 [SMILES: Cc1cnc(CN(C)C(=O)c2c(-c3ccc(Cl)cc3)c(C)c(C(F)(F)F)n2Cc2ccccc2)cn1] | 1-Benzyl-3-(4-chlorophenyl)-N,4-dimethyl-N-[(5-methyl-pyrazin-2-yl)-methyl]-5-(trifluoromethyl)-1H-pyrrole-2-carboxylic acid amide | GP-4 | 120 mg (91%) | |
| SC-152 | 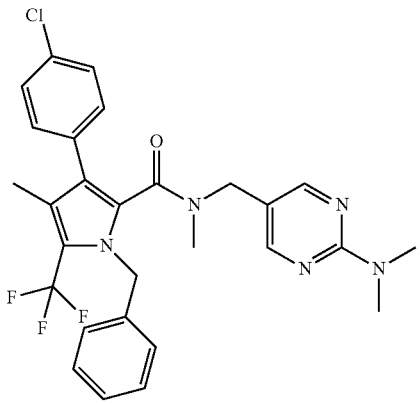 [SMILES: Cc1c(-c2ccc(Cl)cc2)c(C(=O)N(C)Cc2cnc(N(C)C)nc2)n(Cc2ccccc2)c1C(F)(F)F] | 1-Benzyl-3-(4-chlorophenyl)-N-[(2-dimethylamino-pyrimidin-5-yl)-methyl]-N,4-dimethyl-5-(trifluoromethyl)-1H-pyrrole-2-carboxylic acid amide | GP-4 | 110 mg (76%) | |

-continued

Table Synthesis of pyrrole derivatives (SC):

| Example No. | Structure | Name | Synthesis according to | Yield | Comments |
|---|---|---|---|---|---|
| SC-153 | 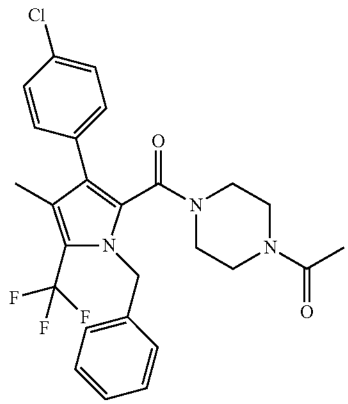 [SMILES: CC(=O)N1CCN(C(=O)c2c(-c3ccc(Cl)cc3)c(C)c(C(F)(F)F)n2Cc2ccccc2)CC1] | 1-[4-[1-Benzyl-3-(4-chlorophenyl)-4-methyl-5-(trifluoromethyl)-1H-pyrrole-2-carbonyl]-piperazin-1-yl]-ethanone | GP-4 | 100 mg (78%) | |
| SC-154 | 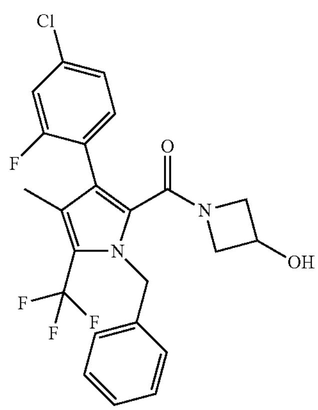 [SMILES: Cc1c(-c2ccc(Cl)cc2F)c(C(=O)N2CC(O)C2)n(Cc2ccccc2)c1C(F)(F)F] | [1-Benzyl-3-(4-chloro-2-fluoro-phenyl)-4-methyl-5-(trifluoromethyl)-1H-pyrrol-2-yl]-(3-hydroxy-azetidin-1-yl)-methanone | GP-4 | 50 mg (44%) | |
| SC-155 | 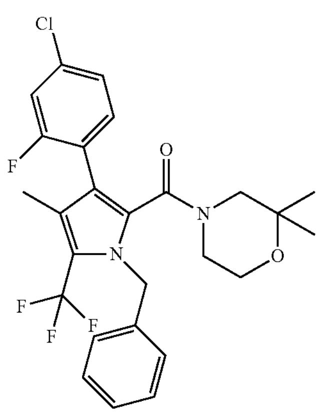 [SMILES: Cc1c(-c2ccc(Cl)cc2F)c(C(=O)N2CCOC(C)(C)C2)n(Cc2ccccc2)c1C(F)(F)F] | [1-Benzyl-3-(4-chloro-2-fluoro-phenyl)-4-methyl-5-(trifluoromethyl)-1H-pyrrol-2-yl]-(2,2-dimethyl-morpholin-4-yl)-methanone | GP-4 | 100 mg (81%) | |

-continued

Table Synthesis of pyrrole derivatives (SC):

| Example No. | Structure | Name | Synthesis according to | Yield | Comments |
|---|---|---|---|---|---|
| SC-156 | 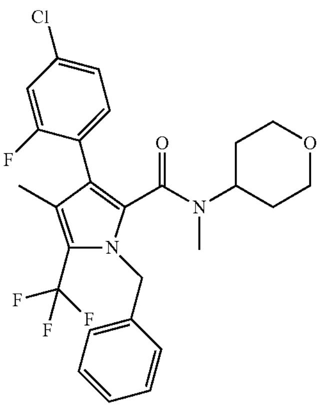 [SMILES: Cc1c(-c2ccc(Cl)cc2F)c(C(=O)N(C)C2CCOCC2)n(Cc2ccccc2)c1C(F)(F)F] | 1-Benzyl-3-(4-chloro-2-fluoro-phenyl)-N,4-dimethyl-N-tetrahydro-pyran-4-yl-5-(trifluoromethyl)-1H-pyrrole-2-carboxylic acid amide | GP-5 | 70 mg (57%) | |
| SC-158 | 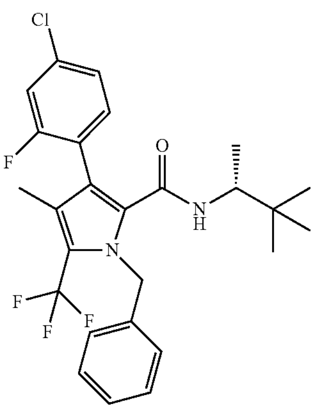 [SMILES: Cc1c(-c2ccc(Cl)cc2F)c(C(=O)N[C@H](C)C(C)(C)C)n(Cc2ccccc2)c1C(F)(F)F] | 1-Benzyl-3-(4-chloro-2-fluoro-phenyl)-4-methyl-5-(trifluoromethyl)-N-[(1R)-1,2,2-trimethyl-propyl]-1H-pyrrole-2-carboxylic acid amide | GP-4 | 190 mg (75%) | |
| SC-159 | 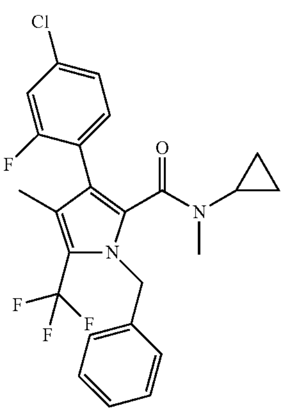 [SMILES: Cc1c(-c2ccc(Cl)cc2F)c(C(=O)N(C)C2CC2)n(Cc2ccccc2)c1C(F)(F)F] | 1-Benzyl-3-(4-chloro-2-fluoro-phenyl)-N-cyclopropyl-N,4-dimethyl-5-(trifluoromethyl)-1H-pyrrole-2-carboxylic acid amide | GP-4 | 50 mg (44%) | |

-continued

Table Synthesis of pyrrole derivatives (SC):

| Example No. | Structure | Name | Synthesis according to | Yield | Comments |
|---|---|---|---|---|---|
| SC-160 | 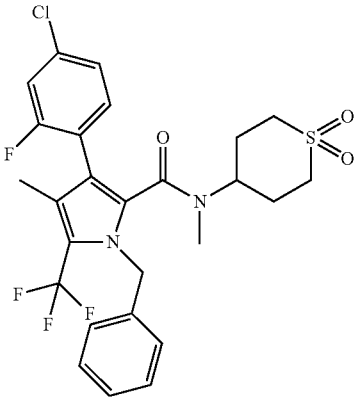 [SMILES: Cc1c(-c2ccc(Cl)cc2F)c(C(=O)N(C)C2CCS(=O)(=O)CC2)n(Cc2ccccc2)c1C(F)(F)F] | 1-Benzyl-3-(4-chloro-2-fluoro-phenyl)-N-(1,1-dioxo-thian-4-yl)-N,4-dimethyl-5-(trifluoromethyl)-1H-pyrrole-2-carboxylic acid amide | GP-4 | 25 mg (18%) | |
| SC-161 | 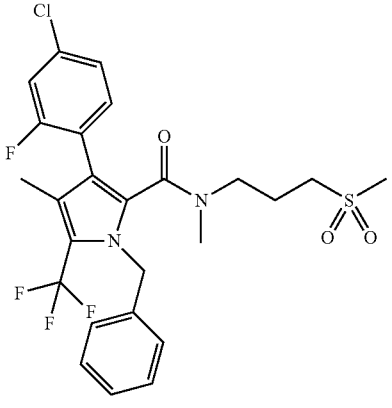 [SMILES: Cc1c(-c2ccc(Cl)cc2F)c(C(=O)N(C)CCCS(C)(=O)=O)n(Cc2ccccc2)c1C(F)(F)F] | 1-Benzyl-3-(4-chloro-2-fluoro-phenyl)-N,4-dimethyl-N-(3-methylsulfonyl-propyl)-5-(trifluoromethyl)-1H-pyrrole-2-carboxylic acid amide | GP-4 | 90 mg (68%) | |
| SC-162 | 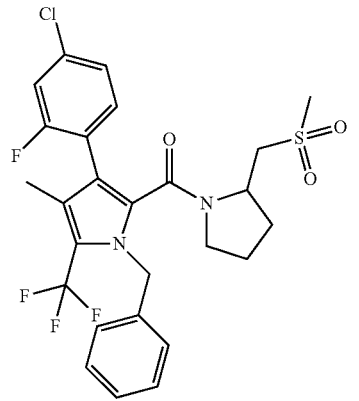 [SMILES: Cc1c(-c2ccc(Cl)cc2F)c(C(=O)N2CCCC2CS(C)(=O)=O)n(Cc2ccccc2)c1C(F)(F)F] | [1-Benzyl-3-(4-chloro-2-fluoro-phenyl)-4-methyl-5-(trifluoromethyl)-1H-pyrrol-2-yl]-[2-(methylsulfonyl-methyl)-pyrrolidin-1-yl]-methanone | GP-4 | 130 mg (96%) | |

-continued

Table Synthesis of pyrrole derivatives (SC):

| Example No. | Structure | Name | Synthesis according to | Yield | Comments |
|---|---|---|---|---|---|
| SC-163 | 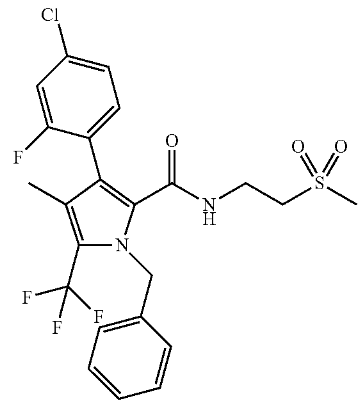 [SMILES: Cc1c(-c2ccc(Cl)cc2F)c(C(=O)NCCS(C)(=O)=O)n(Cc2ccccc2)c1C(F)(F)F] | 1-Benzyl-3-(4-chloro-2-fluoro-phenyl)-4-methyl-N-(2-methylsulfonyl-ethyl)-5-(trifluoromethyl)-1H-pyrrole-2-carboxylic acid amide | GP-4 | 120 mg (96%) | |
| SC-164 | 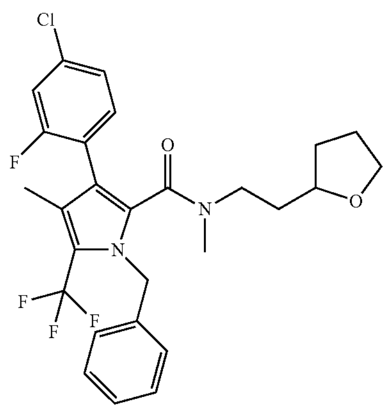 [SMILES: Cc1c(-c2ccc(Cl)cc2F)c(C(=O)N(C)CCC2CCCO2)n(Cc2ccccc2)c1C(F)(F)F] | 1-Benzyl-3-(4-chloro-2-fluoro-phenyl)-N,4-dimethyl-N-(2-tetrahydro-furan-2-yl-ethyl)-5-(trifluoromethyl)-1H-pyrrole-2-carboxylic acid amide | GP-4 | 100 mg (76%) | |
| SC-165 | 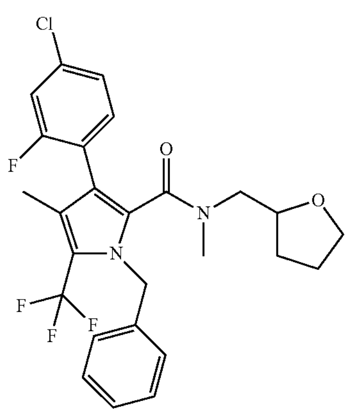 [SMILES: Cc1c(-c2ccc(Cl)cc2F)c(C(=O)N(C)CC2CCCO2)n(Cc2ccccc2)c1C(F)(F)F] | 1-Benzyl-3-(4-chloro-2-fluoro-phenyl)-N,4-dimethyl-N-(tetrahydro-furan-2-yl-methyl)-5-(trifluoromethyl)-1H-pyrrole-2-carboxylic acid amide | GP-4 | 92 mg (74%) | |

Table Synthesis of pyrrole derivatives (SC):

| Example No. | Structure | Name | Synthesis according to | Yield | Comments |
|---|---|---|---|---|---|
| SC-166 | 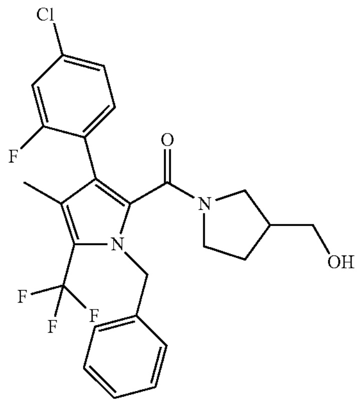 [SMILES: Cc1c(-c2ccc(Cl)cc2F)c(C(=O)N2CCC(CO)C2)n(Cc2ccccc2)c1C(F)(F)F] | [1-Benzyl-3-(4-chloro-2-fluoro-phenyl)-4-methyl-5-(trifluoromethyl)-1H-pyrrol-2-yl]-[3-(hydroxymethyl)-pyrrolidin-1-yl]-methanone | GP-4 | 50 mg (42%) | |
| SC-167 | 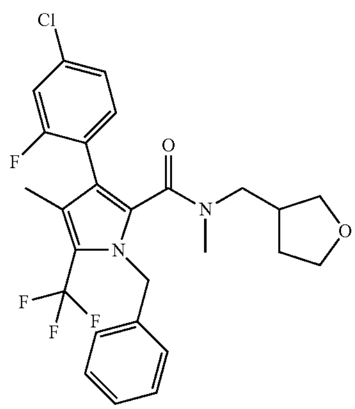 [SMILES: Cc1c(-c2ccc(Cl)cc2F)c(C(=O)N(C)CC2CCOC2)n(Cc2ccccc2)c1C(F)(F)F] | 1-Benzyl-3-(4-chloro-2-fluoro-phenyl)-N,4-dimethyl-N-(tetrahydro-furan-3-yl-methyl)-5-(trifluoromethyl)-1H-pyrrole-2-carboxylic acid amide | GP-6 | 60 mg (61%) | |
| SC-168 | 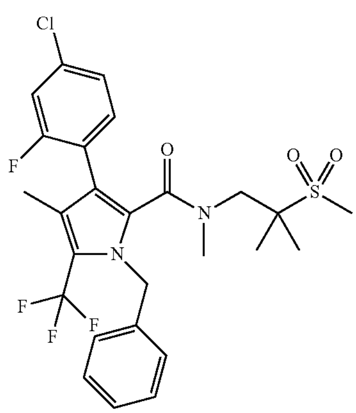 [SMILES: Cc1c(-c2ccc(Cl)cc2F)c(C(=O)N(C)CC(C)(C)S(C)(=O)=O)n(Cc2ccccc2)c1C(F)(F)F] | 1-Benzyl-3-(4-chloro-2-fluoro-phenyl)-N,4-dimethyl-N-(2-methyl-2-methylsulfonyl-propyl)-5-(trifluoromethyl)-1H-pyrrole-2-carboxylic acid amide | GP-6 | 40 mg (37%) | |

-continued

Table Synthesis of pyrrole derivatives (SC):

| Example No. | Structure | Name | Synthesis according to | Yield | Comments |
|---|---|---|---|---|---|
| SC-169 | 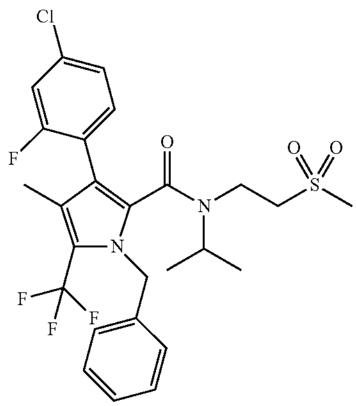 [SMILES: Cc1c(-c2ccc(Cl)cc2F)c(C(=O)N(CCS(C)(=O)=O)C(C)C)n(Cc2ccccc2)c1C(F)(F)F] | 1-Benzyl-3-(4-chloro-2-fluorophenyl)-N-isopropyl-4-methyl-N-(2-methylsulfonyl-ethyl)-5-(trifluoromethyl)-1H-pyrrole-2-carboxylic acid amide | GP-6 | 50 mg (37%) | |
| SC-170 | 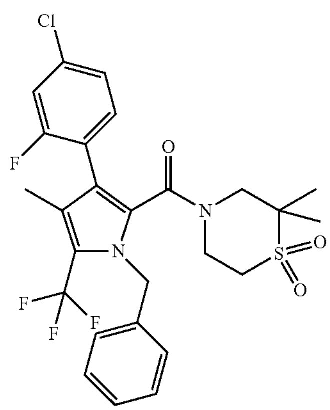 [SMILES: Cc1c(-c2ccc(Cl)cc2F)c(C(=O)N2CCS(=O)(=O)C(C)(C)C2)n(Cc2ccccc2)c1C(F)(F)F] | [1-Benzyl-3-(4-chloro-2-fluorophenyl)-4-methyl-5-(trifluoromethyl)-1H-pyrrol-2-yl]-(2,2-dimethyl-1,1-dioxo-[1,4]thiazinan-4-yl)-methanone | GP-6 | 25 mg (18%) | |
| SC-171 | 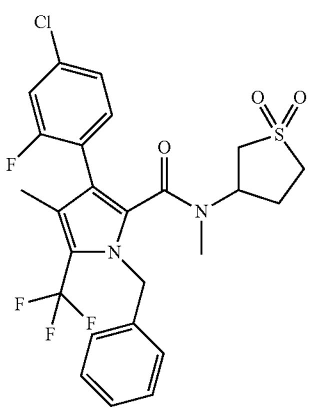 [SMILES: Cc1c(-c2ccc(Cl)cc2F)c(C(=O)N(C)C2CCS(=O)(=O)C2)n(Cc2ccccc2)c1C(F)(F)F] | 1-Benzyl-3-(4-chloro-2-fluorophenyl)-N-(1,1-dioxo-thiolan-3-yl)-N,4-dimethyl-5-(trifluoromethyl)-1H-pyrrole-2-carboxylic acid amide | GP-4 | 50 mg (38%) | |

Table Synthesis of pyrrole derivatives (SC):

| Example No. | Structure | Name | Synthesis according to | Yield | Comments |
|---|---|---|---|---|---|
| SC-172 | 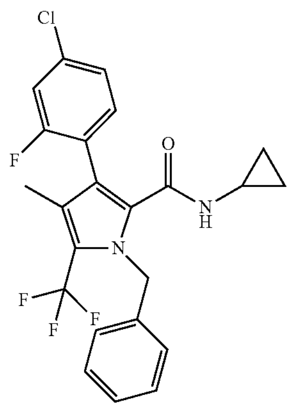 [SMILES: Cc1c(-c2ccc(Cl)cc2F)c(C(=O)NC2CC2)n(Cc2ccccc2)c1C(F)(F)F] | 1-Benzyl-3-(4-chloro-2-fluoro-phenyl)-N-cyclopropyl-4-methyl-5-(trifluoromethyl)-1H-pyrrole-2-carboxylic acid amide | GP-4 | 83 mg (76%) | |
| SC-173 | 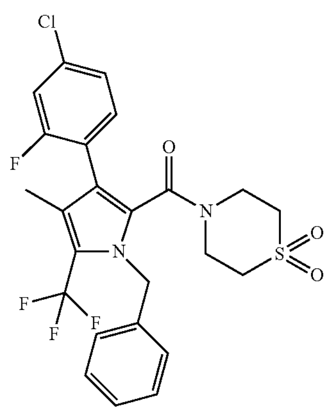 [SMILES: Cc1c(-c2ccc(Cl)cc2F)c(C(=O)N2CCS(=O)(=O)CC2)n(Cc2ccccc2)c1C(F)(F)F] | [1-Benzyl-3-(4-chloro-2-fluoro-phenyl)-4-methyl-5-(trifluoromethyl)-1H-pyrrol-2-yl]-(1,1-dioxo-[1,4]thiazinan-4-yl)-methanone | see below | 32 mg (25%) | |
| SC-174 | 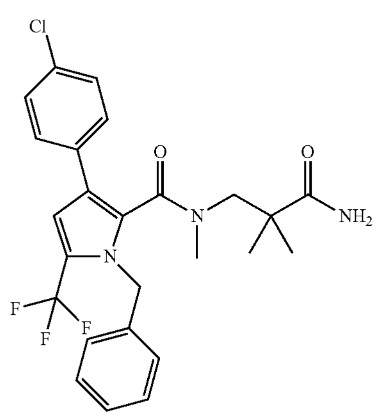 [SMILES: CN(CC(C)(C)C(N)=O)C(=O)c1c(-c2ccc(Cl)cc2)cc(C(F)(F)F)n1Cc1ccccc1] | 1-Benzyl-N-(2-carbamoyl-2-methyl-propyl)-3-(4-chlorophenyl)-N-methyl-5-(trifluoromethyl)-1H-pyrrole-2-carboxylic acid amide | see below | | |

Table Synthesis of pyrrole derivatives (SC):

| Example No. | Structure | Name | Synthesis according to | Yield | Comments |
|---|---|---|---|---|---|
| SC-175 | 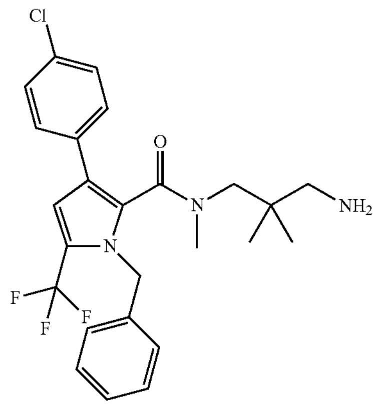 [SMILES: CN(CC(C)(C)CN)C(=O)c1c(-c2ccc(Cl)cc2)cc(C(F)(F)F)n1Cc1ccccc1] | N-(2-Amino-2-methyl-propyl)-1-benzyl-3-(4-chlorophenyl)-N-methyl-5-(trifluoromethyl)-1H-pyrrole-2-carboxylic acid amide | GP-4 | | |
| SC-176 | 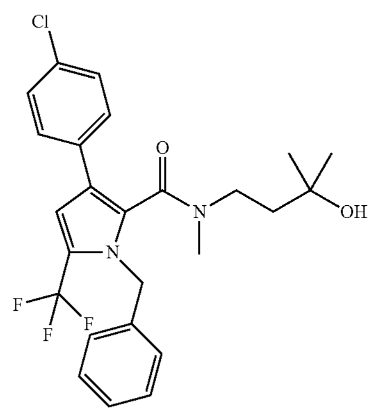 [SMILES: CN(CCC(C)(C)O)C(=O)c1c(-c2ccc(Cl)cc2)cc(C(F)(F)F)n1Cc1ccccc1] | 1-Benzyl-3-(4-chlorophenyl)-N-(3-hydroxy-3-methyl-butyl)-N-methyl-5-(trifluoromethyl)-1H-pyrrole-2-carboxylic acid amide | GP-4 | 90 mg (71%) | |
| SC-177 | 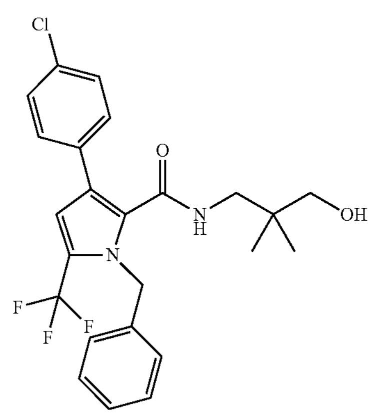 [SMILES: CC(C)(CO)CNC(=O)c1c(-c2ccc(Cl)cc2)cc(C(F)(F)F)n1Cc1ccccc1] | 1-Benzyl-3-(4-chlorophenyl)-N-(3-hydroxy-2,2-dimethyl-propyl)-5-(trifluoromethyl)-1H-pyrrole-2-carboxylic acid amide | GP-4 | 40 mg (33%) | |

-continued

Table Synthesis of pyrrole derivatives (SC):

| Example No. | Structure | Name | Synthesis according to | Yield | Comments |
|---|---|---|---|---|---|
| SC-178 | 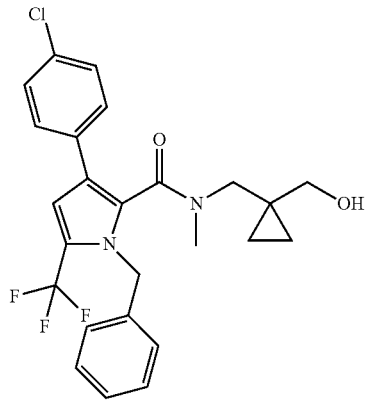 [SMILES: CN(CC1(CO)CC1)C(=O)c1c(-c2ccc(Cl)cc2)cc(C(F)(F)F)n1Cc1ccccc1] | 1-Benzyl-3-(4-chlorophenyl)-N-[[1-(hydroxymethyl)-cyclopropyl]-methyl]-N-methyl-5-(trifluoromethyl)-1H-pyrrole-2-carboxylic acid amide | GP-4 | 70 mg (56%) | |
| SC-179 | 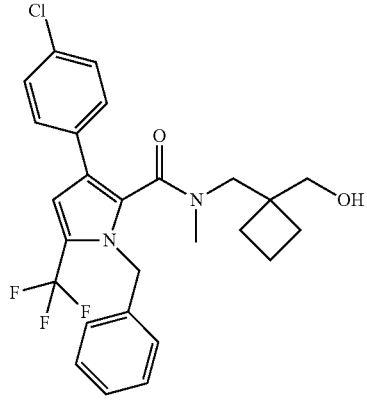 [SMILES: CN(CC1(CO)CCC1)C(=O)c1c(-c2ccc(Cl)cc2)cc(C(F)(F)F)n1Cc1ccccc1] | 1-Benzyl-3-(4-chlorophenyl)-N-[[1-(hydroxymethyl)-cyclobutyl]-methyl]-N-methyl-5-(trifluoromethyl)-1H-pyrrole-2-carboxylic acid amide | GP-4 | 80 mg (62%) | |
| SC-180 | 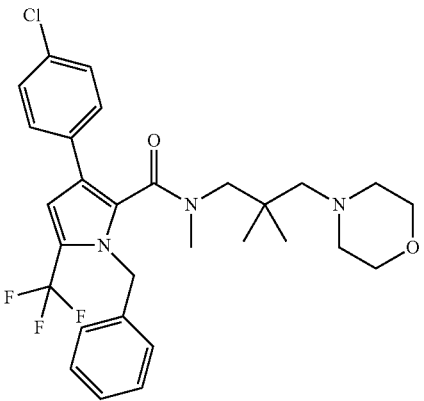 [SMILES: CN(CC(C)(C)CN1CCOCC1)C(=O)c1c(-c2ccc(Cl)cc2)cc(C(F)(F)F)n1Cc1ccccc1] | 1-Benzyl-3-(4-chlorophenyl)-N-(2,2-dimethyl-3-morpholin-4-yl-propyl)-N-methyl-5-(trifluoromethyl)-1H-pyrrole-2-carboxylic acid amide | GP-4 | 120 mg (83%) | |

-continued

Table Synthesis of pyrrole derivatives (SC):

| Example No. | Structure | Name | Synthesis according to | Yield | Comments |
|---|---|---|---|---|---|
| SC-181 | 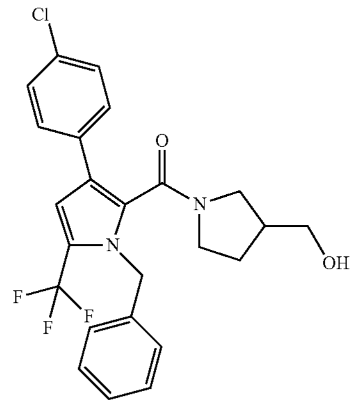 [SMILES: O=C(c1c(-c2ccc(Cl)cc2)cc(C(F)(F)F)n1Cc1ccccc1)N1CCC(CO)C1] | [1-Benzyl-3-(4-chlorophenyl)-5-(trifluoromethyl)-1H-pyrrol-2-yl]-[3-(hydroxymethyl)-pyrrolidin-1-yl]-methanone | GP-4 | 50 mg (41%) | |
| SC-182 | 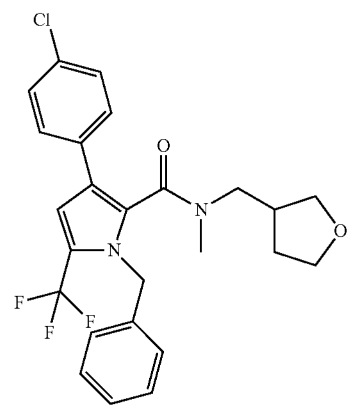 [SMILES: CN(CC1CCOC1)C(=O)c1c(-c2ccc(Cl)cc2)cc(C(F)(F)F)n1Cc1ccccc1] | 1-Benzyl-3-(4-chlorophenyl)-N-methyl-N-(tetrahydro-furan-3-yl-methyl)-5-(trifluoromethyl)-1H-pyrrole-2-carboxylic acid amide | GP-5 | 120 mg (96%) | |
| SC-183 | 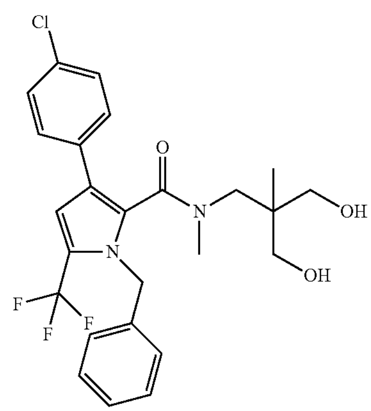 [SMILES: CN(CC(C)(CO)CO)C(=O)c1c(-c2ccc(Cl)cc2)cc(C(F)(F)F)n1Cc1ccccc1] | 1-Benzyl-3-(4-chlorophenyl)-N-[3-hydroxy-2-(hydroxymethyl)-2-methyl-propyl]-N-methyl-5-(trifluoromethyl)-1H-pyrrole-2-carboxylic acid amide | GP-5 | 90 mg (46%) | |

-continued

Table Synthesis of pyrrole derivatives (SC):

| Example No. | Structure | Name | Synthesis according to | Yield | Comments |
|---|---|---|---|---|---|
| SC-184 | 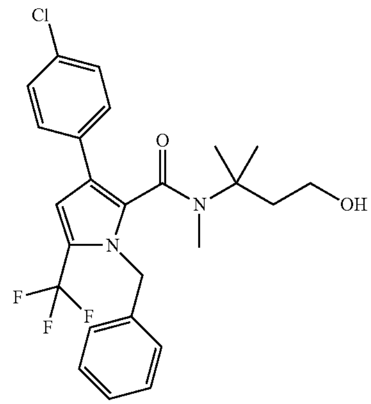 [SMILES: CN(C(=O)c1c(-c2ccc(Cl)cc2)cc(C(F)(F)F)n1Cc1ccccc1)C(C)(C)CCO] | 1-Benzyl-3-(4-chlorophenyl)-N-(3-hydroxy-1,1-dimethyl-propyl)-N-methyl-5-(trifluoromethyl)-1H-pyrrole-2-carboxylic acid amide | GP-4 | 70 mg (37%) | |
| SC-185 | 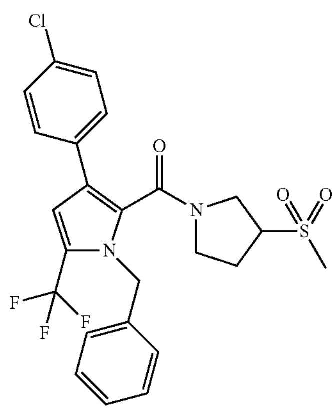 [SMILES: CS(=O)(=O)C1CCN(C(=O)c2c(-c3ccc(Cl)cc3)cc(C(F)(F)F)n2Cc2ccccc2)C1] | [1-Benzyl-3-(4-chlorophenyl)-5-(trifluoromethyl)-1H-pyrrol-2-yl]-(3-methylsulfonyl-pyrrolidin-1-yl)-methanone | GP-6 | 70 mg (65%) | |
| SC-186 | 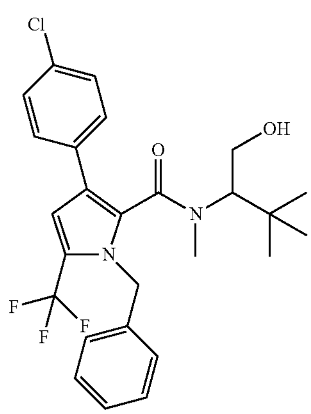 [SMILES: CN(C(=O)c1c(-c2ccc(Cl)cc2)cc(C(F)(F)F)n1Cc1ccccc1)C(CO)C(C)(C)C] | 1-Benzyl-3-(4-chlorophenyl)-N-[1-(hydroxymethyl)-2,2-dimethyl-propyl]-N-methyl-5-(trifluoromethyl)-1H-pyrrole-2-carboxylic acid amide | see below | 80 mg (41%) | |

-continued

Table Synthesis of pyrrole derivatives (SC):

| Example No. | Structure | Name | Synthesis according to | Yield | Comments |
|---|---|---|---|---|---|
| SC-187 | 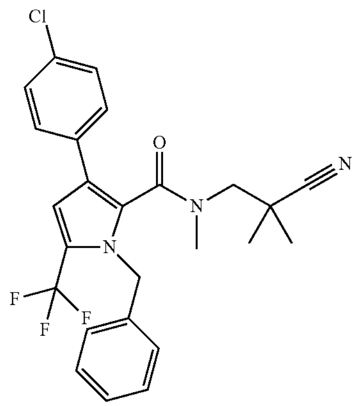 [SMILES: CN(CC(C)(C)C#N)C(=O)c1c(-c2ccc(Cl)cc2)cc(C(F)(F)F)n1Cc1ccccc1] | 1-Benzyl-3-(4-chlorophenyl)-N-(2-cyano-2-methyl-propyl)-N-methyl-5-(trifluoromethyl)-1H-pyrrole-2-carboxylic acid amide | see below | | |
| SC-188 | 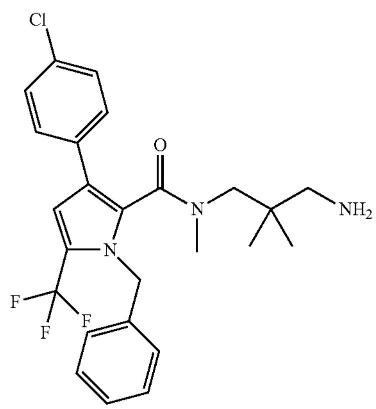 [SMILES: CN(CC(C)(C)CN)C(=O)c1c(-c2ccc(Cl)cc2)cc(C(F)(F)F)n1Cc1ccccc1] | N-(3-Amino-2,2-dimethyl-propyl)-1-benzyl-3-(4-chlorophenyl)-N-methyl-5-(trifluoromethyl)-1H-pyrrole-2-carboxylic acid amide | GP-4 | | |
| SC-189 | 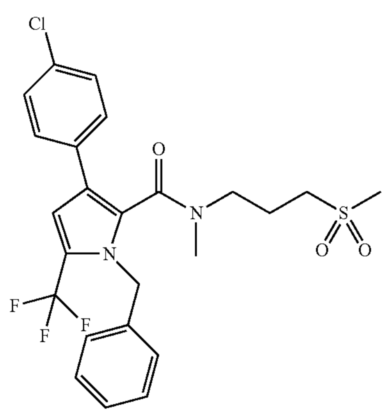 [SMILES: CN(CCCS(C)(=O)=O)C(=O)c1c(-c2ccc(Cl)cc2)cc(C(F)(F)F)n1Cc1ccccc1] | 1-Benzyl-3-(4-chlorophenyl)-N-methyl-N-(3-methylsulfonyl-propyl)-5-(trifluoromethyl)-1H-pyrrole-2-carboxylic acid amide | GP-4 | 100 mg (72%) | |

-continued

Table Synthesis of pyrrole derivatives (SC):

| Example No. | Structure | Name | Synthesis according to | Yield | Comments |
|---|---|---|---|---|---|
| SC-190 | 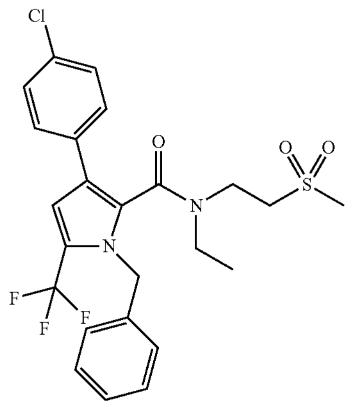 [SMILES: CCN(CCS(C)(=O)=O)C(=O)c1c(-c2ccc(Cl)cc2)cc(C(F)(F)F)n1Cc1ccccc1] | 1-Benzyl-3-(4-chlorophenyl)-N-ethyl-N-(2-methylsulfonyl-ethyl)-5-(trifluoromethyl)-1H-pyrrole-2-carboxylic acid amide | GP-4 | 70 mg (48%) | |
| SC-191 | 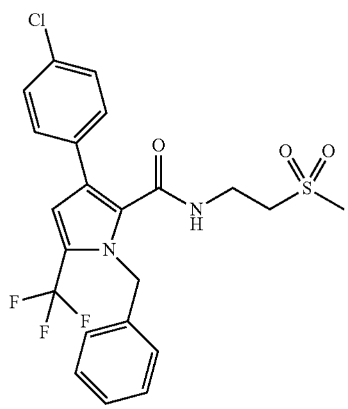 [SMILES: CS(=O)(=O)CCNC(=O)c1c(-c2ccc(Cl)cc2)cc(C(F)(F)F)n1Cc1ccccc1] | 1-Benzyl-3-(4-chlorophenyl)-N-(2-methylsulfonyl-ethyl)-5-(trifluoromethyl)-1H-pyrrole-2-carboxylic acid amide | GP-4 | 90 mg (72%) | |
| SC-192 | 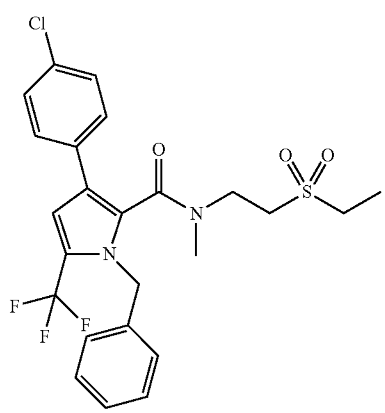 [SMILES: CCS(=O)(=O)CCN(C)C(=O)c1c(-c2ccc(Cl)cc2)cc(C(F)(F)F)n1Cc1ccccc1] | 1-Benzyl-3-(4-chlorophenyl)-N-[2-(ethylsulfonyl)-ethyl]-N-methyl-5-(trifluoromethyl)-1H-pyrrole-2-carboxylic acid amide | GP-4 | 90 mg (65%) | |

-continued

Table Synthesis of pyrrole derivatives (SC):

| Example No. | Structure | Name | Synthesis according to | Yield | Comments |
|---|---|---|---|---|---|
| SC-193 | 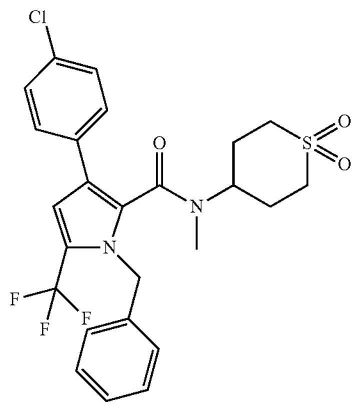 [SMILES: CN(C(=O)c1c(-c2ccc(Cl)cc2)cc(C(F)(F)F)n1Cc1ccccc1)C1CCS(=O)(=O)CC1] | 1-Benzyl-3-(4-chlorophenyl)-N-(1,1-dioxo-thian-4-yl)-N-methyl-5-(trifluoromethyl)-1H-pyrrole-2-carboxylic acid amide | GP-4 | 30 mg (19%) | |
| SC-194 | 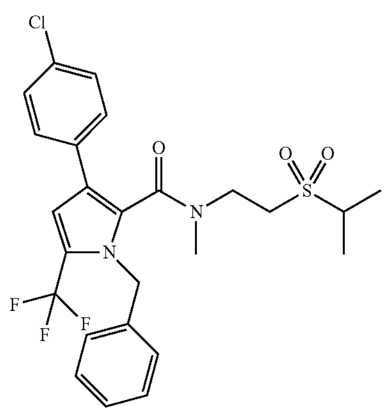 [SMILES: CC(C)S(=O)(=O)CCN(C)C(=O)c1c(-c2ccc(Cl)cc2)cc(C(F)(F)F)n1Cc1ccccc1] | 1-Benzyl-3-(4-chlorophenyl)-N-[2-(isopropylsulfonyl)-ethyl]-N-methyl-5-(trifluoromethyl)-1H-pyrrole-2-carboxylic acid amide | GP-4 | 100 mg (69%) | |
| SC-195 | 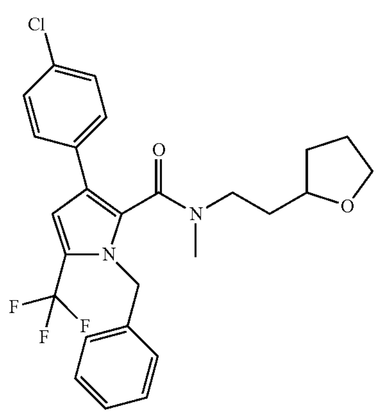 [SMILES: CN(CCC1CCCO1)C(=O)c1c(-c2ccc(Cl)cc2)cc(C(F)(F)F)n1Cc1ccccc1] | 1-Benzyl-3-(4-chlorophenyl)-N-methyl-N-(2-tetrahydro-furan-2-yl-ethyl)-5-(trifluoromethyl)-1H-pyrrole-2-carboxylic acid amide | GP-6 | 80 mg (61%) | |

Table Synthesis of pyrrole derivatives (SC):

| Example No. | Structure | Name | Synthesis according to | Yield | Comments |
|---|---|---|---|---|---|
| SC-196 | 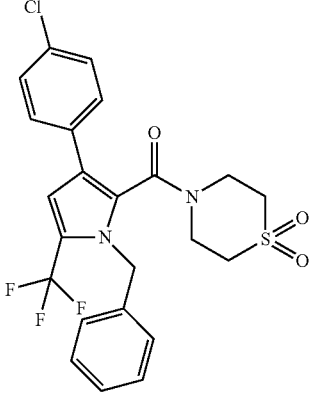 [SMILES: O=C(c1c(-c2ccc(Cl)cc2)cc(C(F)(F)F)n1Cc1ccccc1)N1CCS(=O)(=O)CC1] | [1-Benzyl-3-(4-chlorophenyl)-5-(trifluoromethyl)-1H-pyrrol-2-yl]-(1,1-dioxo-[1,4]thiazinan-4-yl)-methanone | GP-4 | 70 mg (36%) | |
| SC-197 | 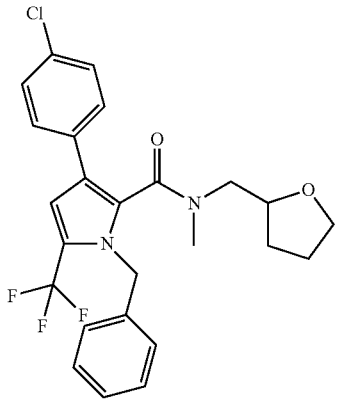 [SMILES: CN(CC1CCCO1)C(=O)c1c(-c2ccc(Cl)cc2)cc(C(F)(F)F)n1Cc1ccccc1] | 1-Benzyl-3-(4-chlorophenyl)-N-methyl-N-(tetrahydro-furan-2-yl-methyl)-5-(trifluoromethyl)-1H-pyrrole-2-carboxylic acid amide | GP-6 | 110 mg (88%) | |
| SC-198 | 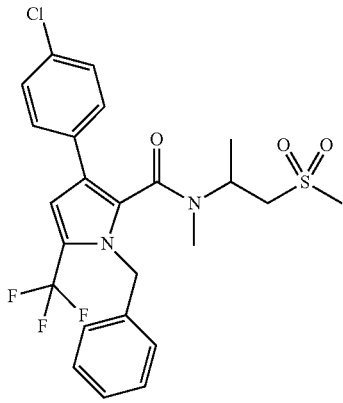 [SMILES: CC(CS(C)(=O)=O)N(C)C(=O)c1c(-c2ccc(Cl)cc2)cc(C(F)(F)F)n1Cc1ccccc1] | 1-Benzyl-3-(4-chlorophenyl)-N-methyl-N-(1-methyl-2-methylsulfonyl-ethyl)-5-(trifluoromethyl)-1H-pyrrole-2-carboxylic acid amide | GP-4 | 60 mg (47%) | |

-continued

Table Synthesis of pyrrole derivatives (SC):

| Example No. | Structure | Name | Synthesis according to | Yield | Comments |
| --- | --- | --- | --- | --- | --- |
| SC-199 | 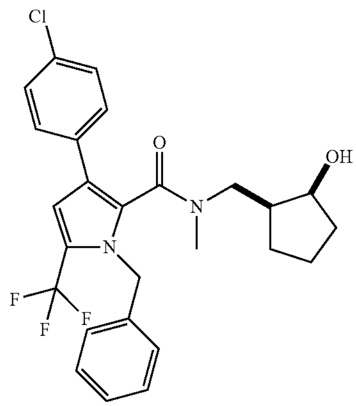 | 1-Benzyl-3-(4-chlorophenyl)-N-[[(1S,2S)-2-hydroxy-cyclopentyl]-methyl]-N-methyl-5-(trifluoromethyl)-1H-pyrrole-2-carboxylic acid amide and 1-Benzyl-3-(4-chlorophenyl)-N-[[(1R,2R)-2-hydroxy-cyclopentyl]-methyl]-N-methyl | GP-4 | 70 mg (54%) | |
| SC-200 | 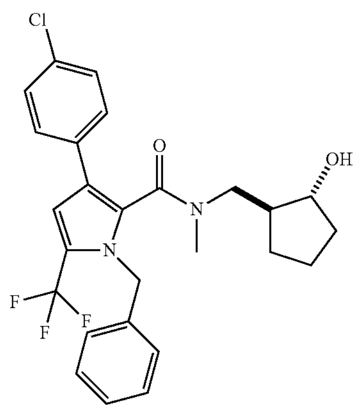 | 1-Benzyl-3-(4-chlorophenyl)-N-[[(1S,2R)-2-hydroxy-cyclopentyl]-methyl]-N-methyl-5-(trifluoromethyl)-1H-pyrrole-2-carboxylic acid amide and 1-Benzyl-3-(4-chlorophenyl)-N-[[(1R,2S)-2-hydroxy-cyclopentyl]-methyl]-N-methyl | GP-4 | 60 mg (46%) | |
| SC-201 | 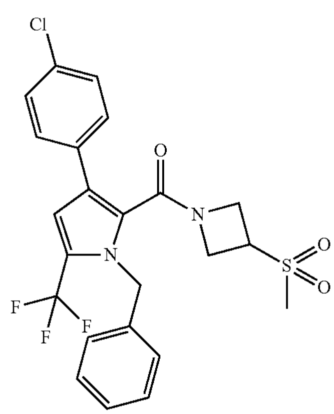 [SMILES: CS(=O)(=O)C1CN(C(=O)c2c(-c3ccc(Cl)cc3)cc(C(F)(F)F)n2Cc2ccccc2)C1] | [1-Benzyl-3-(4-chlorophenyl)-5-(trifluoromethyl)-1H-pyrrol-2-yl]-(3-methylsulfonyl-azetidin-1-yl)-methanone | GP-4 | 90 mg (70%) | |

-continued

Table Synthesis of pyrrole derivatives (SC):

| Example No. | Structure | Name | Synthesis according to | Yield | Comments |
|---|---|---|---|---|---|
| SC-202 | 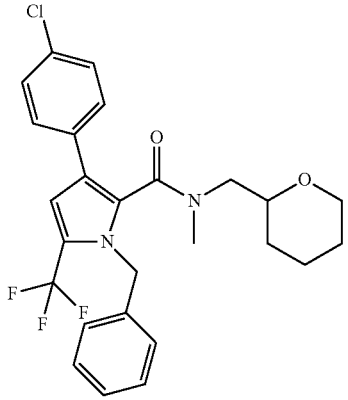 [SMILES: CN(CC1CCCCO1)C(=O)c1c(-c2ccc(Cl)cc2)cc(C(F)(F)F)n1Cc1ccccc1] | 1-Benzyl-3-(4-chlorophenyl)-N-methyl-N-(tetrahydro-pyran-2-yl-methyl)-5-(trifluoromethyl)-1H-pyrrole-2-carboxylic acid amide | GP-6 | 90 mg (71%) | |
| SC-203 | 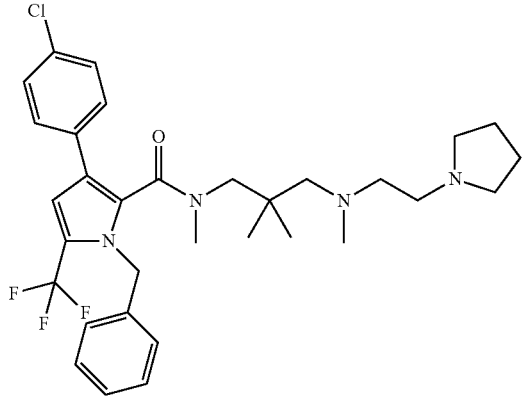 [SMILES: CN(CCN1CCCC1)CC(C)(C)CN(C)C(=O)c1c(-c2ccc(Cl)cc2)cc(C(F)(F)F)n1Cc1ccccc1] | 1-Benzyl-3-(4-chlorophenyl)-N-[2,2-dimethyl-3-[methyl-(2-pyrrolidin-1-yl-ethyl)-amino]-propyl]-N-methyl-5-(trifluoromethyl)-1H-pyrrole-2-carboxylic acid amide | GP-4 | 120 mg (77%) | |
| SC-204 | 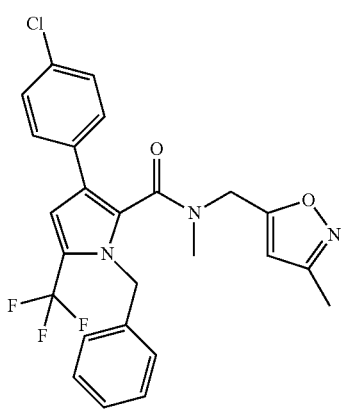 [SMILES: Cc1cc(CN(C)C(=O)c2c(-c3ccc(Cl)cc3)cc(C(F)(F)F)n2Cc2ccccc2)on1] | 1-Benzyl-3-(4-chlorophenyl)-N-methyl-N-[(3-methyl-isoxazol-5-yl)-methyl]-5-(trifluoromethyl)-1H-pyrrole-2-carboxylic acid amide | GP-4 | 73 mg (57%) | |

-continued

Table Synthesis of pyrrole derivatives (SC):

| Example No. | Structure | Name | Synthesis according to | Yield | Comments |
|---|---|---|---|---|---|
| SC-205 | 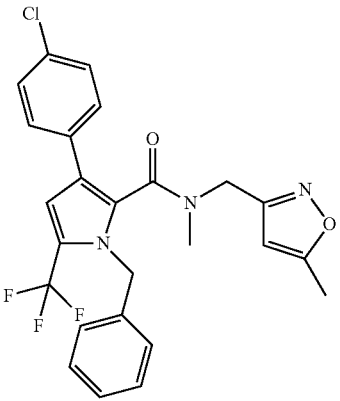 | 1-Benzyl-3-(4-chlorophenyl)-N-methyl-N-[(5-methyl-isoxazol-3-yl)-methyl]-5-(trifluoromethyl)-1H-pyrrole-2-carboxylic acid amide | GP-4 | 80 mg (62%) | |
| SC-206 | 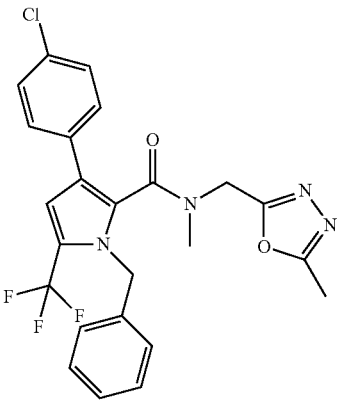 [SMILES: Cc1nnc(CN(C)C(=O)c2c(-c3ccc(Cl)cc3)cc(C(F)(F)F)n2Cc2ccccc2)o1] | 1-Benzyl-3-(4-chlorophenyl)-N-methyl-N-[(5-methyl-[1,3,4]oxadiazol-2-yl)-methyl]-5-(trifluoromethyl)-1H-pyrrole-2-carboxylic acid amide | GP-4 | 46 mg (36%) | |
| SC-207 | 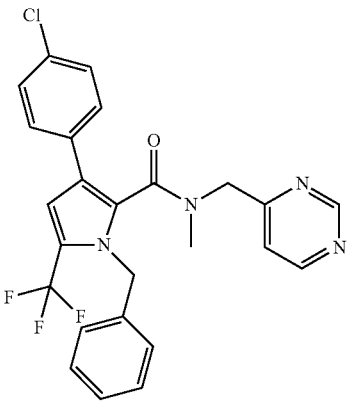 [SMILES: CN(Cc1ccncn1)C(=O)c1c(-c2ccc(Cl)cc2)cc(C(F)(F)F)n1Cc1ccccc1] | 1-Benzyl-3-(4-chlorophenyl)-N-methyl-N-(pyrimidin-4-yl-methyl)-5-(trifluoromethyl)-1H-pyrrole-2-carboxylic acid amide | GP-4 | 65 mg (51%) | |

-continued

Table Synthesis of pyrrole derivatives (SC):

| Example No. | Structure | Name | Synthesis according to | Yield | Comments |
|---|---|---|---|---|---|
| SC-208 | 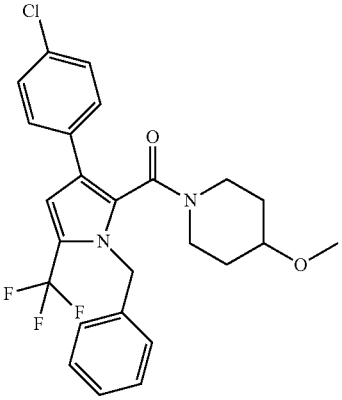 [SMILES: COC1CCN(C(=O)c2c(-c3ccc(Cl)cc3)cc(C(F)(F)F)n2Cc2ccccc2)CC1] | [1-Benzyl-3-(4-chlorophenyl)-5-(trifluoromethyl)-1H-pyrrol-2-yl]-(4-methoxy-piperidin-1-yl)-methanone | GP-4 | 80 mg (64%) | |
| SC-209 | 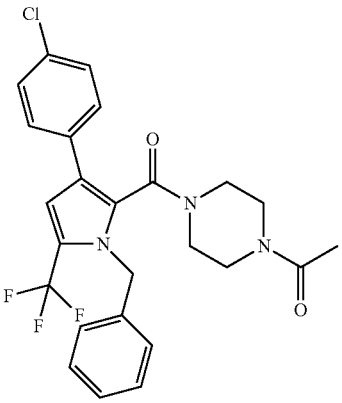 [SMILES: CC(=O)N1CCN(C(=O)c2c(-c3ccc(Cl)cc3)cc(C(F)(F)F)n2Cc2ccccc2)CC1] | 1-[4-[1-Benzyl-3-(4-chlorophenyl)-5-(trifluoromethyl)-1H-pyrrole-2-carbonyl]-piperazin-1-yl]-ethanone | GP-4 | 70 mg (54%) | |
| SC-210 | 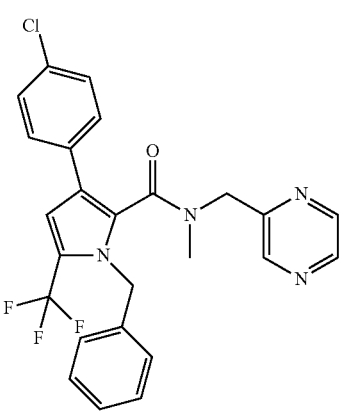 [SMILES: CN(Cc1cnccn1)C(=O)c1c(-c2ccc(Cl)cc2)cc(C(F)(F)F)n1Cc1ccccc1] | 1-Benzyl-3-(4-chlorophenyl)-N-methyl-N-(pyrazin-2-yl-methyl)-5-(trifluoromethyl)-1H-pyrrole-2-carboxylic acid amide | GP-4 | 92 mg (72%) | |

-continued

Table Synthesis of pyrrole derivatives (SC):

| Example No. | Structure | Name | Synthesis according to | Yield | Comments |
|---|---|---|---|---|---|
| SC-211 | 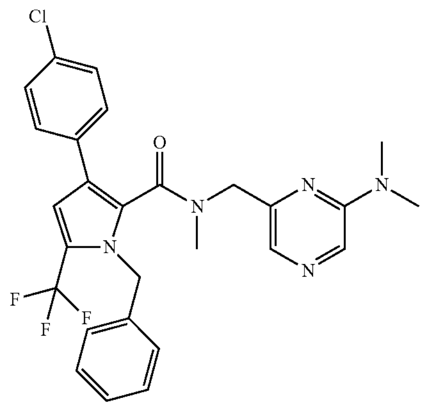 [SMILES: CN(Cc1cncc(N(C)C)n1)C(=O)c1c(-c2ccc(Cl)cc2)cc(C(F)(F)F)n1Cc1ccccc1] | 1-Benzyl-3-(4-chlorophenyl)-N-[(2-dimethylamino-pyrimidin-4-yl)-methyl]-N-methyl-5-(trifluoromethyl)-1H-pyrrole-2-carboxylic acid amide | GP-4 | 118 mg (85%) | |
| SC-212 | 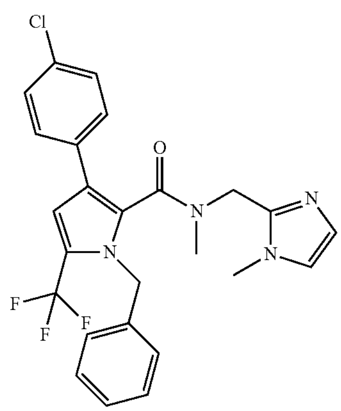 [SMILES: CN(Cc1nccn1C)C(=O)c1c(-c2ccc(Cl)cc2)cc(C(F)(F)F)n1Cc1ccccc1] | 1-Benzyl-3-(4-chlorophenyl)-N-methyl-N-[(1-methyl-1H-imidazol-2-yl)-methyl]-5-(trifluoromethyl)-1H-pyrrole-2-carboxylic acid amide | GP-4 | 107 mg (84%) | |
| SC-213 | 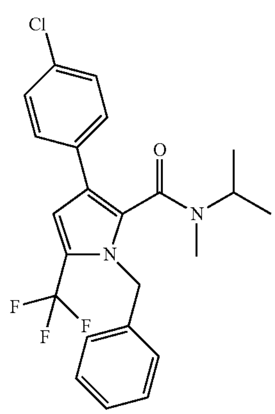 [SMILES: CC(C)N(C)C(=O)c1c(-c2ccc(Cl)cc2)cc(C(F)(F)F)n1Cc1ccccc1] | 1-Benzyl-3-(4-chlorophenyl)-N-isopropyl-N-methyl-5-(trifluoromethyl)-1H-pyrrole-2-carboxylic acid amide | GP-4 | 50 mg (29%) | |

-continued

Table Synthesis of pyrrole derivatives (SC):

| Example No. | Structure | Name | Synthesis according to | Yield | Comments |
|---|---|---|---|---|---|
| SC-214 | 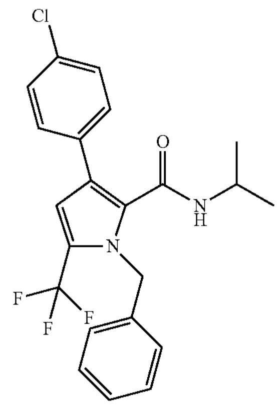 [SMILES: CC(C)NC(=O)c1c(-c2ccc(Cl)cc2)cc(C(F)(F)F)n1Cc1ccccc1] | 1-Benzyl-3-(4-chlorophenyl)-N-isopropyl-5-(trifluoromethyl)-1H-pyrrole-2-carboxylic acid amide | GP-4 | 120 mg (72%) | |
| SC-215 | 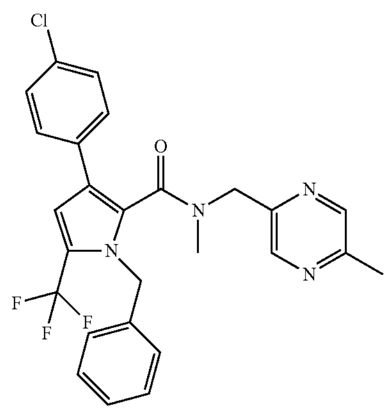 [SMILES: Cc1cnc(CN(C)C(=O)c2c(-c3ccc(Cl)cc3)cc(C(F)(F)F)n2Cc2ccccc2)cn1] | 1-Benzyl-3-(4-chlorophenyl)-N-methyl-N-[(5-methyl-pyrazin-2-yl)-methyl]-5-(trifluoromethyl)-1H-pyrrole-2-carboxylic acid amide | GP-4 | 104 mg (79%) | |
| SC-216 | 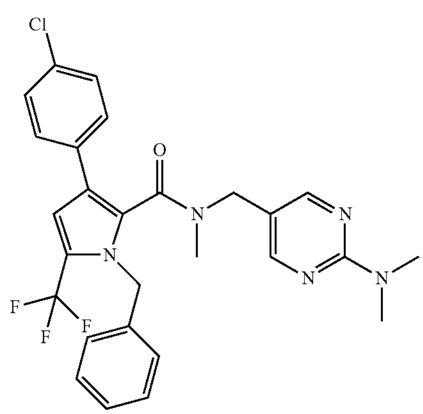 [SMILES: CN(Cc1cnc(N(C)C)nc1)C(=O)c1c(-c2ccc(Cl)cc2)cc(C(F)(F)F)n1Cc1ccccc1] | 1-Benzyl-3-(4-chlorophenyl)-N-[(2-dimethylamino-pyrimidin-5-yl)-methyl]-N-methyl-5-(trifluoromethyl)-1H-pyrrole-2-carboxylic acid amide | GP-4 | 111 mg (79%) | |

-continued

Table Synthesis of pyrrole derivatives (SC):

| Example No. | Structure | Name | Synthesis according to | Yield | Comments |
|---|---|---|---|---|---|
| SC-217 | 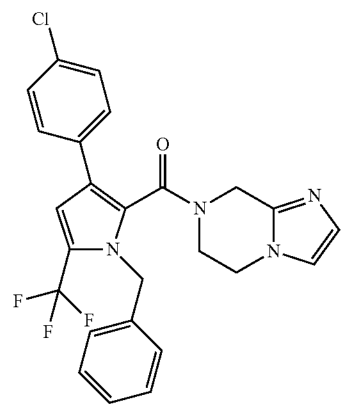 [SMILES: O=C(c1c(-c2ccc(Cl)cc2)cc(C(F)(F)F)n1Cc1ccccc1)N1CCn2ccnc2C1] | [1-Benzyl-3-(4-chlorophenyl)-5-(trifluoromethyl)-1H-pyrrol-2-yl]-(5,6,7,8-tetrahydro-imidazo[1,2-a]pyrazin-7-yl)-methanone | GP-4 | 80 mg (42%) | |
| SC-218 | 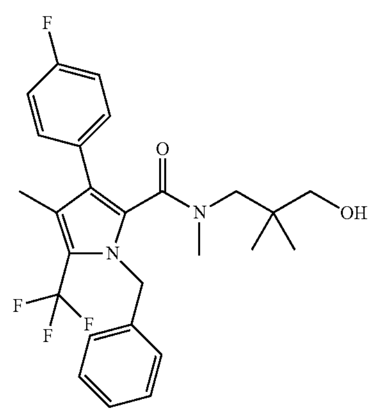 [SMILES: Cc1c(-c2ccc(F)cc2)c(C(=O)N(C)CC(C)(C)CO)n(Cc2ccccc2)c1C(F)(F)F] | 1-Benzyl-3-(4-fluorophenyl)-N-(3-hydroxy-2,2-dimethyl-propyl)-N,4-dimethyl-5-(trifluoromethyl)-1H-pyrrole-2-carboxylic acid amide | GP-4 | 90 mg (71%) | |
| SC-219 | 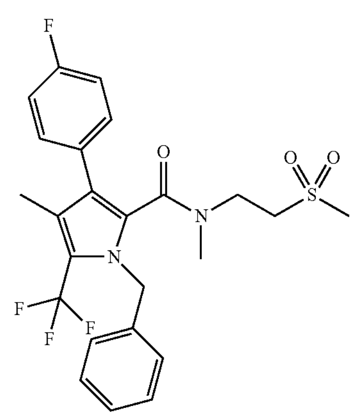 [SMILES: Cc1c(-c2ccc(F)cc2)c(C(=O)N(C)CCS(C)(=O)=O)n(Cc2ccccc2)c1C(F)(F)F] | 1-Benzyl-3-(4-fluorophenyl)-N,4-dimethyl-N-(2-methylsulfonyl-ethyl)-5-(trifluoromethyl)-1H-pyrrole-2-carboxylic acid amide | GP-4 | 80 mg (91%) | |

-continued

Table Synthesis of pyrrole derivatives (SC):

| Example No. | Structure | Name | Synthesis according to | Yield | Comments |
|---|---|---|---|---|---|
| SC-220 | 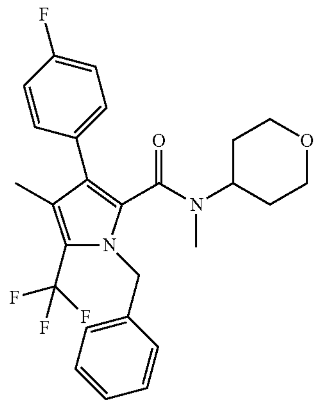 [SMILES: Cc1c(-c2ccc(F)cc2)c(C(=O)N(C)C2CCOCC2)n(Cc2ccccc2)c1C(F)(F)F] | 1-Benzyl-3-(4-fluorophenyl)-N,4-dimethyl-N-tetrahydro-pyran-4-yl-5-(trifluoromethyl)-1H-pyrrole-2-carboxylic acid amide | GP-4 | 110 mg (87%) | |
| SC-221 | 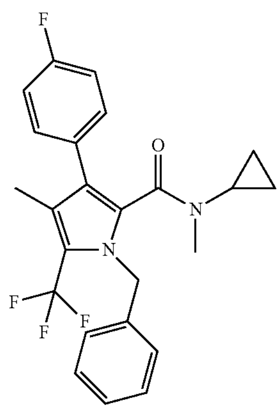 [SMILES: Cc1c(-c2ccc(F)cc2)c(C(=O)N(C)C2CC2)n(Cc2ccccc2)c1C(F)(F)F] | 1-Benzyl-N-cyclopropyl-3-(4-fluorophenyl)-N,4-dimethyl-5-(trifluoromethyl)-1H-pyrrole-2-carboxylic acid amide | GP-6 | 90 mg (79%) | |
| SC-222 | 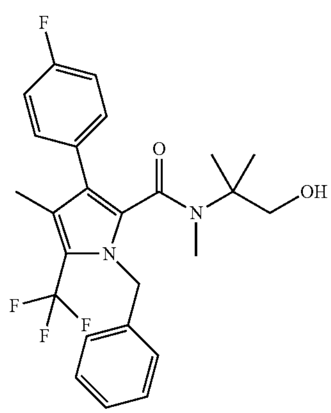 [SMILES: Cc1c(-c2ccc(F)cc2)c(C(=O)N(C)C(C)(C)CO)n(Cc2ccccc2)c1C(F)(F)F] | 1-Benzyl-3-(4-fluorophenyl)-N-(2-hydroxy-1,1-dimethyl-ethyl)-N,4-dimethyl-5-(trifluoromethyl)-1H-pyrrole-2-carboxylic acid amide | GP-4 | 40 mg (33%) | |

-continued

Table Synthesis of pyrrole derivatives (SC):

| Example No. | Structure | Name | Synthesis according to | Yield | Comments |
|---|---|---|---|---|---|
| SC-223 | 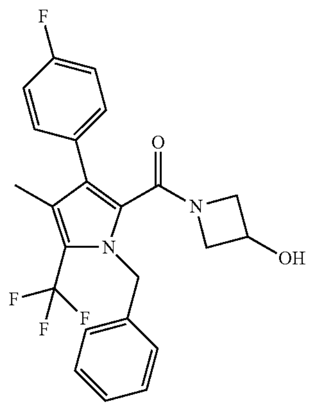 [SMILES: Cc1c(-c2ccc(F)cc2)c(C(=O)N2CC(O)C2)n(Cc2ccccc2)c1C(F)(F)F] | [1-Benzyl-3-(4-fluorophenyl)-4-methyl-5-(trifluoromethyl)-1H-pyrrol-2-yl]-(3-hydroxy-azetidin-1-yl)-methanone | GP-4 | 70 mg (61%) | |
| SC-224 | 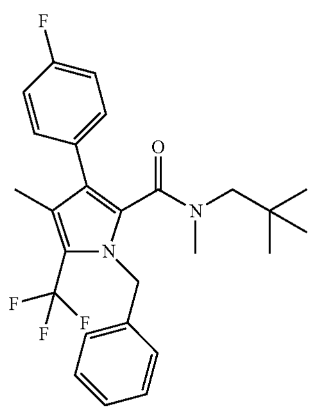 [SMILES: Cc1c(-c2ccc(F)cc2)c(C(=O)N(C)CC(C)(C)C)n(Cc2ccccc2)c1C(F)(F)F] | 1-Benzyl-N-(2,2-dimethyl-propyl)-3-(4-fluorophenyl)-N,4-dimethyl-5-(trifluoromethyl)-1H-pyrrole-2-carboxylic acid amide | GP-4 | 100 mg (82%) | |
| SC-225 | 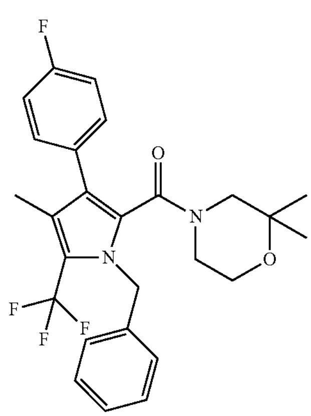 [SMILES: Cc1c(-c2ccc(F)cc2)c(C(=O)N2CCOC(C)(C)C2)n(Cc2ccccc2)c1C(F)(F)F] | [1-Benzyl-3-(4-fluorophenyl)-4-methyl-5-(trifluoromethyl)-1H-pyrrol-2-yl]-(2,2-dimethyl-morpholin-4-yl)-methanone | GP-4 | 90 mg (72%) | |

Table Synthesis of pyrrole derivatives (SC):

| Example No. | Structure | Name | Synthesis according to | Yield | Comments |
|---|---|---|---|---|---|
| SC-226 | 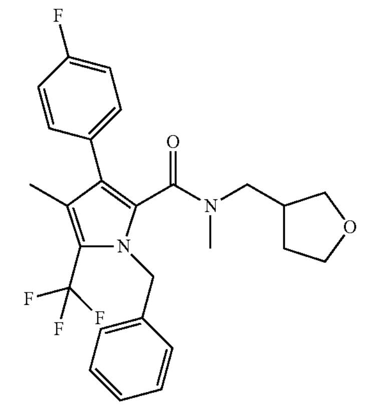 [SMILES: Cc1c(-c2ccc(F)cc2)c(C(=O)N(C)CC2CCOC2)n(Cc2ccccc2)c1C(F)(F)F] | 1-Benzyl-3-(4-fluorophenyl)-N,4-dimethyl-N-(tetrahydro-furan-3-yl-methyl)-5-(trifluoromethyl)-1H-pyrrole-2-carboxylic acid amide | GP-4 | 80 mg (80%) | |
| SC-227 | 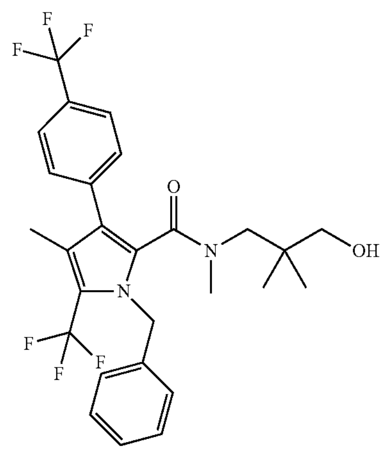 [SMILES: Cc1c(-c2ccc(C(F)(F)F)cc2)c(C(=O)N(C)CC(C)(C)CO)n(Cc2ccccc2)c1C(F)(F)F] | 1-Benzyl-N-(3-hydroxy-2,2-dimethyl-propyl)-N,4-dimethyl-5-(trifluoromethyl)-3-[4-(trifluoromethyl)-phenyl]-1H-pyrrole-2-carboxylic acid amide | GP-4 | 60 mg (49%) | |
| SC-228 | 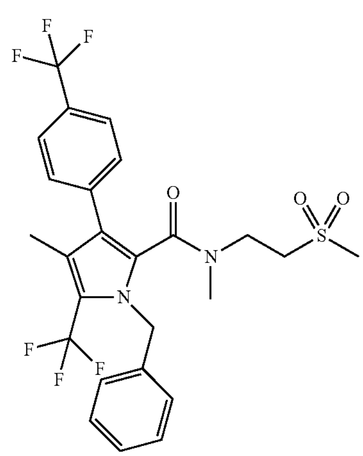 [SMILES: Cc1c(-c2ccc(C(F)(F)F)cc2)c(C(=O)N(C)CCS(C)(=O)=O)n(Cc2ccccc2)c1C(F)(F)F] | 1-Benzyl-N,4-dimethyl-N-(2-methylsulfonyl-ethyl)-5-(trifluoromethyl)-3-[4-(trifluoromethyl)-phenyl]-1H-pyrrole-2-carboxylic acid amide | GP-4 | 110 mg (86%) | |

-continued

Table Synthesis of pyrrole derivatives (SC):

| Example No. | Structure | Name | Synthesis according to | Yield | Comments |
|---|---|---|---|---|---|
| SC-229 | 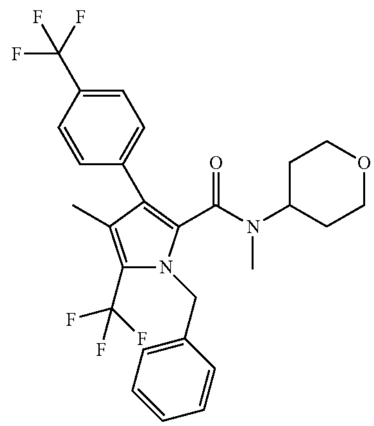 [SMILES: Cc1c(-c2ccc(C(F)(F)F)cc2)c(C(=O)N(C)C2CCOCC2)n(Cc2ccccc2)c1C(F)(F)F] | 1-Benzyl-N,4-dimethyl-N-tetrahydro-pyran-4-yl-5-(trifluoromethyl)-3-[4-(trifluoromethyl)-phenyl]-1H-pyrrole-2-carboxylic acid amide | GP-4 | 90 mg (73%) | |
| SC-230 | 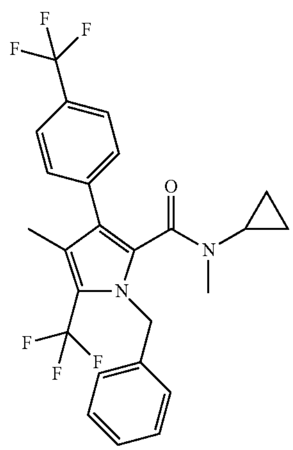 [SMILES: Cc1c(-c2ccc(C(F)(F)F)cc2)c(C(=O)N(C)C2CC2)n(Cc2ccccc2)c1C(F)(F)F] | 1-Benzyl-N-cyclopropyl-N,4-dimethyl-5-(trifluoromethyl)-3-[4-(trifluoromethyl)-phenyl]-1H-pyrrole-2-carboxylic acid amide | GP-6 | 40 mg (36%) | |
| SC-231 | 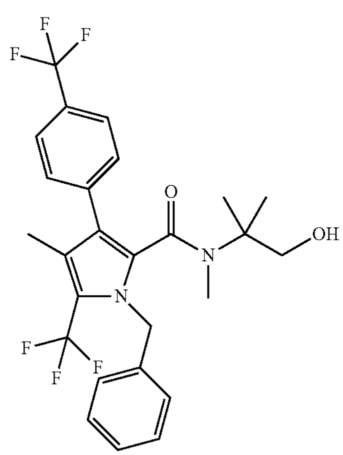 [SMILES: Cc1c(-c2ccc(C(F)(F)F)cc2)c(C(=O)N(C)C(C)(C)CO)n(Cc2ccccc2)c1C(F)(F)F] | 1-Benzyl-N-(2-hydroxy-1,1-dimethyl-ethyl)-N,4-dimethyl-5-(trifluoromethyl)-3-[4-(trifluoromethyl)-phenyl]-1H-pyrrole-2-carboxylic acid amide | GP-4 | 60 mg (50%) | |

-continued

Table Synthesis of pyrrole derivatives (SC):

| Example No. | Structure | Name | Synthesis according to | Yield | Comments |
|---|---|---|---|---|---|
| SC-232 | 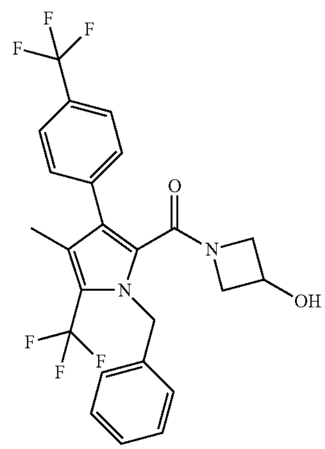 [SMILES: Cc1c(-c2ccc(C(F)(F)F)cc2)c(C(=O)N2CC(O)C2)n(Cc2ccccc2)c1C(F)(F)F] | [1-Benzyl-4-methyl-5-(trifluoromethyl)-3-[4-(trifluoromethyl)-phenyl]-1H-pyrrol-2-yl]-(3-hydroxy-azetidin-1-yl)-methanone | GP-4 | 80 mg (71%) | |
| SC-233 | 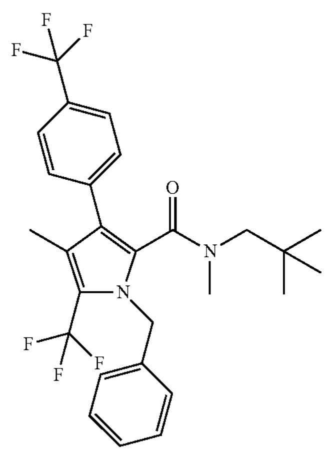 [SMILES: Cc1c(-c2ccc(C(F)(F)F)cc2)c(C(=O)N(C)CC(C)(C)C)n(Cc2ccccc2)c1C(F)(F)F] | 1-Benzyl-N-(2,2-dimethyl-propyl)-N,4-dimethyl-5-(trifluoromethyl)-3-[4-(trifluoromethyl)-phenyl]-1H-pyrrole-2-carboxylic acid amide | GP-4 | 70 mg (59%) | |
| SC-234 | 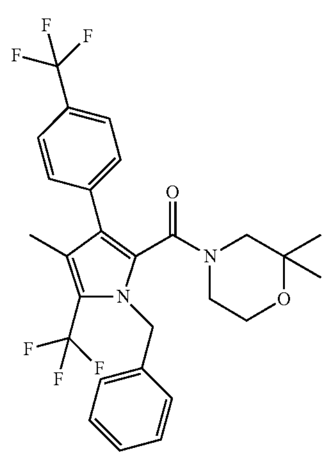 [SMILES: Cc1c(-c2ccc(C(F)(F)F)cc2)c(C(=O)N2CCOC(C)(C)C2)n(Cc2ccccc2)c1C(F)(F)F] | [1-Benzyl-4-methyl-5-(trifluoromethyl)-3-[4-(trifluoromethyl)-phenyl]-1H-pyrrol-2-yl]-(2,2-dimethyl-morpholin-4-yl)-methanone | GP-4 | 70 mg (57%) | |

| Example No. | Structure | Name | Synthesis according to | Yield | Comments |
|---|---|---|---|---|---|
| SC-235 | 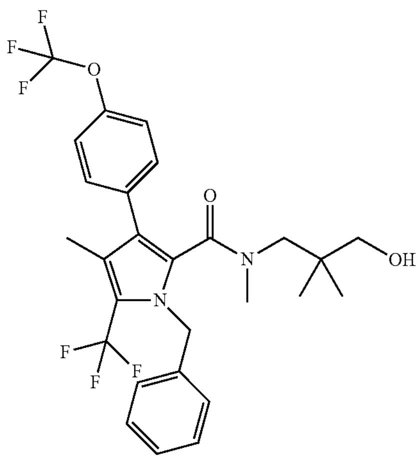 [SMILES: Cc1c(-c2ccc(OC(F)(F)F)cc2)c(C(=O)N(C)CC(C)(C)CO)n(Cc2ccccc2)c1C(F)(F)F] | 1-Benzyl-N-(3-hydroxy-2,2-dimethyl-propyl)-N,4-dimethyl-5-(trifluoromethyl)-3-[4-(trifluoromethyloxy)-phenyl]-1H-pyrrole-2-carboxylic acid amide | GP-4 | 80 mg (65%) | |
| SC-236 | 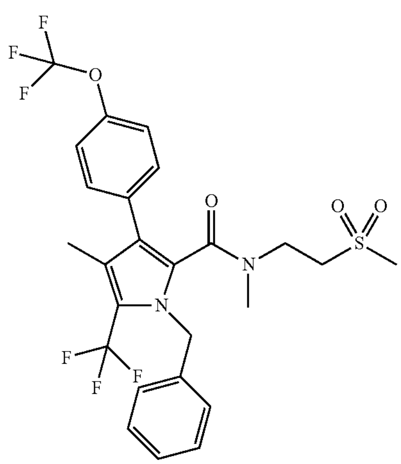 [SMILES: Cc1c(-c2ccc(OC(F)(F)F)cc2)c(C(=O)N(C)CCS(C)(=O)=O)n(Cc2ccccc2)c1C(F)(F)F] | 1-Benzyl-N,4-dimethyl-N-(2-methylsulfonyl-ethyl)-5-(trifluoromethyl)-3-[4-(trifluoromethyloxy)-phenyl]-1H-pyrrole-2-carboxylic acid amide | GP-4 | 110 mg (87%) | |
| SC-237 | 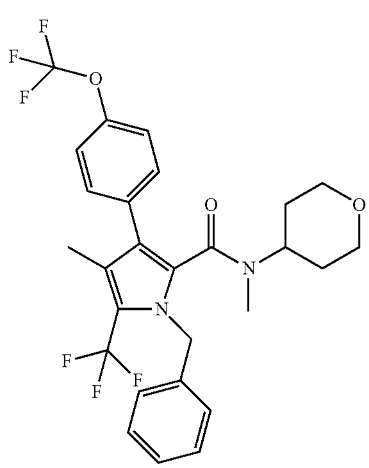 [SMILES: Cc1c(-c2ccc(OC(F)(F)F)cc2)c(C(=O)N(C)C2CCOCC2)n(Cc2ccccc2)c1C(F)(F)F] | 1-Benzyl-N,4-dimethyl-N-tetrahydro-pyran-4-yl-5-(trifluoromethyl)-3-[4-(trifluoromethyloxy)-phenyl]-1H-pyrrole-2-carboxylic acid amide | GP-4 | 90 mg (74%) | |

-continued

Table Synthesis of pyrrole derivatives (SC):

| Example No. | Structure | Name | Synthesis according to | Yield | Comments |
|---|---|---|---|---|---|
| SC-238 | 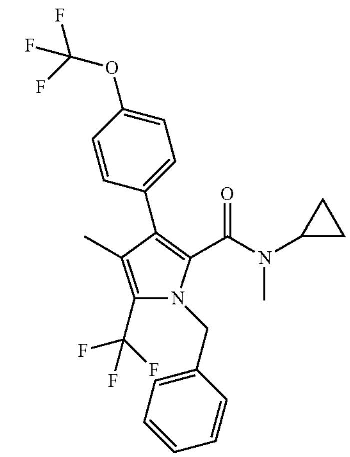 [SMILES: Cc1c(-c2ccc(OC(F)(F)F)cc2)c(C(=O)N(C)C2CC2)n(Cc2ccccc2)c1C(F)(F)F] | 1-Benzyl-N-cyclopropyl-N,4-dimethyl-5-(trifluoromethyl)-3-[4-(trifluoromethyloxy)-phenyl]-1H-pyrrole-2-carboxylic acid amide | GP-4 | 90 mg (80%) | |
| SC-239 | 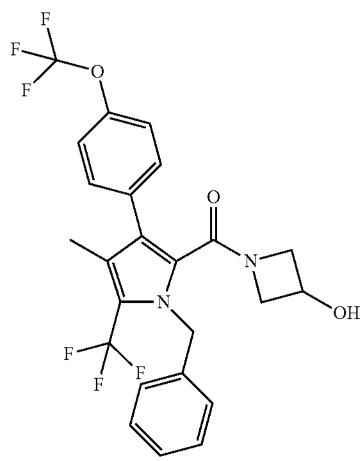 [SMILES: Cc1c(-c2ccc(OC(F)(F)F)cc2)c(C(=O)N2CC(O)C2)n(Cc2ccccc2)c1C(F)(F)F] | [1-Benzyl-4-methyl-5-(trifluoromethyl)-3-[4-(trifluoromethyloxy)-phenyl]-1H-pyrrol-2-yl]-(3-hydroxy-azetidin-1-yl)-methanone | GP-4 | 70 mg (62%) | |
| SC-240 | 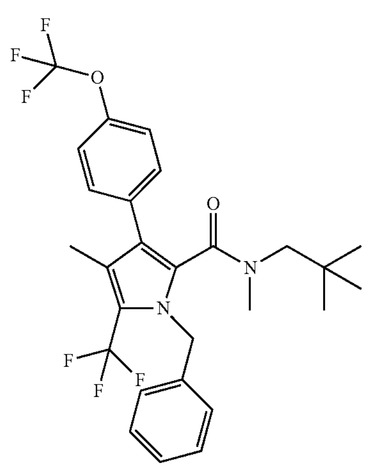 [SMILES: Cc1c(-c2ccc(OC(F)(F)F)cc2)c(C(=O)N(C)CC(C)(C)C)n(Cc2ccccc2)c1C(F)(F)F] | 1-Benzyl-N-(2,2-dimethyl-propyl)-N,4-dimethyl-S-(trifluoromethyl)-3-[4-(trifluoromethyloxy)-phenyl]-1H-pyrrole-2-carboxylic acid amide | GP-6 | 90 mg (76%) | |

-continued

Table Synthesis of pyrrole derivatives (SC):

| Example No. | Structure | Name | Synthesis according to | Yield | Comments |
|---|---|---|---|---|---|
| SC-241 | 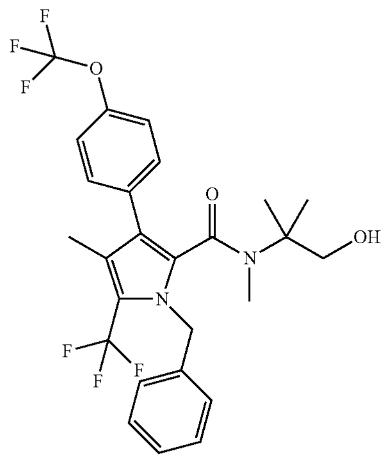 [SMILES: Cc1c(-c2ccc(OC(F)(F)F)cc2)c(C(=O)N(C)C(C)(C)CO)n(Cc2ccccc2)c1C(F)(F)F] | 1-Benzyl-N-(2-hydroxy-1,1-dimethyl-ethyl)-N,4-dimethyl-5-(trifluoromethyl)-3-[4-(trifluoromethyloxy)-phenyl]-1H-pyrrole-2-carboxylic acid amide | GP-4 | 50 mg (42%) | |
| SC-242 | 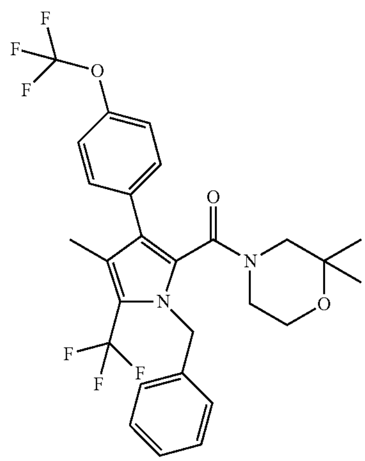 [SMILES: Cc1c(-c2ccc(OC(F)(F)F)cc2)c(C(=O)N2CCOC(C)(C)C2)n(Cc2ccccc2)c1C(F)(F)F] | [1-Benzyl-4-methyl-5-(trifluoromethyl)-3-[4-(trifluoromethyloxy)-phenyl]-1H-pyrrol-2-yl]-(2,2-dimethyl-morpholin-4-yl)-methanone | GP-4 | 80 mg (65%) | |
| SC-243 | 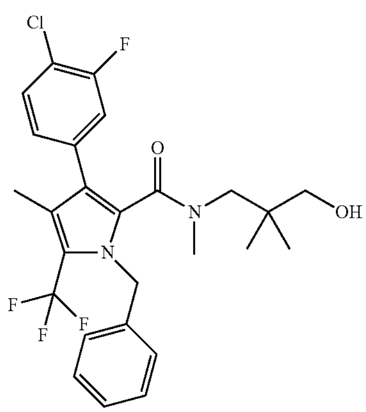 | 1-Benzyl-3-(4-chloro-3-fluoro-phenyl)-N-(3-hydroxy-2,2-dimethyl-propyl)-N,4-dimethyl-5-(trifluoromethyl)-1H-pyrrole-2-carboxylic acid amide | GP-4 | 60 mg (48%) | |

Table Synthesis of pyrrole derivatives (SC):

| Example No. | Structure | Name | Synthesis according to | Yield | Comments |
|---|---|---|---|---|---|
| SC-244 | 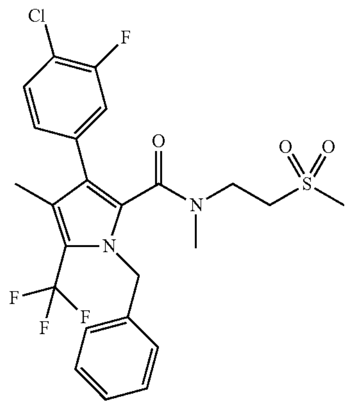 [SMILES: Cc1c(-c2ccc(Cl)c(F)c2)c(C(=O)N(C)CCS(C)(=O)=O)n(Cc2ccccc2)c1C(F)(F)F] | 1-Benzyl-3-(4-chloro-3-fluoro-phenyl)-N,4-dimethyl-N-(2-methylsulfonyl-ethyl)-5-(trifluoromethyl)-1H-pyrrole-2-carboxylic acid amide | GP-4 | 110 mg (87%) | |
| SC-245 | 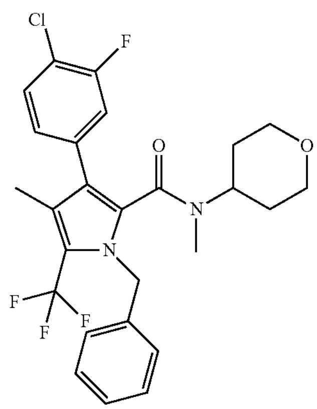 [SMILES: Cc1c(-c2ccc(Cl)c(F)c2)c(C(=O)N(C)C2CCOCC2)n(Cc2ccccc2)c1C(F)(F)F] | 1-Benzyl-3-(4-chloro-3-fluoro-phenyl)-N,4-dimethyl-N-tetrahydro-pyran-4-yl-5-(trifluoromethyl)-1H-pyrrole-2-carboxylic acid amide | GP-4 | 100 mg (81%) | |
| SC-246 | 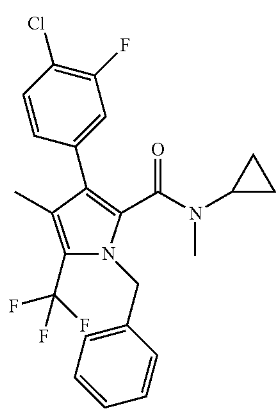 [SMILES: Cc1c(-c2ccc(Cl)c(F)c2)c(C(=O)N(C)C2CC2)n(Cc2ccccc2)c1C(F)(F)F] | 1-Benzyl-3-(4-chloro-3-fluoro-phenyl)-N-cyclopropyl-N,4-dimethyl-5-(trifluoromethyl)-1H-pyrrole-2-carboxylic acid amide | GP-4 | 80 mg (71%) | |

-continued

Table Synthesis of pyrrole derivatives (SC):

| Example No. | Structure | Name | Synthesis according to | Yield | Comments |
|---|---|---|---|---|---|
| SC-247 | 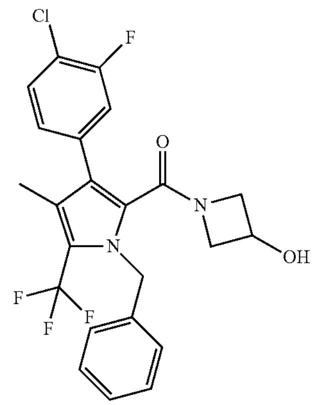 [SMILES: Cc1c(-c2ccc(Cl)c(F)c2)c(C(=O)N2CC(O)C2)n(Cc2ccccc2)c1C(F)(F)F] | [1-Benzyl-3-(4-chloro-3-fluoro-phenyl)-4-methyl-5-(trifluoromethyl)-1H-pyrrol-2-yl]-(3-hydroxy-azetidin-1-yl)-methanone | GP-6 | 80 mg (71%) | |
| SC-248 | 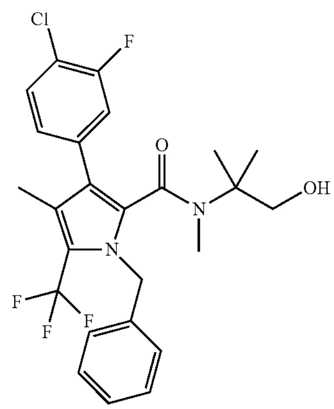 [SMILES: Cc1c(-c2ccc(Cl)c(F)c2)c(C(=O)N(C)C(C)(C)CO)n(Cc2ccccc2)c1C(F)(F)F] | 1-Benzyl-3-(4-chloro-3-fluoro-phenyl)-N-(2-hydroxy-1,1-dimethyl-ethyl)-N,4-dimethyl-5-(trifluoromethyl)-1H-pyrrole-2-carboxylic acid amide | GP-4 | 70 mg (58%) | |
| SC-249 | 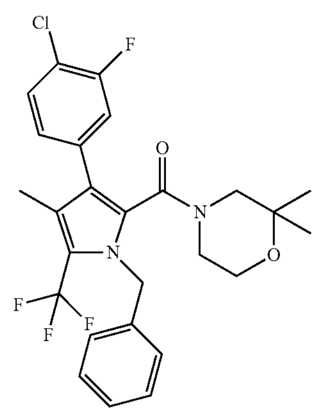 [SMILES: Cc1c(-c2ccc(Cl)c(F)c2)c(C(=O)N2CCOC(C)(C)C2)n(Cc2ccccc2)c1C(F)(F)F] | [1-Benzyl-3-(4-chloro-3-fluoro-phenyl)-4-methyl-5-(trifluoromethyl)-1H-pyrrol-2-yl]-(2,2-dimethyl-morpholin-4-yl)-methanone | GP-4 | 80 mg (65%) | |

Table Synthesis of pyrrole derivatives (SC):

| Example No. | Structure | Name | Synthesis according to | Yield | Comments |
|---|---|---|---|---|---|
| SC-250 | 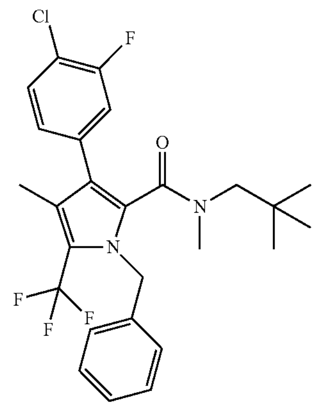 [SMILES: Cc1c(-c2ccc(Cl)c(F)c2)c(C(=O)N(C)CC(C)(C)C)n(Cc2ccccc2)c1C(F)(F)F] | 1-Benzyl-3-(4-chloro-3-fluoro-phenyl)-N-(2,2-dimethyl-propyl)-N,4-dimethyl-5-(trifluoromethyl)-1H-pyrrole-2-carboxylic acid amide | GP-4 | 60 mg (50%) | |
| SC-251 | 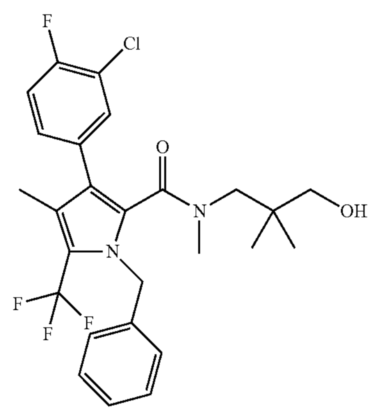 [SMILES: Cc1c(-c2ccc(F)c(Cl)c2)c(C(=O)N(C)CC(C)(C)CO)n(Cc2ccccc2)c1C(F)(F)F] | 1-Benzyl-3-(3-chloro-4-fluoro-phenyl)-N-(3-hydroxy-2,2-dimethyl-propyl)-N,4-dimethyl-5-(trifluoromethyl)-1H-pyrrole-2-carboxylic acid amide | GP-4 | 60 mg (49%) | |
| SC-252 | 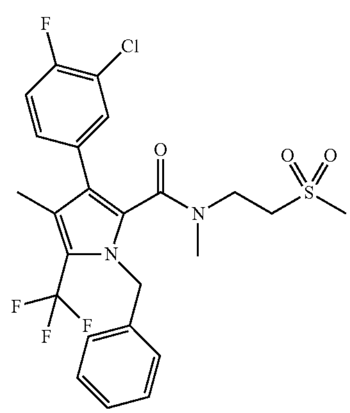 [SMILES: Cc1c(-c2ccc(F)c(Cl)c2)c(C(=O)N(C)CCS(C)(=O)=O)n(Cc2ccccc2)c1C(F)(F)F] | 1-Benzyl-3-(3-chloro-4-fluoro-phenyl)-N,4-dimethyl-N-(2-methylsulfonyl-ethyl)-5-(trifluoromethyl)-1H-pyrrole-2-carboxylic acid amide | GP-4 | 80 mg (62%) | |

Table Synthesis of pyrrole derivatives (SC):

| Example No. | Structure | Name | Synthesis according to | Yield | Comments |
|---|---|---|---|---|---|
| SC-253 | 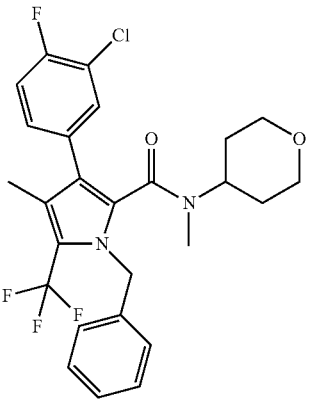 | 1-Benzyl-3-(3-chloro-4-fluoro-phenyl)-N,4-dimethyl-N-tetrahydro-pyran-4-yl-5-(trifluoromethyl)-1H-pyrrole-2-carboxylic acid amide | GP-4 | 110 mg (87%) | |
| SC-254 | 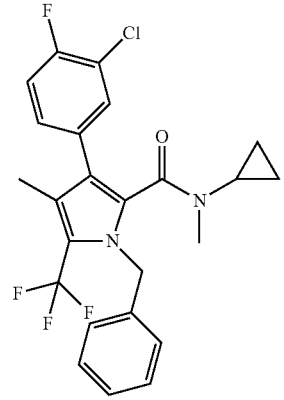 [SMILES: Cc1c(-c2ccc(F)c(Cl)c2)c(C(=O)N(C)C2CC2)n(Cc2ccccc2)c1C(F)(F)F] | 1-Benzyl-3-(3-chloro-4-fluoro-phenyl)-N-cyclopropyl-N,4-dimethyl-5-(trifluoromethyl)-1H-pyrrole-2-carboxylic acid amide | GP-4 | 70 mg (62%) | |
| SC-255 | 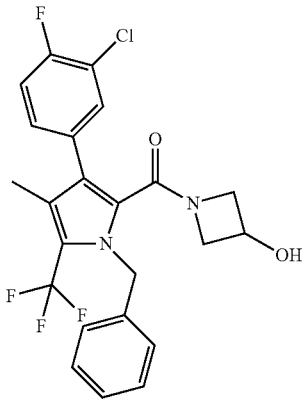 [SMILES: Cc1c(-c2ccc(F)c(Cl)c2)c(C(=O)N2CC(O)C2)n(Cc2ccccc2)c1C(F)(F)F] | [1-Benzyl-3-(3-chloro-4-fluoro-phenyl)-4-methyl-5-(trifluoromethyl)-1H-pyrrol-2-yl]-(3-hydroxy-azetidin-1-yl)-methanone | GP-4 | 65 mg (57%) | |

Table Synthesis of pyrrole derivatives (SC):

| Example No. | Structure | Name | Synthesis according to | Yield | Comments |
|---|---|---|---|---|---|
| SC-256 | 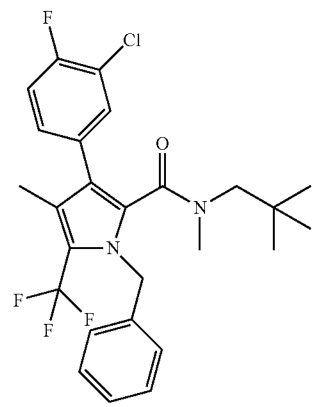 [SMILES: Cc1c(-c2ccc(F)c(Cl)c2)c(C(=O)N(C)CC(C)(C)C)n(Cc2ccccc2)c1C(F)(F)F] | 1-Benzyl-3-(3-chloro-4-fluoro-phenyl)-N-(2,2-dimethyl-propyl)-N,4-dimethyl-5-(trifluoromethyl)-1H-pyrrole-2-carboxylic acid amide | GP-6 | 80 mg (67%) | |
| SC-257 | 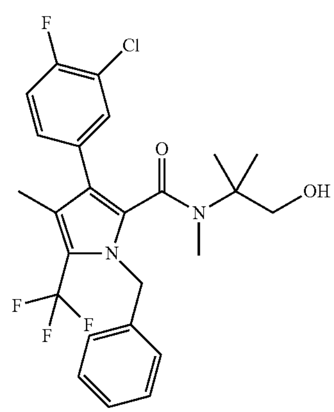 [SMILES: Cc1c(-c2ccc(F)c(Cl)c2)c(C(=O)N(C)C(C)(C)CO)n(Cc2ccccc2)c1C(F)(F)F] | 1-Benzyl-3-(3-chloro-4-fluoro-phenyl)-N-(2-hydroxy-1,1-dimethyl-ethyl)-N,4-dimethyl-5-(trifluoromethyl)-1H-pyrrole-2-carboxylic acid amide | GP-4 | 45 mg (37%) | |
| SC-258 | 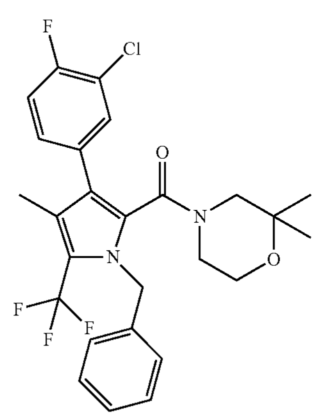 [SMILES: Cc1c(-c2ccc(F)c(Cl)c2)c(C(=O)N2CCOC(C)(C)C2)n(Cc2ccccc2)c1C(F)(F)F] | [1-Benzyl-3-(3-chloro-4-fluoro-phenyl)-4-methyl-5-(trifluoromethyl)-1H-pyrrol-2-yl]-(2,2-dimethyl-morphorin-4-yl)-methanone | see below | 90 mg (73%) | |

-continued

Table Synthesis of pyrrole derivatives (SC):

| Example No. | Structure | Name | Synthesis according to | Yield | Comments |
|---|---|---|---|---|---|
| SC-259 | 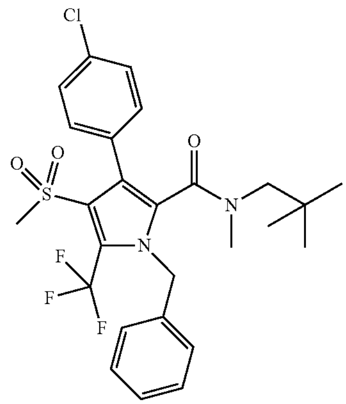 [SMILES: CN(CC(C)(C)C)C(=O)c1c(-c2ccc(Cl)cc2)c(S(C)(=O)=O)c(C(F)(F)F)n1Cc1ccccc1] | 1-Benzyl-3-(4-chlorophenyl)-N-(2,2-dimethyl-propyl)-N-methyl-4-methylsulfonyl-5-(trifluoromethyl)-1H-pyrrole-2-carboxylic acid amide | see below | | |
| SC-260 | 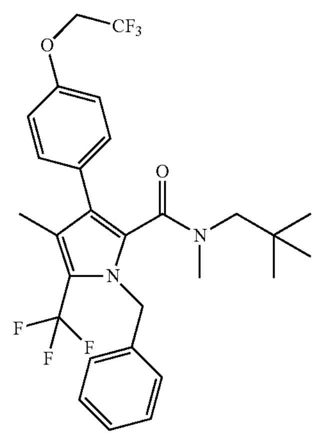 [SMILES: Cc1c(-c2ccc(OCC(F)(F)F)cc2)c(C(=O)N(C)CC(C)(C)C)n(Cc2ccccc2)c1C(F)(F)F] | 1-Benzyl-N-(2,2-dimethyl-propyl)-N,4-dimethyl-3-[4-(2,2,2-trifluoro-ethoxy)-phenyl]-5-(trifluoromethyl)-1H-pyrrole-2-carboxylic acid amide | see below | | |
| SC-261 | 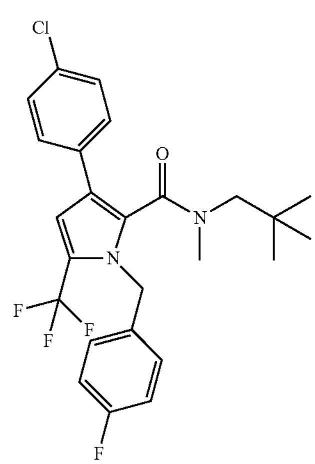 [SMILES: CN(CC(C)(C)C)C(=O)c1c(-c2ccc(Cl)cc2)cc(C(F)(F)F)n1Cc1ccc(F)cc1] | 3-(4-Chlorophenyl)-N-(2,2-dimethyl-propyl)-1-[(4-fluorophenyl)-methyl]-N-methyl-5-(trifluoromethyl)-1H-pyrrole-2-carboxylic acid amide | see below | | |

-continued

Table Synthesis of pyrrole derivatives (SC):

| Example No. | Structure | Name | Synthesis according to | Yield | Comments |
|---|---|---|---|---|---|
| SC-262 | 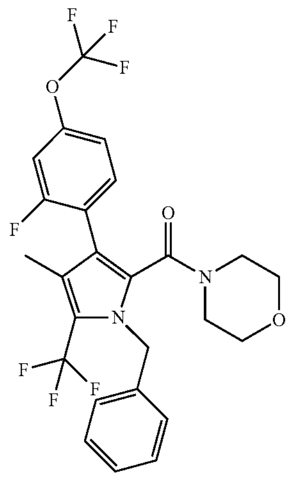 [SMILES: Cc1c(-c2ccc(OC(F)(F)F)cc2F)c(C(=O)N2CCOCC2)n(Cc2ccccc2)c1C(F)(F)F] | [1-Benzyl-3-[2-fluoro-4-(trifluoromethyloxy)-phenyl]-4-methyl-5-(trifluoromethyl)-1H-pyrrol-2-yl]-morpholin-4-yl-methanone | see below | | |
| SC-263 | 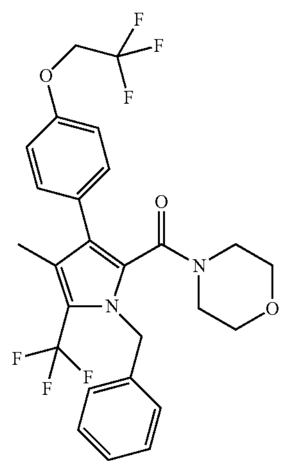 [SMILES: Cc1c(-c2ccc(OCC(F)(F)F)cc2)c(C(=O)N2CCOCC2)n(Cc2ccccc2)c1C(F)(F)F] | [1-Benzyl-4-methyl-3-[4-(2,2,2-trifluoro-ethoxy)-phenyl]-5-(trifluoromethyl)-1H-pyrrol-2-yl]-morpholin-4-yl-methanone | see below | | |
| SC-264 | 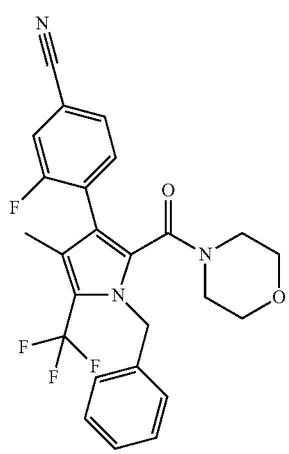 [SMILES: Cc1c(-c2ccc(C#N)cc2F)c(C(=O)N2CCOCC2)n(Cc2ccccc2)c1C(F)(F)F] | 4-[1-Benzyl-4-methyl-2-(morpholine-4-carbonyl)-5-(trifluoromethyl)-1H-pyrrol-3-yl]-3-fluoro-benzonitrile | see below | | |

Table Synthesis of pyrrole derivatives (SC):

| Example No. | Structure | Name | Synthesis according to | Yield | Comments |
|---|---|---|---|---|---|
| SC-265 | 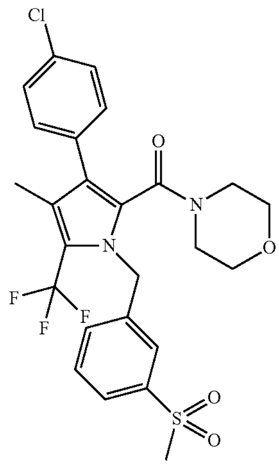 [SMILES: Cc1c(-c2ccc(Cl)cc2)c(C(=O)N2CCOCC2)n(Cc2cccc(S(C)(=O)=O)c2)c1C(F)(F)F] | [3-(4-Chlorophenyl)-4-methyl-1-[(3-methylsulfonyl-phenyl)-methyl]-5-(trifluoromethyl)-1H-pyrrol-2-yl]-morpholin-4-yl-methanone | see below | | |
| SC-266 | 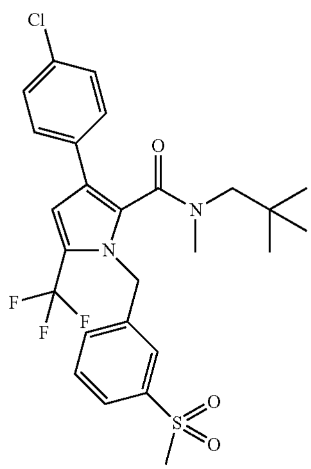 [SMILES: CN(CC(C)(C)C)C(=O)c1c(-c2ccc(Cl)cc2)cc(C(F)(F)F)n1Cc1cccc(S(C)(=O)=O)c1] | 3-(4-Chlorophenyl)-N-(2,2-dimethyl-propyl)-N-methyl-1-[(3-methylsulfonyl-phenyl)-methyl]-5-(trifluoromethyl)-1H-pyrrole-2-carboxylic acid amide | | | |

Synthesis of Example SC-02

Step 1: 1-Benzyl-3-(4-chlorophenyl)-N-methyl-N-neopentyl-1H-pyrrole-2-carboxamide To a suspension of ACI-01 (2 g, 6.42 mmol) in DCM (32 mL) were added N,2,2-trimethylpropan-1-amine (1.06 g, 7.70 mmol) and DIPEA (2.23 mL, 12.83 mmol). To the clear solution were added EDCI (1.353 g, 7.06 mmol) and HOAt (0.087 g, 0.642 mmol) at 0° C. and the yellow solution stirred at room temperature overnight. The mixture was washed with saturated aqueous $NH_4Cl$ and the phases separated. The organic phase was washed with brine, dried over $Na_2SO_4$, filtered and evaporated. The crude mixture was purified by flash chromatography (silica, gradient heptane/EtOAc, 95:5→90:10→80:20) to furnish 2.22 g (88%) of the desired compound.

Step 2: 1-Benzyl-3-(4-chlorophenyl)-N-(2,2-dimethyl-propyl)-N-methyl-5-(trifluoromethyl)-1H-pyrrole-2-carboxylic acid amide (SC-02)

To a solution of 1-benzyl-3-(4-chlorophenyl)-N-methyl-N-neopentyl-1H-pyrrole-2-carboxamide (200 mg, 0.506 mmol) in dry DMSO (10 mL) was added $FeSO_4 \cdot 7H_2O$ (134 mg, 0.481 mmol). $ICF_3$ was bubbled through the reaction mixture for 1 min. After 10 min $H_2O_2$ (35% (w/w) in $H_2O$, 0.266 mL, 3.04 mmol) was added. The mixture was diluted with $Et_2O$ (50 mL) and brine. The organic layer was dried ($Na_2SO_4$) and concentrated. Purification by column chromatography (silica, heptane/EtOAc, 4:1) and trituration from i-$Pr_2O$ (2×2 mL) afforded SC-02 (59 mg, 25%).

Synthesis of Example SC-03

Step 1: (1-Benzyl-3-(4-chlorophenyl)-4-methyl-1H-pyrrol-2-yl)(morpholino)methanone To a solution of ACI-02 (3.60 g, 11.1 mmol) and morpholine (1.02 mL, 11.6 mmol) in DCM (30 mL) was added EDCI (2.22 g, 11.6 mmol) followed by HOAt (0.15 g, 1.1 mmol) while cooling with an ice-bath. The reaction mixture was stirred at room temperature overnight. The reaction mixture was washed with aqueous 1 M HCl (30 mL) and aqueous saturated $NaHCO_3$ (30 mL), dried ($Na_2SO_4$) and concentrated. Crystallisation (heptane/EtOAc) of the residue yielded Step 2: [1-Benzyl-3-(4-chlorophenyl)-4-methyl-5-(trifluoromethyl)-1H-pyrrol-2-yl]-morpholin-4-yl-methanone (SC-03)

To a solution of (1-benzyl-3-(4-chlorophenyl)-4-methyl-1H-pyrrol-2-yl)(morpholino)methanone (500 mg, 1.27 mmol) in DMSO (10 mL) was added $FeSO_4.7H_2O$ (211 mg, 0.760 mmol). While stirring vigorously, $ICF_3$ was bubbled through the reaction mixture for 1 min. The reaction mixture was stirred for 1 min., after which $H_2O_2$ (35% (w/w) in $H_2O$, 0.665 mL, 7.60 mmol) was added. The reaction mixture was stirred for 1 h and $Et_2O$ (50 mL) and brine (30 mL) were added. The organic layer was separated, washed with brine (2×30 mL), dried ($Na_2SO_4$) and concentrated. The residue was first purified by flash column chromatography (silica, heptane/EtOAc, 96:4–>60:40) and then by crystallization (heptane/EtOAc) to give SC-03 (196 mg, 33%).

Synthesis of Example SC-04

Step 1: 1-Benzyl-3-(4-chlorophenyl)-N,4-dimethyl-N-neopentyl-1H-pyrrole-2-carboxamide To a solution of ACI-02 (3.60 g, 11.1 mmol), N,2,2-trimethylpropan-1-amine (2.28 g, 16.6 mmol) and DIPEA (8.11 mL, 46.4 mmol) in DME (30 mL) was added BOP-CI (5.91 g, 23.21 mmol). The reaction mixture was stirred at reflux temperature for 1 h. The reaction mixture was allowed to cool to room temperature and EtOAc (70 mL) and aqueous 1 M HCl (75 mL) were added. After filtration of the solids, the organic layer was separated, washed with aqueous saturated $NaHCO_3$ (75 mL), dried ($Na_2SO_4$) and concentrated. Crystallisation (heptane/EtOAc) gave the first batch of the desired product (1.064 g, 24%). Crystallisation (MeOH) of the mother liquor gave the second (1.686 g, 37%). Final crystallisation (heptane/EtOAc) of the mother liquor gave the third batch of the title compound (750 mg, 17%). Total yield: 3.539 g (78%).

Step 2: 1-Benzyl-3-(4-chlorophenyl)-N-(2,2-dimethyl-propyl)-N,4-dimethyl-5-(trifluoromethyl)-1H-pyrrole-2-carboxylic acid amide (SC-04)

To a solution of 1-benzyl-3-(4-chlorophenyl)-N,4-dimethyl-N-neopentyl-1H-pyrrole-2-carboxamide (400 mg, 0.978 mmol) in DMSO (10 mL) was added $FeSO_4.7H_2O$ (258 mg, 0.929 mmol). While stirring vigorously, $ICF_3$ was bubbled through the reaction mixture for 1 min. The reaction mixture was stirred for 1 min., after which $H_2O_2$ (35% (w/w) in $H_2O$, 0.514 mL, 5.87 mmol) was added. The reaction mixture was stirred for 15 min and $Et_2O$ and brine were added. The organic layer was separated, dried ($Na_2SO_4$) and concentrated. The residue was first purified by column chromategraphy (silica, heptane/EtOAc, 4:1), followed by preparative LMCS and crystallisation (MeOH/$H_2O$) to give SC-04 (126 mg, 27%).

Synthesis of Example SC-09

Step 1: 4-[1-Benzyl-3-(4-chlorophenyl)-4-methyl-5-(trifluoromethyl)-1H-pyrrole-2-carbonyl]-1-methyl-piperazin-2-one (SC-09)

SC-08 (100 mg, 0.210 mmol) was dissolved in dry DMF (2 mL), 60% NaH in mineral oil (20 mg, 0.50 mmol) was added and the slightly foaming mixture was stirred at room temperature for 10 min. Subsequently, MeI (0.04 mL, 0.630 mmol) was added and the mixture was stirred at room temperature for 1 h. The reaction mixture was poured into aqueous 1M $KHSO_4$ (10 mL) and the product was extracted with EtOAc (2×10 mL). The organic layer was washed with aqueous 1M $KHSO_4$ (2×10 mL), aqueous saturated $NaHCO_3$ (2×10 mL) and brine (2×10 mL) before drying over $Na_2SO_4$ and concentration in vacuo to give a yellow oil. The product was purified using flash column chromatography (silica, heptane/EtOAc 80:20 to 40:60) to give SC-09 (31 mg, 30%) as a colorless foam.

Synthesis of Example SC-18

Step 1: 1-Benzyl-3-(4-chlorophenyl)-N,N,4-trimethyl-5-(trifluoromethyl)-1H-pyrrole-2-carboxylic acid amide (SC-18)

ACI-03 (80 mg, 0.203 mmol) was dissolved in dry THF (3 mL). The solution was mixed with $Et_3N$ (71 μL, 0.508 mmol) and stirred for 10 min. at room temperature. 2M Dimethylamine in THF (305 μL, 0.609 mmol) was added, followed by 50% w/w T3P in DMF (178 μL, 305 mmol). The temperature was raised to 50° C. and the reaction mixture was stirred overnight. Additional reagents were added: 2M dimethyl amine in THF (305 μL, 0.609 mmol) and 50% w/w T3P in DMF (178 μL, 305 mmol). The reaction mixture was stirred at 50° C. for 4 d. The temperature was lowered to room temperature; the reaction mixture was concentrated in vacuo. The residue was dissolved in EtOAc (30 mL) and diluted aqueous $Na_2CO_3$ (15 mL) to result in a clear two phase system. The phases were separated, and the organic phase was washed twice with 1M NaOH (10 mL), followed by brine, twice with diluted aqueous $NH_4Cl$ (10 mL) and brine. Drying ($Na_2SO_4$) was followed by concentration in vacuo. The residue was used for preparative TLC (silica, heptane/EtOAc, 4:1), providing 40 mg (47%) of pyrrole SC-18 as a fluffy white solid.

Synthesis of Example SC-19

Step 1: [1-Benzyl-3-(4-chlorophenyl)-4-methyl-5-(trifluoromethyl)-1H-pyrrol-2-yl]-(1-oxo-[1,4]thiazinan-4-yl)-methanone (SC-19)

To a suspension of (1-benzyl-3-(4-chlorophenyl)-4-methyl-5-(trifluoromethyl)-1H-pyrrol-2-yl)(thiomorpholino) methanone [for synthesis see SC-26] (131 mg, 0.28 mmol) in MeOH (4 mL) and $H_2O$ (1 mL) was added oxone (85 mg, 0.138 mmol). The reaction mixture was stirred at room temperature for 2 h. The reaction mixture was diluted with $H_2O$ and extracted with DCM (60 mL). The organic layer was washed with brine, dried ($Na_2SO_4$) and purified by flash column chromatography (silica, heptane/EtOAc, 1:1→0:1) to give SC-19 (48 mg, 35%) as a white foam.

Synthesis of Example SC-22

Step 1: 1-Benzyl-3-(4-chlorophenyl)-N,4-dimethyl-5-(trifluoromethyl)-1H-pyrrole-2-carboxylic acid amide (SC-22)

ACI-03 (80 mg, 0.203 mmol) was dissolved in dry THF (3 mL). The solution was mixed with $Et_3N$ (85 μL, 0.609 mmol) and stirred for 10 min. at room temperature, 2M methyl amine in THF (406 μL, 0.813 mmol) was added, followed by 50% w/w T3P in DMF (237 μL, 0.406 mmol). The temperature was raised to 50° C. and the reaction mixture was stirred for 4 d. Additional reagents were added: 2M methyl amine in THF (203 µL, 0.407 mmol) and 50% w/w T3P in DMF (119 µL, 0.203 mmol). The reaction mixture was stirred at 50° C. overnight. The temperature was lowered to room temperature and the reaction mixture was concentrated in vacuo. The residue was dissolved in EtOAc (30 mL) and diluted with aqueous $Na_2CO_3$ (15 mL) to result in a clear two phase system. The phases were separated, and the organic phase was washed twice with aqueous 1M NaOH (10 mL), followed by brine, twice with diluted aqueous $NH_4Cl$ (10 mL) and again brine. Drying ($Na_2SO_4$) was followed by concentration in vacuo. The residue was used for preparative TLC (silica, heptane/EtOAc, 7:1, 4:1 and 3:1), followed by flash chromatography (silica, heptane/DCM, 3:7) providing 38 mg (46%) of SC-22 as a fluffy white solid.

Synthesis of Example SC-25

Step 1: 3-(4-Chlorophenyl)-4-methyl-1H-pyrrole-2-carboxylic acid

To a solution of ethyl 3-(4-chlorophenyl)-4-methyl-1H-pyrrole-2-carboxylate [for synthesis see ACI-02] (2.0 g, 7.58 mmol) in dry THF (26 mL) and MeOH (26 mL) was added aqueous 6 M NaOH (25.3 mL, 152 mol) and the mixture was stirred at reflux for 3 h. The organic solvents were evaporated and the remainder was acidified with aqueous 6 M HCl (30 mL) at 0° C. The resulting mixture was extracted with EtOAc (2×100 mL). The combined organic layers were dried ($Na_2SO_4$) and concentrated to yield the desired product 1.71 g, 96%).

Step 2: (3-(4-Chlorophenyl)-4-methyl-1H-pyrrol-2-yl)(morpholino)methanone

To a solution of 3-(4-chlorophenyl)-4-methyl-1H-pyrrole-2-carboxylic acid (1.71 g, 7.26 mmol) and DIPEA (1.39 mL, 7.98 mmol) in DCM (50 mL) were added morpholine (664 µL, 7.62 mmol), HOAt (99 mg, 726 µmol) and EDCI (1.53 g, 7.98 mmol) and the reaction mixture was stirred at room temperature for 2 h. The mixture was washed with brine (100 mL) and the organic layer was dried ($Na_2SO_4$) and concentrated. Purification by column chromatography (silica, DCM/(7 M $NH_3$ in MeOH), 98:2) afforded the desired product (1.73 g, 78%).

Step 3:. (3-(4-Chlorophenyl)-4-methyl-5-(trifluoromethyl)-1H-pyrrol-2-yl)(morpholino)methanone A crude batch of (3-(4-chlorophenyl)-4-methyl-1H-pyrrol-2-yl)(morpholino)methanone (260 mg, containing 67% w/w or 0.572 mmol of the desired compound) was dissolved in DMSO (4 mL) and $FeSO_4 7H_2O$ (95 mg, 0.343 mmol) was added. The mixture was stirred at room temperature for 5 min. and $CF_3I$ was bubbled through for 3 min. Then the mixture was cooled in an ice bath and 35% w/w aqueous $H_2O_2$ (300 mL, 3.43 mmol) was added dropwise via a syringe. The reaction was carefully quenched by the addition of brine (30 mL) and the product was extracted with EtOAc twice (50 mL and 10 mL). The combination of organic layers was washed with $H_2O$ (10 mL), brine, dried on $Na_2SO_4$ and concentrated in vacuo. The residue was combined with the residue of another identical reaction (starting from 100 mg or 0.328 mmol of starting material), dissolved in DCM (2 mL). Crystals had formed overnight. Filtration and washing with small portions of DCM gave 58 mg of the desired product. The filtrate was used for flash chromatography (silica, heptane/ EtOAc; 20% to 100% EtOAc) to provide 186 mg desired product. Total yield: 244 mg (73%)

Step 4: [3-(4-Chlorophenyl)-1-[(3-chlorophenyl)-methyl]-4-methyl-5-(trifluoromethyl)-1H-pyrrol-2-yl]-morpholin-4-yl-methanone (SC-25)

(3-(4-Chlorophenyl)-4-methyl-5-(trifluoromethyl)-1H-pyrrol-2-yl)(morpholino)methanone (80 mg, 0.215 mmol) was dissolved in dry MeCN (5 mL). The solution was mixed with $K_2CO_3$ (59 mg, 0.429 mmol), followed by addition of 3-chlorobenzyl bromide (31 µL, 0.236 mmol). The reaction mixture was stirred vigorously at 80° C. overnight. The temperature was lowered to room temperature; the reaction mixture was combined with a few lumps of ice, $Et_2O$ (50 mL) and $H_2O$ (10 mL) to result in a clear two phase system. The phases were separated; the organic phase was washed with brine. Drying ($Na_2SO_4$) was followed by concentration in vacuo. The residue was dissolved in MeCN (30 mL), concentrated in vacuo and used for preparative TLC (silica, heptane/EtOAc, 5:1), providing 96 mg (90%) of SC-25 as a fluffy white solid.

Synthesis of Example SC-26

Step 1: (1-Benzyl-3-(4-chlorophenyl)-4-methyl-5-(trifluoromethyl)-1H-pyrrol-2-yl)(thiomorpholino) methanone To a solution of ACI-03 (150 mg, 0.38 mmol) and thiomorpholine (0.042 mL, 0.419 mmol) in DCM (2 mL) was added EDCI (77 mg, 0.4 mmol) followed by HOAt (5.18 mg, 0.038 mmol). The reaction mixture was stirred at room temperature overnight. The reaction mixture was washed with aqueous 1 M $KHSO_4$ and saturated aqueous $NaHCO_3$, dried ($Na_2SO_4$) and concentrated. The crude product was purified by flash column chromatography (silica, heptane/EtOAc, 9:1→2:1) to give the desired product (162 mg, 89%) as a colourless oil.

Step 2: [1-Benzyl-3-(4-chlorophenyl)-4-methyl-5-(trifluoromethyl)-1H-pyrrol-2-yl]-(1,1-dioxo-[1,4] thiazinan-4-yl)-methanone (SC-26)

To a suspension of (1-benzyl-3-(4-chlorophenyl)-4-methyl-5-(trifluoromethyl)-1H-pyrrol-2-yl)(thiomorpholino) methanone (162 mg, 0.34 mmol) in MeOH (4 mL) and $H_2O$ (1 mL) was added oxone (624 mg, 1.015 mmol). The reaction mixture was stirred at room temperature overnight. The reaction mixture was diluted with $H_2O$ and extracted with DCM (60 mL). The organic layer was washed with brine, dried ($Na_2SO_4$) and purified by flash column chromategraphy (silica, heptane/EtOAc, 4:1→3:2) to give SC-26 (66 mg, 38%) as a white solid.

Synthesis of Example SC-32

Step 1: 3-(4-chlorophenyl)-4-methyl-1H-pyrrole-2-carboxylic acid

To a solution of ethyl 3-(4-chlorophenyl)-4-methyl-1H-pyrrole-2-carboxylate (11 g, 41.7 mmol) in methanol (140 mL,) and tetrahydrofuran (140 mL) was added sodium hydroxide (140 mL, 6M aqueous solution) and the reaction was stirred at 110° C. for 4 hrs. The reaction mixture was allowed to cool and the organics removed under vacuum. The resulting residue was slurried in water (200 mL) and acidified with acetic acid to pH4. The resulting precipitate was collected by filtration and washed with water to afford the title compound as a grey solid (9.8 g, 99% yield)

Step 2: [3-(4-Chlorophenyl)-4-methyl-1H-pyrrol-2-yl]-(3,3-difluoroazetidin-1-yl)methanone A microwave vial was charged with 3-(4-chlorophenyl)-4-methyl-1H-pyrrole-2-carboxylic acid (2 g 8.5 mmol), BOP-CI (2.1 equiv., 4.7 g, 17.8 mmol), 3,3-difluoroazetidine hydrochloride (1.6 equiv., 1.8 g, 13.6 mmol), DIPEA (5 equiv., 7.4 mL, 42.4 mmol) and DCM (20 mL) and the reaction mixture was heated to reflux for 1 hour.

The reaction mixture was cooled and partitioned with dichloromethane (100 mL) and water (100 mL). The aqueous was washed with DCM (2×100 mL) and the organics combined, dried over magnesium sulphate then then concentrated under vacuum to afford a brown solid. The residue was purified by flash chromatography (150 g SNAP silica column, Gradient; 0-35% EtOAc/Petrol Ether over 40 minutes) to afford the title compound as a brown solid (2 g, 76% yield).

Step 3: [3-(4-Chlorophenyl)-1-(3-methoxyphenyl)-4-methyl-pyrrol-2-yl]-(3,3-difluoroazetidin-1-yl)methanone A 5 mL microwave vial was charged with [3-(4-chlorophenyl)-4-methyl-1H-pyrrol-2-yl]-(3,3-difluoroazetidin-1-yl)methanone (200 mg, 0.6 mmol), N,N'-dimethylethylenediamine (11 mg, 0.13 mmol), potassium phosphate tri-basic (0.29 g, 1.4 mmol), 3-Iodoanisole (1.97 g, 1 mL, 8.3 mmol) followed by copper (I) iodide (0.1 equiv., 12 mg, 0.06 mmol) and NMP (1 mL, 1.033 g, 1 mL, 10.4 mmol) and the reaction was at 140° C. for 3 hours via Biotage microwave.

The reaction mixture was cooled, diluted with EtOAc (100 ml) and washed with HCl (1N, 100 mL) followed by NaHCO$_3$ (100 mL saturated solution). The aqueous washes were extracted with EtOAc (50 mL) and the organics combined, dried over magnesium sulphate and then concentrated under vacuum. The residue was purified using flash chromatography (50 g SNAP silica column, gradient; 0-15% EtOAc/Petrol Ether over 20 minutes then 15% to 50% over a further 15 minutes) to afford the title compound as an off-white solid (189 mg, 70% yield).

Step 4: 3-(4-Chlorophenyl)-1-(3-methoxyphenyl)-4-methyl-5-(trifluoromethyl)-1H-pyrrol-2-yl]-(3,3-difluoro-azetidin-1-yl)-methanone

[3-(4-Chlorophenyl)-1-(3-methoxyphenyl)-4-methyl-pyrrol-2-yl]-(3,3-difluoroazetidin-1-yl)methanone (126 mg, 0.3 mmol) followed by Sodium Trifluoromethanesulfinate (0.146 mg, 0.9 mmol), was added to a mixture of DMSO (1.8 mL) and water (0.8 mL) and then stirred vigorously at 0° C. (ice/water bath). Tert-butyl hydroperoxide (70% in H2O) (0.21 mL, 1.5 mmol) was added drop wise and reaction mixture stirred vigorously. DCM (1.8 mL) was added and reaction mixture stirred at room temperature for 18 hours. The reaction mixture was cooled to 0° C. (ice/water bath) and additional Sodium Trifluoromethanesulfinate (0.15 g, 0.9 mmol) followed by Tert-butyl hydroperoxide (70% in H2O) (0.21 mL, 1.5 mmol) was added and reaction stirred at room temperature for 20 hours.

The reaction mixture was quenched by the addition of sodium metabisulfite (100 mL saturated solution). The aqueous solution was extracted with DCM (2×100 mL) and the organics combined, dried over magnesium sulphate and then concentrated under vacuum. The residue was purified using preparative HPLC (preparative Agilent 1200 Series HPLC system using 30%-95% acetonitrile/water (0.1% Ammonia aq.) over 15 minutes, collecting at 254 nm).). The title compound was obtained as a cream solid (44 mg, 30% yield).

Synthesis of Example SC-33

Step 1: [1-(3-chlorophenyl)-3-(4-chlorophenyl)-4-methyl-pyrrol-2-yl]-(3,3-difluoroazetidin-1-yl)methanone

[1-(3-chlorophenyl)-3-(4-chlorophenyl)-4-methyl-pyrrol-2-yl]-(3,3-difluoroazetidin-1-yl)methanone was synthesised according to the procedure described for [3-(4-Chlorophenyl)-1-(3-methoxyphenyl)-4-methyl-pyrrol-2-yl]-(3,3-difluoroazetidin-1-yl)methanone (SC-32) using 1-chloro-3-iodobenzene (1 mL, 8 mmol) and [3-(4-chlorophenyl)-4-methyl-1H-pyrrol-2-yl]-(3,3-difluoroazetidin-1-yl)methanone (200 mg, 0.6 mmol). The product was purified by preparative HPLC (preparative Agilent 1200 Series HPLC system using 30%-95% acetonitrile/water (0.1% Ammonia aq.) over 15 minutes, collecting at 254 nm) to afford the title compound as an off-white solid (223 mg, 89% yield).

Step 2: [1-(3-Chlorophenyl)-3-(4-chlorophenyl)-4-methyl-5-(trifluoromethyl)-1H-pyrrol-2-yl]-(3,3-difluoro-azetidin-1-yl)-methanone

[1-(3-Chlorophenyl)-3-(4-chlorophenyl)-4-methyl-5-(trifluoromethyl)-1H-pyrrol-2-yl]-(3,3-difluoro-azetidin-1-yl)-methanone was synthesised according to the procedure described for 3-(4-Chlorophenyl)-1-(3-methoxyphenyl)-4-methyl-5-(trifluoromethyl)-1H-pyrrol-2-yl]-(3,3-difluoro-azetidin-1-yl)-methanone (SC-32) using [1-(3-chlorophenyl)-3-(4-chlorophenyl)-4-methyl-pyrrol-2-yl]-(3,3-difluoroazetidin-1-yl)methanone (161 mg, 0.4 mmol) to afford the title compound as an off-white solid (62 mg, 33% yield).

Synthesis of Example SC-37

Step 1: tert-Butyl 2-(1-benzyl-3-(4-chlorophenyl)-N,4-dimethyl-5-(trifluoromethyl)-1H-pyrrole-carboxamido)ethylcarbamate ACI-03 (500 mg, 1.27 mmol) and tert-butyl 2-(methylamino)ethylcarbamate HCl (401 mg, 1.905 mmol) were dissolved in DME (2 mL) and BOP-CI (679 mg, 2.67 mmol) and DIPEA (0.929 mL, 5.33 mmol) were added. The reaction mixture was stirred at 60° C. for 1.5 h and then cooled to room temperature. Saturated aqueous NaHCO$_3$ and EtOAc were added. The aqueous layer was extracted with EtOAc, the organic layers were combined, dried (Na$_2$SO$_4$) and evaporated. The product was purified by flash column chromatography (silica, gradient heptane/EtOAc, 1:0→3:1) to afford 587 mg (84%) of the desired product.

Step 2: N-(2-Aminoethyl)-1-benzyl-3-(4-chlorophenyl)-N,4-dimethyl-5-(trifluoromethyl)-1H-pyrrole-2-carboxamide hydrochloride 4 M HCl in dioxane (1.067 mL, 4.27 mmol) was added dropwise to a solution of tert-butyl 2-(1-benzyl-3-(4-chlorophenyl)-N,4-dimethyl-5-(trifluoromethyl)-1H-pyrrole-2-carboxamido)ethylcarbamate (587 mg, 1.067 mmol) in dry dioxane (5 mL) under a N$_2$ atmosphere. The mixture was stirred at room temperature for 5 d. The mixture was evaporated to dryness and the residue was stirred in Et$_2$O. The solids were filtered off to obtain 400 mg (77%) of the desired product as a white solid.

Step 3: N-(2-Acetylamino-ethyl)-1-benzyl-3-(4-chlorophenyl)-N,4-dimethyl-5-(trifluoromethyl)-1H-pyrrole-2-carboxylic acid amide (SC-37)

To a suspension of N-(2-aminoethyl)-1-benzyl-3-(4-chlorophenyl)-N,4-dimethyl-5-(trifluoromethyl)-1H-pyrrole-2-carboxamide hydrochloride (150 mg, 0.308 mmol) in DCM (2 mL) were added dropwise Et$_3$N (0.094 mL, 0.679 mmol) and acetyl chloride (0.024 mL, 0.339 mmol). The reaction mixture was stirred at room temperature overnight. The mixture was diluted with DCM and saturated aqueous NaHCO$_3$. The layers were separated using a phase separator and the solvents were evaporated. The product was purified by flash column chromatography (silica, gradient heptane/EtOAc, 1:2→0:1) to afford 106 mg (70%) of SC-37.

Synthesis of Example SC-38

To a suspension of N-(2-aminoethyl)-1-benzyl-3-(4-chlorophenyl)-N,4-dimethyl-5-(trifluoromethyl)-1H-pyrrole-2-carboxamide hydrochloride [for synthesis see SC-37] (150 mg, 0.308 mmol) in DCM (2 mL) were added dropwise Et$_3$N (0.129 mL, 0.925 mmol) and methanesulfonylchloride (0.048 mL, 0.617 mmol). The reaction mixture was stirred at room temperature for 3 h. The mixture was diluted with DCM and saturated aqueous NaHCO$_3$. The layers were separated using a phase separator and the solvents were evaporated. The product was purified by flash column chromatography (silica, gradient heptane/EtOAc, 2:1→1:2) to afford 139 mg (85%) of SC-38.

Synthesis of Example SC-41

Step 1: 1-Benzyl-4-(4-chlorophenyl)-3-methyl-5-(morpholine-4-carbonyl)-1H-pyrrole-2-carbaldehyde To an ice-cold solution of DMF (0.441 mL, 5.70 mmol) in DCM (5 mL) was added POCl$_3$ (0.425 mL, 4.56 mmol). After stirring the reaction mixture at 0° C. for 15 min, a solution of (1-benzyl-3-(4-chlorophenyl)-4-methyl-1H-pyrrol-2-yl)(morpholino)methanone [obtained via standard EDI/HOAt coupling of ACI-02 with morpholine] (900 mg, 2.28 mmol) in DCM (1 mL) was dropwise added. The reaction was stirred for 30 min, then the ice-bath was removed and stirring was continued at room temperature for 1 h. The reaction mixture was cooled to 0° C., then saturated aqueous NaHCO$_3$ was added while vigorously stirring, until the mixture was neutralised. The mixture was extracted with DCM, washed with brine and concentrated. The residue was dissolved in i-PrOH and precipitated with H$_2$O. The precipitate was filtered, washed with i-PrOH/H$_2$O (1:1, 2×) and MeOH (2×) and dried on for a couple of hours to give the desired product (761 mg, 79%).

Step 2: [1-Benzyl-3-(4-chlorophenyl)-5-(difluoromethyl)-4-methyl-1H-pyrrol-2-yl]-morpholin-4-yl-methanone (SC-41)

Deoxo-Fluor, 50% in toluene (2.1 g, 4.7 mmol) was added to 1-benzyl-4-(4-chlorophenyl)-3-methyl-5-(morpholine-4-carbonyl)-1H-pyrrole-2-carbaldehyde (200 mg, 0.473 mmol) and the reaction mixture was stirred at 60° C. overnight. The reaction mixture was allowed to cool to room temperature and acidified with aqueous 1M KHSO$_4$ while cooling with an ice-bath. The mixture was extracted with EtOAc, washed with brine, dried (Na$_2$SO$_4$) and concentrated. The residue was purified by flash column chromatography (silica, gradient heptane/EtOAc, 96:4–>60:40). The crude product was dissolved in i-PrOH and precipitated with H$_2$O. The precipitate was washed with i-PrOH/H$_2$O (~1:3) (2×) and dried on the filter overnight. Crystallisation (MeOH) of the precipitate failed and was combined with its mother liquor and this was concentrated. Flash column chromatography (silica, gradient heptane/EtOAc, 94:6→34:66) of the residue gave SC-41 (113 mg, 54%).

Synthesis of Example SC-44

Step 1: 1,3-Bis(4-chlorophenyl)-3-(4-chlorophenyl)-4-methyl-pyrrol-2-yl]-(3,3-difluoroazetidin-1-yl)methanone 1,3-Bis(4-chlorophenyl)-3-(4-chlorophenyl)-4-methyl-pyrrol-2-yl]-(3,3-difluoroazetidin-1-yl)methanone was synthesised according to the procedure described for [3-(4-Chlorophenyl)-1-(3-methoxyphenyl)-4-methyl-pyrrol-2-yl]-(3,3-difluoroazetidin-1-yl)methanone (SC-32) using 1-chloro-4-iodobenzene (1 mL, 8 mmol) and [3-(4-chlorophenyl)-4-methyl-1H-pyrrol-2-yl]-(3,3-difluoroazetidin-1-yl)methanone (200 mg, 0.6 mmo) to afford the title compound as pink solid (109 mg, 40% yield).

Step 2: [1,3-Bis(4-chlorophenyl)-4-methyl-5-(trifluoromethyl)-1H-pyrrol-2-yl]-(3,3-difluoro-azetidin-1-yl)-methanone (SC-44)

[1,3-Bis(4-chlorophenyl)-4-methyl-5-(trifluoromethyl)-1H-pyrrol-2-yl]-(3,3-difluoro-azetidin-1-yl)-methanone was synthesised according to the procedure described for 3-(4-Chlorophenyl)-1-(3-methoxyphenyl)-4-methyl-5-(trifluoromethyl)-1H-pyrrol-2-yl]-(3,3-difluoro-azetidin-1-yl)-methanone (SC-32) using [1,3-Bis(4-chlorophenyl)-3-(4-chlorophenyl)-4-methyl-pyrrol-2-yl]-(3,3-difluoroazetidin-1-yl)methanone (133 mg, 0.3 mmol) to afford the title compound as an off-white solid (68 mg, 44% yield).

Synthesis of Example SC-48

Step 1: 1-Benzyl-3-(4-chlorophenyl)-N-[1-(hydroxymethyl)-cyclopropyl]-N,4-dimethyl-5-(trifluoromethyl)-1H-pyrrole-2-carboxylic acid amide (SC-48)

To a solution of SC-52 (200 mg, 0.385 mmol) in dry THF (2 mL) was added 2 M LiBH$_4$ in THF (0.963 mL, 1.93 mmol) and the reaction mixture was stirred for 4 d. The reaction mixture was quenched with aqueous 1 M HCl, extracted with DCM and the organic layer was concentrated. The residue was purified by flash column chromatography (silica, heptane/EtOAc, 93:7–>34:66) yielding SC-48 (126 mg, 69%).

Synthesis of Example SC-49

Step 1: 1-Benzyl-N-(1-carbamoyl-cyclopropyl)-3-(4-chlorophenyl)-N,4-dimethyl-5-(trifluoromethyl)-1H-pyrrole-2-carboxylic acid amide (SC-49)

Respectively, EDCI (47 mg, 0.24 mmol) and HOAt (28 mg, 0.20 mmol) were added to a solution of 0.4 M ammonia in THF (1.53 mL, 0.611 mmol) and 1-01 [for synthesis see SC-52] (100 mg, 0.204 mmol) while cooling with an ice-bath. The reaction mixture was stirred at room temperature overnight, diluted with H$_2$O, extracted with DCM and concentrated. The residue was purified by flash column chromatography (silica, heptane/EtOAc, 88:12→0:1) and freeze-dried (MeCN) resulting in SC-49 (65 mg, 65%).

Synthesis of Example SC-50

Step 1: tert-Butyl 2-(1-benzyl-3-(4-chlorophenyl)-N-(2-hydroxyethyl)-4-methyl-5-(trifluoromethyl)-1H-pyrrole-2-carboxamido)acetate To a mixture of ACI-03 (220 mg, 0.559 mmol), tert-butyl 2-(2-hydroxyethylamino)acetate (139 mg, max. 0.72 mmol) and DIPEA (0.191 mL, 1.117 mmol) in DCM (10 mL) was added BOP-CI (171 mg, 0.670 mmol). The reaction mixture was stirred at room temperature overnight. Aqueous 1 M KHSO$_4$ (50 mL) and DCM (50 mL) were added. The aqueous layer was extracted with DCM (2×50 mL). The organic layers were combined, dried (Na$_2$SO$_4$) and evaporated under reduced pressure. The product was purified by flash chromatography (silica, gradient heptane/EtOAc, 1:0→2:1), to afford 171 mg (56%) of the desired product.

Step 2: 4-[1-Benzyl-3-(4-chlorophenyl)-4-methyl-5-(trifluoromethyl)-1H-pyrrole-2-carbonyl]-morpholin-2-one (SC-50)

tert-Butyl 2-(1-benzyl-3-(4-chlorophenyl)-N-(2-hydroxyethyl)-4-methyl-5-(trifluoromethyl)-1H-pyrrole-2-carboxamido)acetate (171 mg, 0.310 mmol) was dissolved in DCM (18 mL). TFA (2 mL) was added and the reaction mixture was stirred at room temperature for 3 h. The solvent was removed under reduced pressure and the residue co-evaporated with DCM (2×). The product was purified by flash chromategraphy (silica, gradient heptane/EtOAc, 1:0→2:1), to give 97 mg (66%) of SC-50.

Synthesis of Example SC-51

Step 1: [3-(4-Chlorophenyl)-1-[2-(4-fluoro-phenoxy)-ethyl]-4-methyl-5-(trifluoromethyl)-1H-pyrrol-2-yl]-morpholin-4-yl-methanone (SC-51)

(3-(4-Chlorophenyl)-4-methyl-5-(trifluoromethyl)-1H-pyrrol-2-yl)(morpholino)methanone [for synthesis see SC-25] (130 mg, 0.349 mmol) was dissolved in dry MeCN (4 mL). The solution was mixed with K$_2$CO$_3$ (120 mg, 0.872 mmol) and KI (8.7 mg, 0.052 mmol), followed by addition of 4-fluorophenoxy-ethylbromide (153 mg, 0.697 mmol). The reaction mixture was stirred vigorously at 80° C. for 2 d. The temperature was lowered to room temperature; the reaction mixture was combined with the reaction mixture of another identical reaction (starting from 20 mg or 0.054 mmol (3-(4-chlorophenyl)-4-methyl-5-(trifluoromethyl)-1H-pyrrol-2-yl)(morpholino)methanone), followed by concentration in vacuo. The residue was used for flash chromatography (silica, gradient heptane/EtOAc, 1:0→1:1). The product was purified by preparative TLC (silica, DCM twice) to result in 60 mg (29%) of SC-51.

Synthesis of Example SC-52

Step 1: Ethyl 1-(1-benzyl-3-(4-chlorophenyl)-4-methyl-5-(trifluoromethyl)-1H-pyrrole-2-carboxamido)cyclopropanecarboxylate BOP-CI (776 mg, 3.05 mmol) was added to ACI-03 (1.00 g, 2.54 mmol), DIPEA (1.77 mL, 10.2 mmol) and ethyl 1-aminocyclopropanecarboxylate hydrochloride (0.631 g, 3.81 mmol) in DME (10 mL). The reaction mixture was stirred at 60° C. for 1 h, after which the reaction mixture was allowed to cool to room temperature. The reaction mixture was diluted with EtOAc, washed with aqueous 1M KHSO$_4$ and saturated aqueous NaHCO$_3$, dried (Na$_2$SO$_4$) and concentrated. The residue was purified by crystallisation (EtOAc/heptane) to give the desired product (821 mg, 64%).

Step 2: 1-[[1-Benzyl-3-(4-chlorophenyl)-4-methyl-5-(trifluoromethyl)-1H-pyrrole-2-carbonyl]-methyl-amino]-cyclopropane-1-carboxylic acid ethyl ester (SC-52) and 1-(1-Benzyl-3-(4-chlorophenyl)-N,4-dimethyl-5-(trifluoromethyl)-1H-pyrrole-2-carboxamido)cyclopropanecarboxylic acid (I-01)

A solution of ethyl 1-(1-benzyl-3-(4-chlorophenyl)-4-methyl-5-(trifluoromethyl)-1H-pyrrole-2-carboxamido)cyclopropanecarboxylate (818 mg, 1.62 mmol) in dry DMF (3 mL) was added to a suspension of 60% NaH in mineral oil (81 mg, 2.0 mmol) in dry DMF (1 mL) while cooling with an ice-bath. The reaction mixture was stirred for 0.5 h while cooling with an ice-bath and MeI (0.111 mL, 1.78 mmol) was added while still cooling with an ice-bath. The reaction mixture was stirred at room temperature for 2 h, quenched with saturated aqueous NH$_4$Cl and extracted with EtOAc. The organic layer was washed with brine (3×), dried (Na$_2$SO$_4$) and concentrated. The residue was purified by column chromatography (silica, heptane/EtOAc/acetic acid, 4:1:0→2:1:0.06) to give SC-52 (497 mg, 59%) and I-01 (259 mg, 33%).

Synthesis of Example SC-82

Step 1: tert-Butyl 4-(1-benzyl-3-(4-chlorophenyl)-5-(trifluoromethyl)-1H-pyrrole-2-carbonyl)-2,2-dimethylpiperazine-1-carboxylate ACI-06 (100 mg, 0.263 mmol) was dissolved in DME (3 mL) and BOP-CI (141 mg, 0.553 mmol) was added, followed by DIPEA (0.193 mL, 1.106 mmol) and tert-butyl 2,2-dimethylpiperazine-1-carboxylate (56.4 mg, 0.263 mmol). The white suspension was stirred at 60° C. for 3 h. To the reaction mixture was added H$_2$O (50 mL) and EtOAc (10 mL). The aqueous layer was separated and extracted with EtOAc (10 mL). The combined organic layer was washed with brine (20 mL) and subsequently dried (Na$_2$SO$_4$). Concentration in vacuo was followed by flash chromatography (silica, gradient heptane/EtOAc, 1:0→3:1) and provided the desired product (103 mg, 68%) as a white foam.

Step 2: [1-Benzyl-3-(4-chlorophenyl)-5-(trifluoromethyl)-1H-pyrrol-2-yl]-(3,3-dimethyl-piperazin-1-yl)-methanone (SC-82)

To tert-butyl 4-(1-benzyl-3-(4-chlorophenyl)-5-(trifluoromethyl)-1H-pyrrole-2-carbonyl)-2,2-dimethylpiperazine-1-carboxylate (103 mg, 0.178 mmol) in DCM (2 mL) was added TFA (0.234 mL, 3.03 mmol). The reaction mixture was stirred for 1 h and then cooled to 0° C. Saturated aqueous NaHCO$_3$ (15 mL) was added. The aqueous layer was separated and extracted twice with DCM (10 mL). The combined organic phases were washed with brine (20 mL) and dried over Na$_2$SO$_4$. Concentration in vacuo was followed by flash chromatography (silica, gradient heptane/EtOAc, 1:0→0:1). Appropriate fractions were combined, solvents removed in vacuo and the product was placed with MeOH (5 mL) in a vial. The remaining oil was dried in vacuo at 40° C. over 6 h. SC-82 (58 mg, 67%) was obtained as a white foam.

Synthesis of Example SC-119

Step 1: 1-Benzyl-4-bromo-3-(4-chlorophenyl)-N-(2,2-dimethylpropyl)-N-methyl-5-(trifluoromethyl)pyrrole-2-carboxamide Bromine (1.5 equiv., 1.06 g, 0.340 mL, 6.64 mmol) was added dropwise to a cold solution of SC-002 (2.05 g, 2.05 g, 4.43 mmol) in acetic acid (60 mL, 60 mL). The reaction was stirred at 10° C. for 5 mins and then allowed to warm to room temperature and stirred overnight for 18 hours at room temperature. LCMS shows a small amount of SM remaining therefore a few drops (approximately 100 ul) of bromine were added and stirred at room temperature for a further 2 hours. Workup: The reaction mixture was poured into a saturated solution of (L)-ascorbic acid and the precipitate which crashed out was filtered off and washed through with copious amounts of water. Solid then dried in the vacuum oven at 45° C. overnight to give 2.33 g (97%) of a bright yellow solid.

Step 2: 1-Benzyl-3-(4-chlorophenyl)-N-(2,2-dimethyl-propyl)-4-ethyl-N-methyl-5-(trifluoromethyl)-1H-pyrrole-2-carboxylic acid amide (SC-119)

To a solution of 1-benzyl-4-bromo-3-(4-chlorophenyl)-N-(2,2-dimethylpropyl)-N-methyl-5-(trifluoromethyl)pyrrole-2-carboxamide (240 mg, 0.44 mmol) in Toluene (1.5 mL) was added ethylboronic acid (1.5 equiv., 0.66 mmol), Palladium (II) acetate (0.1 equiv., 0.022 mmol) and 2-(DICYCLOHEXYLPHOSPHINO)-2',4',6'-TRI-I-PROPYL-1,1'-BIPHENYL (0.2 equiv., 0.09 mmol) in a reactivial. The reaction was heated to 120° C. overnight. Work up: Filtered and evaporated to give a pale yellow gum. Purification: The gum was purified on a 25 g SNAP silica cartridge on the Isolera eluting with a gradient from 100% pet. ether to
80% DCM in pet. ether to give 134 mgs of a colourless gum. This was further purified on the preparative HPLC with acidic modifier. The clean fractions were combined and evaporated urp to give 37.2 mgs (29%) of an off-white solid.

Synthesis of Example SC-120

Step 1: 1-Benzyl-3-(4-chlorophenyl)-4-cyclopropyl-N-(2,2-dimethyl-propyl)-N-methyl-5-(trifluoromethyl)-1H-pyrrole-2-carboxylic acid amide (SC-120)

To a solution of 1-benzyl-4-bromo-3-(4-chlorophenyl)-N-(2,2-dimethylpropyl)-N-methyl-5-(trifluoromethyl)pyrrole-2-carboxamide (100 mg, 0.18 mmol) in Toluene (1 mL) was added cyclopropylboronic acid (2 equiv., 0.032 g, 0.37 mmol), Palladium(II) acetate (0.1 equiv., 0.004 g, 0.018 mmol), 2-(DICYCLOHEXYLPHOSPHINO)-2',4',6'-TRI-I-PROPYL-1,1'-BIPHENYL (0.2 equiv., 0.01796 g, 0.03691 mmol) and POTASSIUM PHOSPHATE TRIBASIC (3 equiv., 0.1212 g, 0.04726 mL, 0.5537 mmol) in a Reactivial. The reaction was heated to 120° C. overnight. Work up: Reaction mixture cooled to room temperature and diluted with Ethyl Acetate. Filtered through celite and celite washed, through 3× Ethyl Acetate. Organics reduced under vacuum to residue. Purification: Purified via 25 g Silica Column using 0-100% Petrol Ether/(10% Ethyl Acetate/Petrol Ether) over 30 minutes collecting at 254 nm. Major peak isolated and reduced under vacuum to yield ~90 mg (45%) white foam. Purified further via preparative HPLC using 70-95% acetonitrile/water (0.1% formic acid) over 20 min collecting at 254 nm. Pure fractions combined and reduced under vacuum.

Synthesis of Example SC-174

Step 1: 3-(tert-Butoxycarbonyl(methyl)amino)propanoic acid

60% NaH in mineral oil (0.528 g, 13.21 mmol) was washed with hexane (2×10 mL). It was suspended in dry THF (6 mL) and cooled to 0° C. before BOC-BETA-ALA-OH (1 g, 5.29 mmol) in dry THF (6 mL) was added. MeI (0.823 mL, 13.21 mmol) in dry THF (6 mL) was dropwise added after 5 min. and the resulting suspension was stirred at 0° C. to room temperature over the weekend. The reaction mixture was quenched with ice cold $H_2O$ (50 mL) and washed with $Et_2O$ (25 mL). The aqueous layer was acidified with concentrated aqueous HCl (3 mL) and extracted with EtOAc (3×20 mL). The combined EtOAc extracts were dried ($Na_2SO_4$) and concentrated to afford the desired product (1.095 g, quantitative) as a yellow oil.

Step 2: Methyl 3-(tert-butoxycarbonyl(methyl)amino)propanoate

To a cooled (0° C.) solution of 3-(tert-butoxycarbonyl(methyl)amino)propanoic acid (1.095 g, max. 5.29 mmol) in extra dry MeOH (0.24 mL, 5.93 mmol) and DCM (5 mL) was added DMAP (0.066 g, 0.539 mmol). EDCI (1.239 g, 6.47 mmol) was added and the reaction mixture allowed to warm up to room temperature. The reaction mixture was washed with aqueous 0.5 N HCl (3×10 mL), and brine (25 mL). The organic phase was dried over $Na_2SO_4$, filtered, and evaporated in vacuo to afford the desired product (1.129 g, 98% over two steps) as a colourless oil.

Step 3: Methyl 3-(tert-butoxycarbonyl(methyl)amino)-2,2-dimethylpropanoate

A solution of methyl 3-(tert-butoxycarbonyl(methyl)amino)propanoate (250 mg, 1.151 mmol) in dry THF (1 mL) was dropwise added under an nitrogen atmosphere to 1.0 M LiHMDS in THF (4.60 mL, 4.60 mmol) at −78° C. MeI (0.287 mL, 4.60 mmol) in dry THF (1 mL) was added dropwise. The reaction mixture is stirred at −75° C. for 1 h. The mixture was slowly allowed to warm up to room temperature overnight. The reaction mixture was quenched with saturated aqueous $NH_4Cl$ (10 mL). The product was extracted with $Et_2O$ (2×10 mL). The organic layer was washed with brine (10 mL) before drying on $Na_2SO_4$ and concentration in vacuo to give the desired product (256 mg, 89%) as a yellow oil.

Step 4: Methyl 2,2-dimethyl-3-(methylamino)propanoate

Under an nitrogen atmosphere, methyl 3-(tert-butoxycarbonyl(methyl)amino)-2,2-dimethylpropanoate (250 mg, 1.019 mmol) was suspended in dry THF (5 mL) and cooled to −10° C. 4.0 M HCl in dioxane (5.10 mL, 20.38 mmol) was added and the reaction mixture was stirred at room temperature for 3 h. The solvent was evaporated under reduced pressure and the residue co-evaporated with DCM (5 mL) to give 185 mg of crude product as a yellow solid.

Step 5: Methyl 3-(1-benzyl-3-(4-chlorophenyl)-N-methyl-5-(trifluoromethyl)-1H-pyrrole-2-carboxamido)-2,2-dimethylpropanoate To a suspension of ACI-06 (385 mg, 1.014 mmol), BOP-CI (542 mg, 2.129 mmol) and DIPEA (0.742 mL, 4.26 mmol) in DME (3 mL) was added methyl 2,2-dimethyl-3-(methylamino)propanoate (184 mg, 1.014 mmol). The reaction mixture was stirred in a closed vial at 80° C. for 3 h and at room temperature overnight. $H_2O$ (10 mL) and EtOAc (10 mL) were added and the aqueous layer was separated and extracted twice with EtOAc (10 mL). The combined organic layers were washed twice with brine (10 mL) and dried ($Na_2SO_4$), filtered and concentrated in vacuo. Purification of the residue by flash column chromatography (silica, gradient heptane/EtOAc, 10:1→3:1) gave the title compound (266 mg, 51%) as a white solid.

Step 6: 3-(1-Benzyl-3-(4-chlorophenyl)-N-methyl-5-(trifluoromethyl)-1H-pyrrole-2-carboxamido)-2,2-dimethylpropanoic acid (I-02)

A solution of LiOH $H_2O$ (214 mg, 5.11 mmol) in $H_2O$ (3 mL) was added to a stirred solution of methyl 3-(1-benzyl-3-(4-chlorophenyl)-N-methyl-5-(trifluoromethyl)-1H-pyrrole-2-carboxamido)-2,2-dimethylpropanoate (259 mg, 0.511 mmol) in THF (3 mL). The reaction mixture was stirred at room temperature overnight. An extra portion of LiOH $H_2O$ (107 mg, 2.55 mmol) was added, followed by the addition of $H_2O$ (11 mL) and THF (11 mL). The reaction mixture was stirred at room temperature for 2 d and then acidified with aqueous 0.5 M $KHSO_4$ (10 mL). The product was extracted with DCM (3×20 mL). The organic layers were combined and washed with brine (3×10 mL). The combined organic layers were dried on $Na_2SO_4$ and filtered. Solvents were removed in vacuo to give the desired product (233 mg, 93%) as a white foam.

Step 7: 1-Benzyl-N-(2-carbamoyl-2-methyl-propyl)-3-(4-chlorophenyl)-N-methyl-5-(trifluoromethyl)-1H-pyrrole-2-carboxylic acid amide (SC-174)

To a stirred solution of 3-(1-benzyl-3-(4-chlorophenyl)-N-methyl-5-(trifluoromethyl)-1H-pyrrole-2-carboxamido)-2,2-dimethylpropanoic acid (100 mg, 0.203 mmol) in DCM (1 mL) was added added 0.4 N $NH_3$ in THF (0.583 mL, 0.233 mmol) under an nitrogen atmosphere. To the solution was added EDCI (52.5 mg, 0.274 mmol) followed by HOAt (27.6 mg, 0.203 mmol). The reaction mixture was stirred overnight, $H_2O$ (5 mL) was and the product was extracted with DCM (3×2 mL). The organic layers were combined and washed with brine (3×10 mL). The combined organic layers were dried on $Na_2SO_4$ and filtered. Solvents were removed in vacuo. Purification of the residue was performed by flash chromatography (silica, gradient heptane/EtOAc, 10:1→3:1). The product was co-evaporated with $Et_2O$ to give end product SC-174 (46 mg, 46%) as a white solid.

Synthesis of Example SC-175

Step 1: 3-(1-Benzyl-3-(4-chlorophenyl)-N-methyl-5-(trifluoromethyl)-1H-pyrrole-2-carboxamido)-2,2-dimethylpropanoyl azide To a stirred solution of I-02 [see step 4 SC-174] (110 mg, 0.223 mmol) in dry toluene (4 mL) was added $Et_3N$ (62 µL, 0.446 mmol) and DPPA (63 µL, 0.290 mmol). The reaction mixture was stirred overnight and concentrated in vacuo to give the desired product as a yellow oil.

Step 2: N-(2-Amino-2-methyl-propyl)-1-benzyl-3-(4-chlorophenyl)-N-methyl-5-(trifluoromethyl)-1H-pyrrole-2-carboxylic acid amide (SC-175)

Crude 3-(1-benzyl-3-(4-chlorophenyl)-N-methyl-5-(trifluoromethyl)-1H-pyrrole-2-carboxamido)-2,2-dimethylpropanoyl azide (max. 0.223 mmol) was dissolved in 1,4-dioxane (3 mL) and 5 M aqueous HCl (6 mL) was added. The mixture was stirred at 50° C. for 3 h and than cooled to room temperature. The reaction mixture was extracted with EtOAc (2×10 mL). The organic layer was washed with aqueous 3 N NaOH (15 mL) and brine (15 mL) and dried over $Na_2SO_4$. After filtration, the filtrate was concentrated in vacuo. The product was co-evaporated with $Et_2O$ to give SC-175 (71 mg, 68%).

Synthesis of Example SC-187

Step 1: 1-Benzyl-3-(4-chlorophenyl)-N-(2-cyano-2-methyl-propyl)-N-methyl-5-(trifluoromethyl)-1H-pyrrole-2-carboxylic acid amide (SC-187)

To a stirred solution of SC-174 (235 mg, 0.478 mmol) in pyridine (4.83 mL) was added at 0° C. TFAA (0.153 mL, 1.099 mmol) under a nitrogen atmosphere. The reaction mixture was stirred at room temperature for 30 min. Aqueous 1 M HCl (20 mL) and DCM (10 mL) were added and the aqueous layer was set to pH 2 with aqueous 5 M HCl (10 mL). The layers were separated and extracted twice with DCM (10 mL). The combined organic layers were concentrated in vacuo. Purification was performed with flash chromatography (silica, gradient heptane/EtOAc, 1:0→0:1). The appropriate fractions were combined and solvents removed in vacuo to give SC-187 (187 mg, 82%) as a yellow foam.

Synthesis of Example SC-188

Step 1: N-(3-Amino-2,2-dimethyl-propyl)-1-benzyl-3-(4-chlorophenyl)-N-methyl-5-(trifluoromethyl)-1H-pyrrole-2-carboxylic acid amide (SC-188)

To a stirred solution of SC-187 (31 mg, 0.276 mmol) in dry MeOH (3 mL) was added $CoCl_2$ (54 4, 1.382 mmol) under an inert atmosphere. $NaBH_4$ (199 mg, 5.25 mmol) was added in three equal portions under a nitrogen atmosphere at −5° C. The grey reaction mixture was stirred at room temperature during 30 min. and quenched with ice (20 mL) and aqueous 0.5 M $KHSO_4$ (20 mL). DCM (10 mL) was added and both layers were filtered over Celite. The aqueous layer was extracted twice with DCM (10 mL). The combined organic layers were washed with brine (20 mL), dried ($Na_2SO_4$), filtered and concentrated in vacuo. Purification was performed by flash chromatography (silica, $CH_2Cl_2$/MeOH, 9:1). The appropriate fractions were combined and solvents removed in vacuo. This product was combined with the crude batch from a previous experiment performed under the same reaction conditions. In this previous experiment SC-187 (14 mg, 0.023 mmol, purity: 76%), MeOH (1 mL), $CoCl_2$ (5.72 µL, 0.148 mmol) and $NaBH_4$ (21.2 mg, 0.561 mmol) were used. Further purification was performed by flash chromatography (silica, DCM/MeOH/$Et_3N$, 9:1:0.1). The appropriate fractions were combined and solvents removed in vacuo. Concentration in vacuo gave SC-188 (67 mg, 46%) as a green oil.

Synthesis of Example SC-260

Step 1: Ethyl 4-methyl-5-(trifluoromethyl)-1H-pyrrole-2-carboxylate

Trifluoromethanesulfonyl chloride (40.7 mL, 381.67 mmol) was added to the argon degassed solution of ethyl-4-methyl-1H-pyrrole-2-carboxylate (40 g, 254.45 mmol), $K_2HPO_4$ (132.9 g, 763.35 mmol), dichlorotris(1,10-phenanthroline) ruthenium (II) hydrate (3.6 g, 5.08 mmol) in acetonitrile. The reaction mixture was stirred for 6 d at room temperature adjacent to a fluorescent light bulb (23 W). The reaction mixture was diluted with EtOAc and $H_2O$. The aqueous layer was extracted with EtOAc (2×700 mL). Combined organic layer was dried over anhydrous $Na_2SO_4$, concentrated under reduced pressure to yield crude mass which was then purified by column chromatography (100-200 mesh Silica gel; 20% ethyl acetate/hexane; $R_f$-value 0.7) to afford title compound (25 g, 71.13% yield, white color solid).

Step 2: Ethyl 3-bromo-4-methyl-5-(trifluoromethyl)-1H-pyrrole-2-carboxylate

N-Bromosuccinimide (NBS) (17.7 g, 99.77 mmol) was portion wise added to an ice cooled solution of ethyl 4-methyl-5-(trifluoromethyl)-1H-pyrrole-2-carboxylate (21 g, 95.02 mmol) and $K_2CO_3$ (13.7 g, 99.77 mmol) in acetonitrile. The reaction mixture was stirred for 2 h at RT. The reaction mixture was diluted with EtOAc and $H_2O$. The aqueous layer was extracted with EtOAc (2×300 mL). Combined organic layer was dried over anhydrous $Na_2SO_4$, concentrated under reduced pressure to yield crude mass which was directly used to next step without further purification

Step 3: Ethyl 1-benzyl-3-bromo-4-methyl-5-(trifluoromethyl)-1H-pyrrole-2-carboxylate Benzyl bromide (10.9 mL, 91.66 mmol) was added to the solution of crude ethyl 3-bromo-4-methyl-5-(trifluoromethyl)-1H-pyrrole-2-carboxylate (25 g, 83.33 mmol) and $K_2CO_3$ (23.03 g, 166.66 mmol) in acetonitrile. The reaction mixture was stirred for 13 h at 80° C. Then the reaction mixture was cooled to RT and then diluted with EtOAc and $H_2O$. The aqueous layer was extracted with EtOAc (2×400 mL). Combined organic layer was dried over anhydrous $Na_2SO_4$, concentrated under reduced pressure to yield crude mass which was then purified by column chromatography (100-200 mesh Silica gel; 10% ethyl acetate/hexane; $R_f$-value 0.8) to afford title compound (29 g, 89.18% yield, pale yellow color oil).

Step 4: 1-Benzyl-3-bromo-4-methyl-5-(trifluoromethyl)-1H-pyrrole-2-carboxylic acid Lithium hydroxide monohydrate (8.89 g, 371.6 mmol) was added to the ice cold solution of ethyl 1-benzyl-3-bromo-4-methyl-5-(trifluoromethyl)-1H-pyrrole-2-carboxylate (29 g, 74.32 mmol) in THF (300 mL) and $H_2O$ (100 mL) warmed to RT and then heated at 100° C. for 14 h, cooled to RT and then diluted with $H_2O$ and acidify with 6N HCl (pH-2). The aqueous layer was extracted with EtOAc (2×350 mL). Combined organic layer was dried over anhydrous $Na_2SO_4$, concentrated under reduced pressure to yield crude mass which was triturated with diethyl ether to afford title compound (23 g, 85.48% yield, white color solid).

Step 5: 1-Benzyl-3-bromo-N,4-dimethyl-N-neopentyl-5-(trifluoromethyl)-1H-pyrrole-2-carboxamide HATU (12.6 g, 33.24 mmol) and DIPEA (12.4 ml, 69.25 mmol) were added to the ice cold solution of 1-benzyl-3-bromo-4-methyl-5-(trifluoromethyl)-1H-pyrrole-2-carboxylic acid (10 g, 27.77) in DMF (110 mL) and it was stirred for 10 min at same temperature and then neopentyl amine (3.92 ml, 33.24 mmol) was added to the reaction mixture warmed to RT and then stirred for 15 h. Reaction mixture was diluted with EtOAc and $H_2O$. The aqueous layer was extracted with EtOAc (2×300 mL). Combined organic layer was dried over anhydrous $Na_2SO_4$, concentrated under reduced pressure to yield crude mass of 1-benzyl-3-bromo-4-methyl-N-neopentyl-5-(trifluoromethyl)-1H-pyrrole-2-carboxamide (11 g, 91.9% yield, white color solid) which directly used without further purification. Methyl iodide (3.17 mL, 51.04 mmol) was added to the ice cold solution of 1-benzyl-3-bromo-4-methyl-N-neopentyl-5-(trifluoromethyl)-1H-pyrrole-2-carboxamide (11 g, 25.52 mmol), (100%) NaH (1.2 g, 51.04 mmol) in THF (100 mL) and stirred for 2 h at RT. The reaction mass was poured onto crushed ice, extracted with EtOAc (2×200 mL). Combined organic layer was dried over anhydrous $Na_2SO_4$, concentrated under reduced pressure to yield crude mass which was then purified by column chromatography (100-200 mesh Silica gel; 10% ethyl acetate/hexane $R_f$-value 0.6) to afford title compound (10 g, 88.05% yield, white solid).

Step 6: 1-Benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (2.4 M) n-BuLi (10.89 mL, 26.15 mmol) was added to the cooled (−78° C.) solution of 1-benzyl-3-bromo-N,4-dimethyl-N-neopentyl-5-(trifluoromethyl)-1H-pyrrole-2-carboxamide (9.7 g, 21.79 mmol) in dry THF (100 mL) and it was stirred at same temperature for 30 min. HBPin (17.4 mL, 108.98 mmol) was added to the reaction mixture and stirred for 45 min at −78° C. The reaction mass was quenched with saturated $NH_4Cl$ solution, extracted with ethyl acetate (2×300 mL). Combined organic layer was dried over anhydrous $Na_2SO_4$, concentrated under reduced pressure to yield crude mass which was then purified by column chromatography (230-400 mesh Silica gel; 20% ethyl acetate/hexane; $R_f$ value 0.4) to afford title compound (4.4 g, 40.95% yield, white solid).

Step 7: 1-Benzyl-N,4-dimethyl-N-neopentyl-3-(4-(2,2,2-trifluoroethoxy)phenyl)-5-(trifluoromethyl)-1H-pyrrole-2-carboxamide (SC-260)

Under an nitrogen atmosphere 1-benzyl-N,4-dimethyl-N-neopentyl-3-(4,4,5,5-tetramethyl-1,3,2-dioxaborolan-2-yl)-5-(trifluoromethyl)-1H-pyrrole-2-carboxamide (106 mg, 0.216 mmol) was dissolved in DMF (1 mL) and LiOH (4 mg, 0.216 mmol), bis(tri-tert-butylphosphine)palladium (0) (6 mg, 0.014 mmol) and 1-bromo-4-(2,2,2-trifluoroethoxy)benzene (50 mg, 0.196 mmol) were subsequently added. The reaction mixture was stirred at 80° C. under microwave irridation for 1 h. The mixture was cooled to RT and the reaction was stopped by addition of 1M NaOH solution (2 mL). The crude product was extracted with EtOAc (2×3 mL) and the combined organic layers were washed with water (3×1 mL), dried over $Na_2SO_4$, filtered and the solvent was removed under reduced pressure. The crude mass was purified by flash chromatography to give SC-260 (95 mg, 89.7%).

Synthesis of Example SC-259

Step 1: 1-Benzyl-3-(4-chlorophenyl)-N-(2,2-dimethyl-propyl)-N-methyl-4-methylsulfonyl-5-(trifluoromethyl)-1H-pyrrole-2-carboxylic acid amide (SC-259)

1-Benzyl-4-bromo-3-(4-chlorophenyl)-N-(2,2-dimethyl-propyl)-N-methyl-5-(trifluoromethyl)pyrrole-2-carboxamide (100 mg, 0.18 mmol) followed by SODIUM METHANE-SULFINATE (4.0 equiv., 0.078 g, 0.74 mmol), COPPER(I) TRIFLATE BENZENE COMPLEX (0.1 equiv., 0.010 g, 0.018 mmol), DIMETHYL SULFOXIDE (0.6 mL) and N,N'-DIMETHYLETHYLENEDIAMINE (0.2 equiv., 0.003 g, 0.037 mmol) added to reactivial. Flushed with Nitrogen and heated at 140° C. for 18 hours (overnight). Black solid residue formed. Work Up: Diluted with 50 ml Dichloromethane and 100 ml Water then filtered to remove solids. Dichloromethane/Water shaken and separated. Aqueous extracted 2×50 ml Dichloromethane. Organics combined and filtered through hydrophobic frit, then reduced under vacuum. Purification: Purified via Preparative HPLC over 2 injections using 50-95% acetonitrile/water (0.1% Formic Acid) over 15 minutes collecting at 254 nm. Pure fractions combined and reduced under vacuum to yield product as 51.4 mg (0.09 mmol) beige solid.

Synthesis of Example SC-261

Step 1: 3-(4-Chlorophenyl)-1H-pyrrole-2-carboxylic acid

To a solution of ethyl 3-(4-chlorophenyl)-1H-pyrrole-2-carboxylate [see step 2 ACI-02] (8 g, 32.0 mmol) in DMSO (30 mL) was added NaOH (2.56 g, 64.1 mmol) and the reaction mixture was stirred at 70° C. for 20 h. An additional portion of NaOH (0.5 g, 12.5 mmol) was added and stirring at 70° C. was continued for 30 min. The reaction mixture was cooled in an ice bath and acidified with aqueous 1M $KHSO_4$ (80 mL). The solid was filtered off and washed with aqueous 1M $KHSO_4$ (20 mL), $H_2O$ (3×25 mL) and heptane (3×25 mL) and dried on air. The residue was dissolved in EtOAc (600 mL), dried ($Na_2SO_4$) and the solvent was removed in vacuo. The product was stirred in i-$Pr_2O$/heptane (1:1, 100 mL). The solid was filtered and off dried in vacuo to give the desired product as a a white solid (6.04 g, 85%).

Step 2: 3-(4-Chlorophenyl)-5-(trifluoromethyl)-1H-pyrrole-2-carboxylic acid

In 6 separate tubes, 3-(4-chlorophenyl)-1H-pyrrole-2-carboxylic acid (1 g, 4.51 mmol) and $K_2HPO_4$ (2.36 g, 13.54 mmol) were combined in dry MeCN (40 mL) and degassed with Ar for 10 min. Dichlorotris(1,10-phenanthroline)ruthenium(II) hydrate (0.130 g, 0.180 mmol) was added, followed by trifluoromethanesulfonyl chloride (0.53 mL, 4.96 mmol) and the suspension was irradiated with a fluorescent light bulb (E27-32W, 4000K, 65 mA) at 40° C. for 20 h. More trifluoromethanesulfonyl chloride (0.24 mL, 2.250 mmol) was added and the irradiation was continued for 24 h. More trifluoromethanesulfonyl chloride (0.24 mL, 2.250 mmol) was added and the irradiation was continued for 48 h. More trifluoromethanesulfonyl chloride (0.24 mL, 2.250 mmol) was added and the irradiation was continued for 72 h. More degassed dry MeCN (5-10 mL per vial) was added to fill up the vials and more trifluoromethanesulfonyl chloride (0.5 mL, 4.69 mmol) was added. The irradiation was continued for 20 h. More trifluoromethanesulfonyl chloride (0.5 mL, 4.69 mmol) was added and the irradiation was continued for 24 h. The reaction mixtures were combined and filtered over a short plug of silica (eluent EtOAc). The filtrate was concentrated in vacuo and stirred with i-$Pr_2O$ (100 mL) to give a brown suspension. The solids were filtered off and the filtrate was concentrated in vacuo. The residue was absorbed on hydromatrix and purified using column chromatography (silica, gradient heptane/EtOAc 2:1–>1:2) to give a brown oil which solidified upon standing. The solid was treated with MeCN (5 mL), filtered off and washed with MeCN (3×5 mL) to give the desired product (1.37 g, 17%) as a white solid. The mother liquor was concentrated in vacuo and the residue was triturated with DCM to give the starting material (156 mg, 2%) as a light yellow solid. The mother liquor (4.9 g) was absorbed on hydromatrix and purified using column chromatography (silica, gradient heptane/EtOAc 7:3–>2:3) to give impure fractions which were combined and crystallised from MeCN. The product was filtered off and washed with a mixture of heptane and MeCN (~1:1, 2×3 mL) and dried to give another batch of the desired product (468 mg, 6%) as a white solid. The mother liquor was concentrated in vacuo to give the desired product (1.23 g, 78% pure) as a brown oil. From the column more impure product was retrieved to give the title compound (1.86 g, 51% pure) as a brown oil.

Step 3: 3-(4-Chlorophenyl)-N-methyl-N-neopentyl-5-(trifluoromethyl)-1H-pyrrole-2-carboxamide N-Methyl neopentyl amine (0.781 g, 5.68 mmol) and 3-(4-chlorophenyl)-5-(trifluoromethyl)-1H-pyrrole-2-carboxylic acid (1.37 g, 4.73 mmol) were combined in DME (13 mL). DIPEA (3.47 mL, 19.87 mmol) and BOP-CI (2.53 g, 9.93 mmol) were added. The mixture was stirred at 60° C. for 1 h. The reaction mixture was diluted with EtOAc (50 mL) and washed with aqueous 1M $KHSO_4$ (3×20 mL), aqueous saturated $NaHCO_3$ (3×20 mL) and brine (2×20 mL) before drying on $Na_2SO_4$ and concentration in vacuo to give an oil. The product was dissolved by heating in i-$Pr_2O$ and left to cool for 16 h. A solid had formed which was filtered off and washed with i-$Pr_2O$ (2×5 mL) to give a light yellow solid. The filtrate was combined with the residue and purified using column chromatography (silica, gradient heptane/EtOAc 95:5–>7:3) to give the desired product (604 mg, 34%) as a yellow solid. The mother liquor was concentrated in vacuo and triturated with heptane to give another batch of the desired product (271 mg, 15%) as a white solid.

Step 4: 3-(4-Chlorophenyl)-N-(2,2-dimethyl-propyl)-1-[(4-fluorophenyl)-methyl]-N-methyl-5-(trifluoromethyl)-1H-pyrrole-2-carboxylic acid amide (SC-261)

To a solution of 3-(4-chlorophenyl)-N-methyl-N-neopentyl-5-(trifluoromethyl)-1H-pyrrole-2-carboxamide (100 mg, 0.268 mmol) in dry DMF (1.5 mL) was added 1-(bromomethyl)-4-fluorobenzene (35 µL, 0.282 mmol) and $Cs_2CO_3$ (131 mg, 0.402 mmol). The white suspension was stirred at 60° C. for 1 h. The reaction mixture was poured out in saturated aqueous $NaHCO_3$ (25 mL) and the product was extracted with EtOAc (2×25 mL). The combined organic layers were washed with saturated aqueous $NaHCO_3$ (2×15 mL), aqueous 1M $KHSO_4$ (2×15 mL) and brine (2×15 mL) before drying on $Na_2SO_4$ and concentration in vacuo. The product was purified using flash chromatography (silica, gradient heptane/EtOAc 95:5→7:3). The product containing fractions were combined, concentrated in vacuo and crystallised from hot i-Pr$_2$O to give a first batch of SC-261. The mother liquor was concentrated in vacuo and crystallised from i-Pr$_2$O/heptane (1:1) to give white crystals which were combined with the earlier obtained batch to give SC-261 (58 mg, 45%) as colorless crystals.

Synthesis of Example SC-262

Step 1: (1-Benzyl-3-bromo-4-methyl-5-(trifluoromethyl)-1H-pyrrol-2-yl)(morpholino)methanone HATU (12.59 g 33.14 mmol) and DIPEA (12.3 mL, 33.14 mmol) were added to the ice cold solution of 1-benzyl-3-bromo-4-methyl-5-(trifluoromethyl)-1H-pyrrole-2-carboxylic acid (10 g, 27.62 mmol) in DMF (110 mL) and it was stirred for 10 min at same temperature and then morpholine (2.8 mL, 33.14 mmol) was added to the reaction mixture warmed to RT and then stirred for 14 h. The reaction mixture was diluted with EtOAc and H$_2$O. The aqueous layer was extracted with EtOAc (2×300 mL), washed with water (2×300 mL) and brine (2×300 mL), organic layer was dried over anhydrous Na$_2$SO$_4$, combined organic layer was dried over anhydrous Na$_2$SO$_4$ and concentrated under reduced pressure to yield crude mass which was then purified by column chromatography (100-200 mesh Silica gel; 30% ethyl acetate/hexane; R$_f$-value 0.6) to afford title compound (10 g, 84% yield, white color solid).

Step 2: (1-Benzyl-4-methyl-3-(4,4,5,5-tetramethyl-1,3,2-dioxaborolan-2-yl)-5-(trifluoromethyl)-1H-pyrrol-2-yl)(morpholino)methanone (2.3 M) n-BuLi (7.50 mL, 17.26 mmol) was added to the cooled (−78° C.) solution of (1-benzyl-3-bromo-4-methyl-5-(trifluoromethyl)-1H-pyrrol-2-yl)(morpholino)methanone (6.2 g, 14.38 mmol) in dry THF (80 mL) and it was stirred at same temperature for 30 min. HBPin (11.49 mL, 71.92 mmol) was added to the reaction mixture and stirred for 45 min at −78° C. The reaction mass was quenched with saturated NH$_4$Cl solution, extracted with ethyl acetate (2×300 mL). Combined organic layer was dried over anhydrous Na$_2$SO$_4$, concentrated under reduced pressure to yield crude mass which was then purified by column chromatography (230-400 mesh Silica gel; 20% ethyl acetate/hexane; R$_f$-value 0.4) to afford title compound (10 g, 78.62% yield, white solid).

Step 3: (1-benzyl-3-(2-fluoro-4-(trifluoromethoxy)phenyl)-4-methyl-5-(trifluoromethyl)-1H-pyrrol-2-yl)(morpholino)methanone (SC-262)

Under an nitrogen atmosphere (1-benzyl-4-methyl-3-(4,4,5,5-tetramethyl-1,3,2-dioxaborolan-2-yl)-5-(trifluoromethyl)-1H-pyrrol-2-yl)(morpholino)methanone (50 mg, 0.106 mmol) was dissolved in DMF (0.5 mL) and LiOH (2 mg, 0.106 mmol), bis(tri-tert-butylphosphine)palladium (0) (3 mg, 0.007 mmol) and 1-bromo-2-fluoro-4-(trifluoromethoxy)benzene (24 mg, 0.096 mmol) were subsequently added. The reaction mixture was stirred at 80° C. under microwave irridation for 1 h. The mixture was cooled to RT and the reaction was stopped by addition of 1M NaOH solution (2 mL). The crude product was extracted with EtOAc (2×3 mL) and the combined organic layers were washed with water (3×1 mL), dried over Na$_2$SO$_4$, filtered and the solvent was removed under reduced pressure. The crude mass was purified by flash chromatography to give SC-262 (34 mg, 66.8%).

Synthesis of Example SC-263

Under an nitrogen atmosphere (1-benzyl-4-methyl-3-(4,4,5,5-tetramethyl-1,3,2-dioxaborolan-2-yl)-5-(trifluoromethyl)-1H-pyrrol-2-yl)(morpholino)methanone (50 mg, 0.106 mmol) was dissolved in DMF (0.5 mL) and LiOH (2 mg, 0.106 mmol), bis(tri-tert-butylphosphine)palladium (0) (3 mg, 0.007 mmol) and 1-bromo-4-(2,2,2-trifluoroethoxy)benzene (24 mg, 0.096 mmol) were subsequently added. The reaction mixture was stirred at 80° C. under microwave irridation for 1 h. The mixture was cooled to RT and the reaction was stopped by addition of 1M NaOH solution (2 mL). The crude product was extracted with EtOAc (2×3 mL) and the combined organic layers were washed with water (3×1 mL), dried over Na$_2$SO$_4$, filtered and the solvent was removed under reduced pressure. The crude mass was purified by flash chromatography to give SC-263 (32 mg, 63.3%).

Synthesis of Example SC-264

Under an nitrogen atmosphere (1-benzyl-4-methyl-3-(4,4,5,5-tetramethyl-1,3,2-dioxaborolan-2-yl)-5-(trifluoromethyl)-1H-pyrrol-2-yl)(morpholino)methanone (50 mg, 0.106 mmol) was dissolved in DMF (0.5 mL) and LiOH (2 mg, 0.106 mmol), bis(tri-tert-butylphosphine)palladium (0) (3 mg, 0.007 mmol) and 4-bromo-3-fluorobenzonitrile (19 mg, 0.096 mmol) were subsequently added. The reaction mixture was stirred at 80° C. under microwave irridation for 1 h. The mixture was cooled to RT and the reaction was stopped by addition of 1M NaOH solution (2 mL). The crude product was extracted with EtOAc (2×3 mL) and the combined organic layers were washed with water (3×1 mL), dried over Na$_2$SO$_4$, filtered and the solvent was removed under reduced pressure. The crude mass was purified by flash chromatography to give SC-264 (24 mg, 55.0%).

Synthesis of Example SC-265

To a solution of (3-(4-chlorophenyl)-4-methyl-5-(trifluoromethyl)-1H-pyrrol-2-yl)(morpholino)methanone [see step 3 SC-25] (150 mg, 0.402 mmol) and 1-(bromomethyl)-3-(methylsulfonyl)benzene (110 mg, 0.443 mmol) in dry DMF (2 mL), Cs$_2$CO$_3$ (288 mg, 0.885 mmol) was added and the reaction mixture was stirred at 50° C. for 5 h. The reaction mixture was poured out in H$_2$O (200 mL) and extracted with EtOAc (200 mL). The organic layer was washed with brine (2×100 mL), dried over Na$_2$SO$_4$ and the solvent was removed under reduced pressure. The product was purified using flash chromatography (silica, gradient heptane/EtOAc, 7:3→0:1). The product was co-evaporated with pentane (3×20 mL) to give 191 mg (88%) of SC-265 as a white solid.

Synthesis of Example SC-266

To a solution of 3-(4-chlorophenyl)-N-methyl-N-neopentyl-5-(trifluoromethyl)-1H-pyrrole-2-carboxamide [see step 3 SC-261] (150 mg, 0.402 mmol) and 1-(bromomethyl)-3-(methylsulfonyl)benzene (110 mg, 0.443 mmol) in dry DMF (2 mL), Cs$_2$CO$_3$ (288 mg, 0.885 mmol) was added and the reaction was stirred at 50° C. for 18 h. The reaction mixture was poured out in EtOAc (150 mL) and washed with H$_2$O (2×150 mL) and brine (150 mL). The organic layer was dried over Na$_2$SO$_4$ and the solvent was removed under reduced pressure. The residue was purified using flash chromatography (silica, gradient heptane/EtOAc, 9:1→1:1). The product was co-evaporated with pentane (3×20 mL) to give 197 mg (90%) of SC-266 as a white foam.

Analytical Data:

Material and Methods for LC/MS Analytics:

Hardware: Coupled Agilent 1290 Infinity UHPLC-TOF System; LC-Module: MTP-Handler: Agilent, Model Bench-Cel 2R; Themostatic Control Autoinjector: Agilent, Modell G4226A; Column oven: Agilent, Model G1316C; DAD: Agilent, Model G4212A; Binary Pump: Agilent, Model G4220A; Time Of Flight Mass Spectrometer: Agilent 6224; Ion source: Dual ESI; Column: Supplier: Waters; Type: Acquity UPLC HSS T3 1.8 μm (Part No. 186003538); Dimensions: 2.1×50 mm; Eluents: Eluent A: Water from Millipore Ultrapure water System: Milli-Q Integral 3+0.1% Formic acid; Eluent B: Acetonitrile, Merck KGaA: LiChrosolv Hypergrade for LC-MS (1.00029.9010)+0.1% Formic acid; Formic acid: Merck KGaA: Suprapure 98-100% (1.11670.1000); LC-Method: Flow: 2.5 mL/min; Runtime: 1.2 min; Gradient: Start 2% B, 1 min 100% B, 1.09 min 100% B, 1.11 min 2% B, 1.2 min 2% B Stop; Column temperature: 80° C.; UV: 190-400 nm; MS-Method: Ion Polarity: Positive; Gas Temperature: 325° C.; Gas Flow: 10 mL/min For all exemplified compounds SC-01 to SC-266, the target mass was detected. The purity, determined at UV 254 nm, was found to be >97% for all exemplified compounds SC-01 to SC-266, except for SC-117, SC-123, SC-125, SC-127, SC-128, SC-129, SC-130, SC-136 and SC-186 (>93-97%) and SC-41, SC-42, SC-95, SC-126, SC-135, SC-141, SC-145, SC-199, SC-206 and SC-231 (87-93%).

2. Assay Descriptions and Biological Data 2.1 Fluorescent Assay for CaV2.2 Channels Using Potassium Depolarization to Induce Channel Opening Human CaV2.2 channels were stably expressed in HEK293 cells together with alpha2-delta and beta subunits of voltage gated calcium channels. In addition, an inwardly rectifying potassium channel (Kir2.3) was stably expressed in these cells to augment control of the cell membrane potential by the concentration of extracellular potassium ions. Raise of the extracellular potassium concentration leads to depolarization of the membrane potential and thus regulates the voltage dependent state of CaV2.2 channels. For preparation, cells were seeded in black poly-D-lysine coated 96-well plates (Becton Dickinson, Biocoat 4640) in 100 μl medium [500 ml DMEM/F-12 plus Glutamax (Invitrogen 31331-093) plus 5.5 ml MEM NEAA 100× (Invitrogen 11140-035) plus 50 ml FBS decomplemented (Invitrogen 10270-106) plus 4.4 ml Geneticin (Invitrogen 10131-027) plus 1.1 ml Hygromycin B (Invitrogen 10687-010) plus 68.75 μl Puromycin (Clontech, 631306)] at a cell density of 45.000 cells per well.

Plates were incubated at 37° C. (5% $CO_2$) for 20 to 23 hours. On the day of experiment medium was discarded and cells were loaded with Fluo 4 by addition of 100 μl of basic assay buffer (10 mM HEPES, 30 mM KCl, 120 mM NaCl, 0.8 mM CaCl2, 1.7 mM MgCl2, 10 mM Glucose, 0.1% BSA. pH 7.4) containing 2 μM Fluo 4 (Molecular Probes; F-14201), 0.01% pluronic acid (Molecular Probes; P-6866) and 2.5 mM probenecid (Molecular Probes; P36400). Cells were incubated in the dark at 25° C. for 60 min. Then the dye containing buffer was discarded and 100 μl basic assay buffer was added. Subsequently cells were incubated in the dark at 25° C. for 15 min. 25 μl of basic assay buffer with or without test compound were added and cells were incubated again in the dark at 25° C. for 15 min. Fluorescence intensity was measured on a FLIPR 3 instrument (Molecular Devices Corp., Sunnyvale, Calif.) with excitation at 480 nm and emission at 535 nm. After continuously reading fluorescence for 30 sec, 50 μl of basic assay buffer containing 210 mM KCl (NaCl omitted) were added for depolarization. Peak fluorescent signal intensity was determined and the amplitude of the peak signal, normalized to base line, was used to measure channel inhibition by test compounds.

The following table summarizes the inhibitory activity of exemplified compounds according to the present invention.

| Example No. | %-Inhib* |
| --- | --- |
| SC-01 | A |
| SC-02 | B |
| SC-03 | A |
| SC-04 | B |
| SC-05 | B |
| SC-06 | A |
| SC-08 | B |
| SC-09 | B |
| SC-10 | B |
| SC-11 | A |
| SC-16 | B |
| SC-17 | A |
| SC-18 | B |
| SC-19 | A |
| SC-20 | B |
| SC-21 | A |
| SC-22 | B |
| SC-23 | B |
| SC-24 | A |
| SC-25 | B |
| SC-26 | B |
| SC-29 | A |
| SC-32 | B |
| SC-33 | B |
| SC-34 | A |
| SC-35 | B |
| SC-36 | A |
| SC-37 | A |
| SC-38 | A |
| SC-39 | A |
| SC-40 | A |
| SC-41 | A |
| SC-42 | A |
| SC-44 | B |
| SC-48 | A |
| SC-49 | A |
| SC-50 | B |
| SC-51 | A |
| SC-52 | A |
| SC-53 | B |
| SC-54 | A |
| SC-55 | A |
| SC-56 | A |
| SC-57 | A |
| SC-58 | A |
| SC-59 | A |
| SC-60 | A |
| SC-61 | A |
| SC-62 | A |
| SC-63 | A |
| SC-64 | A |
| SC-65 | A |
| SC-66 | B |
| SC-67 | A |
| SC-68 | A |
| SC-69 | B |
| SC-70 | A |
| SC-71 | B |
| SC-72 | B |
| SC-73 | A |
| SC-74 | A |
| SC-75 | B |
| SC-76 | B |
| SC-77 | B |
| SC-78 | A |
| SC-79 | A |
| SC-80 | B |
| SC-81 | A |

-continued

| Example No. | %-Inhib* |
|---|---|
| SC-82 | B |
| SC-83 | A |
| SC-84 | C |
| SC-85 | A |
| SC-86 | A |
| SC-87 | A |
| SC-88 | B |
| SC-89 | B |
| SC-90 | A |
| SC-92 | A |
| SC-93 | B |
| SC-94 | B |
| SC-95 | B |
| SC-96 | C |
| SC-97 | C |
| SC-98 | C |
| SC-99 | C |
| SC-100 | B |
| SC-101 | A |
| SC-102 | B |
| SC-103 | B |
| SC-104 | B |
| SC-105 | B |
| SC-106 | A |
| SC-107 | A |
| SC-108 | A |
| SC-109 | B |
| SC-110 | B |
| SC-111 | A |
| SC-112 | B |
| SC-113 | A |
| SC-114 | A |
| SC-115 | A |
| SC-116 | A |
| SC-117 | B |
| SC-118 | A |
| SC-119 | B |
| SC-120 | B |
| SC-121 | A |
| SC-122 | A |
| SC-123 | A |
| SC-124 | A |
| SC-125 | A |
| SC-126 | A |
| SC-127 | A |
| SC-128 | A |
| SC-129 | B |
| SC-130 | A |
| SC-131 | A |
| SC-132 | A |
| SC-133 | A |
| SC-134 | A |
| SC-135 | A |
| SC-136 | A |
| SC-137 | B |
| SC-138 | B |
| SC-139 | A |
| SC-140 | A |
| SC-141 | A |
| SC-142 | A |
| SC-143 | A |
| SC-144 | A |
| SC-145 | A |
| SC-146 | B |
| SC-147 | B |
| SC-148 | A |
| SC-149 | A |
| SC-150 | B |
| SC-151 | A |
| SC-152 | A |
| SC-154 | B |
| SC-155 | A |
| SC-156 | A |
| SC-158 | B |
| SC-159 | A |
| SC-160 | A |
| SC-161 | A |

-continued

| Example No. | %-Inhib* |
|---|---|
| SC-162 | A |
| SC-163 | A |
| SC-164 | A |
| SC-165 | A |
| SC-166 | A |
| SC-167 | A |
| SC-168 | A |
| SC-169 | B |
| SC-170 | A |
| SC-171 | A |
| SC-172 | B |
| SC-173 | A |
| SC-174 | A |
| SC-175 | B |
| SC-176 | A |
| SC-177 | A |
| SC-178 | A |
| SC-179 | A |
| SC-180 | B |
| SC-181 | B |
| SC-182 | A |
| SC-183 | A |
| SC-184 | B |
| SC-185 | A |
| SC-186 | A |
| SC-187 | A |
| SC-188 | B |
| SC-189 | A |
| SC-190 | A |
| SC-191 | B |
| SC-192 | A |
| SC-193 | A |
| SC-194 | A |
| SC-195 | A |
| SC-196 | A |
| SC-197 | A |
| SC-198 | A |
| SC-199 | A |
| SC-200 | A |
| SC-201 | B |
| SC-202 | B |
| SC-203 | A |
| SC-204 | B |
| SC-205 | A |
| SC-206 | B |
| SC-207 | A |
| SC-208 | A |
| SC-209 | A |
| SC-210 | B |
| SC-211 | C |
| SC-212 | A |
| SC-213 | A |
| SC-214 | B |
| SC-215 | A |
| SC-216 | B |
| SC-217 | A |
| SC-218 | A |
| SC-219 | A |
| SC-220 | A |
| SC-221 | A |
| SC-222 | A |
| SC-223 | B |
| SC-224 | B |
| SC-225 | A |
| SC-226 | A |
| SC-227 | B |
| SC-228 | B |
| SC-229 | B |
| SC-230 | C |
| SC-231 | A |
| SC-232 | C |
| SC-233 | D |
| SC-234 | B |
| SC-235 | B |
| SC-236 | A |
| SC-237 | B |
| SC-238 | C |

-continued

| Example No. | %-Inhib* |
|---|---|
| SC-239 | B |
| SC-240 | D |
| SC-241 | A |
| SC-242 | B |
| SC-243 | A |
| SC-244 | B |
| SC-245 | A |
| SC-246 | B |
| SC-247 | C |
| SC-248 | B |
| SC-249 | B |
| SC-250 | C |
| SC-251 | B |
| SC-252 | A |
| SC-253 | A |
| SC-254 | B |
| SC-255 | C |
| SC-256 | D |
| SC-257 | B |
| SC-258 | B |
| SC-259 | B |
| SC-260 | C |
| SC-261 | B |
| SC-262 | B |
| SC-263 | B |
| SC-264 | B |
| SC-266 | B |

*%-Inhib (CaV2.2) @3 μM @30 mM KCl: "A": %-Inhibition >95%; "B": %-Inhibition >75% up to ≤95%; "C": %-Inhibition >40% up to ≤75%; "D": %-Inhibition >30% up to ≤40%.

2.2 Electrophysiological Assessment of Calcium Channel Activity

Patch-clamp recordings were performed using HEK293 cells stably expressing human Cav2.2. Cells were plated in T150 flasks and grown a humidified incubator at 37° C. and under 5% $CO_2$ to approximately 50-60% confluency. Cells were maintained at 30° C. for 48 hrs prior to recording. On the day of the experiment, cells were harvested with TrypLE cell detachment solution (Invitrogen) diluted to 25% with phosphate buffered saline and maintained in 50% cell culture media, 50% NaCl based external saline (in mM, 140 NaCl, 4 KCl, 1 $MgCl_2$, 2 $CaCl_2$, 5 Glucose, 10 HEPES, pH 7.4) up to several hours prior to experiment.

Currents were recorded at room temperature (21-23° C.) using the Patchliner planar array technology (Nanion). Patchliner is a multi-well whole-cell automated patch clamp device that operates asyn-chronously with fully integrated fluidics. Capacitance and series resistance compensation was automated and no correction for liquid junction potential was employed. Leak was subtracted on-line. Whole-cell patch-clamp recordings were obtained using extracellular saline consisting of (mM): 145 TEA-Cl, 10 $BaCl_2$, 10 HEPES, 10 glucose. The pH was adjusted to 7.35 with NaOH and the osmolarity was adjusted to 310 mOsm with sucrose. Intracellular solution consisted of (mM): 50 CsCl, 60 CsF, 10 NaCl, 20 EGTA, 5 BAPTA, 10 HEPES. Prior to an experiment, 5 mM MgATP and 0.3 NaGTP were added, the pH was adjusted to 7.2 with CsOH and the osmolarity was adjusted to 290 mOsm with sucrose.

A voltage pulse protocol was utilised to assess compound inhibition. Cells were held at a holding potential of −60 mV and channels were activated using a 10 ms test pulse to +30 mV activated every 10 seconds (0.1 Hz). Increasing concentrations of compound were applied to individual cells with 5 minutes at each test concentration. Compounds were prepared in DMSO as 10 mM stock solutions and subsequent 1:3 serial dilutions performed. Final dilution of 1:1000 in external solution resulted in a final DMSO concentration of 0.1%.

For each cell, current responses were normalised to dimethyl sulfoxide vehicle control to generate concentration-response curves. When multiple doses were achieved per cell, IC50 values were calculated from the fits of the Hill equation to the data. The form of the Hill equation used was: Relative current=(100/(1+(IC50/conc)^Slope)). A selection of the foregoing exemplified compounds was tested under these conditions: Several compounds are potent inhibitors (IC50<5 μM) or even very potent inhibitors (IC50<2 μM).

The invention claimed is:
1. A compound of general formula (I),

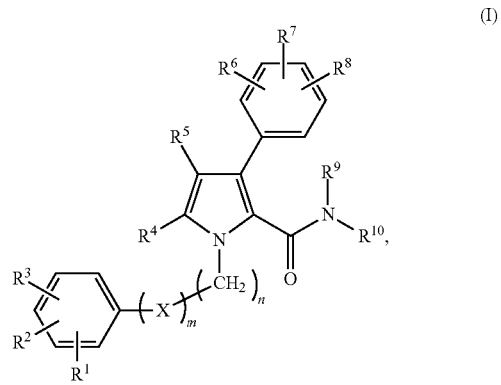

wherein
n represents 1 or 2;
m represents 0 or 1 with the proviso that n≥m;
X is;
$R^1$, $R^2$ and $R^3$, are each independently of one another selected from the group consisting of H; F; Cl; Br; I; O—$C_{1-6}$-alkyl; S—$C_{1-6}$-alkyl; S(=O)—$C_{1-6}$-alkyl; S(=O)$_2$—$C_{1-6}$-alkyl; whereby in each case $C_{1-6}$-alkyl may be branched or unbranched; unsubstituted or mono- or poly-substituted with one or more substituents independently of one another selected from the group consisting of F; Cl; $CF_3$; OH and O—$C_{1-6}$-alkyl;
$R^4$ represents $CH_2F$; $CHF_2$, or $CF_3$;
$R^5$ represents H; $C_{1-6}$-alkyl, branched or unbranched, unsubstituted a $C_{3-6}$ cycloaliphatic residue unsubstituted;
$R^6$, $R^7$ and $R^8$, are each independently of one another selected from the group consisting of H; F; Cl; Br; I; CN; $CF_3$; $CF_2H$; $CFH_2$; $CF_2Cl$; $CFCl_2$; $OCF_3$; $OCF_2H$; $OCFH_2$; $OCF_2Cl$; $OCFCl_2$; O—$C_{1-6}$-alkyl, whereby $C_{1-6}$-alkyl may be branched or unbranched; unsubstituted or mono-or poly-substituted with one or more substituents independently of one another selected from the group consisting of F; Cl; $CF_3$; OH and O—$C_{1-6}$-alkyl;
$R^9$ represents H; or a $C_{1-6}$ aliphatic residue, branched or unbranched, unsubstituted;
$R^{10}$ represents H; or a $C_{1-6}$ aliphatic residue, branched or unbranched, unsubstituted or substituted with 1, 2, 3, 4 or 5 substituents independently from one another selected from the group consisting of F, Cl, $CF_3$, CN, OH, =O, O—$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H) $C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)$_2$—$C_{1-6}$-alkyl, N($C_{1-6}$-alkyl)-S(=O)$_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, N(H)—C(=O)—O—$C_{1-6}$-alkyl; C(=O)—$NH_2$, C(=O)—N(H)($C_{1-6}$-alkyl), C(=O)—N(C$_{1-6}$-alkyl)$_2$, N(H)—C(=O)—C$_{1-6}$-alkyl, and N(C$_{1-6}$-alkyl)-C(=O)—C$_{1-6}$-alkyl; or a C$_{3-6}$ cycloaliphatic residue, unsubstituted or substituted with 1, 2, 3, 4 or 5 substituents independently from one another selected from the group consisting of F, Cl, CN, CF$_3$, =O, OCF$_3$, C$_{1-6}$-alkylen-OH, C$_{1-6}$ alkyl, OH, O—C$_{1-6}$-alkyl, O—(C=O)C$_{1-6}$-alkyl, S(=O)—C$_{1-6}$-alkyl, S(=O)$_2$-C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)$_2$—C$_{1-6}$-alkyl, C(=O)—NH$_2$, C(=O)—N(H)(C$_{1-6}$alkyl), C(=O)—N(C$_{1-6}$-alkyl)$_2$, C(=O)—O—C$_{1-6}$-alkyl; N(H)—C(=O)—C$_{1-6}$-alkyl, and N(C$_{1-6}$-alkyl)-C(=O)—C$_{1-6}$-alkyl; wherein said heteroary residue is optionally connected via a C$_{1-6}$-alkylene group, branched or unbranched, unsubstituted a 3-7-membered heterocycloaliphatic residue, which is unsubstituted or substituted with 1, 2, 3, 4 or 5 substituents independently from one another selected from the group consisting of F, Cl, CN, CF$_3$, =O, OCF$_3$, C$_{1-6}$-alkylen-OH, C$_{1-6}$ alkyl, OH, O—C$_{1-6}$-alkyl, O—(C=O)C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$-N(C$_{1-6}$-alkyl)$_2$, NH$_2$, NH(C$_{1-6}$-alkyl), N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl, and N(C$_{1-6}$-alkyl)-C(=O)—C$_{1-6}$-alkyl, wherein said 3-7-membered heterocycloaliphatic residue is optionally connected via a C$_{1-6}$-alkylene group, branched or unbranched, unsubstituted;

or a heteroaryl residue, which is unsubstituted or substituted with 1, 2, 3, 4 or 5 substituents independently from one another selected from the group consisting of F, Cl, CN, CF$_3$, OCF$_3$, C$_{1-6}$-alkylen-OH, C$_{1-6}$alkyl, OH, O—C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)$_2$—C$_{1-6}$-alkyl, N(C$_{1-6}$-alkyl)-S(=O)$_2$—C$_{1-6}$-alkyl, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl, and N(C$_{1-6}$-alkyl)-C(=O)—C$_{1-6}$-alkyl, wherein said heteroaryl residue is optionally connected via a C$_{1-6}$-alkylene group, branched or unbranched, unsubstituted;

or

R$^9$ and R$^{10}$ together with the nitrogen atom connecting them form a 3-7-membered heterocycloaliphatic residue selected from the group consisting of

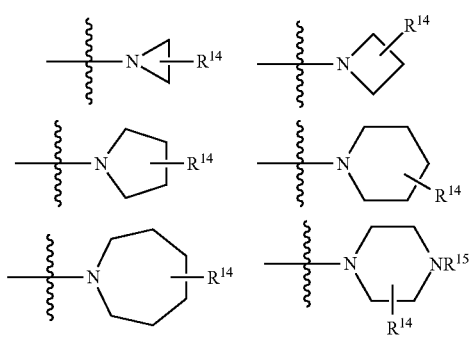

-continued

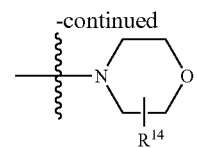

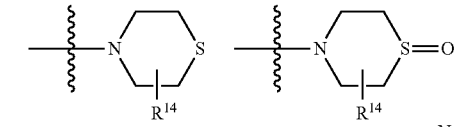

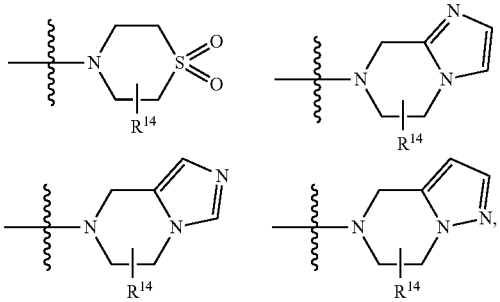

wherein
R$^{14}$ denotes 0, 1, 2, 3 or 4 substituents which are in each case independently of each other selected from the group consisting of F, Cl, CF$_3$, =O, OCF$_3$, OH, O—C$_{1-6}$-alkyl, C$_{1-6}$-alkylen-OH, C$_{1-6}$-alkylen-SO$_2$(C$_{1-6}$-alkyl), SO$_2$(C$_{1-6}$-alkyl) and C$_{1-6}$-alkyl; and
R$^{15}$ represents H, C$_{1-6}$-alkyl or (C=O)C$_{1-6}$-alkyl;
optionally in the form of a single stereoisomer or a mixture of stereoisomers, in form of the free compound and/or a physiologically acceptable salt and/or a physiologically acceptable solvate thereof.

2. A pharmaceutical composition comprising at least one compound according to claim 1.

3. A compound according to claim 1, wherein R$^4$ represents CHF$_2$ or CF$_3$.

4. A compound according to claim 1, wherein R$^5$ is selected from the group consisting of H, methyl, ethyl, n-propyl, iso-propyl, n-butyl, sec-butyl, iso-butyl, tert-butyl, and cyclopropyl.

5. A compound according to claim 1, wherein
R$^6$, R$^7$ and R$^8$ are each independently of one another selected from the group consisting of H; F; Cl; CN; CF$_3$; CF$_2$H; CFH$_2$; OCF$_3$; and O—C$_{1-6}$-alkyl, unsubstituted or mono- or polysubstituted with one or more substituents independently of one another selected from the group consisting of F; Cl; CF$_3$; OH and O—C$_{1-6}$-alkyl.

6. A compound according to claim 1, wherein
n represents 1 and m represents 0.

7. A compound according to claim 1, wherein
R$^9$ represents H or C$_{1-6}$-alkyl; and
R$^{10}$ represents a C$_{3-6}$-cycloaliphatic residue, which is unsubstituted or substituted as specified in claim 1;
or
R$^9$ and R$^{10}$ together with the nitrogen atom connecting them form a 3-7-membered heterocycloaliphatic residue selected from the group consisting of

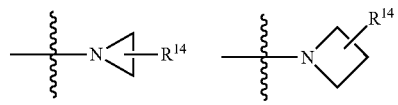

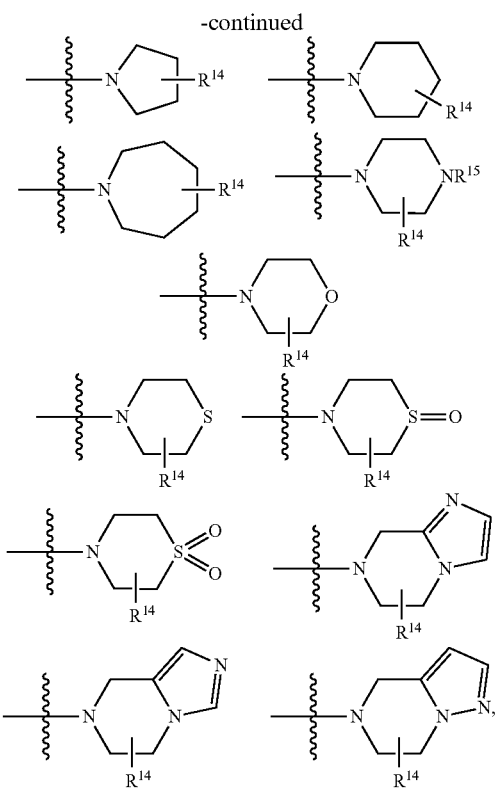

wherein
R$^{14}$ denotes 0, 1, 2, 3 or 4 substituents which are in each case independently of each other selected from the group consisting of F, Cl, CF$_3$, =O, OCF$_3$, OH, O—C$_{1-6}$-alkyl, C$_{1-6}$-alkylen-OH, C$_{1-6}$-alkylen-SO$_2$(C$_{1-6}$-alkyl), SO$_2$(C$_{1-6}$-alkyl) and C$_{1-6}$-alkyl.

8. A compound according to claim 1 selected from the group consisting of:
- [1-Benzyl-3-(4-chlorophenyl)-5-(trifluoromethyl)-1H-pyrrol-2-yl]-morpholin-4-yl-methanone;
- 1-Benzyl-3-(4-chlorophenyl)-N-(2,2-dimethyl-propyl)-N-methyl-5-(trifluoro-methyl)-1H-pyrrole-2-carboxylic acid amide;
- [1-Benzyl-3-(4-chlorophenyl)-4-methyl-5-(trifluoromethyl)-1H-pyrrol-2-yl]-morpholin-4-yl-methanone;
- 1-Benzyl-3-(4-chlorophenyl)-N-(2,2-dimethyl-propyl)-N,4-dimethyl-5-(trifluoromethyl)-1H-pyrrole-2-carboxylic acid amide;
- [1-Benzyl-3-(4-chlorophenyl)-4-methyl-5-(trifluoromethyl)-1H-pyrrol-2-yl]-(3-hydroxy-azetidin-1-yl)-methanone;
- 1-Benzyl-3-(4-chlorophenyl)-N,4-dimethyl-N-(2-methylsulfonyl-ethyl)-5-(trifluoromethyl)-1H-pyrrole-2-carboxylic acid amide;
- 4-[1-Benzyl-3-(4-chlorophenyl)-4-methyl-5-(trifluoromethyl)-1H-pyrrole-2-carbonyl]-piperazin-2-one;
- 4-[1-Benzyl-3-(4-chlorophenyl)-4-methyl-5-(trifluoromethyl)-1H-pyrrole-2-carbonyl]-1-methyl-piperazin-2-one;
- 1-Benzyl-3-(4-chlorophenyl)-4-methyl-N-tetrahydro-pyran-4-yl-5-(trifluoro-methyl)-1H-pyrrole-2-carboxylic acid amide;
- 1-Benzyl-3-(4-chlorophenyl)-N,4-dimethyl-N-tetrahydro-pyran-4-yl-5-(trifluoromethyl)-1H-pyrrole-2-carboxylic acid amide;
- 1-Benzyl-3-(4-chlorophenyl)-N-[1-(hydroxymethyl)-cyclopropyl]-4-methyl-5-(trifluoromethyl)-1H-pyrrole-2-carboxylic acid amide;
- [1-Benzyl-3-(4-chlorophenyl)-4-methyl-5-(trifluoromethyl)-1H-pyrrol-2-yl]-(4-hydroxy-piperidin-1-yl)-methanone;
- 1-Benzyl-3-(4-chlorophenyl)-N,N,4-trimethyl-5-(trifluoromethyl)-1H-pyrrole-2-carboxylic acid amide;
- [1-Benzyl-3-(4-chlorophenyl)-4-methyl-5-(trifluoromethyl)-1H-pyrrol-2-yl]-(1-oxo-[1,4]thiazinan-4-yl)-methanone;
- [1-Benzyl-3-(4-chlorophenyl)-4-methyl-5-(trifluoromethyl)-1H-pyrrol-2-yl]-[2-(hydroxymethyl)-morpholin-4-yl]-methanone;
- 1-Benzyl-3-(4-chlorophenyl)-N,4-dimethyl-N-(tetrahydro-pyran-4-yl-methyl)-5-(trifluoromethyl)-1H-pyrrole-2-carboxylic acid amide;
- 1-Benzyl-3-(4-chlorophenyl)-N,4-dimethyl-5-(trifluoromethyl)-1H-pyrrole-2-carboxylic acid amide;
- [1-Benzyl-3-(4-chlorophenyl)-4-methyl-5-(trifluoromethyl)-1H-pyrrol-2-yl]-(3-hydroxy-pyrrolidin-1-yl)-methanone;
- 1-Benzyl-3-(4-chlorophenyl)-N-(2-hydroxy-ethyl)-N,4-dimethyl-5-(trifluoromethyl)-1H-pyrrole-2-carboxylic acid amide;
- [3-(4-Chlorophenyl)-1-[(3-chlorophenyl)-methyl]-4-methyl-5-(trifluoromethyl)-1H-pyrrol-2-yl]-morpholin-4-yl-methanone;
- [1-Benzyl-3-(4-chlorophenyl)-4-methyl-5-(trifluoromethyl)-1H-pyrrol-2-yl]-(1,1-dioxo-[1,4]thiazinan-4-yl)-methanone;
- [1-Benzyl-3-(4-chlorophenyl)-4-methyl-5-(trifluoromethyl)-1H-pyrrol-2-yl]-(3,3-dimethyl-piperazin-1-yl)-methanone;
- [3-(4-Chlorophenyl)-1-(3-methoxyphenyl)-4-methyl-5-(trifluoromethyl)-1H-pyrrol-2-yl]-(3,3-difluoro-azetidin-1-yl)-methanone;
- [1-(3-Chlorophenyl)-3-(4-chlorophenyl)-4-methyl-5-(trifluoromethyl)-1H-pyrrol-2-yl]-(3,3-difluoro-azetidin-1-yl)-methanone;
- 1-Benzyl-3-(4-chlorophenyl)-N-cyclopropyl-N,4-dimethyl-5-(trifluoromethyl)-1H-pyrrole-2-carboxylic acid amide;
- 1-Benzyl-3-(4-chlorophenyl)-N-cyclopropyl-4-methyl-5-(trifluoromethyl)-1H-pyrrole-2-carboxylic acid amide;
- 1-Benzyl-3-(4-chlorophenyl)-N-[(1-methoxy-cyclopropyl)-methyl]-4-methyl-5-(trifluoromethyl)-1H-pyrrole-2-carboxylic acid amide;
- N-(2-Acetylamino-ethyl)-1-benzyl-3-(4-chlorophenyl)-N,4-dimethyl-5-(trifluoro-methyl)-1H-pyrrole-2-carboxylic acid amide;
- 1-Benzyl-3-(4-chlorophenyl)-N-[2-(methanesulfonamido)-ethyl]-N,4-dimethyl-5-(trifluoromethyl)-1H-pyrrole-2-carboxylic acid amide;
- 1-Benzyl-3-(4-chlorophenyl)-N,4-dimethyl-N-(1-methyl-piperidin-4-yl)-5-(trifluoromethyl)-1H-pyrrole-2-carboxylic acid amide;
- [1-Benzyl-3-(4-chlorophenyl)-4-methyl-5-(trifluoromethyl)-1H-pyrrol-2-yl]-(2,2-dimethyl-morpholin-4-yl)-methanone;
- [1-Benzyl-3-(4-chlorophenyl)-5-(difluoro-methyl)-4-methyl-1H-pyrrol-2-yl]-morpholin-4-yl-methanone;
- 1-Benzyl-3-(4-chlorophenyl)-5-(difluoro-methyl)-N-(2,2-dimethyl-propyl)-N,4-dimethyl-1H-pyrrole-2-carboxylic acid amide;

[1,3-Bis(4-chlorophenyl)-4-methyl-5-(trifluoromethyl)-1H-pyrrol-2-yl]-(3,3-difluoro-azetidin-1-yl)-methanone;

1-Benzyl-3-(4-chlorophenyl)-N-[1-(hydroxymethyl)-cyclopropyl]-N,4-dimethyl-5-(trifluoromethyl)-1H-pyrrole-2-carboxylic acid amide;

1-Benzyl-N-(1-carbamoyl-cyclopropyl)-3-(4-chlorophenyl)-N,4-dimethyl-5-(trifluoromethyl)-1H-pyrrole-2-carboxylic acid amide;

4-[1-Benzyl-3-(4-chlorophenyl)-4-methyl-5-(trifluoromethyl)-1H-pyrrole-2-carbonyl]-morpholin-2-one;

[3-(4-Chlorophenyl)-1-[2-(4-fluoro-phenoxy)-ethyl]-4-methyl-5-(trifluoromethyl)-1H-pyrrol-2-yl]-morpholin-4-yl-methanone;

1-[[1-Benzyl-3-(4-chlorophenyl)-4-methyl-5-(trifluoromethyl)-1H-pyrrole-2-carbonyl]-methyl-amino]-cyclopropane-1-carboxylic acid ethyl ester;

3-(4-Chlorophenyl)-1-[(3-chlorophenyl)-methyl]-N-(2,2-dimethyl-propyl)-N,4-dimethyl-5-(trifluoromethyl)-1H-pyrrole-2-carboxylic acid amide;

1-Benzyl-3-(4-chlorophenyl)-N-(2-hydroxy-2-methyl-propyl)-N,4-dimethyl-5-(trifluoromethyl)-1H-pyrrole-2-carboxylic acid amide;

4-[3-(4-Chlorophenyl)-1-[(3-chlorophenyl)-methyl]-4-methyl-5-(trifluoromethyl)-1H-pyrrole-2-carbonyl]-piperazin-2-one;

3-(4-Chlorophenyl)-1-[(3-chlorophenyl)-methyl]-N,4-dimethyl-N-(2-methylsulfonyl-ethyl)-5-(trifluoromethyl)-1H-pyrrole-2-carboxylic acid amide;

3-(4-Chlorophenyl)-1-[(3-chlorophenyl)-methyl]-N-(2-hydroxy-2-methyl-propyl)-N,4-dimethyl-5-(trifluoromethyl)-1H-pyrrole-2-carboxylic acid amide;

1-Benzyl-3-(4-chloro-2-fluoro-phenyl)-N-(2-hydroxy-2-methyl-propyl)-N,4-dimethyl-5-(trifluoromethyl)-1H-pyrrole-2-carboxylic acid amide;

1-Benzyl-3-(4-chloro-2-fluoro-phenyl)-N-(2,2-dimethyl-propyl)-N,4-dimethyl-5-(trifluoromethyl)-1H-pyrrole-2-carboxylic acid amide;

1-Benzyl-3-(4-chlorophenyl)-N,4-dimethyl-N-[(3-methyl-oxetan-3-yl)-methyl]-5-(trifluoromethyl)-1H-pyrrole-2-carboxylic acid amide;

4-[1-Benzyl-3-(4-chloro-2-fluoro-phenyl)-4-methyl-5-(trifluoromethyl)-1H-pyrrole-2-carbonyl]-piperazin-2-one;

[1-Benzyl-3-(4-chloro-2-fluoro-phenyl)-4-methyl-5-(trifluoromethyl)-1H-pyrrol-2-yl]-morpholin-4-yl-methanone;

1-Benzyl-3-(4-chlorophenyl)-N-(1,1-dioxo-thiolan-3-yl)-N,4-dimethyl-5-(trifluoromethyl)-1H-pyrrole-2-carboxylic acid amide;

1-Benzyl-3-(4-chloro-2-fluoro-phenyl)-N,4-dimethyl-N-(2-methylsulfonyl-ethyl)-5-(trifluoromethyl)-1H-pyrrole-2-carboxylic acid amide;

1-Benzyl-3-(4-chlorophenyl)-N-[(1-hydroxy-cyclopropyl)-methyl]-N,4-dimethyl-5-(trifluoromethyl)-1H-pyrrole-2-carboxylic acid amide;

4-[1-Benzyl-3-(4-chlorophenyl)-5-(trifluoromethyl)-1H-pyrrole-2-carbonyl]-piperazin-2-one;

1-Benzyl-3-(4-chlorophenyl)-N-methyl-N-(2-methylsulfonyl-ethyl)-5-(trifluoromethyl)-1H-pyrrole-2-carboxylic acid amide;

1-Benzyl-3-(4-chlorophenyl)-N-(2-hydroxy-2-methyl-propyl)-N-methyl-5-(trifluoromethyl)-1H-pyrrole-2-carboxylic acid amide;

3-(4-Chlorophenyl)-1-[(3-chlorophenyl)-methyl]-N-methyl-N-(2-methylsulfonyl-ethyl)-5-(trifluoromethyl)-1H-pyrrole-2-carboxylic acid amide;

3-(4-Chlorophenyl)-1-[(3-chlorophenyl)-methyl]-N-(2-hydroxy-2-methyl-propyl)-N-methyl-5-(trifluoromethyl)-1H-pyrrole-2-carboxylic acid amide;

3-(4-Chlorophenyl)-1-[(3-chlorophenyl)-methyl]-N-(2,2-dimethyl-propyl)-N-methyl-5-(trifluoromethyl)-1H-pyrrole-2-carboxylic acid amide;

[1-Benzyl-3-(4-chlorophenyl)-5-(trifluoromethyl)-1H-pyrrol-2-yl]-(3-hydroxy-azetidin-1-yl)-methanone;

1-Benzyl-3-(4-chlorophenyl)-N-methyl-N-tetrahydro-pyran-4-yl-5-(trifluoromethyl)-1H-pyrrole-2-carboxylic acid amide;

[3-(4-Chlorophenyl)-1-[(3-chlorophenyl)-methyl]-5-(trifluoromethyl)-1H-pyrrol-2-yl]-morpholin-4-yl-methanone;

[1-Benzyl-3-(4-chlorophenyl)-5-(trifluoromethyl)-1H-pyrrol-2-yl]-(2,2-dimethyl-morpholin-4-yl)-methanone;

1-Benzyl-3-(4-chlorophenyl)-N-(cyclopropyl-methyl)-N-methyl-5-(trifluoro-methyl)-1H-pyrrole-2-carboxylic acid amide;

1-Benzyl-N-tert-butyl-3-(4-chlorophenyl)-N-methyl-5-(trifluoromethyl)-1H-pyrrole-2-carboxylic acid amide;

1-Benzyl-3-(4-chlorophenyl)-N-methyl-N-[(3-methyl-oxetan-3-yl)-methyl]-5-(trifluoromethyl)-1H-pyrrole-2-carboxylic acid amide;

1-Benzyl-3-(4-chlorophenyl)-N-(3-hydroxy-2,2-dimethyl-propyl)-N-methyl-5-(trifluoromethyl)-1H-pyrrole-2-carboxylic acid amide;

1-Benzyl-3-(4-chlorophenyl)-N,N-dimethyl-5-(trifluoromethyl)-1H-pyrrole-2-carboxylic acid amide;

4-[3-(4-Chlorophenyl)-1-[(3-chlorophenyl)-methyl]-5-(trifluoromethyl)-1H-pyrrole-2-carbonyl]-piperazin-2-one;

[1-Benzyl-3-(4-chlorophenyl)-5-(trifluoromethyl)-1H-pyrrol-2-yl]-(3,3-dimethyl-piperazin-1-yl)-methanone;

1-Benzyl-3-(4-chlorophenyl)-N-(1,1-dioxo-thiolan-3-yl)-N-methyl-5-(trifluoro-methyl)-1H-pyrrole-2-carboxylic acid amide;

1-Benzyl-3-(4-chlorophenyl)-N-(3,3-dimethyl-butyl)-N-methyl-5-(trifluoro-methyl)-1H-pyrrole-2-carboxylic acid amide;

1-Benzyl-3-(4-chlorophenyl)-N-methyl-N-(2-methyl-2-morpholin-4-yl-propyl)-5-(trifluoromethyl)-1H-pyrrole-2-carboxylic acid amide;

[1-Benzyl-3-(4-chloro-2-fluoro-phenyl)-5-(trifluoromethyl)-1H-pyrrol-2-yl]-morpholin-4-yl-methanone;

1-Benzyl-3-(4-chloro-2-fluoro-phenyl)-N-(2-hydroxy-2-methyl-propyl)-N-methyl-5-(trifluoromethyl)-1H-pyrrole-2-carboxylic acid amide;

1-Benzyl-3-(4-chloro-2-fluoro-phenyl)-N-(2,2-dimethyl-propyl)-N-methyl-5-(trifluoromethyl)-1H-pyrrole-2-carboxylic acid amide;

4-[1-Benzyl-3-(4-chloro-2-fluoro-phenyl)-5-(trifluoromethyl)-1H-pyrrole-2-carbonyl]-piperazin-2-one;

1-Benzyl-3-(4-chloro-2-fluoro-phenyl)-N-methyl-N-(2-methylsulfonyl-ethyl)-5-(trifluoromethyl)-1H-pyrrole-2-carboxylic acid amide;

1-Benzyl-3-(4-chlorophenyl)-N-methyl-N-(2-methyl-2-methylsulfonyl-propyl)-5-(trifluoromethyl)-1H-pyrrole-2-carboxylic acid amide;

[1-Benzyl-3-(4-chlorophenyl)-4-methyl-5-(trifluoromethyl)-1H-pyrrol-2-yl]-(3,3-difluoro-azetidin-1-yl)-methanone;

[1-Benzyl-3-(4-chlorophenyl)-5-(trifluoromethyl)-1H-pyrrol-2-yl]-(3,3-difluoro-azetidin-1-yl)-methanone;

[1-Benzyl-3-(4-fluorophenyl)-4-methyl-5-(trifluoromethyl)-1H-pyrrol-2-yl]-(3,3-difluoro-azetidin-1-yl)-methanone;
[1-Benzyl-4-methyl-5-(trifluoromethyl)-3-[4-(trifluoromethyl)-phenyl]-1H-pyrrol-2-yl]-(3,3-difluoro-azetidin-1-yl)-methanone;
[1-Benzyl-4-methyl-5-(trifluoromethyl)-3-[4-(trifluoromethyloxy)-phenyl]-1H-pyrrol-2-yl]-(3,3-difluoro-azetidin-1-yl)-methanone;
[1-Benzyl-3-(4-chloro-3-fluoro-phenyl)-4-methyl-5-(trifluoromethyl)-1H-pyrrol-2-yl]-(3,3-difluoro-azetidin-1-yl)-methanone;
[1-Benzyl-3-(3-chloro-4-fluoro-phenyl)-4-methyl-5-(trifluoromethyl)-1H-pyrrol-2-yl]-(3,3-difluoro-azetidin-1-yl)-methanone;
[1-Benzyl-3-(4-chloro-2-fluoro-phenyl)-4-methyl-5-(trifluoromethyl)-1H-pyrrol-2-yl]-(3,3-difluoro-azetidin-1-yl)-methanone;
[1-Benzyl-3-(4-fluorophenyl)-4-methyl-5-(trifluoromethyl)-1H-pyrrol-2-yl]-morpholin-4-yl-methanone;
[1-Benzyl-4-methyl-5-(trifluoromethyl)-3-[4-(trifluoromethyl)-phenyl]-1H-pyrrol-2-yl]-morpholin-4-yl-methanone;
[1-Benzyl-3-(4-chloro-3-fluoro-phenyl)-4-methyl-5-(trifluoromethyl)-1H-pyrrol-2-yl]-morpholin-4-yl-methanone;
[1-Benzyl-3-(3-chloro-4-fluoro-phenyl)-4-methyl-5-(trifluoromethyl)-1H-pyrrol-2-yl]-morpholin-4-yl-methanone;
[1-Benzyl-4-methyl-5-(trifluoromethyl)-3-[4-(trifluoromethyloxy)-phenyl]-1H-pyrrol-2-yl]-morpholin-4-yl-methanone;
1-Benzyl-3-(4-chlorophenyl)-N-(3-hydroxy-2,2-dimethyl-propyl)-N,4-dimethyl-5-(trifluoromethyl)-1H-pyrrole-2-carboxylic acid amide;
1-Benzyl-3-(4-chloro-2-fluoro-phenyl)-N-(3-hydroxy-2,2-dimethyl-propyl)-N,4-dimethyl-5-(trifluoromethyl)-1H-pyrrole-2-carboxylic acid amide;
1-Benzyl-3-(4-fluorophenyl)-N-(2-hydroxy-2-methyl-propyl)-N,4-dimethyl-5-(trifluoromethyl)-1H-pyrrole-2-carboxylic acid amide;
1-Benzyl-N-(2-hydroxy-2-methyl-propyl)-N,4-dimethyl-5-(trifluoromethyl)-3-[4-(trifluoromethyl)-phenyl]-1H-pyrrole-2-carboxylic acid amide;
1-Benzyl-N-(2-hydroxy-2-methyl-propyl)-N,4-dimethyl-5-(trifluoromethyl)-3-[4-(trifluoromethyloxy)-phenyl]-1H-pyrrole-2-carboxylic acid amide;
1-Benzyl-3-(4-chloro-3-fluoro-phenyl)-N-(2-hydroxy-2-methyl-propyl)-N,4-dimethyl-5-(trifluoromethyl)-1H-pyrrole-2-carboxylic acid amide;
1-Benzyl-3-(3-chloro-4-fluoro-phenyl)-N-(2-hydroxy-2-methyl-propyl)-N,4-dimethyl-5-(trifluoromethyl)-1H-pyrrole-2-carboxylic acid amide;
1-Benzyl-3-(4-chlorophenyl)-N-(3-hydroxy-3-methyl-butyl)-N,4-dimethyl-5-(trifluoromethyl)-1H-pyrrole-2-carboxylic acid amide;
1-Benzyl-3-(4-chlorophenyl)-N-(3-hydroxy-2,2-dimethyl-propyl)-4-methyl-5-(trifluoromethyl)-1H-pyrrole-2-carboxylic acid amide;
1-Benzyl-3-(4-chlorophenyl)-N-[[1-(hydroxymethyl)-cyclopropyl]-methyl]-N,4-dimethyl-5-(trifluoromethyl)-1H-pyrrole-2-carboxylic acid amide;
1-Benzyl-3-(4-chlorophenyl)-N-[[1-(hydroxymethyl)-cyclobutyl]-methyl]-N,4-dimethyl-5-(trifluoromethyl)-1H-pyrrole-2-carboxylic acid amide;
[1-Benzyl-3-(4-chlorophenyl)-4-methyl-5-(trifluoromethyl)-1H-pyrrol-2-yl]-[3-(hydroxymethyl)-pyrrolidin-1-yl]-methanone;
1-Benzyl-3-(4-chlorophenyl)-N-(2,2-dimethyl-3-morpholin-4-yl-propyl)-N,4-dimethyl-5-(trifluoromethyl)-1H-pyrrole-2-carboxylic acid amide;
1-Benzyl-3-(4-chlorophenyl)-N-(2,2-dimethyl-propyl)-4-ethyl-N-methyl-5-(trifluoromethyl)-1H-pyrrole-2-carboxylic acid amide;
1-Benzyl-3-(4-chlorophenyl)-4-cyclopropyl-N-(2,2-dimethyl-propyl)-N-methyl-5-(trifluoromethyl)-1H-pyrrole-2-carboxylic acid amide;
1-Benzyl-3-(4-chlorophenyl)-N,4-dimethyl-N-(tetrahydro-furan-3-yl-methyl)-5-(trifluoromethyl)-1H-pyrrole-2-carboxylic acid amide;
1-Benzyl-3-(4-chlorophenyl)-N-(3-hydroxy-1,1-dimethyl-propyl)-N,4-dimethyl-5-(trifluoromethyl)-1H-pyrrole-2-carboxylic acid amide;
[1-Benzyl-3-(4-chlorophenyl)-4-methyl-5-(trifluoromethyl)-1H-pyrrol-2-yl]-(3-methylsulfonyl-pyrrolidin-1-yl)-methanone;
1-Benzyl-3-(4-chlorophenyl)-N-[1-(hydroxymethyl)-2,2-dimethyl-propyl]-N,4-dimethyl-5-(trifluoromethyl)-1H-pyrrole-2-carboxylic acid amide;
1-Benzyl-3-(4-chlorophenyl)-N-[3-hydroxy-2-(hydroxymethyl)-2-methyl-propyl]-N,4-dimethyl-5-(trifluoromethyl)-1H-pyrrole-2-carboxylic acid amide;
1-Benzyl-3-(4-chlorophenyl)-N-(2-hydroxy-1,1-dimethyl-ethyl)-N,4-dimethyl-5-(trifluoromethyl)-1H-pyrrole-2-carboxylic acid amide;
1-Benzyl-3-(4-chlorophenyl)-N,4-dimethyl-N-(3-methylsulfonyl-propyl)-5-(trifluoromethyl)-1H-pyrrole-2-carboxylic acid amide;
1-Benzyl-3-(4-chlorophenyl)-N-ethyl-4-methyl-N-(2-methylsulfonyl-ethyl)-5-(trifluoromethyl)-1H-pyrrole-2-carboxylic acid amide;
1-Benzyl-3-(4-chlorophenyl)-4-methyl-N-(2-methylsulfonyl-ethyl)-5-(trifluoromethyl)-1H-pyrrole-2-carboxylic acid amide;
1-Benzyl-3-(4-chlorophenyl)-N-[2-(isopropylsulfonyl)-ethyl]-N,4-dimethyl-5-(trifluoromethyl)-1H-pyrrole-2-carboxylic acid amide;
1-Benzyl-3-(4-chlorophenyl)-N-(1,1-dioxo-thian-4-yl)-N,4-dimethyl-5-(trifluoromethyl)-1H-pyrrole-2-carboxylic acid amide;
1-Benzyl-3-(4-chlorophenyl)-N-[2-(ethylsulfonyl)-ethyl]-N,4-dimethyl-5-(trifluoromethyl)-1H-pyrrole-2-carboxylic acid amide;
1-Benzyl-3-(4-chlorophenyl)-N,4-dimethyl-N-(2-tetrahydro-furan-2-yl-ethyl)-5-(trifluoromethyl)-1H-pyrrole-2-carboxylic acid amide;
1-Benzyl-3-(4-chlorophenyl)-N,4-dimethyl-N-(tetrahydro-furan-2-yl-methyl)-5-(trifluoromethyl)-1H-pyrrole-2-carboxylic acid amide;
1-Benzyl-3-(4-chlorophenyl)-N-[[(2S)-2-hydroxy-cyclopentyl]-methyl]-N,4-dimethyl-5-(trifluoromethyl)-1H-pyrrole-2-carboxylic acid amide;
1-Benzyl-3-(4-chlorophenyl)-N-[[(2R)-2-hydroxy-cyclopentyl]-methyl]-N,4-dimethyl-5-(trifluoromethyl)-1H-pyrrole-2-carboxylic acid amide;
[1-Benzyl-3-(4-chlorophenyl)-4-methyl-5-(trifluoromethyl)-1H-pyrrol-2-yl]-(3-methylsulfonyl-azetidin-1-yl)-methanone;
1-Benzyl-3-(4-chlorophenyl)-N,4-dimethyl-N-(tetrahydro-pyran-2-yl-methyl)-5-(trifluoromethyl)-1H-pyrrole-2-carboxylic acid amide;

1-Benzyl-3-(4-chlorophenyl)-N-[2,2-dimethyl-3-[methyl-(2-pyrrolidin-1-yl-ethyl)-amino]-propyl]-N,4-dimethyl-5-(trifluoromethyl)-1H-pyrrole-2-carboxylic acid amide;
1-Benzyl-3-(4-chlorophenyl)-N,4-dimethyl-N-[(3-methyl-isoxazol-5-yl)-methyl]-5-(trifluoromethyl)-1H-pyrrole-2-carboxylic acid amide;
1-Benzyl-3-(4-chlorophenyl)-N,4-dimethyl-N-(1-methyl-2-methylsulfonyl-ethyl)-5-(trifluoromethyl)-1H-pyrrole-2-carboxylic acid amide;
1-Benzyl-3-(4-chlorophenyl)-N,4-dimethyl-N-[(5-methyl-isoxazol-3-yl)-methyl]-5-(trifluoromethyl)-1H-pyrrole-2-carboxylic acid amide;
1-Benzyl-3-(4-chlorophenyl)-N,4-dimethyl-N-[(5-methyl-[1,3,4]oxadiazol-2-y1)-methyl]-5-(trifluoromethyl)-1H-pyrrole-2-carboxylic acid amide;
1-Benzyl-3-(4-chlorophenyl)-N,4-dimethyl-N-(pyrimidin-4-yl-methyl)-5-(trifluoromethyl)-1H-pyrrole-2-carboxylic acid amide;
[1-Benzyl-3-(4-chlorophenyl)-4-methyl-5-(trifluoromethyl)-1H-pyrrol-2-yl]-(4-methoxy-piperidin-1-yl)-methanone;
1-Benzyl-3-(4-chlorophenyl)-N,4-dimethyl-N-(pyrazin-2-yl-methyl)-5-(trifluoromethyl)-1H-pyrrole-2-carboxylic acid amide;
1-Benzyl-3-(4-chlorophenyl)-N-[(2-dimethylamino-pyrimidin-4-yl)-methyl]-N,4-dimethyl-5-(trifluoromethyl)-1H-pyrrole-2-carboxylic acid amide;
1-Benzyl-3-(4-chlorophenyl)-N,4-dimethyl-N-[(1-methyl-1H-imidazol-2-yl)-methyl]-5-(trifluoromethyl)-1H-pyrrole-2-carboxylic acid amide;
1-Benzyl-3-(4-chlorophenyl)-N-isopropyl-N,4-dimethyl-5-(trifluoromethyl)-1H-pyrrole-2-carboxylic acid amide;
1-Benzyl-3-(4-chlorophenyl)-N-isopropyl-4-methyl-5-(trifluoromethyl)-1H-pyrrole-2-carboxylic acid amide;
1-Benzyl-3-(4-chlorophenyl)-N,4-dimethyl-N-[(5-methyl-pyrazin-2-yl)-methyl]-5-(trifluoromethyl)-1H-pyrrole-2-carboxylic acid amide;
1-Benzyl-3-(4-chlorophenyl)-N-[(2-dimethylamino-pyrimidin-5-yl)-methyl]-N,4-dimethyl-5-(trifluoromethyl)-1H-pyrrole-2-carboxylic acid amide;
1-[4-[1-Benzyl-3-(4-chlorophenyl)-4-methyl-5-(trifluoromethyl)-1H-pyrrole-2-carbonyl]-piperazin-1-yl]-ethanone;
[1-Benzyl-3-(4-chloro-2-fluoro-phenyl)-4-methyl-5-(trifluoromethyl)-1H-pyrrol-2-yl]-(3-hydroxy-azetidin-1-yl)-methanone;
[1-Benzyl-3-(4-chloro-2-fluoro-phenyl)-4-methyl-5-(trifluoromethyl)-1H-pyrrol-2-yl]-(2,2-dimethyl-morpholin-4-yl)-methanone;
1-Benzyl-3-(4-chloro-2-fluoro-phenyl)-N,4-dimethyl-N-tetrahydro-pyran-4-y1-5-(trifluoromethyl)-1H-pyrrole-2-carboxylic acid amide;
1-Benzyl-3-(4-chloro-2-fluoro-phenyl)-4-methyl-5-(trifluoromethyl)-N-[(1R)-1,2,2-trimethyl-propyl]-1H-pyrrole-2-carboxylic acid amide;
1-Benzyl-3-(4-chloro-2-fluoro-phenyl)-N-cyclopropyl-N,4-dimethyl-5-(trifluoromethyl)-1H-pyrrole-2-carboxylic acid amide;
1-Benzyl-3-(4-chloro-2-fluoro-phenyl)-N-(1,1-dioxo-thian-4-yl)-N,4-dimethyl-5-(trifluoromethyl)-1H-pyrrole-2-carboxylic acid amide;
1-Benzyl-3-(4-chloro-2-fluoro-phenyl)-N,4-dimethyl-N-(3-methylsulfonyl-propyl)-5-(trifluoromethyl)-1H-pyrrole-2-carboxylic acid amide;
[1-Benzyl-3-(4-chloro-2-fluoro-phenyl)-4-methyl-5-(trifluoromethyl)-1H-pyrrol-2-yl]-[2-(methylsulfonyl-methyl)-pyrrolidin-1-yl]-methanone;
1-Benzyl-3-(4-chloro-2-fluoro-phenyl)-4-methyl-N-(2-methylsulfonyl-ethyl)-5-(trifluoromethyl)-1H-pyrrole-2-carboxylic acid amide;
1-Benzyl-3-(4-chloro-2-fluoro-phenyl)-N,4-dimethyl-N-(2-tetrahydro-furo-2-yl-ethyl)-5-(trifluoromethyl)-1H-pyrrole-2-carboxylic acid amide;
1-Benzyl-3-(4-chloro-2-fluoro-phenyl)-N,4-dimethyl-N-(tetrahydro-furan-2-yl-methyl)-5-(trifluoromethyl)-1H-pyrrole-2-carboxylic acid amide;
[1-Benzyl-3-(4-chloro-2-fluoro-phenyl)-4-methyl-5-(trifluoromethyl)-1H-pyrrol-2-yl]-[3-(hydroxymethyl)-pyrrolidin-1-yl]-methanone;
1-Benzyl-3-(4-chloro-2-fluoro-phenyl)-N,4-dimethyl-N-(tetrahydro-furan-3-yl-methyl)-5-(trifluoromethyl)-1H-pyrrole-2-carboxylic acid amide;
1-Benzyl-3-(4-chloro-2-fluoro-phenyl)-N,4-dimethyl-N-(2-methyl-2-methylsulfonyl-propyl)-5-(trifluoromethyl)-1H-pyrrole-2-carboxylic acid amide;
1-Benzyl-3-(4-chloro-2-fluoro-phenyl)-N-isopropyl-4-methyl-N-(2-methylsulfonyl-ethyl)-5-(trifluoromethyl)-1H-pyrrole-2-carboxylic acid amide;
[1-Benzyl-3-(4-chloro-2-fluoro-phenyl)-4-methyl-5-(trifluoromethyl)-1H-pyrrol-2-yl]-(2,2-dimethyl-1,1-dioxo-[1,4]thiazinan-4-yl)-methanone;
1-Benzyl-3-(4-chloro-2-fluoro-phenyl)-N-(1,1-dioxo-thiolan-3-yl)-N,4-dimethyl-5-(trifluoromethyl)-1H-pyrrole-2-carboxylic acid amide;
1-Benzyl-3-(4-chloro-2-fluoro-phenyl)-N-cyclopropyl-4-methyl-5-(trifluoromethyl)-1H-pyrrole-2-carboxylic acid amide;
[1-Benzyl-3-(4-chloro-2-fluoro-phenyl)-4-methyl-5-(trifluoromethyl)-1H-pyrrol-2-yl]-(1,1-dioxo-[1,4]thiazinan-4-yl)-methanone;
1-Benzyl-N-(2-carbamoyl-2-methyl-propyl)-3-(4-chlorophenyl)-N-methyl-5-(trifluoromethyl)-1H-pyrrole-2-carboxylic acid amide;
N-(2-Amino-2-methyl-propyl)-1-benzyl-3-(4-chlorophenyl)-N-methyl-5-(trifluoromethyl)-1H-pyrrole-2-carboxylic acid amide;
1-Benzyl-3-(4-chlorophenyl)-N-(3-hydroxy-3-methyl-butyl)-N-methyl-5-(trifluoromethyl)-1H-pyrrole-2-carboxylic acid amide;
1-Benzyl-3-(4-chlorophenyl)-N-(3-hydroxy-2,2-dimethyl-propyl)-5-(trifluoromethyl)-1H-pyrrole-2-carboxylic acid amide;
1-Benzyl-3-(4-chlorophenyl)-N-[[1-(hydroxymethyl)-cyclopropyl]-methyl]-N-methyl-5-(trifluoromethyl)-1H-pyrrole-2-carboxylic acid amide;
1-Benzyl-3-(4-chlorophenyl)-N-[[1-(hydroxymethyl)-cyclobutyl]-methyl]-N-methyl-5-(trifluoromethyl)-1H-pyrrole-2-carboxylic acid amide;
1-Benzyl-3-(4-chlorophenyl)-N-(2,2-dimethyl-3-morpholin-4-yl-propyl)-N-methyl-5-(trifluoromethyl)-1H-pyrrole-2-carboxylic acid amide;
[1-Benzyl-3-(4-chlorophenyl)-5-(trifluoromethyl)-1H-pyrrol-2-yl]-[3-(hydroxymethyl)-pyrrolidin-1-yl]-methanone;
1-Benzyl-3-(4-chlorophenyl)-N-methyl-N-(tetrahydrofuran-3-yl-methyl)-5-(trifluoromethyl)-1H-pyrrole-2-carboxylic acid amide;
1-Benzyl-3-(4-chlorophenyl)-N-[3-hydroxy-2-(hydroxymethyl)-2-methyl-propyl]-N-methyl-5-(trifluoromethyl)-1H-pyrrole-2-carboxylic acid amide;

1-Benzyl-3-(4-chlorophenyl)-N-(3-hydroxy-1,1-dimethyl-propyl)-N-methyl-5-(trifluoromethyl)-1H-pyrrole-2-carboxylic acid amide;
[1-Benzyl-3-(4-chlorophenyl)-5-(trifluoromethyl)-1H-pyrrol-2-yl]-(3-methylsulfonyl-pyrrolidin-1-yl)-methanone;
1-Benzyl-3-(4-chlorophenyl)-N-[1-(hydroxymethyl)-2,2-dimethyl-propyl]-N-methyl-5-(trifluoromethyl)-1H-pyrrole-2-carboxylic acid amide;
1-Benzyl-3-(4-chlorophenyl)-N-(2-cyano-2-methyl-propyl)-N-methyl-5-(trifluoromethyl)-1H-pyrrole-2-carboxylic acid amide;
N-(3-Amino-2,2-dimethyl-propyl)-1-benzyl-3-(4-chlorophenyl)-N-methyl-5-(trifluoromethyl)-1H-pyrrole-2-carboxylic acid amide;
1-Benzyl-3-(4-chlorophenyl)-N-methyl-N-(3-methylsulfonyl-propyl)-5-(trifluoromethyl)-1H-pyrrole-2-carboxylic acid amide;
1-Benzyl-3-(4-chlorophenyl)-N-ethyl-N-(2-methylsulfonyl-ethyl)-5-(trifluoromethyl)-1H-pyrrole-2-carboxylic acid amide;
1-Benzyl-3-(4-chlorophenyl)-N-(2-methylsulfonyl-ethyl)-5-(trifluoromethyl)-1H-pyrrole-2-carboxylic acid amide;
1-Benzyl-3-(4-chlorophenyl)-N-[2-(ethylsulfonyl)-ethyl]-N-methyl-5-(trifluoromethyl)-1H-pyrrole-2-carboxylic acid amide;
1-Benzyl-3-(4-chlorophenyl)-N-(1,1-dioxo-thian-4-yl)-N-methyl-5-(trifluoromethyl)-1H-pyrrole-2-carboxylic acid amide;
1-Benzyl-3-(4-chlorophenyl)-N-[2-(isopropylsulfonyl)-ethyl]-N-methyl-5-(trifluoromethyl)-1H-pyrrole-2-carboxylic acid amide;
1-Benzyl-3-(4-chlorophenyl)-N-methyl-N-(2-tetrahydro-furan-2-yl-ethyl)-5-(trifluoromethyl)-1H-pyrrole-2-carboxylic acid amide;
[1-Benzyl-3-(4-chlorophenyl)-5-(trifluoromethyl)-1H-pyrrol-2-yl]-(1,1-dioxo-[1,4]thiazinan-4-yl)-methanone;
1-Benzyl-3-(4-chlorophenyl)-N-methyl-N-(tetrahydrofuran-2-yl-methyl)-5-(trifluoromethyl)-1H-pyrrole-2-carboxylic acid amide;
1-Benzyl-3-(4-chlorophenyl)-N-methyl-N-(1-methyl-2-methylsulfonyl-ethyl)-5-(trifluoromethyl)-1H-pyrrole-2-carboxylic acid amide;
1-Benzyl-3-(4-chlorophenyl)-N-[[(2S)-2-hydroxy-cyclopentyl]-methyl]-N-methyl-5-(trifluoromethyl)-1H-pyrrole-2-carboxylic acid amide;
1-Benzyl-3-(4-chlorophenyl)-N-[[(2R)-2-hydroxy-cyclopentyl]-methyl]-N-methyl-5-(trifluoromethyl)-1H-pyrrole-2-carboxylic acid amide;
[1-Benzyl-3-(4-chlorophenyl)-5-(trifluoromethyl)-1H-pyrrol-2-yl]-(3-methylsulfonyl-azetidin-1-yl)-methanone;
1-Benzyl-3-(4-chlorophenyl)-N-methyl-N-(tetrahydro-pyran-2-yl-methyl)-5-(trifluoromethyl)-1H-pyrrole-2-carboxylic acid amide;
1-Benzyl-3-(4-chlorophenyl)-N-[2,2-dimethyl-3-[methyl-(2-pyrrolidin-1-yl-ethyl)-amino]-propyl]-N-methyl-5-(trifluoromethyl)-1H-pyrrole-2-carboxylic acid amide;
1-Benzyl-3-(4-chlorophenyl)-N-methyl-N-[(3-methyl-isoxazol-5-yl)-methyl]-5-(trifluoromethyl)-1H-pyrrole-2-carboxylic acid amide;
1-Benzyl-3-(4-chlorophenyl)-N-methyl-N-[(5-methyl-isoxazol-3-yl)-methyl]-5-(trifluoromethyl)-1H-pyrrole-2-carboxylic acid amide;
1-Benzyl-3-(4-chlorophenyl)-N-methyl-N-[(5-methyl-[1,3,4]oxadiazol-2-yl)-methyl]-5-(trifluoromethyl)-1H-pyrrole-2-carboxylic acid amide;
1-Benzyl-3-(4-chlorophenyl)-N-methyl-N-(pyrimidin-4-yl-methyl)-5-(trifluoromethyl)-1H-pyrrole-2-carboxylic acid amide;
[1-Benzyl-3-(4-chlorophenyl)-5-(trifluoromethyl)-1H-pyrrol-2-yl]-(4-methoxy-piperidin-1-yl)-methanone;
1-[4-[1-Benzyl-3-(4-chlorophenyl)-5-(trifluoromethyl)-1H-pyrrole-2-carbonyl]-piperazin-1-yl]-ethanone;
1-Benzyl-3-(4-chlorophenyl)-N-methyl-N-(pyrazin-2-yl-methyl)-5-(trifluoromethyl)-1H-pyrrole-2-carboxylic acid amide;
1-Benzyl-3-(4-chlorophenyl)-N-[(2-dimethylamino-pyrimidin-4-yl)-methyl]-N-methyl-5-(trifluoromethyl)-1H-pyrrole-2-carboxylic acid amide;
1-Benzyl-3-(4-chlorophenyl)-N-methyl-N-[(1-methyl-1H-imidazol-2-yl)-methyl]-5-(trifluoromethyl)-1H-pyrrole-2-carboxylic acid amide;
1-Benzyl-3-(4-chlorophenyl)-N-isopropyl-N-methyl-5-(trifluoromethyl)-1H-pyrrole-2-carboxylic acid amide;
1-Benzyl-3-(4-chlorophenyl)-N-isopropyl-5-(trifluoromethyl)-1H-pyrrole-2-carboxylic acid amide;
1-Benzyl-3-(4-chlorophenyl)-N-methyl-N-[(5-methyl-pyrazin-2-yl)-methyl]-5-(trifluoromethyl)-1H-pyrrole-2-carboxylic acid amide;
1-Benzyl-3-(4-chlorophenyl)-N-[(2-dimethylamino-pyrimidin-5-yl)-methyl]-N-methyl-5-(trifluoromethyl)-1H-pyrrole-2-carboxylic acid amide;
[1-Benzyl-3-(4-chlorophenyl)-5-(trifluoromethyl)-1H-pyrrol-2-yl]-(5,6,7,8-tetrahydro-imidazo[1,2-a]pyrazin-7-yl)-methanone;
1-Benzyl-3-(4-fluorophenyl)-N-(3-hydroxy-2,2-dimethyl-propyl)-N,4-dimethyl-5-(trifluoromethyl)-1H-pyrrole-2-carboxylic acid amide;
1-Benzyl-3-(4-fluorophenyl)-N,4-dimethyl-N-(2-methylsulfonyl-ethyl)-5-(trifluoromethyl)-1H-pyrrole-2-carboxylic acid amide;
1-Benzyl-3-(4-fluorophenyl)-N,4-dimethyl-N-tetrahydro-pyran-4-yl-5-(trifluoromethyl)-1H-pyrrole-2-carboxylic acid amide;
1-Benzyl-N-cyclopropyl-3-(4-fluorophenyl)-N,4-dimethyl-5-(trifluoromethyl)-1H-pyrrole-2-carboxylic acid amide;
1-Benzyl-3-(4-fluorophenyl)-N-(2-hydroxy-1,1-dimethyl-ethyl)-N,4-dimethyl-5-(trifluoromethyl)-1H-pyrrole-2-carboxylic acid amide;
[1-Benzyl-3-(4-fluorophenyl)-4-methyl-5-(trifluoromethyl)-1H-pyrrol-2-yl]-(3-hydroxy-azetidin-1-yl)-methanone;
1-Benzyl-N-(2,2-dimethyl-propyl)-3-(4-fluorophenyl)-N,4-dimethyl-5-(trifluoromethyl)-1H-pyrrole-2-carboxylic acid amide;
[1-Benzyl-3-(4-fluorophenyl)-4-methyl-5-(trifluoromethyl)-1H-pyrrol-2-yl]-(2,2-dimethyl-morpholin-4-yl)-methanone;
1-Benzyl-3-(4-fluorophenyl)-N,4-dimethyl-N-(tetrahydro-furan-3-yl-methyl)-5-(trifluoromethyl)-1H-pyrrole-2-carboxylic acid amide;
1-Benzyl-N-(3-hydroxy-2,2-dimethyl-propyl)-N,4-dimethyl-5-(trifluoromethyl)-3-[4-(trifluoromethyl)-phenyl]-1H-pyrrole-2-carboxylic acid amide;
1-Benzyl-N,4-dimethyl-N-(2-methylsulfonyl-ethyl)-5-(trifluoromethyl)-3-[4-(trifluoromethyl)-phenyl]-1H-pyrrole-2-carboxylic acid amide;

1-Benzyl-N,4-dimethyl-N-tetrahydro-pyran-4-yl-5-(trifluoromethyl)-3-[4-(trifluoromethyl)-phenyl]-1H-pyrrole-2-carboxylic acid amide;

1-Benzyl-N-cyclopropyl-N,4-dimethyl-5-(trifluoromethyl)-3-[4-(trifluoromethyl)-phenyl]-1H-pyrrole-2-carboxylic acid amide;

1-Benzyl-N-(2-hydroxy-1,1-dimethyl-ethyl)-N,4-dimethyl-5-(trifluoromethyl)-3-[4-(trifluoromethyl)-phenyl]-1H-pyrrole-2-carboxylic acid amide;

[1-Benzyl-4-methyl-5-(trifluoromethyl)-3-[4-(trifluoromethyl)-phenyl]-1H-pyrrol-2-yl]-(3-hydroxy-azetidin-1-yl)-methanone;

1-Benzyl-N-(2,2-dimethyl-propyl)-N,4-dimethyl-5-(trifluoromethyl)-3-[4-(trifluoromethyl)-phenyl]-1H-pyrrole-2-carboxylic acid amide;

[1-Benzyl-4-methyl-5-(trifluoromethyl)-3-[4-(trifluoromethyl)-phenyl]-1H-pyrrol-2-yl]-(2,2-dimethyl-morpholin-4-yl)-methanone;

1-Benzyl-N-(3-hydroxy-2,2-dimethyl-propyl)-N,4-dimethyl-5-(trifluoromethyl)-3-[4-(trifluoromethyloxy)-phenyl]-1H-pyrrole-2-carboxylic acid amide;

1-Benzyl-N,4-dimethyl-N-(2-methylsulfonyl-ethyl)-5-(trifluoromethyl)-3-[4-(trifluoromethyloxy)-phenyl]-1H-pyrrole-2-carboxylic acid amide;

1-Benzyl-N,4-dimethyl-N-tetrahydro-pyran-4-yl-5-(trifluoromethyl)-3-[4-(trifluoromethyloxy)-phenyl]-1H-pyrrole-2-carboxylic acid amide;

1-Benzyl-N-cyclopropyl-N,4-dimethyl-5-(trifluoromethyl)-3-[4-(trifluoromethyloxy)-phenyl]-1H-pyrrole-2-carboxylic acid amide;

[1-Benzyl-4-methyl-5-(trifluoromethyl)-3-[4-(trifluoromethyloxy)-phenyl]-1H-pyrrol-2-yl]-(3-hydroxy-azetidin-1-yl)-methanone;

1-Benzyl-N-(2,2-dimethyl-propyl)-N,4-dimethyl-5-(trifluoromethyl)-3-[4-(trifluoromethyloxy)-phenyl]-1H-pyrrole-2-carboxylic acid amide;

1-Benzyl-N-(2-hydroxy-1,1-dimethyl-ethyl)-N,4-dimethyl-5-(trifluoromethyl)-3-[4-(trifluoromethyloxy)-phenyl]-1H-pyrrole-2-carboxylic acid amide;

[1-Benzyl-4-methyl-5-(trifluoromethyl)-3-[4-(trifluoromethyloxy)-phenyl]-1H-pyrrol-2-yl]-(2,2-dimethyl-morpholin-4-yl)-methanone;

1-Benzyl-3-(4-chloro-3-fluoro-phenyl)-N-(3-hydroxy-2,2-dimethyl-propyl)-N,4-dimethyl-5-(trifluoromethyl)-1H-pyrrole-2-carboxylic acid amide;

1-Benzyl-3-(4-chloro-3-fluoro-phenyl)-N,4-dimethyl-N-(2-methylsulfonyl-ethyl)-5-(trifluoromethyl)-1H-pyrrole-2-carboxylic acid amide;

1-Benzyl-3-(4-chloro-3-fluoro-phenyl)-N,4-dimethyl-N-tetrahydro-pyran-4-yl-5-(trifluoromethyl)-1H-pyrrole-2-carboxylic acid amide;

1-Benzyl-3-(4-chloro-3-fluoro-phenyl)-N-cyclopropyl-N,4-dimethyl-5-(trifluoromethyl)-1H-pyrrole-2-carboxylic acid amide;

[1-Benzyl-3-(4-chloro-3-fluoro-phenyl)-4-methyl-5-(trifluoromethyl)-1H-pyrrol-2-yl]-(3-hydroxy-azetidin-1-yl)-methanone;

1-Benzyl-3-(4-chloro-3-fluoro-phenyl)-N-(2-hydroxy-1,1-dimethyl-ethyl)-N,4-dimethyl-5-(trifluoromethyl)-1H-pyrrole-2-carboxylic acid amide;

[1-Benzyl-3-(4-chloro-3-fluoro-phenyl)-4-methyl-5-(trifluoromethyl)-1H-pyrrol-2-yl]-(2,2-dimethyl-morpholin-4-yl)-methanone;

1-Benzyl-3-(4-chloro-3-fluoro-phenyl)-N-(2,2-dimethyl-propyl)-N,4-dimethyl-5-(trifluoromethyl)-1H-pyrrole-2-carboxylic acid amide;

1-Benzyl-3-(3-chloro-4-fluoro-phenyl)-N-(3-hydroxy-2,2-dimethyl-propyl)-N,4-dimethyl-5-(trifluoromethyl)-1H-pyrrole-2-carboxylic acid amide;

1-Benzyl-3-(3-chloro-4-fluoro-phenyl)-N,4-dimethyl-N-(2-methylsulfonyl-ethyl)-5-(trifluoromethyl)-1H-pyrrole-2-carboxylic acid amide;

1-Benzyl-3-(3-chloro-4-fluoro-phenyl)-N,4-dimethyl-N-tetrahydro-pyran-4-y1-5-(trifluoromethyl)-1H-pyrrole-2-carboxylic acid amide;

1-Benzyl-3-(3-chloro-4-fluoro-phenyl)-N-cyclopropyl-N,4-dimethyl-5-(trifluoromethyl)-1H-pyrrole-2-carboxylic acid amide;

[1-Benzyl-3-(3-chloro-4-fluoro-phenyl)-4-methyl-5-(trifluoromethyl)-1H-pyrrol-2-yl]-(3-hydroxy-azetidin-1-yl)-methanone;

1-Benzyl-3-(3-chloro-4-fluoro-phenyl)-N-(2,2-dimethyl-propyl)-N,4-dimethyl-5-(trifluoromethyl)-1H-pyrrole-2-carboxylic acid amide;

1-Benzyl-3-(3-chloro-4-fluoro-phenyl)-N-(2-hydroxy-1,1-dimethyl-ethyl)-N,4-dimethyl-5-(trifluoromethyl)-1H-pyrrole-2-carboxylic acid amide;

[1-Benzyl-3-(3-chloro-4-fluoro-phenyl)-4-methyl-5-(trifluoromethyl)-1H-pyrrol-2-yl]-(2,2-dimethyl-morpholin-4-yl)-methanone;

1-Benzyl-3-(4-chlorophenyl)-N-(2,2-dimethyl-propyl)-N-methyl-4-methylsulfonyl-5-(trifluoromethyl)-1H-pyrrole-2-carboxylic acid amide;

1-Benzyl-N-(2,2-dimethyl-propyl)-N,4-dimethyl-3-[4-(2,2,2-trifluoro-ethoxy)-phenyl]-5-(trifluoromethyl)-1H-pyrrole-2-carboxylic acid amide;

3-(4-Chlorophenyl)-N-(2,2-dimethyl-propyl)-1-[(4-fluorophenyl)-methyl]-N-methyl-5-(trifluoromethyl)-1H-pyrrole-2-carboxylic acid amide;

[1-Benzyl-3-[2-fluoro-4-(trifluoromethyloxy)-phenyl]-4-methyl-5-(trifluoromethyl)-1H-pyrrol-2-yl]-morpholin-4-yl-methanone;

[1-Benzyl-4-methyl-3-[4-(2,2,2-trifluoro-ethoxy)-phenyl]-5-(trifluoromethyl)-1H-pyrrol-2-yl]-morpholin-4-yl-methanone;

4-[1-Benzyl-4-methyl-2-(morpholine-4-carbonyl)-5-(trifluoromethyl)-1 H-pyrrol-3-yl]-3-fluoro-benzonitrile;

[3-(4-Chlorophenyl)-4-methyl-1-[(3-methylsulfonyl-phenyl)-methyl]-5-(trifluoromethyl)-1H-pyrrol-2-yl]-morpholin-4-yl-methanone; and 3-(4-Chlorophenyl)-N-(2,2-dimethyl-propyl)-N-methyl-1-[(3-methylsulfonyl-phenyl)-methyl]-5-(trifluoromethyl)-1H-pyrrole-2-carboxylic acid amide;

optionally in the form of a single stereoisomer or a mixture of stereoisomers, in the form of the free compound and/or a physiologically acceptable salt or solvate thereof.

9. A pharmaceutical composition comprising at least one compound according to claim 8.

* * * * *